United States Patent
Kuo et al.

(10) Patent No.: US 6,710,048 B2
(45) Date of Patent: Mar. 23, 2004

(54) PYRAZINE DERIVATIVES AS MODULATORS OF TYROSINE KINASES

(75) Inventors: Gee-Hong Kuo, Scotch Plains, NJ (US); Peter J. Connolly, New Providence, NJ (US); Catherine Prouty, Doylestown, PA (US); Alan DeAngelis, Pennington, NJ (US); Aihua Wang, Jamison, PA (US); Linda Jolliffe, Hillsborough, NJ (US); Steve Middleton, Flemington, NJ (US); Stuart Emanuel, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/955,780

(22) Filed: Sep. 19, 2001

(65) Prior Publication Data

US 2003/0060629 A1 Mar. 27, 2003

Related U.S. Application Data

(60) Provisional application No. 60/233,968, filed on Sep. 20, 2000.

(51) Int. Cl.$^7$ ...................... A61K 31/505; C07D 239/00
(52) U.S. Cl. ............................ 514/252.11; 514/235.8; 514/255.05; 544/120; 544/357; 544/405
(58) Field of Search .................. 544/405, 357, 544/120; 514/252.11, 255.05, 235.8

(56) References Cited

U.S. PATENT DOCUMENTS

| | | | | |
|---|---|---|---|---|
| 4,514,400 | A | 4/1985 | Campbell | 514/257 |
| 5,843,942 | A | * 12/1998 | Breault et al. | 514/247 |
| 5,939,359 | A | * 8/1999 | Engel et al. | 544/405 |
| 6,358,972 | B1 | * 3/2002 | Filla et al. | 514/300 |
| 2003/0032647 | A1 | * 2/2003 | Yamada et al. | 544/405 |

FOREIGN PATENT DOCUMENTS

| WO | WO 9900385 A1 | 1/1999 |
|---|---|---|
| WO | WO 0160806 A2 | 8/2001 |

OTHER PUBLICATIONS

Burke, Stem Cells, vol. 12, p. 1–6 (1994).*
Brower, Nature Biotechnology vol. 17, p. 963–968 (1999).*
Hennequin et al. J.Med. Chem. vol. 42, p. 5369–5389 (1999).*
Heldin, Carl–Henrik, "Dimerization of Cell Surface Receptors in Signal Transduction," Cell, 80:213–223 1995.
Kelly, T. Ross, et al., "Synthesis of Schumanniophytine and Isoschumanniophytine," J. Org. Chem., 57:1593–1597 1992.
Lohse, Olivier, "Improved Large–Scale Preparation of 4–Iodopicolinic Acid," Synthethic Communications, 26(10):2017–2025 1996.
Nicosia, Roberto F., et al., "Growth of Microvessels in Serum–Free Matrix Culture of Rat Aorta," Laboratory Inves. 63(1):115 1990.
Nissanov, Jonathan, et al., "Methods in Laboratory Investigation," Laboratory Invest. 73(5):734 1995.
Sato, Nobuhiro, et al., "Studies on Pyrazines. 29[1]. High Regioselective Synthesis of Chloropyrazines from 3–Substituted Pyrazine 1–Oxides," J. Heterocyc Chem, 31:1177 1994.
Tessler, Shoshana, et al., "Heparin Modulates the Interaction of VEGF (165) with Soluble and Cell Associated flk–1 Receptors," Journal of Biological Chem. 269(17): 12456–12461 (1994).
Torrado, Alicia, et al., "General Synthesis of Retinoids and Arotinoids via Palladium–Catalyzed Cross–Coupling f Boronic Acids with Electrophiles," Synthesis, 285–293 1995.
Torrado, Alicia et al., "New Synthetic amino Acids for the Design and Synthesis of Peptide–Based Metal Ion Sensors," J. Org. Chem., 61:8940–8948 1996.
Turck, A., et al., "A New Route to Arglecin by Metalation and Cross Coupling of Pyrazines, Metalation of Diazines, XII," J. Heterocyc Chem. 31(6):1449–1453 1994.
Wuest, H. M. & Sakal, E. H., Some Derivatives of 3–Pyridol with Parasympathomimetic Properties(1), 73:1210 1951.
GenBank Accession #U93306 1998.

* cited by examiner

*Primary Examiner*—Richard L. Raymond

(57) ABSTRACT

The present invention provides pyrazine derivatives that inhibit tyrosine kinase activity. Certain pyrazine derivatives are selective inhibitors of vascular endothelial growth factor (VEGF) receptor tyrosine kinase. The present invention also provides pharmaceutical formulations containing the pyrazine derivatives and methods of use of these formulations as anti-tumor agents and to treat solid-tumor cancers, angiogenesis, diabetic retinopathy, rheumatoid arthritis, endometriosis and psoriasis.

71 Claims, 1 Drawing Sheet

FIGURE 1/1
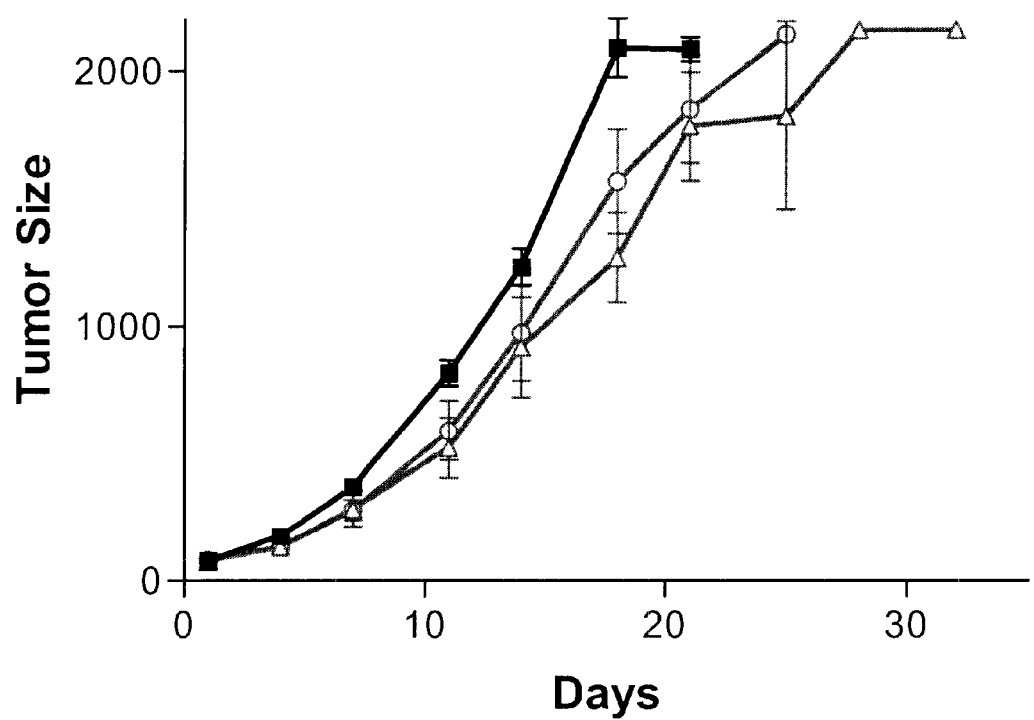

SEQUENCE LISTING

```
<160> NUMBER OF SEQ ID NOS: 12

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:VEGF-R
      substrate

<400> SEQUENCE: 1

Lys His Lys Lys Leu Ala Glu Gly Ser Ala Tyr Glu Glu Val
 1               5                  10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: CDK-1
      substrate

<400> SEQUENCE: 2

Lys Thr Pro Lys Lys Ala Lys Lys Pro Lys Thr Pro Lys Lys Ala Lys
 1               5                  10                  15

Lys Leu

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:EGF-R
      substrate

<400> SEQUENCE: 3

Asp Arg Val Tyr Ile His Pro Phe
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:Protein
      Kinase A substrate

<400> SEQUENCE: 4

Gly Arg Thr Gly Arg Arg Asn Ser Ile
 1               5
```

```
<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:PKC-gamma
      substrate

<400> SEQUENCE: 5

Arg Phe Ala Arg Lys Gly Ser Leu Arg Gln Lys Asn Val
 1               5                  10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:Casein
      Kinase 1 substrate

<400> SEQUENCE: 6

Lys Arg Arg Arg Ala Leu Ser
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:Casein
      Kinase 2 substrate

<400> SEQUENCE: 7

Arg Arg Glu Glu Glu Thr Glu Glu Glu
 1               5

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:Calmodulin
      Kinase substrate

<400> SEQUENCE: 8

Lys Lys Arg Ala Leu Arg Arg Gln Glu Thr Val Asp Ala Leu
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:GSK-3
      substrate

<400> SEQUENCE: 9

Lys Arg Arg Glu Ile Leu Ser Arg Arg Pro
 1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:MAP Kinase
      ERK-2 substrate

<400> SEQUENCE: 10
```

```
Ala Pro Arg Thr Pro Gly Gly Arg Arg
  1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:Insulin
      Kinase substrate

<400> SEQUENCE: 11

Thr Arg Asp Ile Tyr Glu Thr Asp Tyr Tyr Arg Lys
  1               5                  10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence:PDGF-R
      substrate

<400> SEQUENCE: 12

Lys His Lys Lys Leu Ala Glu Gly Ser Ala Tyr Glu Glu Val
  1               5                  10
```

PYRAZINE DERIVATIVES AS MODULATORS OF TYROSINE KINASES

FIELD OF THE INVENTION

This invention claims priority from U.S. Provisional Application No. 60/233,968 filed Sep. 20, 2000 and entitled "Pyrazine Derivatives as Modulators of Tyrosine Kinases."

The present invention provides pyrazine derivatives that inhibit tyrosine kinase activity. Certain pyrazine derivatives are selective inhibitors of the vascular endothelial growth factor (VEGF) receptor tyrosine kinase. The present invention also provides pharmaceutical formulations containing the pyrazine derivatives and methods for use of these formulations as anti-tumor agents, and to treat diabetic retinopathy, rheumatoid arthritis, endometriosis, and psoriasis.

BACKGROUND OF THE INVENTION

Angiogenesis plays a role in various processes including development of the vasculature, wound healing and maintenance of the female reproductive system. Pathological angiogenesis is associated with disease states such as cancer, diabetic retinopathy, rheumatoid arthritis, endometriosis and psoriasis. Solid-tumor cancers, in particular, are dependent on angiogenesis for their growth. The vascular endothelial growth factors (VEGFs) are mediators of both normal and pathologic angiogenesis. VEGF transmits signals into cells through their cognate receptors, which belong to the receptor tyrosine kinase (RTK) family of transmembrane receptors. These receptors are tripartite, consisting of an extracellular ligand-binding domain, a transmembrane domain, which anchors the receptor in the membrane of the cell, and an intracellular tyrosine kinase domain. One subfamily of RTKs comprises the receptors Flt1/VEGF-R1 and KDR/Flk1/VEGF-R2, which bind VEGFs. Binding of the VEGF ligand to the receptor results in stimulation of the receptor tyrosine kinase activity and transduction of biological signals into the cell. The KDR/Flk1/VEGF-R2 receptor mediates the biological activities of mitogenesis and proliferation of endothelial cells while the Flt1/VEGF-R1 receptor mediates functions such as endothelial cell adhesion. Inhibition of KDR/Flk1/VEGF-R2 signalling has been shown to inhibit the process of angiogenesis. Inhibitors of this receptor are likely useful in controlling or limiting angiogenesis.

SUMMARY OF THE INVENTION

The present invention provides pyrazine derivative compounds that display activity as kinase inhibitors of the formula:

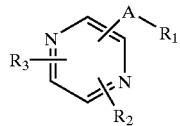

where the substituents are defined herein. These pyrazine derivatives are useful as kinase inhibitors; particularly, as inhibitors against the kinase domain of the Vascular Endothelial Growth Factor Receptor (VEGF-R), inhibiting the activity of the VEGF receptor in vitro and in vivo.

In a preferred embodiment, the invention relates to compounds of Formula 1:

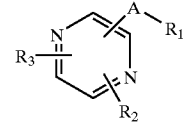

Formula 1 or a pharmaceutically acceptable salt thereof, wherein $R_1$ is selected from the group consisting of cycloalkyl, heterocyclyl, biheterocyclyl, aryl, biaryl, heteroaryl and biheteroaryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkenyl, heterocyclylalkynyl, heterocyclylalkoxy, aryl, arylalkyl, arylalkenyl, arylalkynyl, arylalkoxy, heteroaryl, heteroarylalkyl, heteroarylalkenyl, heteroarylalkynyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, (hydroxyalkoxy)carbonyl, trihalo substituted lower alkyl and trihalo substituted lower alkoxy;

A is selected from the group consisting of —N($R_4$)-($CH_2$)$_x$—, —O($CH_2$)$_x$—, —S($CH_2$)$_x$—, —$SO_2$-($CH_2$)$_x$—, —$SO_2$N($CH_2$)$_x$—, —$NSO_2$($CH_2$)$_x$—, —N($R_4$)($CH_2$)$_x$—, —N($R_4$)($CH_2$)$_{1-4}$NH($CH_2$)$_x$—, —N($R_4$)CONH($CH_2$)$_x$— and —N($R_4$)CNNH-($CH_2$)$_x$—; wherein x is an integer from 0 to 4;

$R_4$ is selected from the group consisting of H, lower alkyl, alkyl, hydroxyalkyl, alkoxyalkyl, arylalkyl, lower alkenyl, alkenyl, aryl and heteroaryl; wherein aryl and heteroaryl are optionally substituted with 1 to 5 substituents independently selected from the group consisting of OH, halogen, cyano, nitro, amino, alkylamino, di(alkyl)amino, (hydroxyalkyl)amino, di(hydroxyalkyl)amino, alkyl, lower alkyl, alkoxy, lower alkoxy, tri(halo)substituted lower alkyl and tri(halo)substituted lower alkoxy;

$R_2$ is selected from the group consisting of heteroaryl and biheteroaryl optionally substituted with 1 to 2 substituents independently selected from $R_7$ and 1 substituent selected from $R_8$;

$R_7$ is selected from the group consisting of alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy;

$R_8$ is selected from the group consisting of alkyl, OH, hydroxyalkyl, halogen, cyano, amino, alkylamino, di(alkyl)amino, (hydroxyalkyl)amino, di(hydroxyalkyl)amino, carbamoyl, alkylcarbonylamino, alkylcarbonyl, alkoxycarbonyl, (hydroxyalkyl)carbonyl, (hydroxyalkoxy)carbonyl, $O(CH_2)_nR_5$, $O(CH_2)_nO(CH_2)_mR_5$, $O(CH_2)_nCH[(CH_2)_mR_5]_2$, $O(CH_2)_nN[(CH_2)_mR_5]_2$, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH(CH_2)_nCH(OH)(CH_2)_mOR_5$, $NH(CH_2)_nCH(OH)(CH_2)_mN[(CH_2)_mR_5]_2$, $NH(CH_2)_nCO(CH_2)_mN[(CH_2)_mR_5]_2$, $NH(CH_2)_nCO_2(CH_2)_mR_5$, $NH(CH_2)_nCO(CH_2)_mSO_2NH(CH_2)_nR_5$, $NHCO(CH_2)_nCH(R_5)_2$, $NHCO(CH_2)_nR_5$, $NHCO(CH_2)_nO(CH_2)_mR_5$, $NHCO(CH_2)_nO(CH_2)_mO(CH_2)_mR_5$, $NHCO(CH_2)_nO(CH_2)_mCO(CH_2)_mR_5$, $NHCO(CH_2)_nN[(CH_2)_mR_5]_2$, $CONH(CH_2)_nO(CH_2)_mR_5$, and $CONH(CH_2)_nN[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino;

$R_5$ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents; and, $R_3$ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo) substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

In one aspect of this embodiment, the compound of claim 1 includes $R_1$ wherein $R_1$ is selected from the group consisting of cycloalkyl, heterocyclyl, biheterocyclyl, aryl, biaryl, heteroaryl and biheteroaryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkoxy, aryl, arylalkyl, arylalkoxy, heteroaryl, heteroarylalkyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, trihalo substituted lower alkyl and trihalo substituted lower alkoxy.

In another aspect of this embodiment, $R_1$ is selected from the group consisting of aryl optionally substituted with 1 to 5 substituents independently selected from the group consisting of lower alkyl, lower alkoxy, heterocyclyl, heterocyclylalkyl, aryl, arylalkyl, heteroaryl, heteroarylalkyl, OH, halogen, cyano, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, trihalo substituted lower alkyl and trihalo substituted lower alkoxy.

Preferably $R_1$ is selected from the group consisting of phenyl optionally substituted with 1 to 5 substituents independently selected from the group consisting of lower alkyl, lower alkoxy, OH, halogen, cyano, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, trihalo substituted lower alkyl and trihalo substituted lower alkoxy. In another aspect, $R_1$ is selected from the group consisting of phenyl optionally substituted with 1 to 5 substituents independently selected from the group consisting of methoxy, chlorine and fluorine. Still further in a preferred aspect of this embodiment, A is selected from the group consisting of —$N(R_4)(CH_2)_x$—, —$O(CH_2)_x$—, —$S(CH_2)_x$—, —$SO_2(CH_2)_x$—, —$SO_2N(CH_2)_x$—, —$NSO_2(CH_2)_x$—, —$N(R_4)(CH_2)_{1-4}O(CH_2)_x$— and —$N(R_4)(CH_2)_{1-4}NH(CH_2)_x$—; wherein x is an integer from 0 to 3. In another aspect, A is selected from the group consisting of —$N(R_4)(CH_2)_x$—, —$O(CH_2)_x$—, —$S(CH_2)_x$—, —$SO_2(CH_2)_x$—, —$SO_2N(CH_2)_x$—, —$NSO_2(CH_2)_x$—, —$N(R_4)(CH_2)_{1-4}O(CH_2)_x$— and —$N(R_4)(CH_2)_{1-4}NH(CH_2)_x$—; wherein x is an integer from 0 to 1. Alternatively, A is selected from the group consisting of —$N(R_4)(CH_2)_x$— and —$O(CH_2)_x$—; wherein x is an integer from 0 to 1.

Preferably, $R_4$ is selected from the group consisting of H, alkyl, lower alkyl, alkoxyalkyl, alkenyl, lower alkenyl, hydroxyalkyl, aryl, arylalkyl and heteroaryl and still more preferably $R_4$ is selected from the group consisting of H, lower alkyl and hydroxyalkyl. Most preferably, $R_4$ is H.

In another aspect of this embodiment, $R_2$ is selected from the group consisting of heteroaryl and biheteroaryl optionally substituted with 1 to 2 substituents independently selected from $R_7$ and optionally substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$. Preferably $R_2$ is selected from the group consisting of heteroaryl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

In one aspect $R_2$ is selected from the group consisting of thienyl, pyrrolyl, oxazolyl, thiazolyl, imidazolyl, pyrazolyl, isoxazolyl, isothiazolyl, pyridinyl, pyridazinyl, pyrimidinyl and pyrazinyl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$. Preferably $R_2$ is selected from the group consisting of pyridinyl, pyridazinyl, pyrimidinyl and pyrazinyl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

Also preferably $R_7$ is selected from the group consisting of lower alkyl, lower alkoxy, heterocyclylalkyl, aryl, arylalkyl, OH, hydroxyalkyl, halogen, cyano, nitro, amino, alkylamino, di(alkyl)amino, (hydroxyalkyl)amino, di(hydroxyalkyl)amino, acyl, carboxyl, tri(halo)substituted lower alkyl and tri(halo)substituted lower alkoxy. In a preferred embodiment, $R_7$ is selected from the group consisting of lower alkyl, OH, halogen, cyano, nitro, amino, tri(halo) substituted lower alkyl and tri(halo)substituted lower alkoxy. In yet another embodiment, $R_7$ is selected from the group consisting of methyl, ethyl, OH, bromine, chlorine, fluorine, cyano, nitro, amino, trifluoromethyl and trifluoromethoxy.

$R_8$ is preferably selected from the group consisting of OH, amino, (hydroxyalkyl)amino, alkoxycarbonyl, OCON$[(CH_2)_mR_5]_2$, NH$(CH_2)_nR_5$, NH$(CH_2)_nCH(R_5)_2$, NH$(CH_2)_n$SO$_2(CH_2)_mR_5$, NH$(CH_2)_nO(CH_2)_mR_5$, NH$(CH_2)_n$OCH$[(CH_2)_mR_5]_2$, NH$(CH_2)_nO(CH_2)_mO(CH_2)_mR_5$, NH$(CH_2)_n$N$[(CH_2)_mR_5]_2$, NH$(CH_2)_n$SO$_2$NH$(CH_2)_mR_5$, NH$(CH_2)_n$CH(OH)$(CH_2)_mR_5$, NH$(CH_2)_n$CH(OH)$(CH_2)_m$OR$_5$, NH$(CH_2)_n$CH(OH)$(CH_2)_m$N$[(CH_2)_mR]_2$, NH$(CH_2)_n$CO$(CH_2)_m$N$[(CH_2)_mR_5]_2$, NH$(CH_2)_n$CO$_2(CH_2)_mR_5$, NH$(CH_2)_n$CO$(CH_2)_m$SO$_2$NH$(CH_2)_mR_5$, NHCO$(CH_2)_nR_5$, NHCO$(CH_2)_nO(CH_2)_mR_5$, NHCO$(CH_2)_nO(CH_2)_mO(CH_2)_mR_5$, NHCO$(CH_2)_nO(CH_2)_m$CO$(CH_2)_mR_5$, CONH$(CH_2)_nO(CH_2)_mR_5$ and CONH$(CH_2)_n$N$[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino. In one aspect of this embodiment, $R_8$ is selected from the group consisting of OH, amino, (hydroxyalkyl)amino, alkoxycarbonyl, OCON$[(CH_2)_mR_5]_2$, NH$(CH_2)_nR_5$, NH$(CH_2)_n$CH(R$_5$)$_2$, NH$(CH_2)_n$SO$_2(CH_2)_mR_5$, NH$(CH_2)_n$O$(CH_2)_mR_5$, NH$(CH_2)_n$OCH$[(CH_2)_mR_5]_2$, NH$(CH_2)_n$O$(CH_2)_mO(CH_2)_mR_5$, NH$(CH_2)_n$N$[(CH_2)_mR_5]_2$, NH$(CH_2)_n$SO$_2$NH$(CH_2)_mR_5$, NH$(CH_2)_n$CH(OH)$(CH_2)_mR_5$, NH$(CH_2)_n$CH(OH)$(CH_2)_m$OR$_5$, NH$(CH_2)_n$CH(OH)$(CH_2)_m$N$[(CH_2)_mR_5]_2$, NH$(CH_2)_n$CO$(CH_2)_m$N$[(CH_2)_mR_5]_2$, NH$(CH_2)_n$CO$_2(CH_2)_mR_5$, NH$(CH_2)_n$CO$(CH_2)_m$SO$_2$NH$(CH_2)_mR_5$, NHCO$(CH_2)_nR_5$, NHCO$(CH_2)_nO(CH_2)_mR_5$, NHCO$(CH_2)_nO(CH_2)_mO(CH_2)_mR_5$, NHCO$(CH_2)_nO$-$(CH_2)_m$CO$(CH_2)_mR_5$, CONH$(CH_2)_nO(CH_2)_mR_5$ and CONH$(CH_2)_n$N$[(CH_2)_mR_5]_2$; wherein n is an integer from 0 to 5 and m is an integer from 0 to 2; with the proviso, that m is at least 1 when $R_5$ is selected from the group consisting of OH, amino, alkylamino and di(alkyl)amino. Still more preferably, $R_8$ is selected from the group consisting of OH, amino, (2-hydroxyethyl)amino, (3-hydroxy-n-propyl) amino, (4-hydroxy-n-butyl)amino, ethoxycarbonyl, OCON$(R_5)_2$, NH$[(CH_2)_{1-4}R_5]$, NH$[(CH_2)_{1-3}$SO$_2(CH_2)_{0-1}R_5]$, NH$[(CH_2)_{1-3}$O$(CH_2)_{0-1}R_5]$, NH$[(CH_2)_{1-4}$OCH$[(CH_2)_{1-2}R_5]_2$, NH$[(CH_2)_{1-3}$O$(CH_2)_{1-2}$O$(CH_2)_{1-2}R_5]$, NH$[(CH_2)_{1-4}$N$[(CH_2)_{0-2}R_5]_2$, NH$[(CH_2)_{1-4}$SO$_2$NH$(CH_2)_{1-2}R_5]$, NH$[(CH_2)_{1-4}$CH(OH)-$(CH_2)_{1-2}R_5]$, NH$[(CH_2)_{1-4}$CH(OH)$(CH_2)_{1-2}$OR$_5]$, NH-$(CH_2)_{1-4}$CH(OH)$(CH_2)_{1-2}$N$[(CH_2)_{0-1}R_5]_2$, NH$[(CH_2)_{1-3}$CO $(CH_2)_{0-1}$N$[(CH_2)_{0-1}R_5]_2$, NH$[(CH_2)_{1-3}$CO$_2(CH_2)_{0-1}R_5]$, NH$[(CH_2)_{1-4}$CO$(CH_2)_{1-2}$SO$_2$NH$(CH_2)_{1-2}R_5]$, NHCO-$(CH_2)_{0-1}R_5$, NHCO$(CH_2)_{1-3}$O$(CH_2)_{0-2}R_5$, NHCO$(CH_2)_{1-2}$O$(CH_2)_{1-2}$O$(CH_2)_{1-2}R_5$, NHCO$(CH_2)_{1-2}$O$(CH_2)_{0-1}$CO $(CH_2)_{1-2}R_5$, CONH$(CH_2)_{1-3}$O$(CH_2)_{0-2}R_5$ and CONH-$(CH_2)_{1-3}$N$[(CH_2)_{1-2}R_5]_2$; with the proviso, that the $R_5$ alkylene linking group is at least methylene when $R_5$ is selected from the group consisting of OH, amino, alkylamino and di(alkyl)amino.

In another embodiment of this invention, $R_5$ is selected from the group consisting of H, OH, lower alkyl, amino, alkylamino, di(alkyl)amino, aryl, heteroaryl and heterocyclyl; wherein aryl, heteroaryl and heterocyclyl are optionally substituted with 1 to 3 substituents independently selected from the group consisting of lower alkyl, acyl, carboxyl, aryl (optionally substituted with one halogen substituent), di(alkyl)amino; alkylsulfonyl, aminosulfonyl, alkylaminosulfonyl and aminosulfonylalkyl; and, wherein heterocyclyl is further optionally substituted with 1 to 3 oxo substituents. Preferably $R_5$ is selected from the group consisting of H, OH, lower alkyl, heteroaryl and heterocyclyl; wherein heterocyclyl is optionally substituted with 1 to 3 substituents independently selected from the group consisting of lower alkyl, acyl, carboxyl, aryl (optionally substituted with one halogen substituent), di(alkyl)amino, alkylsulfonyl, aminosulfonyl, alkylaminosulfonyl, aminosulfonylalkyl and oxo. In a preferred embodiment, $R_5$ is selected from the group consisting of H, OH, methyl, ethyl, t-butyl, 1H-azetidinyl, 1H-pyrrolidinyl, 4-tetrahydro-2H-pyranyl, hexahydro-1H-azepinyl, 1,3-dioxolanyl, 1,3-dioxanyl, piperidinyl, piperazinyl, imidazolyl, pyrazolyl, triazolyl and pyridinyl; wherein 1,3-dioxolanyl, 1,3-dioxanyl, piperazinyl and piperidinyl are optionally substituted with 1 to 2 substituents independently selected from the group consisting of methyl, acetyl, carboxyl, phenyl (optionally substituted with chlorine), di(methyl)amino, methylsulfonyl, methylaminosulfonyl and oxo.

In other embodiments, $R_3$ is selected from the group consisting of H, lower alkyl, lower alkoxy, OH, halogen, cyano, amino, alkylamino and di(alkyl)amino. Preferably, $R_3$ is selected from the group consisting of H, lower alkyl, lower alkoxy, OH, halogen, amino and di(alkyl)amino and more preferably, $R_3$ is selected from the group consisting of H and methyl.

Preferred compounds include:

3-[[5-[6-[(3-chlorophenyl)amino]pyrazinyl]-3-pyridinyl] amino]-11-propanol;

3-[[5-[2-[(3-chlorophenyl)amino]-6-methyl-4-pyrimidinyl]-3-pyridinyl]amino]-1-propanol;

2-[[5-[6-[(3-chlorophenyl)amino]pyrazinyl]-3-pyridinyl] amino]-ethanol;

4-[[5-[6-[(3-chlorophenyl)amino]pyrazinyl]-3-pyridinyl] amino]-1-butanol;

3-[[5-[6-[(3-fluorophenyl)amino]pyrazinyl]-3-pyridinyl] amino]-1-propanol;

3-[[5-[6-[(3-methoxyphenyl)amino]pyrazinyl]-3-pyridinyl]amino]-1-propanol;

3-[[5-[6-[(phenylmethyl)amino]pyrazinyl]-3-pyridinyl] amino]-1-propanol;

3-[[6'-[(3-chlorophenyl)amino][2,2'-bipyrazin]-6-yl] amino]-1-propanol;

3-[[4-[6-[(3-chlorophenyl)amino]pyrazinyl]-3-pyridinyl] amino]-1-propanol;

3-[[5-[6-[(3-chlorophenyl)amino]pyrazinyl]-2-thiazolyl] amino]-1-propanol; and,

2-[2-[2-[[5-[6-[(3-chlorophenyl)amino]pyrazinyl]-3-pyridinyl]amino]ethoxy]ethoxy]-ethanol.

Additional preferred compounds include:

6-(5-amino-3-pyridinyl)-N-(3-chlorophenyl)-2-pyrazinamine;

N'-[5-[6-[(3-chlorophenyl)amino]pyrazinyl]-3-pyridinyl]-$N^2,N^2$-dimethyl-1,2-ethanediamine;

N-[5-[6-[(3-chlorophenyl)amino]pyrazinyl]-3-pyridinyl]-4-morpholinepropanamine;

N-[5-[6-[(3-chlorophenyl)amino]pyrazinyl]-3-pyridinyl]-$N^3,N^3$-dimethyl-1,3-propanediamine;

N-(3-chlorophenyl)-6-[5-[[3-(1-piperazinyl)propyl]amino]-3-pyridinyl]-2-pyrazinamine;

N-(3-chlorophenyl)-6-[5-[[4-(4-pyridinyl)butyl]amino]-3-pyridinyl]-2-pyrazinamine;

N-(3-chlorophenyl)-6-[5-[[3-(4-pyridinyl)propyl]amino]-3-pyridinyl]-2-pyrazinamine;

N-(3-chlorophenyl)-6-[5-[[3-(3-pyridinyl)propyl]amino]-3-pyridinyl]-2-pyrazinamine;

N-(3-chlorophenyl)-6-[5-[[3-(1H-pyrazol-1-yl)propyl] amino]-3-pyridinyl]-2-pyrazinamine;

N-(3-chlorophenyl)-6-[5-[[3-(1H-1,2,4-triazol-1-yl) propyl]amino]-3-pyridinyl]-2-pyrazinamine;

N-(3-chlorophenyl)-6-[5-[[3-(1H-imidazol-1-yl)propyl] amino]-3-pyridinyl]-2-pyrazinamine;

N-(3-chlorophenyl)-6-[5-[[(tetrahydro-2H-pyran-4-yl) methyl]amino]-3-pyridinyl]-2-pyrazinamine;

N-(3-chlorophenyl)-6-[5-[[2-(2-methoxyethoxy)ethyl] amino]-3-pyridinyl]-2-pyrazinamine;

N-(4-methoxyphenyl)-6-[5-[[3-(4-pyridinyl)propyl] amino]-3-pyridinyl]-2-pyrazinamine;

N-(3,4-dichlorophenyl)-6-[5-[[3-(4-pyridinyl)propyl] amino]-3-pyridinyl]-2-pyrazinamine;

N-[5-[6-[(3-chlorophenyl)amino]pyrazinyl]-3-pyridinyl]-2-(2-methoxyethoxy)acetamide;

N-[5-[6-[(3-chlorophenyl)amino]pyrazinyl]-3-pyridinyl]-2-ethoxy-acetamide;

N-[5-[6-[(3-chlorophenyl)amino]pyrazinyl]-3-pyridinyl]-3-methoxy-propanamide; and, N-[5-[6-[(3-chlorophenyl)amino]pyrazinyl]-3-pyridinyl]-2-hydroxy-acetamide.

Further preferred compounds include:

N-[5-[6-[(3-chlorophenyl)amino]pyrazinyl]-3-pyridinyl]-2-methoxy-acetamide;

N-[5-[6-[(3-chlorophenyl)amino]pyrazinyl]-3-pyridinyl]-3-pyridinecarboxamide;

N-[5-[6-[(3-chlorophenyl)amino]pyrazinyl]-3-pyridinyl]-1-pyrrolidinecarboxamide; and, 4-[[5-[6-[(3-chlorophenyl)amino]pyrazinyl]-3-pyridinyl] amino]-butanoic acid ethyl ester.

In another aspect of the invention, the invention relates to compounds of Formula 2:

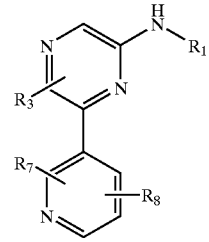

Formula 2 or a pharmaceutically acceptable salt thereof, wherein $R_1$ is selected from the group consisting of cycloalkyl, heterocyclyl, biheterocyclyl, aryl, biaryl, heteroaryl and biheteroaryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkenyl, heterocyclylalkynyl, heterocyclylalkoxy, aryl, arylalkyl, arylalkenyl, arylalkynyl, arylalkoxy, heteroaryl, heteroarylalkyl, heteroarylalkenyl, heteroarylalkynyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl) carbonyl, (hydroxyalkoxy)carbonyl, trihalo substituted lower alkyl and trihalo substituted lower alkoxy;

$R_7$ is selected from the group consisting of alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy;

$R_8$ is selected from the group consisting of alkyl, OH, hydroxyalkyl, halogen, cyano, amino, alkylamino, di(alkyl)amino, (hydroxyalkyl)amino, di(hydroxyalkyl)amino, carbamoyl, alkylcarbonylamino, alkylcarbonyl, alkoxycarbonyl, (hydroxyalkyl) carbonyl, (hydroxyalkoxy)carbonyl, $O(CH_2)_nR_5$, $O(CH_2)_nO(CH_2)_mR_5$, $O(CH_2)_nCH[(CH_2)_mR_5]_2$, $O(CH_2)_nN[(CH_2)_mR_5]_2$, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH$

[(CH$_2$)$_m$R$_5$]$_2$, NH(CH$_2$)$_n$O(CH$_2$)$_m$O(CH$_2$)$_m$R$_5$, NH(CH$_2$)$_n$N[(CH$_2$)$_m$R$_5$]$_2$, NH(CH$_2$)$_n$SO$_2$NH(CH$_2$)$_m$R$_5$, NH(CH$_2$)$_n$CH(OH)(CH$_2$)$_m$R$_5$, NH(CH$_2$)$_n$CH(OH)(CH$_2$)$_m$OR$_5$, NH(CH$_2$)$_n$CH(OH)(CH$_2$)$_m$N[(CH$_2$)$_m$R$_5$]$_2$, NH(CH$_2$)$_n$CO(CH$_2$)$_m$N[(CH$_2$)$_m$R$_5$]$_2$, NH(CH$_2$)$_n$CO$_2$(CH$_2$)$_m$R$_5$]$_2$, NH(CH$_2$)$_n$CO(CH$_2$)$_m$SO$_2$NH(CH$_2$)$_m$R$_5$, NHCO(CH$_2$)$_m$CH(R$_5$)$_2$, NHCO(CH$_2$)$_n$R$_5$, NHCO(CH$_2$)$_n$O(CH$_2$)$_m$R$_5$, NHCO(CH$_2$)$_n$O(CH$_2$)$_m$O(CH$_2$)$_m$R$_5$, NHCO(CH$_2$)$_n$O(CH$_2$)$_m$CO(CH$_2$)$_m$R$_5$, NHCO(CH$_2$)$_n$N[(CH$_2$)$_m$R$_5$]$_2$, CONH(CH$_2$)$_n$O(CH$_2$)$_m$R$_5$, and CONH(CH$_2$)$_n$N[(CH$_2$)$_m$R$_5$]$_2$; wherein n is an integer from 0 to 6 and m is an integer from 0 to 4; with the proviso, that m is at least 1 when R$_5$ is selected from the group consisting of OH, amino, alkylamino and di(alkyl)amino;

R$_5$ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents; and, R$_3$ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

In a preferred embodiment of this invention, the compounds are provided as pharmaceutical compositions comprising a pharmaceutically acceptable carrier.

The invention further relates to a method for inhibiting the vascular endothelial growth factor (VEGF) receptor tyrosine kinase comprising the step of administering a therapeutically effective amount of the compounds of this invention. In a preferred embodiment, the method is used to treat a disease selected from the group consisting of aberrant angiogenesis, tumors, diabetic retinopathy, rheumatoid arthritis, endometriosis and psoriasis.

The invention also relates to a method of treating angiogenesis in a subject in need thereof comprising administering a therapeutically effective amount of the compounds of this invention. Methods for treating tumors, including solid-tumors is also contemplated in this invention. The invention also relates to methods of treating diabetic retinopathy in a subject in need thereof comprising administering a therapeutically effective amount of a compound of this invention. Further methods for treating rheumatoid arthritis, psoriasis and endometriosis in a subject in need thereof comprising administering a therapeutically effective amount of the compound of claim 1.

In a further method of this invention, the invention relates to a method of inhibiting the vascular endothelial growth factor (VEGF) receptor tyrosine kinase comprising the step of administering a composition of this invention. Preferred diseases associated with this method include aberrant angiogenesis, tumors, diabetic retinopathy, rheumatoid arthritis, endometriosis and psoriasis.

The compounds of the present invention are useful in treating conditions mediated by the activity of the VEGF-R including, but not limited to, solid-tumor cancers, aberrant angiogenesis, diabetic retinopathy, rheumatoid arthritis, endometriosis and psoriasis.

BRIEF DESCRIPTION OF THE DRAWINGS

FIG. 1: A375 cell line tumor growth delay by compound 33. Black square represents control samples; Open triangle represents compound 33 used at 50 mg/Kg; Open circle represents compound 33 used at 5 mg/Kg.

DETAILED DESCRIPTION

Definitions

Unless specified otherwise, the term "alkyl" refers to a saturated straight, branched or cyclic substituent consisting solely of carbon and H containing 1 to carbon atoms for a carbon chain and 3 to 8 carbon atoms for a cyclic substituent; preferably, 1 to 8 carbon atoms for a carbon chain and 4 to 7 carbon atoms for a cyclic substituent; and, most preferably, 1 to 6 carbon atoms for a carbon chain and 5 to 6 carbon atoms for a cyclic substituent. The term "lower alkyl" refers to an alkyl chain substituent containing 1 to 4 carbon atoms; preferably, 1 to 2 carbon atoms, where alkyl is defined supra. The term "alkenyl" refers to an unsaturated straight, branched or cyclic substituent consisting solely of carbon and H atoms containing at least one double bond. The term "alkynyl" refers to an unsaturated straight, branched or cyclic substituent consisting solely of carbon and H atoms containing at least one triple bond. The term "alkoxy" refers to O-alkyl where alkyl is as defined supra. The term "alkthio" refers to S-alkyl where alkyl is as defined supra. The term "carboxyl" refers to an acidic alkyl carbon chain with a terminal COOH group. The term "acyl" refers to a carbonyl linking group —C(=O)— with a terminal alkyl chain, wherein alkyl is as defined supra. The terms "alkylamino," "di(alkyl)amino," "(hydroxyalkyl)amino" and "di(hydroxyalkyl)amino" refer to a nitrogen heteroatom linking group with a terminal alkyl chain or chains (substituted or unsubstituted on the terminal carbon with hydroxy). Alkyl, alkenyl, alkynyl and alkoxycarbon chains are substituted, unless indicated otherwise, on the terminal carbon atom of the chain.

The term "cycloalkyl" refers to alkyl, alkenyl and alkynyl cyclic ring systems as defined supra. The term "heterocyclyl" refers to saturated or partially saturated ring systems containing 4 to 7 ring atoms wherein at least 1 to 3 atoms are independently N, S, or O atoms and the remaining ring atoms are C and H. The term "biheterocyclyl" refers to bicyclic saturated or partially saturated ring systems containing 9 to 12 ring atoms wherein at least 1 to 3 atoms are independently N, S, or O atoms and the remaining ring atoms are C and H and includes bicyclic ring systems comprising a heterocyclyl ring fused to a benzene ring. Embodiments for compounds of the present invention include those wherein heterocyclyl are selected from 2H-pyrrole, pyrrolinyl (selected from 2-pyrrolinyl, 3-pyrrolinyl), pyrrolidinyl, dioxlanyl, 2-imidazolinyl, imidazolidinyl, 2-pyrazolinyl, pyrazolidinyl, 2H-pyranyl, 4H-pyranyl, piperidinyl, dioxolanyl, morpholinyl, dithianyl, thiomorpholinyl and piperazinyl. The term "cycloalkylalkyl" and "heterocyclylalkyl" refers to an alkyl chain substituted on the terminal carbon atom with a cycloalkyl and heterocyclyl group, respectively; where alkyl, cycloalkyl and heterocyclyl are as defined supra.

The term "aryl" refers to aromatic ring systems containing 5 to 10 carbon atoms and H. The term "biaryl" refers to bicyclic aromatic ring systems containing 9 to 12 carbon atoms and H. The term "arylalkyl" and "biarylalkyl" refers to an alkyl chain substituted on the terminal carbon atom with an aryl and biaryl group, respectively; where alkyl, aryl and biaryl are as defined supra. Embodiments for compounds of the present invention include those wherein aryl and biaryl are selected from phenyl and naphthalenyl.

The term "heteroaryl" refers to aromatic ring systems containing 5 to 7 ring atoms wherein at least 1 to 3 atoms are independently N, S, or O atoms and the remaining ring atoms are C and H. The term "biheteroaryl" refers to bicyclic aromatic ring systems containing 9 to 12 ring atoms wherein at least 1 to 4 atoms are independently N, S, or O atoms and the remaining ring atoms are C and H. Embodiments for compounds of the present invention include those wherein heteroaryl and biheteroaryl are selected from furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, benzo[b]furyl, benzo[b]thiophenyl, 1H-indazolyl, benzimidazolyl, benzthiazolyl, quinolinyl, isoquinolinyl and quinazolinyl. The term "heteroarylalkyl" and "biheteroarylalkyl" refers to an alkyl chain substituted on the terminal carbon atom with a heteroaryl and biheteroaryl group, respectively; where alkyl, heteroaryl and biheteroaryl are as defined supra.

The term "halo" or "halogen" means fluoro, chloro, bromo and iodo. "Independently" means that when there is more than one substituent that the substituents may be the same or different. When a group is "substituted", that group may have one or more substituents, preferably from one to five, more preferably one to three, and most preferably at least one substituent independently selected from the list of substituents provided for the group.

| Abbreviations | |
|---|---|
| "Ph"or "PH" | Phenyl |
| "Boc" | t-Butoxycarbonyl |
| "Cbz" | benzyloxycarbonyl |
| "Ts" | Toluenesulfonyl |
| "Fmoc" | N-(9-fluorenylmethoxycarbonyl) |
| "P(o-tol)$_3$" | Tri-o-tolylphosphine |
| "PdCl$_2$(PPh$_3$)$_2$" | Dichlorobis(triphenylphosphine)palladium(II) |
| "Pd$_2$(dba)$_3$" | Tris(dibenzylideneacetone)-dipalladium(0) |
| "Pd$_2$(dba)$_3$" adduct | Tris(dibenzylideneacetone)dipalladium(0)-chloroform |
| "DMAP" | 4-(dimethylamino)pyridine |
| "DPPF" | 1,1'-Bis(diphenylphosphino)-ferrocene |
| "DPPA" | Diphenylphosphoryl azide |
| "OTf" | Trifluorosulfonyloxy |
| "OTBS" | t-Butyldimethylsilyloxy |
| "OTBDMS" | t-Butyldimethylsilyloxy |
| "TFA" | Trifluoroacetic acid |
| triflate | Trifluorosulfonyloxy |
| "AsPPh$_3$" | Triphenylarsine |
| "EDCI" | 1-(3-Dimethylaminopropyl)-3-ethylcarbodiimide |
| "TMEDA" | Tetramethylethylenediamine |
| "HATU" | o-(7-Azabenzotriazol-1-yl)-1,1,3,3-tetramethyluronium |
| "BINAP" | 2,2'-Bis(diphenylphosphino)-1,1'-binaphthyl |
| "Pd(OAc)$_2$" | Palladium acetate |
| "DMAP" | Dimethylaminopyridine |

-continued

| Abbreviations | |
|---|---|
| "NMP" | 1-Methyl-2-pyrrolidinone |
| "Cmd" | Compound |
| "THF" | Tetrahydrofuran |
| "CDI" | Carbonyl diimidazoyl |

The term "subject" includes, without limitation, any animal or artificially modified animal. In a preferred embodiment, the subject is a human.

The compounds of the present invention may also be present in the form of pharmaceutically acceptable salts. For use in medicine, the salts of the compounds of this invention refer to non-toxic "pharmaceutically acceptable salts" (Ref International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

To the extent that certain compounds of the present invention may have at least one chiral center, the compounds may thus exist as enantiomers. In addition, the compounds of the present invention may also possess two or more chiral centers and thus may also exist as diastereomers or as exo or endo isomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention includes compounds that are useful in the treatment of diseases associated with the stimulation and presentation of inappropriate, abnormal or increased angiogenesis; for example excessive angiogenesis that is associated with some proliferative diseases or disease states including, but not limited to diabetic retinopathy, rheumatoid arthritis, endometriosis and psoriasis.

Inappropriate or aberrant angiogenesis is also associated with cancer, and in particular, cancers associated with foci of proliferating cells. For purposes of this invention the term "cancer" refers to angiogenesis associated with uncontrolled cell proliferation. Cancers can be benign or malignant and refers to any group for cells that have lost their normal regulatory controls that would otherwise govern the rate of cell growth. Some cancer cells stimulate ingrowth of the vasculature, also referred to as neovascularization, to facilitate survival. Neovascularization further facilitates metastasis. The cancer cells spread throughout the body and invade normal tissues where they proliferate and form secondary cancers. These masses of cancer cells are also referred to as tumors. Tumors, and in particular, solid tumors, require the process of angiogenesis to supply oxygen and nutrients. Without a blood supply a tumor can only grow to the size of a few millimeters. Angiogenesis inhibitors inhibit neovascularization and therefor effectively inhibit cancer cell growth in a variety of cancers that require the ingrowth of the microvasculature. Such tumors include for example, breast cancers, pancreatic cancer, skin cancers, including melanomas and basal cell carcinomas, a variety of cancers of the lung, prostate cancers, ovarian cancers, brain cancers, liver cancers, renal and hepatic cancers, uterine cancers, cancers of the gastrointestinal system, colorectal cancers, cancers of the head and neck, including cancers of the mouth and throat.

In these diseases, aberrant angiogenesis can be controlled through the use of angiogenesis inhibitors. These inhibitors are molecules that bind to cell receptors, generally on endothelial cells, that are known to be associated with the formation of neovasculature and inhibit receptor signalling pathways resulting in an inhibition of neovascularization. Such receptors include the Vascular Endothelial Growth Factors, such as VEGF-1, 2, 3 and others described below that have been implicated in angiogenesis.

Pyrazine Derivative Compounds

Certain pyrazine compounds, described herein, are useful as tyrosine kinase inhibitors, particularly as inhibitors of the kinase domain of VEGF-R (Vascular endothelial growth factor receptor-2, Genbank Accession number X61656), EGFR (epidermal growth factor receptor), GSK-3β (glycogen synthase kinase-3 beta subunit), PDGF-R (platelet derived growth factor receptor), and FGF-R2 (fibroblast growth factor receptor-2). Preferably, compounds of the present invention are selective inhibitors of the VEGF-R.

Useful inhibitory activity is defined herein as an $IC_{50}$ of less than 10 μM (10 micromolar); preferably, inhibitory activity is less than or equal to 5 μM; and, more preferably, inhibitory activity is less than or equal to 1 μM. Using methods well known in the art and/or using the methods provided in the example infra, compounds of the present invention may be tested for their ability to inhibit the enzymatic activity of other kinases.

The present invention provides novel compounds of Formula 1:

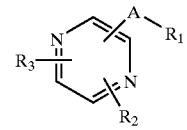

Formula 1 or a pharmaceutically acceptable salt thereof, wherein $R_1$ is selected from the group consisting of cycloalkyl, heterocyclyl, biheterocyclyl, aryl, biaryl, heteroaryl and biheteroaryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkenyl, heterocyclylalkynyl, heterocyclylalkoxy, aryl, arylalkyl, arylalkenyl, arylalkynyl, arylalkoxy, heteroaryl, heteroarylalkyl, heteroarylalkenyl, heteroarylalkynyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo) substituted lower alkoxy), aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, (hydroxyalkoxy)carbonyl, trihalo substituted lower alkyl and trihalo substituted lower alkoxy;

A is selected from the group consisting of —N(R$_4$)-(CH$_2$)$_x$—, —O(CH$_2$)$_x$—, —S(CH$_2$)$_x$—, —SO$_2$-(CH$_2$)$_x$—, —SO$_2$N(CH$_2$)$_x$—, —NSO$_2$(CH$_2$)$_x$—, —N(R$_4$)(CH$_2$)$_{1-4}$O(CH$_2$)$_x$—, —N(R$_4$)(CH$_2$)$_{1-4}$NH(CH$_2$)$_x$—, —N(R$_4$)CONH(CH$_2$)$_x$— and —N(R$_4$)CNNH(CH$_2$)$_x$—, wherein x is an integer from 0 to 4;

$R_4$ is selected from the group consisting of H, lower alkyl, alkyl, hydroxyalkyl, alkoxyalkyl, arylalkyl, lower alkenyl, alkenyl, aryl and heteroaryl; wherein aryl and heteroaryl are optionally substituted with 1 to 5 substituents independently selected from the group consisting of OH, halogen, cyano, nitro, amino, alkylamino, di(alkyl)amino, (hydroxyalkyl)amino, di(hydroxyalkyl)amino, alkyl, lower alkyl, alkoxy, lower alkoxy, tri(halo)substituted lower alkyl and tri (halo)substituted lower alkoxy;

$R_2$ is selected from the group consisting of heteroaryl and biheteroaryl optionally substituted with 1 to 2 substituents independently selected from $R_7$ and 1 substituent selected from $R_8$;

$R_7$ is selected from the group consisting of alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy;

$R_8$ is selected from the group consisting of alkyl, OH, hydroxyalkyl, halogen, cyano, amino, alkylamino, di(alkyl)amino, (hydroxyalkyl)amino, di(hydroxyalkyl)amino, carbamoyl, alkylcarbonylamino, alkylcarbonyl, alkoxycarbonyl, (hydroxyalkyl)carbonyl, (hydroxyalkoxy)carbonyl, $O(CH_2)_nR_5$, $O(CH_2)_nO(CH_2)_mR_5$, $O(CH_2)_nCH[(CH_2)_mR_5]_2$, $O(CH_2)_nN[(CH_2)_mR_5]_2$, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH(CH_2)_nCH(OH)(CH_2)_mOR_5$, $NH(CH_2)_nCH(OH)(CH_2)_mN[(CH_2)_mR_5]_2$, $NH(CH_2)_nCO(CH_2)_mN[(CH_2)_mR_5]_2$, $NH(CH_2)_nCO_2(CH_2)_mR_5$, $NH(CH_2)_nCO(CH_2)_mSO_2NH(CH_2)_mR_5$, $NHCO(CH_2)_mCH(R_5)_2$, $NHCO(CH_2)_nR_5$, $NHCO(CH_2)_nO(CH_2)_mR_5$, $NHCO(CH_2)_nO(CH_2)_mO(CH_2)_mR_5$, $NHCO(CH_2)_nO(CH_2)_mCO(CH_2)_mR_5$, $NHCO(CH_2)_nN[(CH_2)_mR_5]_2$, $CONH(CH_2)_nO(CH_2)_mR_5$, and $CONH(CH_2)_nN[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino;

$R_5$ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents;

$R_3$ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

Preferred embodiments for compounds of the present invention include compounds of Formula 1 selected from a compound of Formula 2:

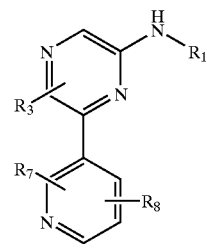

Formula 2 wherein all variables are as defined previously.

Embodiments for compounds of the present invention include compounds of Formula 1 wherein $R_1$ is selected from the group consisting of cycloalkyl, heterocyclyl, biheterocyclyl, aryl, biaryl, heteroaryl and biheteroaryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkoxy, aryl, arylalkyl, arylalkoxy, heteroaryl, heteroarylalkyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, trihalo substituted lower alkyl and trihalo substituted lower alkoxy.

Preferably, $R_1$ is selected from the group consisting of aryl optionally substituted with 1 to 5 substituents independently selected from the group consisting of lower alkyl, lower alkoxy, heterocyclyl, heterocyclylalkyl, aryl, arylalkyl, heteroaryl, heteroarylalkyl, OH, halogen, cyano, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, trihalo substituted lower alkyl and trihalo substituted lower alkoxy.

More preferably, $R_1$ is selected from the group consisting of phenyl optionally substituted with 1 to 5 substituents independently selected from the group consisting of lower alkyl, lower alkoxy, OH, halogen, cyano, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, trihalo substituted lower alkyl and trihalo substituted lower alkoxy.

Most preferably, $R_1$ is selected from the group consisting of phenyl optionally substituted with 1 to 5 substituents independently selected from the group consisting of methoxy, chlorine and fluorine.

Preferred embodiments for compounds of the present invention include compounds of Formula 1 wherein A is selected from the group consisting of —$N(R_4)(CH_2)_x$—, —$O(CH_2)_x$—, —$S(CH_2)_x$—, —$SO_2(CH_2)_x$—, —$N(R_4)(CH_2)_{1-4}O(CH_2)_x$— and —$N(R_4)(CH_2)_{1-4}NH(CH_2)_x$—; wherein x is an integer from 0 to 3.

More preferably, A is selected from the group consisting of —N($R_4$)($CH_2$)$_x$—, —O($CH_2$)$_x$—, —S($CH_2$)$_x$—, —$SO_2$($CH_2$)$_x$—, —$SO_2$N($CH_2$)$_x$—, —$NSO_2$($CH_2$)$_x$—, —N($R_4$)($CH_2$)$_{1-4}$O($CH_2$)$_x$— and —N($R_4$)($CH_2$)$_{1-4}$NH($CH_2$)$_x$—; wherein x is an integer from 1 to 1.

Most preferably, A is selected from the group consisting of —N($R_4$)($CH_2$)$_x$— and —O($CH_2$)$_x$—; wherein x is an integer from 0 to 1.

Preferred embodiments for compounds of the present invention include compounds of Formula 1 wherein $R_4$ is selected from the group consisting of H, alkyl, lower alkyl, alkoxyalkyl, alkenyl, lower alkenyl, hydroxyalkyl, aryl, arylalkyl and heteroaryl.

More preferably, $R_4$ is selected from the group consisting of H, lower alkyl and hydroxyalkyl.

Most preferably, $R_4$ is H.

Embodiments for compounds of the present invention include compounds of Formula 1 wherein $R_2$ is selected from the group consisting of heteroaryl and biheteroaryl optionally substituted with 1 to 2 substituents independently selected from $R_7$ and optionally substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

Preferably, $R_2$ is selected from the group consisting of heteroaryl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

More preferably, $R_2$ is selected from the group consisting of thienyl, pyrrolyl, oxazolyl, thiazolyl, imidazolyl, pyrazolyl, isoxazolyl, isothiazolyl, pyridinyl, pyridazinyl, pyrimidinyl and pyrazinyl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

Most preferably, $R_2$ is selected from the group consisting of pyridinyl, pyridazinyl, pyrimidinyl and pyrazinyl optionally substituted with 1 substituent selected from $R_7$ and substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

Preferred embodiments for compounds of the present invention include compounds of Formula 1 wherein $R_7$ is selected from the group consisting of lower alkyl, lower alkoxy, heterocyclylalkyl, aryl, arylalkyl, OH, hydroxyalkyl, halogen, cyano, nitro, amino, alkylamino, di(alkyl)amino, (hydroxyalkyl)amino, di(hydroxyalkyl)amino, acyl, carboxyl, tri(halo)substituted lower alkyl and tri(halo) substituted lower alkoxy.

More preferably, $R_7$ is selected from the group consisting of lower alkyl, OH, halogen, cyano, nitro, amino, tri(halo)substituted lower alkyl and tri(halo)substituted lower alkoxy.

Most preferably, $R_7$ is selected from the group consisting of methyl, ethyl, OH, bromine, chlorine, fluorine, cyano, nitro, amino, trifluoromethyl and trifluoromethoxy.

Preferred embodiments for compounds of the present invention include compounds of Formula 1 wherein $R_8$ is selected from the group consisting of OH, amino, (hydroxyalkyl)amino, alkoxycarbonyl, OCON[($CH_2$)$_m R_5$]$_2$, NH($CH_2$)$_n R_5$, NH($CH_2$)$_n$CH($R_5$)$_2$, NH($CH_2$)$_n$SO$_2$($CH_2$)$_m R_5$, NH($CH_2$)$_n$O($CH_2$)$_m R_5$, NH($CH_2$)$_n$OCH[($CH_2$)$_m R_5$]$_2$, NH($CH_2$)$_n$O($CH_2$)$_m$O($CH_2$)$_m R_5$, NH($CH_2$)$_n$N[($CH_2$)$_m R_5$]$_2$, NH($CH_2$)$_n$SO$_2$NH($CH_2$)$_m R_5$, NH($CH_2$)$_n$CH(OH)($CH_2$)$_m R_5$, NH($CH_2$)$_n$CH(OH)($CH_2$)$_m$OR$_5$, NH($CH_2$)$_n$CH(OH)($CH_2$)$_m$N[($CH_2$)$_m R_5$]$_2$, NH($CH_2$)$_n$CO($CH_2$)$_m$N[($CH_2$)$_m R_5$]$_2$, NH($CH_2$)$_n$CO$_2$($CH_2$)$_m R_5$, NH($CH_2$)$_n$CO($CH_2$)$_m$SO$_2$NH($CH_2$)$_m R_5$, NHCO($CH_2$)$_n R_5$, NHCO($CH_2$)$_n$O($CH_2$)$_m R_5$, NHCO($CH_2$)$_n$O($CH_2$)$_n$O($CH_2$)$_m R_5$, NHCO($CH_2$)$_n$O($CH_2$)$_m$CO($CH_2$)$_m R_5$, CONH($CH_2$)$_n$O($CH_2$)$_m R_5$ and CONH-($CH_2$)$_n$N[($CH_2$)$_m R_5$]$_2$; wherein n is an integer from 0 to 6 and m is an integer from 0 to 4; with the proviso, that m is at least 1 when $R_5$ is selected from the group consisting of OH, amino, alkylamino and di(alkyl)amino.

More preferably, $R_8$ is selected from the group consisting of OH, amino, (hydroxyalkyl)amino, alkoxycarbonyl, OCON[($CH_2$)$_m R_5$]$_2$, NH($CH_2$)$_n R_5$, NH($CH_2$)$_n$CH($R_5$)$_2$, NH($CH_2$)$_n$SO$_2$($CH_2$)$_m R_5$, NH($CH_2$)$_n$O($CH_2$)$_m R_5$, NH-($CH_2$)$_n$OCH[($CH_2$)$_m R_5$]$_2$, NH($CH_2$)$_n$O($CH_2$)$_m$O($CH_2$)$_m R_5$, NH($CH_2$)$_n$N[($CH_2$)$_m R_5$]$_2$, NH($CH_2$)$_n$SO$_2$NH($CH_2$)$_m R_5$, NH($CH_2$)$_n$CH(OH)($CH_2$)$_m R_5$, NH($CH_2$)$_n$CH(OH)($CH_2$)$_m$OR$_5$, NH($CH_2$)$_n$CH(OH)($CH_2$)$_m$N[($CH_2$)$_m R_5$]$_2$, NH($CH_2$)$_n$CO($CH_2$)$_m$N[($CH_2$)$_m R_5$]$_2$, NH($CH_2$)$_n$CO$_2$($CH_2$)$_m R_5$, NH($CH_2$)$_n$CO($CH_2$)$_m$SO$_2$NH($CH_2$)$_m R_5$, NHCO($CH_2$)$_n R_5$, NHCO($CH_2$)$_n$O($CH_2$)$_m R_5$, NHCO($CH_2$)$_n$O($CH_2$)$_n$O($CH_2$)$_m R_5$, NHCO($CH_2$)$_n$O($CH_2$)$_m$CO($CH_2$)$_m R_5$, CONH($CH_2$)$_n$O ($CH_2$)$_m$R and CONH($CH_2$)$_n$N[($CH_2$)$_m R_5$]$_2$; wherein n is an integer from 0 to 5 and m is an integer from 0 to 2; with the proviso, that m is at least 1 when $R_5$ is selected from the group consisting of OH, amino, alkylamino and di(alkyl)amino.

Most preferably, $R_8$ is selected from the group consisting of OH, amino, (2-hydroxyethyl)amino, (3-hydroxy-n-propyl)amino, (4-hydroxy-n-butyl)amino, ethoxycarbonyl, OCON($R_5$)$_2$, NH($CH_2$)$_{1-4}$R$_5$, NH($CH_2$)$_{1-3}$SO$_2$($CH_2$)$_{0-1}$R$_5$, NH($CH_2$)$_{1-3}$O($CH_2$)$_{0-1}$R$_5$, NH($CH_2$)$_{1-4}$OCH[($CH_2$)$_{1-2}$R$_5$]$_2$, NH($CH_2$)$_{1-3}$O($CH_2$)$_{1-2}$O($CH_2$)$_{1-2}$R$_5$, NH($CH_2$)$_{1-4}$N-[($CH_2$)$_{0-2}$R$_5$]$_2$, NH($CH_2$)$_{1-4}$SO$_2$NH($CH_2$)$_{1-2}$R$_5$, NH($CH_2$)$_{1-4}$CH(OH)($CH_2$)$_{1-2}$R$_5$, NH($CH_2$)$_{1-4}$CH(OH)($CH_2$)$_{1-2}$OR$_5$, NH($CH_2$)$_{1-4}$CH(OH)($CH_2$)$_{1-2}$N[($CH_2$)$_{0-1}$R$_5$]$_2$, NH($CH_2$)$_{1-3}$CO($CH_2$)$_{0-1}$N[($CH_2$)$_{0-1}$R$_5$]$_2$, NH($CH_2$)$_{1-3}$CO$_2$($CH_2$)$_{0-1}$R$_5$, NH($CH_2$)$_{1-4}$CO($CH_2$)$_{1-2}$SO$_2$NH($CH_2$)$_{1-2}$R$_5$, NHCO-($CH_2$)$_{0-1}$R$_5$, NHCO($CH_2$)$_{1-3}$O($CH_2$)$_{0-2}$R$_5$, NHCO($CH_2$)$_{1-2}$O($CH_2$)$_{1-2}$O($CH_2$)$_{1-2}$R$_5$, NHCO($CH_2$)$_{1-2}$O($CH_2$)$_{0-1}$CO($CH_2$)$_{1-2}$R$_5$, CONH($CH_2$)$_{1-3}$O($CH_2$)$_{0-2}$R$_5$ and CONH-($CH_2$)$_{1-3}$N[($CH_2$)$_{1-2}$R$_5$]$_2$; with the proviso, that the $R_5$ alkylene linking group is at least methylene when $R_5$ is selected from the group consisting of OH, amino, alkylamino and di(alkyl)amino.

Preferred embodiments for compounds of the present invention include compounds of Formula 1 wherein $R_5$ is selected from the group consisting of H, OH, lower alkyl, amino, alkylamino, di(alkyl)amino, aryl, heteroaryl and heterocyclyl; wherein aryl, heteroaryl and heterocyclyl are optionally substituted with 1 to 3 substituents independently selected from the group consisting of lower alkyl, acyl, carboxyl, aryl (optionally substituted with one halogen substituent), di(alkyl)amino; alkylsulfonyl, aminosulfonyl, alkylaminosulfonyl and aminosulfonylalkyl; and, wherein heterocyclyl is further optionally substituted with 1 to 3 oxo substituents.

More preferably, $R_5$ is selected from the group consisting of H, OH, lower alkyl, heteroaryl and heterocyclyl; wherein heterocyclyl is optionally substituted with 1 to 3 substituents independently selected from the group consisting of lower alkyl, acyl, carboxyl, aryl (optionally substituted with one halogen substituent), di(alkyl)amino, alkylsulfonyl, aminosulfonyl, alkylaminosulfonyl, aminosulfonylalkyl and oxo.

Most preferably, $R_5$ is selected from the group consisting of H, OH, methyl, ethyl, t-butyl, 1H-azetidinyl, 1H-pyrrolidinyl, 4-tetrahydro-2H-pyranyl, hexahydro-1H-azepinyl, 1,3-dioxolanyl, 1,3-dioxanyl, piperidinyl, piperazinyl, imidazolyl, pyrazolyl, triazolyl and pyridinyl; wherein 1,3-dioxolanyl, 1,3-dioxanyl, piperazinyl and piperidinyl are optionally substituted with 1 to 2 substituents independently selected from the group consisting of methyl, acetyl, carboxyl, phenyl (optionally substituted with chlorine), di(methyl)amino, methylsulfonyl, methylaminosulfonyl and oxo.

Preferred embodiments for compounds of the present invention include compounds of Formula 1 wherein $R_3$ is selected from the group consisting of H, lower alkyl, lower alkoxy, OH, halogen, cyano, amino, alkylamino and di(alkyl)amino.

More preferably, $R_3$ is selected from the group consisting of H, lower alkyl, lower alkoxy, OH, halogen, amino and di(alkyl)amino.

Most preferably, $R_3$ is selected from the group consisting of H and methyl.

Preferred embodiments for compounds of the present invention include those compounds of Formula 1 selected from the group consisting of:

| Cmd | |
|---|---|
| 4 | 3-[[5-[6-[(3-chlorophenyl)amino]pyrazinyl]-3-pyridinyl]amino]-1-propanol |
| 5 | 6-(5-amino-3-pyridinyl)-N-(3-chlorophenyl)-2-pyrazinamine |
| 10 | 3-[[5-[2-[(3-chlorophenyl)amino]-6-methyl-4-pyrimidinyl]-3-pyridinyl]amino]-1-propanol |
| 31 | 2-[[5-[6-[(3-chlorophenyl)amino]pyrazinyl]-3-pyridinyl]amino]-ethanol |
| 32 | 4-[[5-[6-[(3-chlorophenyl)amino]pyrazinyl]-3-pyridinyl]amino]-1-butanol |
| 33 | $N^1$-[5-[6-[(3-chlorophenyl)amino]pyrazinyl]-$N^2,N^2$-dimethyl-1,2-ethanediamine |
| 34 | N-[5-[6-[(3-chlorophenyl)amino]pyrazinyl]-3-puridinyl]-4-morpholinepropanamine |
| 35 | $N^1$-[5-[6-[(3-chlorophenyl)amino]pyrazinyl]-3-pyridinyl]-$N^3,N^3$-dimethyl-1,3-propanediamine |
| 41 | N-[5-[6-[(3-chlorophenyl)amino]pyrazinyl]3-pyridinyl]-2-methoxy-acetamide |
| 43 | N-[5-[6-[(3-chlorophenyl)amino]pyrazinyl]3-pyridinyl]-3-pyridinecarboxamide |
| 52 | 3-[[5-[6-[(3-fluorophenyl)amino]pyrazinyl]-3-pyridinyl]amino]-1-propanol |
| 57 | 3-[[5-[6-[(3-methoxyphenyl)amino]pyrazinyl]-3-pyridinyl]amino]-1-propanol |
| 62 | 3-[[5-[6-[(phenylmethyl)amino]pyrazinyl]-3-pyridinyl]amino]-1-propanol |
| 69 | N-(3-chlorophenyl)-6-[5-[[3-(1-piperazinyl)propyl]amino]-3-pyridinyl]-2-pyrazinamine |
| 70 | N-(3-chlorophenyl)-6-[5-[[4-(4-pyridinyl)butyl]amino]-3-pyridinyl]-2-pyrazinamine |
| 71 | N-(3-chlorophenyl)-6-[5-[[3-(4-pyridinyl)propyl]amino]-3-pyridinyl]-2-pyrazinamine |
| 72 | N-(3-chlorophenyl)-6-[5-[[3-(3-pyridinyl)propyl]amino]-3-pyridinyl]-2-pyrazinamine |
| 74 | N-[5-[6-[(3-chlorophenyl)amino]pyrazinyl]-3-pyridinyl-1-pyrrolidinecarboxamide |
| 75 | N-(3-chlorophenyl)-6-[5-[[3-(1H-pyrazol-1-yl)propyl]amino]-3-pyridinyl]-2-pyrazinamine |
| 76 | N-(3-chlorophenyl)-6-[5-[[3-(1H-1,2,4-triazol-1-yl)propyl]amino]-3-pyridinyl]-2-pyrazinamine |
| 77 | N-(3-chlorophenyl)-6-[5-[[3-(1H-imidazol-1-yl)propyl]amino]-3-pyridinyl]-2-pyrazinamine |
| 78 | 2-[2-[2-[[5-[6-[(3-chlorophenyl)amino]pyrazinyl]-3-pyridinyl]amino]ethoxy]ethoxy]-ethanol |
| 79 | N-(3-chlorophenyl)-6-[5-[[(tetrahydro-2H-pyran-4-yl)methyl]amino]-3-pyridinyl]-2-pyrazinamine |
| 84 | 4-[[5-[6-[(3-chlorophenyl)amino]pyrazinyl]-3-pyridinyl]amino]-butanoic acid ethyl ester |
| 85 | N-(3-chlorophenyl)-6-[5-[[2-(2-methoxyethoxy)ethyl]amino]3-pyridinyl]-2-pyrazinamine |
| 88 | N-(4-methoxyphenyl)-6-[5-[[3-(4-pyridinyl)propyl]amino]-3-pyridinyl]-2-pyrazinamine |
| 89 | N-(3,4-dichlorophenyl)-6-[5-[[3-(4-pyridinyl)propyl]amino]-3-pyridinyl]-2-pyrazinamine |
| 90 | 3-[[6'-[(3-chlorophenyl)amino][2,2'-bipyrazin]-6-yl]amino]-1-propanol |
| 93 | 3-[[4-[6-[(3-chlorophenyl)amino]pyrazinyl]-3-pyridinyl]amino]-1-propanol |
| 95 | 3-[[5-[6-[(3-chlorophenyl)amino]pyrazinyl]-2-thiazolyl]amino]-1-propanol |
| 98 | N-[5-[6-[(3-chlorophenyl)amino]pyrazinyl]-3-pyridinyl]-2-(2-methoxyethoxy)-acetamide |
| 102 | N-[5-[6-[(3-chlorophenyl)amino]pyrazinyl]-3-pyridinyl]-2-ethoxy-acetamide |
| 103 | N-[5-[6-[(3-chlorophenyl)amino]pyrazinyl]-3-pyridinyl]-3-methoxy-propanamide |
| and | |
| 105 | N-[5-[6-[(3-chlorophenyl)amino]pyrazinyl]-3-pyridinyl]-2-hydroxy-acetamide |

Intermediates

The present invention also is directed towards compounds used to synthesize the compounds of Formula I. Thus, the present invention provides intermediate compounds of Formula 3:

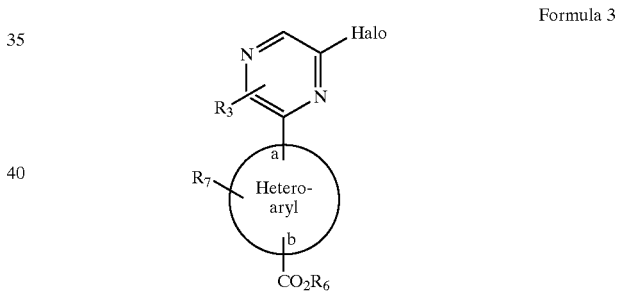

Formula 3 wherein

Halo is selected from the group consisting of chloro, fluoro, bromo and iodo;

Heteroaryl is selected from the group consisting of thienyl, furyl, pyrrole, oxazolyl, thiazolyl, imidazolyl, pyrazolyl, isoxazolyl, isothiazolyl, oxadiazolyl, triazolyl, thiadiazolyl, 2H-pyranyl, pyridinyl, pyrazinyl, pyridazinyl, pyrimidinyl, indolizinyl, isoindoyl and 3H-indolyl;

"a" is the position of attachment for Heteroaryl to the pyrazine ring and "b" is the position of attachment for $CO_2R_6$ to the Heteroaryl ring wherein "a" and "b" are carbon atoms;

$R_6$ is lower alkyl; and, all other variables are as defined previously.

In particular, the present invention provides an intermediate useful in the synthesis of substituted 3-pyridinyl-pyrazine derivatives of the formula:

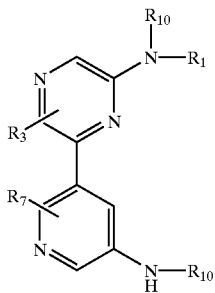

wherein $R_{10}$ is a protecting group selected from the group consisting of t-butoxycarbonyl, benzyloxycarbonyl, and N-(9-fluorenylmethoxycarbonyl); and, all other variables are as defined previously.

Nomenclature

Compounds are named according to nomenclature well known in the art, exemplified using ring numbering as follows:

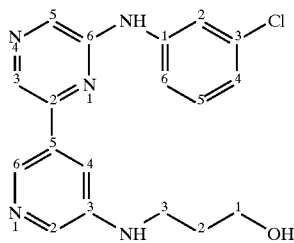

3-[[5-[6-[(3-chlorophenyl)amino]pyrazinyl]-3-pyridinyl]amino]-1-propanol Names can be generated using a nomeclature system based on this example, or may be generated using commercial chemical naming software, preferably ACD/Index Name (Advanced Chemistry Development, Inc., Toronto, Ontario).

General Synthetic Schemes

The invention can be better understood by way of the following schemes. These schemes are representative of the preferred synthetic methods, but are not to be construed as limiting the scope of the invention.

Scheme 1

A mixture of 5-bromonicotinate Compound 1A (substituted or unsubstituted with $R_7$), bis(tributyltin), palladium acetate, tri-o-tolylphosphine and triethylamine in a suitable solvent, such as acetonitrile, is stirred under nitrogen. The cooled reaction mixture is filtered, washed, and the mixture is concentrated under vacuum. The residue is diluted with a suitable solvent, such as dichloromethane, washed with a suitable aqueous solvent, and concentrated. The residue is further diluted with a suitable solvent, such as hexane, filtered, and the filtrate is concentrated. The product is purified by column chromatography to give Compound 1B. A mixture of Compound 1B, 2,6-dichloropyrazine (Compound 1C), dichloro-bis(triphenylphosphine) palladium and LiCl in anhydrous toluene is stirred under nitrogen. The cooled reaction mixture is concentrated under vacuum. Aqueous solvent is added to the residue and stirred and then extracted with a suitable solvent, such as dichloromethane. The combined solution is filtered, dried, and concentrated. The product is purified by column chromatography to give Compound 1D as an off-white solid.

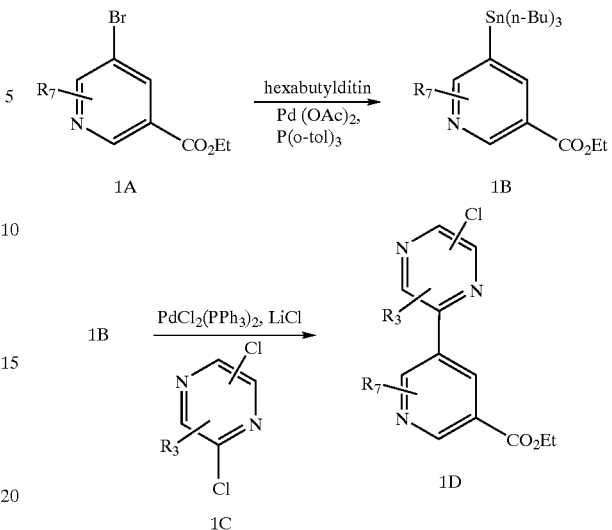

A mixture of Compound 1D, Compound 1E, $Pd_2(dba)_3$, DPPF, and $Cs_2CO_3$ in anhydrous dioxane is stirred under nitrogen. The reaction is cooled and a suitable solvent, such as dichloromethane, is added. The diluted reaction is filtered, washed with more solvent, and the combined filtrate is concentrated to give Compound 1F. The Compound 1F is diluted with a small amount of a suitable solvent, such as dichloromethane. The solid is collected through filtration, and the filtrate is concentrated. The Compound 1F may be recrystallized from EtOAc/hexane.

A mixture of Compound 1F, $Boc_2O$, and DMAP in a suitable solvent, such as dichloromethane is stirred. The reaction mixture is concentrated and the product is purified by column chromatography (EtOAc/hexane as solvent) to give Compound 1G.

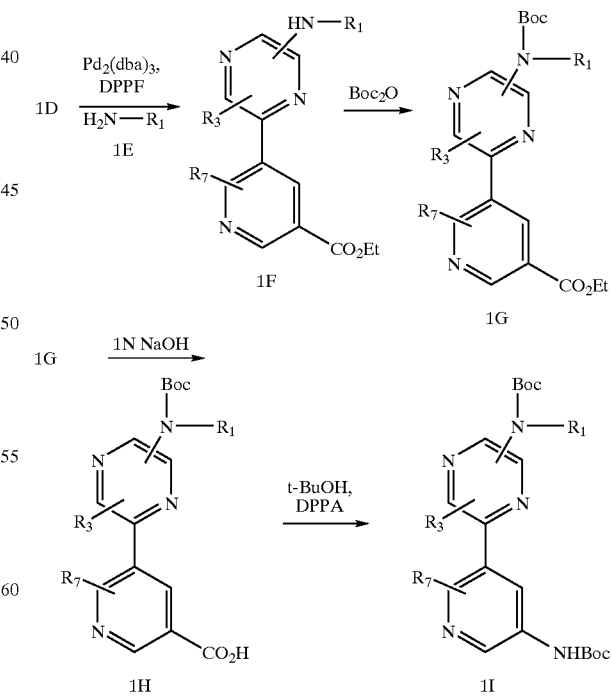

Compound 1G is dissolved in a suitable solvent, such as methanol, and stirred, and then cooled to about 0° C. A NaOH$_{(aq)}$ (1 N) solution is added slowly and the mixture is stirred at about 0° C., followed by stirring at about 20° C. Glacial acetic acid is slowly added to the reaction mixture at about 0° C. followed by the addition of water. A solid is formed, and is collected through filtration, washed with water, and then dried in a vacuum oven to give the carboxylic acid Compound 1H.

A mixture of the carboxylic acid Compound 1H, DPPA, triethylamine, and t-BuOH in toluene is stirred under nitrogen at about 70° C., and then stirred at about 100° C. The reaction mixture is concentrated under vacuum. The product is purified by column chromatography to give Compound 1I.

Scheme 1 Alternate Substituent Pattern #1

A mixture of Compound 1I, (haloalkoxy)-t-butyldimethylsilane, and Cs$_2$CO$_3$ in DMF is stirred at about 70° C. under nitrogen. The reaction mixture is diluted with water, extracted, dried, and concentrated. The product is purified by column chromatography to give a silylated-product. The silylated-product is dissolved in a suitable solvent, such as TFA, stirred, and then concentrated. An ammonium hydroxide solution is added to the residue until the pH is about 10–11, water is added, and a solid is formed. The solid is collected through filtration, washed with water, and dried under vacuum to give Compound 1J. Alternatively, the same procedure can be performed with a substituted aminoalkylhalo replacing the (haloalkoxy)-t-butyl-dimethylsilane to yield Compound 1K.

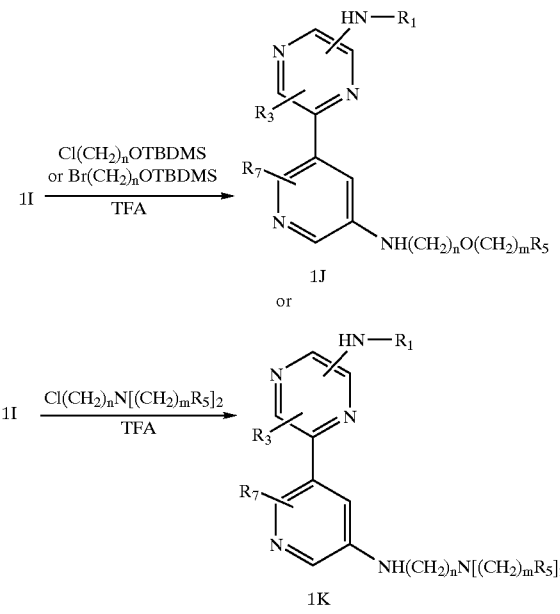

Scheme 1 Alternate Substituent Pattern #2

Compound 1I is dissolved in anhydrous THF at about 0° C. and NaH is added (60% oil dispersion). R$_5$(CH$_2$)$_n$COCl is added and the reaction is stirred at about 0° C. under N$_2$, and then allowed to warm up. NH$_4$Cl$_{(aq)}$ is added to quench the reaction. Solvent is removed and the product is extracted into CH$_2$Cl$_2$, washed with water, and dried. Product is purified by column chromatography to give a solid. The product is dissolved in a solvent, such as TFA, stirred, and concentrated. An ammonium hydroxide solution is added to the residue until the pH is about 10–11 and a solid is formed. The solid is collected through filtration, washed with water and dried under vacuum to give Compound 1L1. Alternatively, the same procedure can be performed with R$_5$(CH$_2$)$_m$O(CH$_2$)$_n$COCl replacing R$_5$(CH$_2$)$_n$COCl to yield Compound 1L2.

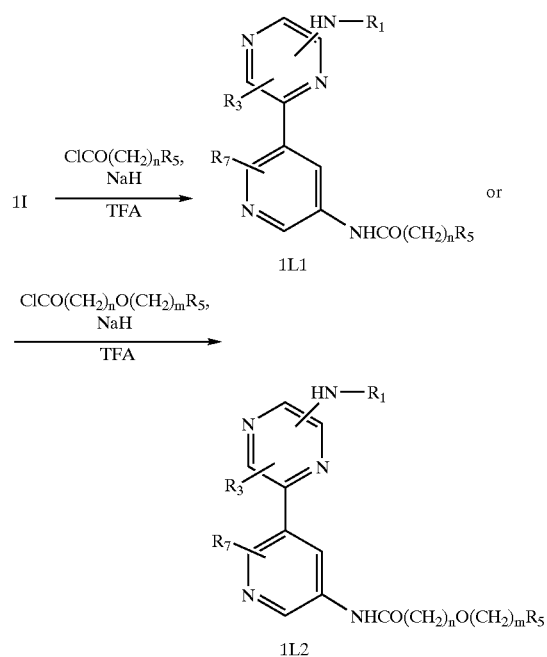

Scheme 1 Alternate Substituent Pattern #3

A mixture of Compound 1H, alkoxyamine (NH$_2$(CH$_2$)$_n$O(CH$_2$)R$_5$), diisopropylethylamine and HATU in DMF is stirred under N$_2$. Solvent is removed and the product is purified by column chromatography to generate a solid product. The solid is dissolved in a suitable solvent, stirred, and concentrated. An ammonium hydroxide solution is added to the residue until the pH is about 10–11. The solid is collected through filtration, washed with water and dried under vacuum to give the final, purified product of Compound 1N. Alternatively, using a substituted aminoalkylamine (NH$_2$(CH$_2$)$_m$N[(CH$_2$)$_m$R$_5$]$_2$) in this scheme yields Compound 1M.

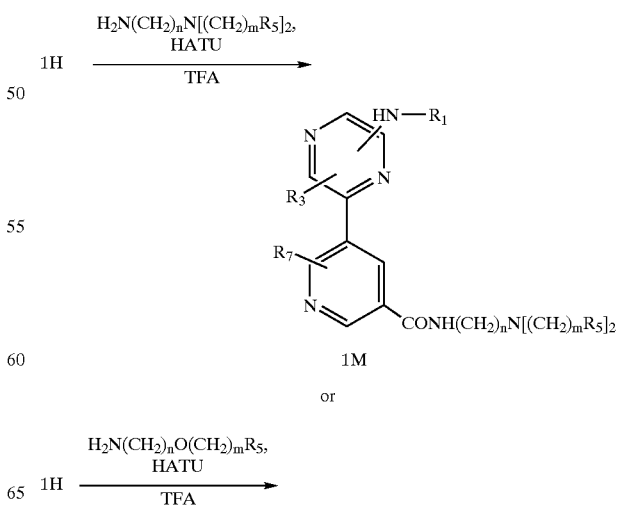

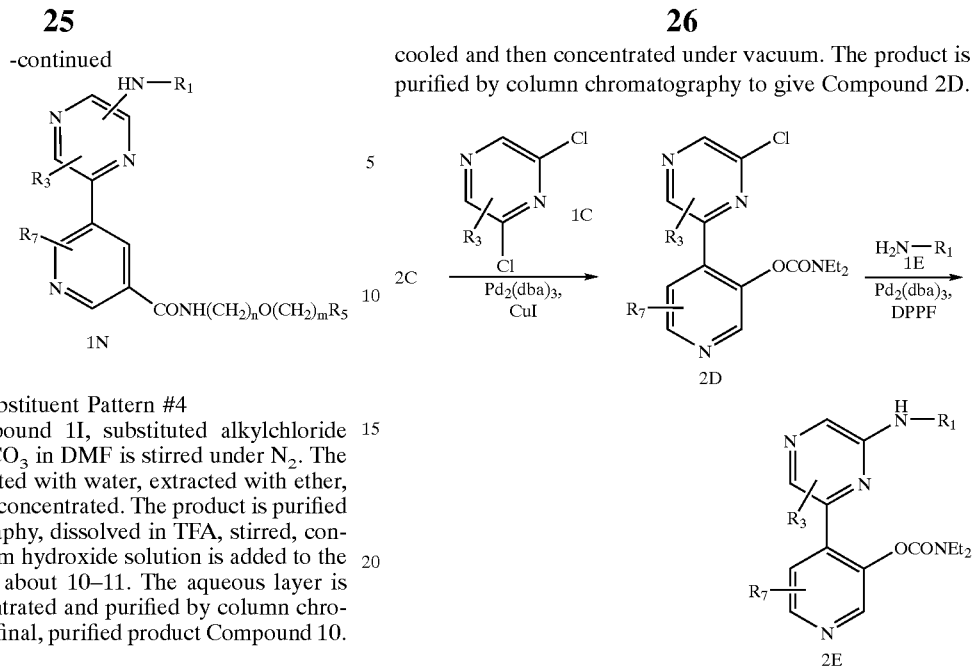

Scheme 1 Alternate Substituent Pattern #4

A mixture of Compound 1I, substituted alkylchloride (Cl(CH$_2$)$_n$R$_5$) and Cs$_2$CO$_3$ in DMF is stirred under N$_2$. The reaction mixture is diluted with water, extracted with ether, dried with Na$_2$SO$_4$ and concentrated. The product is purified by column chromatography, dissolved in TFA, stirred, concentrated and ammonium hydroxide solution is added to the residue until the pH is about 10–11. The aqueous layer is extracted, dried, concentrated and purified by column chromatography to give the final, purified product Compound 10.

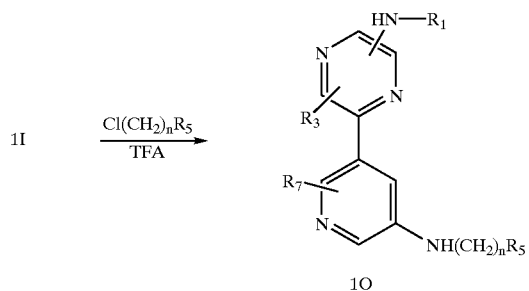

Scheme 2

3-Pyridyl diethyl carbamate (Compound 2B) (1.0 g, 5.1 mmol) is prepared using commercially available Compound 2A and standard methods (Wuest, H. M., Sakal, E. H. *J Am Chem Soc* 73 1210 1951) and is dissolved in a suitable solvent. This is cooled to about −78° C., and then sec-BuLi and TMEDA are added under nitrogen. The reaction mixture is stirred at about −78° C. Trimethyltin chloride in anhydrous solvent is added slowly and the reaction is allowed to warm up. NH$_4$Cl$_{(aq)}$ is added to quench the reaction and the product is extracted, dried, and concentrated under vacuum. The product is purified by column chromatography to provide Compound 2C.

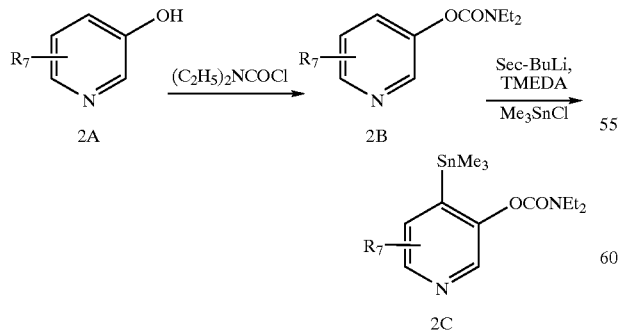

A mixture of Compound 2C, 2,6-dichloropyrazine (Compound 1C), tris-2-furyl phosphine, CuI, and Pd$_2$(dba)$_3$ in anhydrous NMP is stirred under nitrogen. The reaction is cooled and then concentrated under vacuum. The product is purified by column chromatography to give Compound 2D.

A mixture of Compound 2D, Compound 1E, Pd$_2$(dba)$_3$, DPPF and Cs$_2$CO$_3$ in anhydrous dioxane is stirred under nitrogen. The reaction is cooled and a suitable solvent, such as dichloromethane, is added. The diluted reaction is filtered, washed with more solvent, and the combined filtrate is concentrated to give Compound 2E. Compound 2E is diluted with a small amount of a suitable solvent, such as dichloromethane. The solid is collected through filtration and the filtrate is concentrated. Compound 2E is then dissolved in a suitable solvent, such as methanol, stirred and cooled to about 0° C. A NaOH$_{(aq)}$ solution is added slowly and the mixture is stirred first at about 0° C. and then stirred at about 20° C. Glacial acetic acid is slowly added to the reaction mixture at about 0° C. followed by the addition of water. A solid is formed, and is collected through filtration, washed with water, and then dried in a vacuum oven to give Compound 2F.

Compound 2F is dissolved in a cooled suitable solvent, such as in anhydrous CH$_2$Cl$_2$ (5 mL) at 0° C., and (CF$_3$SO$_2$)$_2$O and triethylamine are added. The reaction is stirred under nitrogen and then concentrated under vacuum. The product is purified by column chromatography to give the triflate Compound 2G.

Compound 2G is dissolved in solvent and treated with Boc$_2$O and DMAP by mixing the reaction under nitrogen. The solvent is removed under vacuum and the product is purified by column chromatography to give Compound 2H.

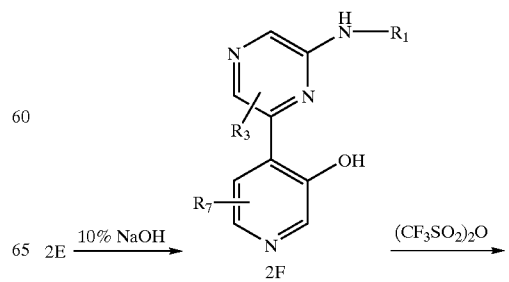

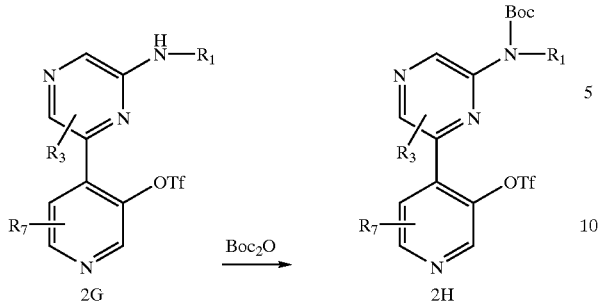 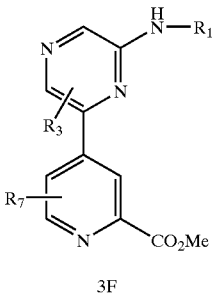

Scheme 3

A mixture of Compound 3A, 4-iodopicolinic acid (hemi-hydroiodide hydrate) and CDI in THF is stirred. The reaction mixture is cooled, and then a solvent, such as methanol, is added. Next triethylamine is added slowly. The reaction is stirred and then concentrated under vacuum. The product is purified by column chromatography to give Compound 3B as a solid. A mixture of Compound 3B, bis(tributyltin), palladium acetate, tri-o-tolylphosphine and triethylamine in a suitable solvent such as acetonitrile is stirred under nitrogen. The cooled reaction mixture is concentrated under vacuum. The residue is purified by column chromatography to give Compound 3C.

Scheme 4

A mixture of 2-methoxy-6-(tributyltin)pyridine (Compound 4A), Compound 5B, $Pd_2(dba)_3$, triphenylarsine, and THF is refluxed under nitrogen. The product is purified by column chromatography and recrystallized from a solvent, such as hexane, to give a solid Compound 4B. A mixture of Compound 4B and pyridine hydrochloride is heated under nitrogen. The mixture is cooled, and then triturated in a mixture of a suitable solvent, such as dichloromethane, and 30% ammonium hydroxide. Then the solvent is removed under vacuum. Solids are collected through filtration and dried under vacuum to give Compound 4C.

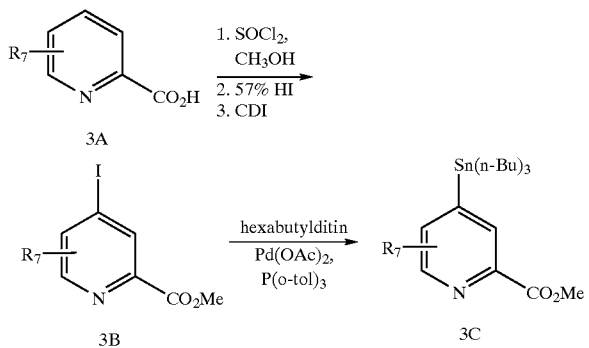

A mixture of Compound 3C, 2,6-diiodopyrazine Compound 3D, $Pd_2(dba)_3$, and triphenylarsine in THF is stirred at reflux under nitrogen. Aqueous solvent is added and stirred and then extracted with a suitable solvent, such as dichloromethane. The product is purified by column chromatography to give Compound 3E as a solid. A mixture of Compound 3E, Compound 1E, $Pd_2(dba)_3$, DPPF, $Cs_2CO_3$ in anhydrous dioxane is stirred under nitrogen. The reaction mixture is concentrated under vacuum and purified by column chromatography to give Compound 3F.

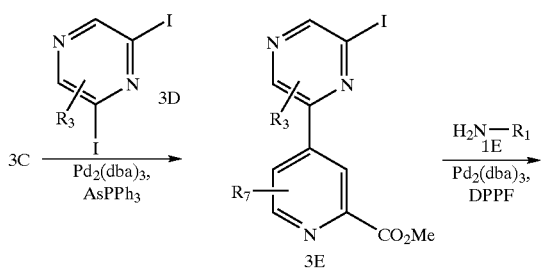

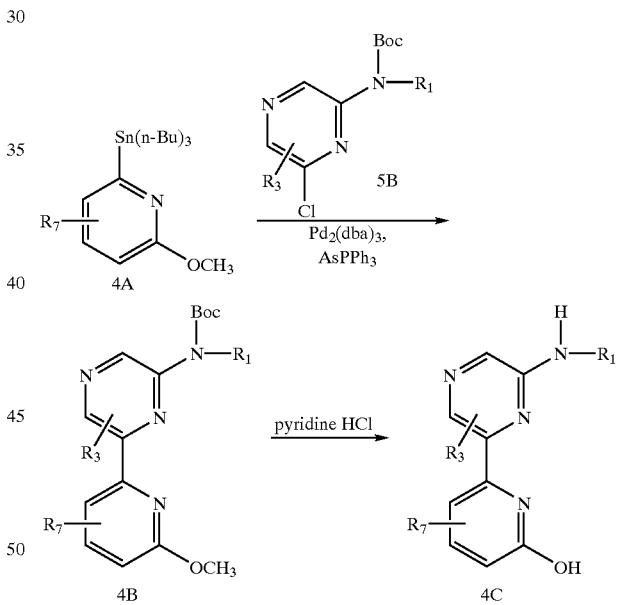

Scheme 5 Intermediate Product 5B

Palladium acetate, BINAP, t-BuONa, 2,6-dichloropyrazine (Compound 1C), and Compound 1E in a solvent is stirred at about 80° C. for about 22 hours under Nitrogen. $CH_2Cl_2$ is added, the reaction mixture is filtered through celite, and the solvent is evaporated. Product is purified by column chromatography to give Compound 5A. A mixture of Compound 5A, $Boc_2O$, and DMAP in a suitable solvent, such as dichloromethane, is stirred at about 20° C. for about 16 hours. The reaction mixture is concentrated and the product is purified by column chromatography to give Compound 5B.

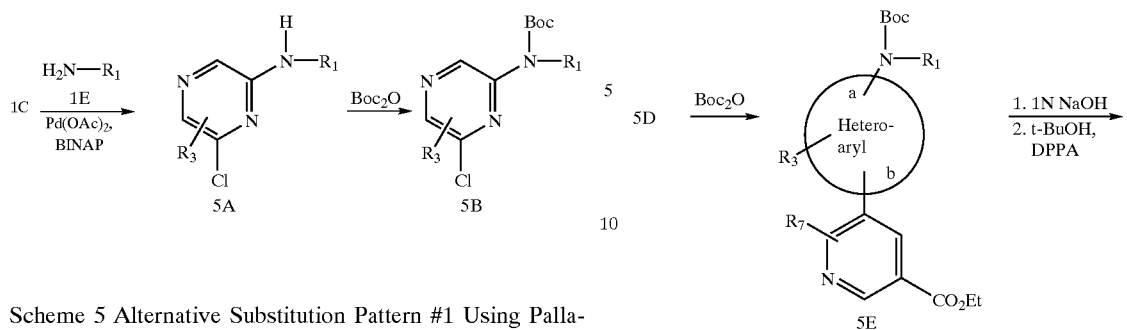

Scheme 5 Alternative Substitution Pattern #1 Using Palladium Chemistry

A mixture of Compound 1B, a dihaloheteroaryl compound, dichloro-bis(triphenylphosphine)palladium and LiCl in anhydrous toluene is stirred under nitrogen. The reaction is cooled and then concentrated under vacuum. Aqueous solvent is added to the residue, stirred, and then extracted with a suitable solvent, such as dichloromethane. The solution is filtered, dried, and concentrated. The product is purified by column chromatography to give Compound 5C.

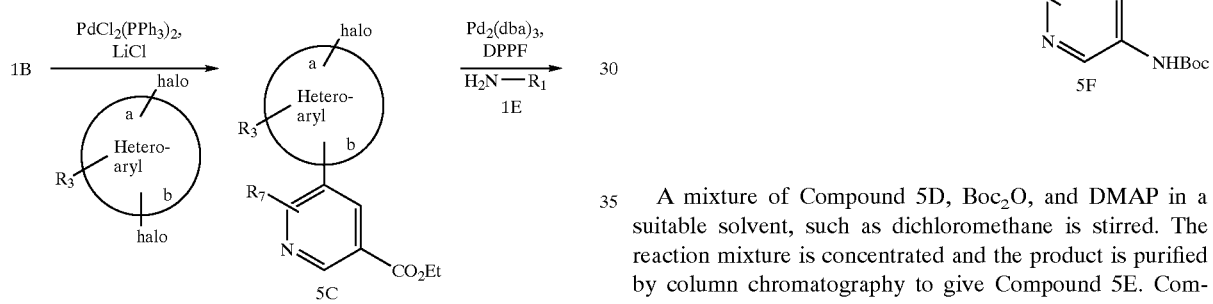

A mixture of Compound 5C, Compound 1E, $Pd_2(dba)_3$, DPPF and $Cs_2CO_3$ in anhydrous dioxane is stirred under nitrogen. The reaction is cooled and a suitable solvent, such as dichloromethane, is added. The diluted reaction is filtered and the filtrate is concentrated to give a product. The product is diluted with a small amount of a suitable solvent, such as dichloromethane. A solid is collected through filtration, the filtrate is concentrated and Compound 5D may be recrystallized from EtOAc/hexane.

A mixture of Compound 5D, $Boc_2O$, and DMAP in a suitable solvent, such as dichloromethane is stirred. The reaction mixture is concentrated and the product is purified by column chromatography to give Compound 5E. Compound 5E is dissolved in a suitable solvent, such as methanol, stirred, and then cooled to 0° C. A $NaOH_{(aq)}$ (1 N) solution is added slowly and the mixture is stirred at about 0° C. for 20 min. and then stirred for an additional 18 hours at about 20° C. Glacial acetic acid is added to the reaction mixture at about 0° C. slowly followed by the addition of water. A solid is formed and is collected through filtration, washed with water, and then dried in a vacuum oven to give a carboxylic acid derivative. The carboxylic acid derivative, DPPA, triethylamine, and t-BuOH in toluene is stirred under nitrogen, and then stirred at about 100° C. The reaction mixture is concentrated under vacuum. The product is purified by column chromatography to give Compound 5F. Other compounds of the invention may be obtained by substituting Compound 5F for Compound 1I in any of the reactions described for use of Compound 1I in Scheme 1.

Scheme 5 Alternative Substitution Pattern #2 Using Palladium Chemistry

Using the methodology of Scheme 1, other compounds of the invention may have a heterocylic substituent Compound 5G attached to a pyrazine ring Compound 1C to yield a target Compound 5H. Compound 7B is further used analogously to Compound 1D in the methods of Scheme 1.

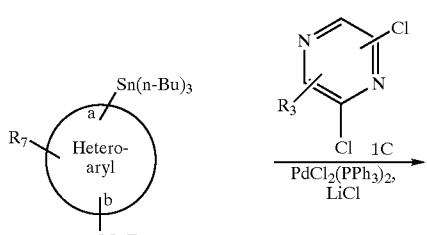

5G

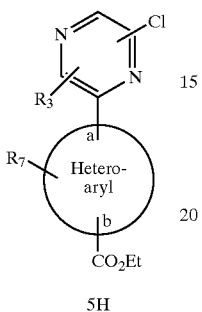

5H

Scheme 6

To compounds of the invention wherein the "A" linking group is varied, a Compound 5H is reacted with Compound 6A, Pd$_2$(dba)$_3$, DPPF and Cs$_2$CO$_2$ in anhydrous dioxane by stirring the mixture under nitrogen. The reaction is cooled and a suitable solvent is added. The diluted reaction is filtered and the filtrate is concentrated to give Compound 6B. Other compounds of the invention may be obtained by substituting Compound 6B for Compound 1G in any of the reactions described for use of Compound 1G in Scheme 1.

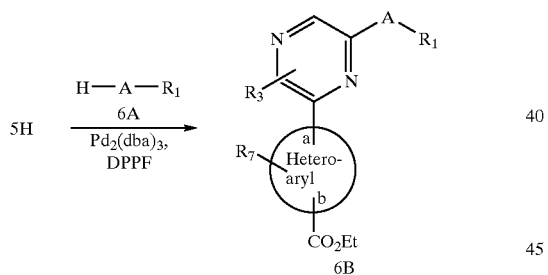

6B

Scheme 7

Alternatively to Scheme 5 and 6, using palladium chemistry, target compounds of the invention may be obtained by mixing 2-amino-6-bromopyridine Compound 7A (optionally substituted with R$_7$), an R$_{10}$ protecting group such as di-tert-butyl dicarbonate and 4-(dimethylamino) pyridine in t-BuOH and stirring at room temperature for more than 24 h. Concentrating and purifying the solution by flash chromatography (using a solvent such as EtOAc/hexane) gives N-(R$_{10}$)-2-amino-6-bromopyridine which is then mixed with dry DMF and to the solution is added bromo-(CH$_2$)$_m$-tert-butyldimethylsilane and Cs$_2$CO$_3$. The mixture is stirred at 70° C. for 18 h, the solvent is evaporated under reduced pressure and the residue is purified by column chromatography to provide Compound 7B as a clear oil.

A mixture of Compound 7B, bis(tributyltin), tetrakis (triphenylphosphine)palladium, LiCl and 2,6-di-tert-butyl-4-methylphenol in anhydrous 1,4-dioxane is refluxed at 100° C. for 4 h under nitrogen. The solvent is removed under reduced pressure and the residue chromatographed over silica gel (using a solvent such as ethyl acetate/hexane) to give Compound 7C as a clear oil. A mixture of Compound 7C, Compound 5B, dichlorobis(triphenylphosphine) palladium and LiCl in anhydrous toluene is stirred at 100° C. for 3 h under nitrogen. The cooled reaction mixture is concentrated under vacuum and purified by flash chromatography to give Compound 7D as a yellow oil. Compound 7D is dissolved in TFA and the solution stirred at room temperature for 2 h before concentration. A saturated NH$_4$OH solution is added to the residue until made basic and is followed by adding water to precipitate the solid. The precipitated solid is collected through filtration, washed with water and Et$_2$O, and dried under vacuum to provide the target Compound 7E as a yellow solid.

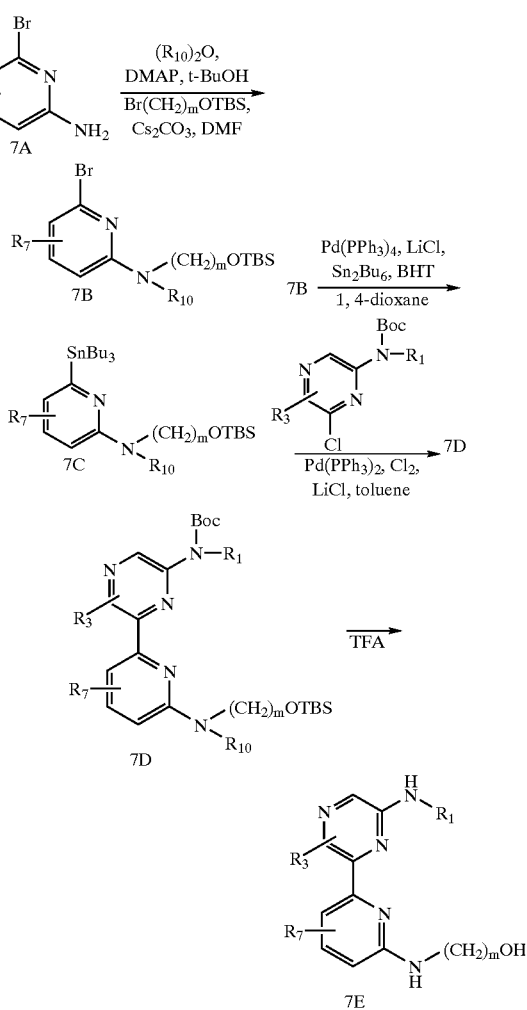

Scheme 8

As an alternate substitution pattern for Scheme 7, target compounds of the invention may be obtained by mixing 4-iodopicolinic acid Compound 8A (optionally substituted with R$_7$) (prepared as described in Lohse, O. *Synth. Commun.* 1996, 26, 2017), DPPA and triethylamine in t-BuOH and toluene, heating the mixture at 65° C. for 1.5 h and then at 100° C. for 4 h. After concentrating the reaction mixture and purification by flash chromatography (using a solvent such as EtOAc/hexane), Compound 8B is obtained as a white solid. A mixture of Compound 8B, bromo-(CH$_2$)$_m$-tert-butyldimethylsilane and Cs$_2$CO$_3$ in dry DMF is stirred at 70° C. for 3 h. The solvent is evaporated under reduced pressure and the residue purified by column chromatography (using a solvent such as EtOAc/hexane) to provide Compound 8C as a clear oil. A mixture of Compound 8C, bis(trimethyltin), tetrakis(triphenylphosphine)palladium, LiCl and BHT (2,6-di-tert-butyl-4-methylphenol) in anhydrous 1,4-dioxane is heated at 90° C. for 1.5 h under nitrogen. The solvent is removed under reduced pressure and the residue chromatographed over silica gel (using a solvent such as EtOAc/hexane) to give Compound 8D as a clear oil. Other compounds of the invention may be obtained by substituting Compound 8D for Compound 7C in the reaction described for use of Compound 7C in Scheme 7.

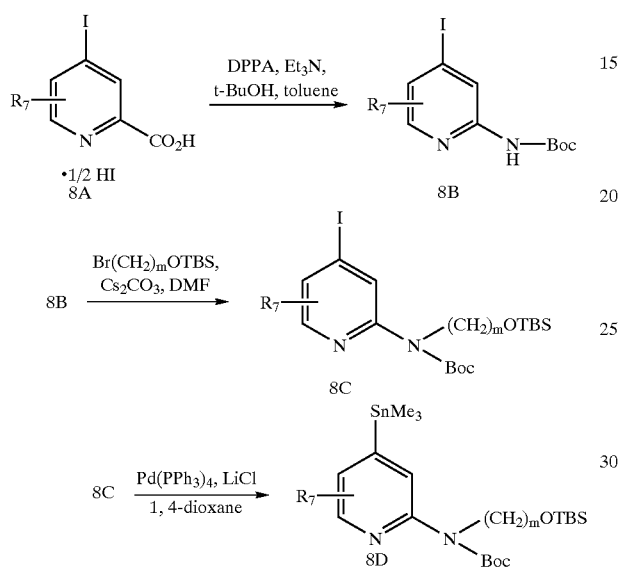

Scheme 9

As an alternate substitution pattern for Scheme 7, target compounds of the invention wherein $R_7$ is selected from halogen may be obtained by adding bromine dropwise to a suspension of 6-aminonicotinic acid Compound 9A in water at 4° C. After completion of the addition, the cooling bath is removed and the reaction mixture is stirred at room temperature for 4.5 h. Saturated $Na_2S_2O_5$ is added slowly to the stirred mixture. The solid is then collected through filtration, washed with water, and dried under vacuum overnight to give a 6-amino-5-bromonicotinic acid intermediate along with a 3,5-dibromo-2-aminopyridine intermediate in approximately a 1:1 ratio as a greenish solid. A mixture of the solid containing the 6-amino-5-bromonicotinic acid intermediate, DPPA, triethylamine, an $R_{10}$ protecting group such as benzyl alcohol and toluene is heated at 70° C. for 1 h, then 100° C. for 1 h. After concentrating the reaction mixture and purification by flash chromatography (using a solvent such as EtOAc/hexane), the Compound 9B is obtained as a yellow solid. A mixture of Compound 9B, bromo-$(CH_2)_m$-tert-butyldiphenylsilane and and $Cs_2CO_3$ in dry DMF is heated at 70° C. for 3 h. The reaction mixture is concentrated and purified by column chromatography (using a solvent such as EtOAc/hexane) to give Compound 9C as a yellow oil. To the solution of Compound 9C in $CH_2Cl_2$ at 4° C. is added $NOBF_4$ (nitrosonium tetrafluoroborate). After 1 h at 4° C., more $NOBF_4$ is added followed by the same amount of $NOBF_4$ after another 1 h. After stirring for a total of 3 h at 4° C., water is added. The aqueous solution is extracted with a solvent such as $CH_2Cl_2$. The combined organic layers are dried, concentrated and flash chromatographed (using a solvent such as EtOAc/hexane) to give Compound 9D as a yellow oil. Other compounds of the invention may be obtained by substituting Compound 9D for Compound 7C in the reaction described for use of Compound 7C in Scheme 7.

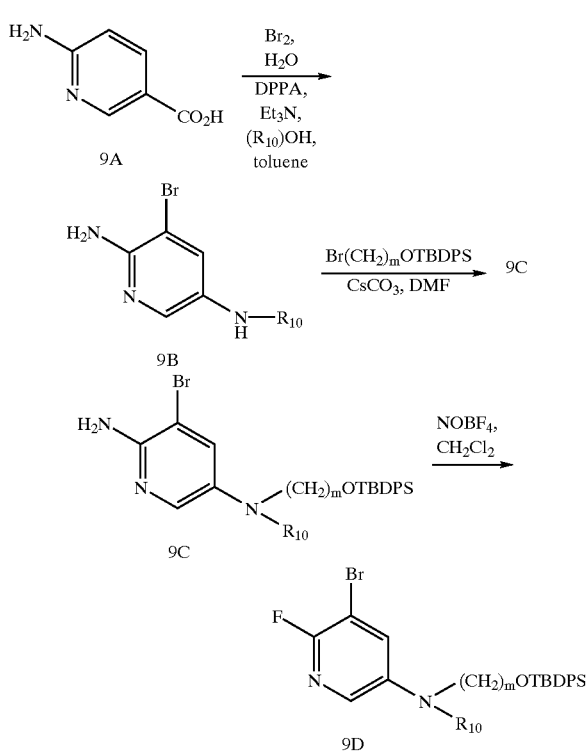

ProDrugs

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Pharmaceutical Formulations

The instant pharmaceutical composition can be prepared according to conventional pharmaceutical techniques. A pharmaceutically acceptable carrier may be used in the composition of the invention. The composition may take a wide variety of forms depending on the form of preparation desired for administration including, but not limited to, intravenous (both bolus and infusion), oral, nasal, transdermally, topical with or without occlusion, intraperitoneal, subcutaneous, intramuscular, or parenteral, all using forms well known to those of ordinary skill in the pharmaceutical arts. In preparing the compositions in oral dosage form, one or more of the usual pharmaceutical carriers may be employed, such as water, glycols, oils, alcohols, flavoring agents, preservatives, coloring agents, syrup and the like in the case of oral liquid preparations (for example, suspensions, elixirs and solutions), or carriers such as starches, sugars, diluents, granulating agents, lubricants, binders, disintegrating agents and the like in the case of oral solid preparations (for example, powders, capsules and tablets).

The compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cotton seed oil, sesame oil, and the like, as well as organic solvents such as solketal, glycerol formal, and the like. As an alternative, aqueous parenteral formulations may also be used. For example, acceptable aqueous solvents include water, Ringer's solution and an isotonic aqueous saline solution. Further, a sterile non-volatile oil can usually be employed as solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

The compounds may alternatively be administered occularly via application of a formulation consisting of the active ingredient dissolved in an inert aqueous liquid carrier. Such aqueous liquid formulations are useful, for example in the treatment of diabetic retinopathy. Acceptable aqueous solvents include water, Ringer's solution, and an isotonic aqueous saline solution. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

As used herein, a "therapeutically effective amount" of the instant pharmaceutical composition, or compound therein, means an amount that inhibits the function of the kinase enzymatic activity. The instant pharmaceutical composition will generally contain a per dosage unit (e.g., tablet, capsule, powder, injection, teaspoonful and the like) from about 0.001 to about 100 mg/kg. In one embodiment, the instant pharmaceutical composition contains a per dosage unit of from about 0.01 to about 50 mg/kg of compound, and preferably from about 0.05 to about 20 mg/kg. Methods are known in the art for determining therapeutically effective doses for the instant pharmaceutical composition. The effective dose for administering the pharmaceutical composition to a human, for example, can be determined mathematically from the results of animal studies. Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Oral Dosage Forms

Because of their ease of administration, tablets and capsules represent an advantageous oral dosage unit form, wherein solid pharmaceutical carriers are employed. If desired, tablets may be sugar-coated or enteric-coated by standard techniques.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like.

Skin Care Compositions

In one embodiment of the present invention, compounds of the present invention are formulated as skin care compositions, particularly for use in treating psoriasis.

Skin care compositions of the present invention preferably comprise, in addition to the active compound of the present invention, a cosmetically- or pharmaceutically-acceptable carrier.

Herein, "cosmetically-acceptable carrier" means one or more compatible solid or liquid filler diluents or encapsulating substances which are suitable for use in contact with the skin of humans and lower animals without undue toxicity, incompatibility, instability, irritation, allergic response, and the like, commensurate with a reasonable benefit/risk ratio.

Herein, "compatible" means that the components of the cosmetic or pharmaceutical compositions are capable of being commingled with the active compound of the present invention, and with each other, in a manner such that there is no interaction which would substantially reduce the cosmetic or pharmaceutical efficacy of the composition under ordinary use situations.

Preferably the skin care compositions of the present invention are topical compositions., ie., they are applied topically by the direct laying on or spreading of the composition on skin. Preferably such topical compositions comprise a cosmetically- or pharmaceutically-acceptable topical carrier.

The topical composition may be made into a wide variety of product types. These include, but are not limited to, lotions, creams, beach oils, gels, sticks, sprays, ointments, pastes, mousses, and cosmetics; hair care compositions such as shampoos and conditioners; and personal cleansing compositions.

Preferably the carrier is a cosmetically- or pharmaceutically-acceptable aqueous or organic solvent. Water is a preferred solvent. Examples of suitable organic solvents include: propylene glycol, polyethylene glycol (200–600), polypropylene glycol (425–2025), propylene glycol-14 butyl ether, glycerol, 1,2,4-butanetriol, sorbitol esters, 1,2,6-hexanetriol, ethanol, isopropanol, butanediol, and mixtures thereof. Such solutions useful in the present invention preferably contain from about 0.001% to about 25% of the active compound, more preferably from about 0.1% to about 10% more preferably from about 0.5% to about 5%; and preferably from about 50% to about 99.99% of an acceptable aqueous or organic solvent, more preferably from about 90% to about 99%.

Skin care compositions of the present invention may further include a wide variety of additional oil-soluble materials and/or water-soluble materials conventionally used in topical compositions, at their art-established levels. Such additional components include, but are not limited to: thickeners, pigments, fragrances, humectants, proteins and polypeptides, preservatives, pacifiers, penetration enhancing agents, collagen, hylauronic acid, elastin, hydrolysates, primrose oil, jojoba oil, epidermal growth factor, soybean saponins, mucopolysaccharides, Vitamin A and derivatives thereof, Vitamin B2, biotin, pantothenic acid, Vitamin D, and mixtures thereof.

Inhalant Compositions

In a particular embodiment, the instant pharmaceutical composition is administered by inhalation. For inhalation therapy, the composition may be in a solution useful for administration by metered dose inhalers, or in a form suitable for a dry powder inhaler or insufflator. More particularly, the instant composition is conveniently delivered in the form of an aerosol spray delivered, for example from a pressurized container, a pack or a nebuliser, with the use of a suitable propellant, e.g., dichlorodifluoromethane, trichlorofluoromethane, dichlorotetrafluoroethane, carbon dioxide or other suitable gas inside such container. The dosage unit may be determined by providing a valve to deliver a metered amount. Capsules and cartridges made of a pharmaceutically acceptable material such as gelatin for use in an inhaler or insufflator may be formulated containing a powder mix of the compound and a suitable powder base such as lactose or starch.

Coadministration of Pharmaceutical Agents

In a preferrred embodiment of this invention, VEGF-R selective agents of the present invention are advantageously co-administered with at least one other anti-tumor agent to facilitate eradication or stasis of a malignancy. For example, but not to limit the present invention, an anti-VEGF-R compound of the present invention, acting, for example, as anti-angiogenic compound, can be administered in a dosing regimin with a cytotoxic compound, such as a DNA alkylating agent. Preferred anti-tumor agents are selected from the group consisting of cladribine (2-chloro-2'-deoxy-(beta)-D-adenosine), Chlorambucil (4-[bis(2-chlorethyl)amino]benzenebutanoic acid), DTIC-Dome (5-(3,3-dimethyl-1-triazeno)-imidazole-4-carboxamide), platinum chemotherapeutics and nonplatinum chemotherapeutics. Platinum containing anti-tumor agents include, but are not limited to, cisplatin (cis-dichlorodiamineplatinum). Non-platinum containing anti-tumor agents include, but are not limited to, cyclophosphamide, fluorouracil, epirubicin, methotrexate, vincristine, doxorubicin, bleomycin, and etoposide. Each anti-tumor agent is administered within therapeutically effective amounts, which are well known in the art, and vary based on the agent used, the type of malignancy, and other conditions Specific Synthetic Examples The invention can be better understood by way of the following examples. These examples are representative of the preferred embodiments, but are not to be construed as limiting the scope of the invention.

General $^1$H NMR spectra were measured on a Bruker AC-300 (300 MHz) spectrometer using tetramethylsilane as an internal standard. Elemental analyses were obtained by Quantitative Technologies Inc. (Whitehouse, N.J.), and the results were within 0.4% of the calculated values unless otherwise mentioned. Melting points were determined in open capillary tubes with a Thomas-Hoover apparatus and were uncorrected. Optical rotations were measured at 25° C. with an Autopol III polarimeter. Electrospray mass spectra (MS-ES) were recorded on a Hewlett Packard 59987A spectrometer. High resolution mass spectra (HRMS) were obtained on a Micromass Autospec. E. spectrometer.

EXAMPLE 1

Synthesis of Intermediate Compound 1B

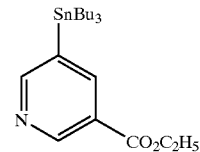

A mixture of 5-bromonicotinate (25 g, 108.7 mmol), bis(tributyltin) (63.05 g, 108.7 mmol), palladium acetate (1.1 g, 4.89 mmol), tri-o-tolylphosphine (8.6 g, 28.26 mmol) and triethylamine (21.96 g, 217.4 mmol) in acetonitrile (350 mL) was stirred at 95–100° C. for 22 h under nitrogen. The cooled reaction mixture was filtered through celite. Then the celite was washed with more acetonitrile and the combined acetonitrile was concentrated under vacuum. The residue was diluted with a suitable solvent, such as dichloromethane, washed with aqueous sodium carbonate and concentrated. The residue was further diluted with hexane. The solid was filtered off and the filtrate was concentrated. The product was purified by column chromatography (twice, $SiO_2$, dichloromethane/hexane as solvent) to give 19.09 g (40%) of 1B as a light orange oil; $^1$H NMR (300 MHz, $CDCl_3$) δ9.11 (brs, 1H), 8.74 (brs, 1H), 8.35 (brs, 1H), 4.41 (q, J=6.9 Hz, 2H), 1.72–1.05 (m, 21H), 0.89 (t, J=7.2 Hz, 9H); MS (ES) m/z: 442 (M+H$^+$).

EXAMPLE 2

Synthesis of Intermediate Compound 1D

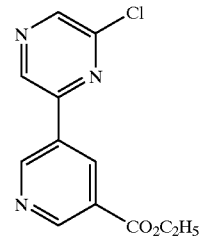

A mixture of 1B (10 g, 22.7 mmol), 2,6-dichloropyrazine (6.76 g, 45.4 mmol), dichloro-bis(triphenylphosphine) palladium (797 mg, 1.14 mmol) and LiCl (4.77 g, 113.5 mmol) in anhydrous toluene (85 mL) was stirred at 100° C. for 23 h under nitrogen. The cooled reaction mixture was concentrated under vacuum. Aqueous sodium carbonate was added to the residue and stirred for 10 min. and extracted with dichloromethane (3x). The combined dichloromethane solution was filtered through celite, dried ($Na_2SO_4$) and concentrated. The product was purified by column chromatography (EtOAc/hexane as solvent) to give 3.56 g (60%) of 1D as an off-white solid; $^1$H NMR (300 MHz, $CDCl_3$) δ9.43 (brs, 1H), 9.35 (brs, 1H), 9.05 (s, 1H), 8.91 (s, 1H), 8.64 (s, 1H), 4.48 (q, J=7.3 Hz, 2H), 1.47 (t, J=7.2 Hz, 3H); MS (ES) m/z: 264 (M+H$^+$). Anal. Calcd. For $C_{12}H_{10}N_3O_2Cl$: C, 54.66; H, 3.82; N, 15.94. Found: C, 54.62; H, 3.77; N, 15.57.

EXAMPLE 3

COMPOUND 1

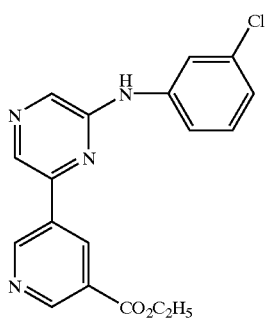

A mixture of 1D (24.3 g, 92.4 mmol), 3-chloroaniline (16.6 g, 129 mmol), Pd$_2$(dba)$_3$ (2.39 g, 2.31 mmol), DPPF (4.1 g, 7.4 mmol), Cs$_2$CO$_3$ (60.2 g, 185 mmol) in anhydrous dioxane (230 mL) was stirred at 110° C. for 46 h under nitrogen. Dichloromethane (100 mL) was added to the cooled reaction mixture. The mixture was then filtered through celite, the celite cake was washed with more dichloromethane and the combined filtrate was concentrated to give a yellow-brown solid. Small amounts of dichloromethane was added, the solid was collected through filtration and the filtrate was concentrated. The solid collected was recrystallized from EtOAc/hexane to give 21.83 g (67%) of Cmd 1 as a yellow solid; $^1$H NMR (300 MHz, CDCl$_3$) δ9.44 (brs, 1H), 9.31 (brs, 1H), 8.90 (s, 1H), 8.57 (s, 1H), 8.26 (s, 1H), 7.72 (s, 1H), 7.44 (d, J=8.1 Hz, 1H), 7.31 (t, J=8.0 Hz, 1H), 7.08 (d, J=8.0 Hz, 1H), 7.04 (s, 1H), 4.48 (q, J=7.2 Hz, 2H), 1.46 (t, J=7.0 Hz, 3H); MS (ES) m/z: 355 (M+H$^+$). Anal. Calcd. For C$_{18}$H$_{15}$N$_4$O$_2$Cl: C, 60.94; H, 4.26; N, 15.79 Found: C, 60.54; H, 4.33; N, 15.58.

EXAMPLE 4

COMPOUND 2

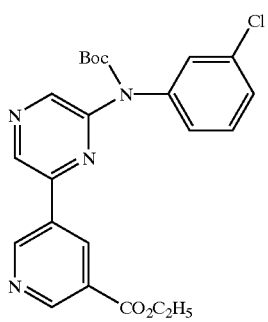

A mixture of Cmd 1 (21.83 g, 61.7 mmol), Boc$_2$O (26.9 g, 123 mmol), and DMAP (~3 g, cat.) in dichloromethane (500 mL) was stirred at 20° C. for 4 h. The reaction mixture was concentrated and the product was purified by column chromatography (EtOAc/hexane as solvent) to give 26.7 g (95%) of Cmd 2 as yellowish oil; $^1$H NMR (300 MHz, CDCl$_3$) δ9.22 (d, J=2.0 Hz, 1H), 9.15 (d, J=2.2 Hz, 1H), 9.10 (s, 1H), 8.84 (s, 1H), 8.64 (t, J=2.1 Hz, 1H), 7.35 (m, 3H), 7.18 (brd, J=7.3 Hz, 1H), 4.44 (q, J=7.1 Hz, 2H), 1.50 (s, 9H), 1.44 (t, J=7.1 Hz, 3H); MS (ES) m/z: 455 (M+H$^+$).

EXAMPLE 5

COMPOUND 3

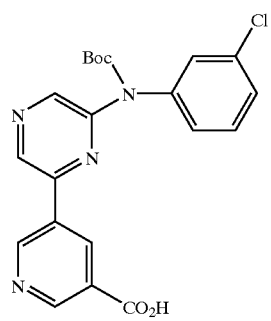

Compound Cmd 2 (32.2 g, 71 mmol) was dissolved in methanol (200 mL) and stirred for 10 min then cooled to 0° C. A NaOH$_{(aq)}$ (1 N, 118 mL) solution was added slowly and the mixture was stirred at 0° C. for 20 min then stirred at 20° C. for another 18 h. Glacial acetic acid (95 mL) was added to the reaction mixture at 0° C. slowly followed by the addition of water (350 mL). A yellow solid was formed. The yellow solid was collected through filtration, washed with water (5×), dried in vacuum oven overnight to give 28.3 g (94%) of the carboxylic acid Cmd 3 as a yellow solid; $^1$H NMR (300 MHz, D$^6$-DMSO) δ9.27 (d, J=1.9 Hz, 1H), 9.22 (s, 1H), 9.09 (d, J=1.6 Hz, 1H), 9.03 (s, 1H), 8.65 (brs, 1H), 7.52–7.31 (m, 4H), 1.44 (s, 9H); MS (ES) m/z: 425 (M–H$^+$). Anal. Calcd. For C$_{21}$H$_{19}$N$_4$O$_4$Cl: C, 59.09; H, 4.49; N, 13.13. Found: C, 58.82; H, 4.38; N, 12.98.

EXAMPLE 6

COMPOUND 67

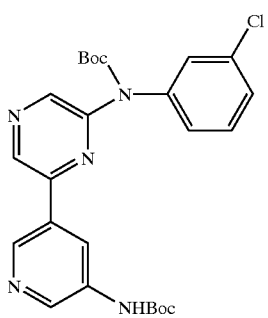

A mixture of the carboxylic acid Cmd 3 (28.3 g, 66.5 mmol), DPPA (21.95 g, 80 mmol), triethylamine (13.43 g, 133 mmol), t-BuOH (280 mL) in toluene (200 mL) was stirred under nitrogen at 70° C. for 30 min then stirred at 100° C. for 4 h. The reaction mixture was concentrated under vacuum. The product was purified by column chromatography (EtOAc/hexane as solvent) to give 29.28 g (89%) of Cmd 67 as a yellowish foam; $^1$H NMR (300 MHz, CDCl$_3$) δ8.99 (s, 1H), 8.80 (s, 1H), 8.67 (d, J=1.7 Hz, 1H), 8.49 (d, J=2.4 Hz, 1H), 8.41 (brs, 1H), 7.29 (m, 3H), 7.17 (d, J=7.5 Hz, 1H), 7.08 (s, 1H), 1.54 (s, 9H), 1.49 (s, 9H); MS (ES) m/z: 498 (M+H$^+$). Anal. Calcd. For C$_{25}$H$_{28}$N$_5$O$_4$Cl: C, 60.30; H, 5.67; N, 14.06. Found: C, 60.14; H, 5.49; N, 13.91.

EXAMPLE 7

COMPOUND 4

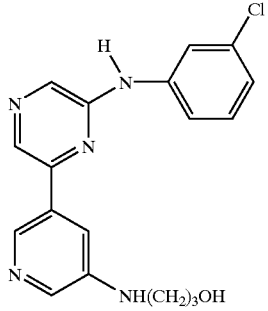

3-[[5-[6-[(3-chlorophenyl)amino]pyrazinyl]-
3-pyridinyl]amino]-1-propanol (Cmd 4)

A mixture of Cmd 67 (3 g, 6 mmol), (3-bromopropoxy)-t-butyl-dimethylsilane (2.28 g, 9 mmol) and $Cs_2CO_3$ (5.9 g, 18 mmol) in DMF (60 mL) was stirred at 70° C. under nitrogen for 36 h. The reaction mixture was diluted with water, extracted with ether (3×), dried ($Na_2SO_4$) and concentrated. The product was purified by column chromatography (EtOAc/hexane as solvent) to give 3.04 g of the silylated-product as orange oil. The silylated-product was dissolved in TFA (30 mL) and stirred at 20° C. for 1 h before it was concentrated. An ammonium hydroxide solution was added to the residue until the pH was about 10–11, water was added and a yellow solid was formed. The yellow solid was collected through filtration, washed with water and dried under vacuum. The yellow solid was recrystallized from $CH_3OH$/EtOAc to give 1.25 g (59%) of Cmd 4 as a light yellow solid; $^1$H NMR (300 MHz, $CD_3OD$) δ8.45 (s, 1H), 8.41 (d, J=1.6 Hz, 1H), 8.12 (brs, 2H), 8.00 (d, J=2.7 Hz, 1H), 7.66 (brs, 1H), 7.55 (d, J=8.3 Hz, 1H), 7.30 (t, J=8.1 Hz, 1H), 6.99 (d, J=7.9 Hz, 1H), 3.72 (t, J=6.3 Hz, 2H), 3.33 (t, J=6.8 Hz, 2H), 1.91 (m, 2H); MS (ES) m/z: 356 (M+H$^+$). Anal. Calcd. For $C_{18}H_{18}N_5OCl \cdot 0.5H_2O$: C, 59.26; H, 5.25; N, 19.20. Found: C, 59.30; H, 4.95; N, 18.95.

EXAMPLE 8

COMPOUND 5

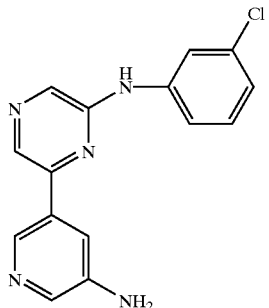

6-(5-amino-3-pyridinyl)-
N-(3-chlorophenyl)-2-pyrazinamine (Cmd 5)

Compound Cmd 67 (100 mg, 0.2 mmol) was dissolved in TFA (2 mL) and stirred at 20° C. for 2 hours before it was concentrated. An ammonium hydroxide solution was added to the residue until the pH was about 10–11, water was added and a yellow solid was formed. The yellow solid was collected through filtration, washed with water and dried under vacuum to give 54 mg (91%) of Cmd 5 as a light yellow solid; MS (ES) m/z: 298 (M+H$^+$).

EXAMPLE 9

COMPOUND 6

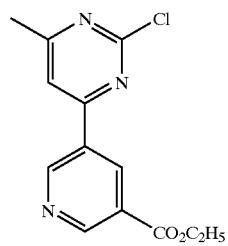
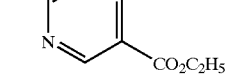

A mixture of Compound 1B (500 mg, 1.14 mmol), 2,4-dichloro-6-methylpyrimidine (as in Scheme 5, Alternate Substitution Pattern #1, to replace Compound 1C, where $R_3$ is methyl) (370 mg, 2.27 mmol), dichloro-bis(triphenylphosphine)palladium (40 mg, 0.057 mmol) and LiCl (239 mg, 5.68 mmol) in anhydrous toluene (5 mL) was stirred at 100° C. for 23 h under nitrogen. The cooled reaction mixture was concentrated under vacuum. Aqueous sodium carbonate was added to the residue and stirred for 10 min. then extracted with dichloromethane (3×). The combined dichloromethane solution was filtered through celite, dried ($Na_2SO_4$) and concentrated. The product was purified by column chromatography (EtOAc/hexane as solvent) to give 281 mg (52%) of Cmd 6 as an off-white solid; $^1$H NMR (300 MHz, $CDCl_3$) δ9.43 (d, J=1.9 Hz, 1H), 9.35 (d, J=1.4 Hz, 1H), 8.92 (d, J=1.5 Hz, 1H), 7.60 (s, 1H), 4.48 (q, J=7.1 Hz, 2H), 2.66 (s, 3H), 1.46 (t, J=7.0 Hz, 3H); MS (ES) m/z: 278 (M+H$^+$).

EXAMPLE 10

COMPOUND 7

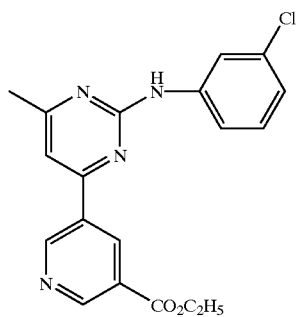
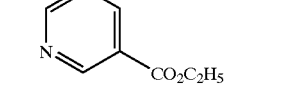

A mixture of Cmd 6 (1.41 g, 5.09 mmol), 3-chloroaniline (782 mg, 6.11 mmol), $Pd_2(dba)_3$ (132 mg, 0.127 mmol), DPPF (226 mg, 0.407 mmol), $Cs_2CO_3$ (3.32 g, 10.2 mmol) in anhydrous dioxane (15 mL) was stirred at 110° C. for 26 h under nitrogen. Dichloromethane (30 mL) was added to the cooled reaction mixture which was then filtered through celite and the celite cake was washed with more dichloromethane. The combined filtrate was concentrated to give a yellow-brown solid. The product was purified by column chromatography (EtOAc/hexane as solvent) to give 1.03 g (55%) of Cmd 7 as a yellow-brown solid; $^1$H NMR (300 MHz, $CDCl_3$) δ9.44 (d, J=2.1 Hz, 1H), 9.32 (d, J=1.9 Hz, 1H), 8.91 (m, 1H), 7.93 (t, J=1.9 Hz, 1H), 7.51 (d, J=8.2 Hz, 1H), 7.28 (m, 2H), 7.16 (s, 1H), 7.03 (d, J=7.9 Hz, 1H), 4.48 (q, J=7.1 Hz, 2H), 2.54 (s, 3H), 1.46 (t, J=7.1 Hz, 3H); MS (ES) m/z: 369 (M+H$^+$). Anal. Calcd. For $C_{19}H_{17}N_4O_2Cl$: C, 61.88; H, 4.65; N, 15.19. Found: C, 61.74; H, 4.63; N, 14.79.

EXAMPLE 11

COMPOUND 8

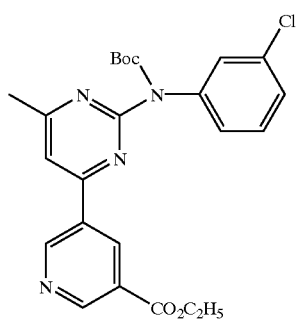

A mixture of Cmd 7 (1 g, 2.72 mmol), Boc₂O (3.56 g, 16.29 mmol), and DMAP (0.3 g, cat.) in dichloromethane (90 mL) was stirred at 20° C. for 24 h. The reaction mixture was concentrated and the product was purified by column chromatography (EtOAc/hexane as solvent) to give 1.16 g (91%) of Cmd 8 as a yellow brown foam; $^1$H NMR (300 MHz, CDCl₃) δ9.34 (d, J=2.2 Hz, 1H), 9.30 (d, J=2.0 Hz, 1H), 8.82 (m, 1H), 7.46 (s, 1H), 7.32–7.18 (m, 4H), 4.46 (q, J=7.1 Hz, 2H), 2.60 (s, 3H), 1.49 (s, 9H), 1.44 (t, J=7.1 Hz, 3H); MS (ES) m/z: 469 (M+H⁺), 369 (M+H⁺-Boc).

EXAMPLE 12

COMPOUND 9

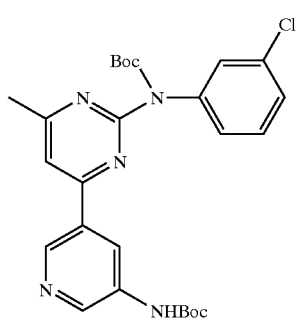

Compound Cmd 8 (1.16 g, 2.49 mmol) was dissolved in methanol (30 mL) and stirred for 10 min then cooled to 0° C. A NaOH$_{(aq)}$ (1 N, 18 mL) solution was added slowly and the mixture was stirred at 0° C. for 20 min then stirred at 20° C. for another 18 h. Glacial acetic acid (16 mL) was added to the reaction mixture at 0° C. slowly followed by the addition of water (200 mL). A yellowish-white solid was formed. The yellowish-white solid was collected through filtration, and washed with water (5×) then dried in vacuum oven overnight to give 1.04 g (95%) of Cmd 63 as a light-brown solid; MS (ES) m/z: 439 (M–H⁺). Anal. Calcd. For C₂₂H₂₁N₄O₄Cl·0.5H₂O: C, 58.73; H, 4.93; N, 12.45. Found: C, 59.04; H, 4.88; N, 12.23. A mixture of Cmd 63 (1.02 g, 2.32 mmol), DPPA (766 mg, 2.78 mmol), triethylamine (398 mg, 3.9 mmol), and t-BuOH (10 mL) in toluene (8 mL) was stirred under nitrogen at 70° C. for 30 min then stirred at 100° C. for 18 h. The reaction mixture was concentrated under vacuum. The product was purified by column chromatography (EtOAc/hexane as solvent) to give 883 mg (75%) of Cmd 9 as a yellowish foam; $^1$H NMR (300 MHz, CDCl₃) δ8.86 (d, J=1.4 Hz, 1H), 8.55 (m, 2H), 7.42 (s, 1H), 7.27 (m, 4H), 6.80 (brs, 1H), 2.58 (s, 3H), 1.54 (s, 9H), 1.48 (s, 9H); MS (ES) m/z: 512 (M+H⁺), 412 (M+H⁺−Boc). Anal. Calcd. For C₂₆H₃₀N₅O₄Cl: C, 60.99; H, 5.91; N, 13.68. Found: C, 60.83; H, 5.92; N, 13.33.

EXAMPLE 13

COMPOUND 10

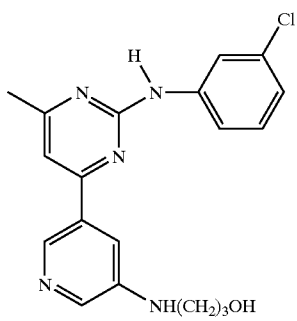

3-[[5-[2-[(3-chlorophenyl)amino]6-methyl-4-pyrimidinyl]-3-pyridinyl]amino]-1-propanol(Cmd 10)

A mixture of Cmd 9 (100 mg, 0.196 mmol), (3-bromopropoxy)-t-butyl-dimethylsilane (75 mg, 0.294 mmol) and Cs₂CO₃ (192 mg, 0.59 mmol) in DMF (4 mL) was stirred at 70° C. under nitrogen for 24 h. The reaction mixture was diluted with water, extracted with ether (3×), dried (Na₂SO₄) and concentrated. The product was purified by column chromatography (EtOAc/hexane as solvent) to give 92 mg of the silylated-product as oil. The silylated-product was dissolved in TFA (4 mL) and stirred at 20° C. for 1 h before it was concentrated. An ammonium hydroxide solution was added to the residue until the pH was about 10–11, water was added and a yellow solid was formed. The yellow solid was collected through filtration, washed with water and dried under vacuum. The product was purified by column chromatography (dichloromethane/methanol as solvent), followed by recrystallization from EtOAc/hexane to give 36 mg (50%) of Cmd 10 as an off-white solid; $^1$H NMR (300 MHz, CD₃OD) δ8.31 (s, 1H), 7.98 (s, 1H), 7.93 (s, 1H), 7.43 (m, 2H), 7.17 (m, 1H), 7.00 (brs, 1H), 6.89 (brd, J=7.2 Hz, 1H), 3.72 (t, J=6.2 Hz, 2H), 3.22 (m, 2H), 2.34 (s, 3H), 1.87 (m, 2H); MS (ES) m/z: 370 (M+H⁺).

EXAMPLE 14

COMPOUND 11

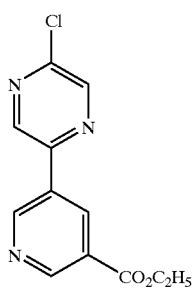

A mixture of 1B (2 g, 4.54 mmol), 2,3-dichloropyrazine (2.03 g, 13.62 mmol), dichloro-bis(triphenylphosphine) palladium (159 mg, 0.227 mmol) and LiCl (953 mg, 22.7 mmol) in anhydrous toluene (20 mL) was stirred at 100° C. for 23 h under nitrogen. The cooled reaction mixture was concentrated under vacuum. Aqueous sodium carbonate was added to the residue and stirred for 10 min. then extracted with dichloromethane (3×). The combined dichloromethane solution was filtered through celite, dried (Na₂SO₄) and concentrated. The product was purified by column chromatography (EtOAc/hexane as solvent) to give 648 mg (54%) of Cmd 11 as an off-white solid; $^1$H NMR (300 MHz, CDCl$_3$) δ9.33 (d, J=2.0 Hz, 1H), 9.23 (d, J=2.2 Hz, 1H), 8.77 (t, J=2.1 Hz 1H), 8.67 (d, J=2.4 Hz, 1H), 8.45 (d, J=2.4 Hz, 1H), 4.46 (q, J=7.1 Hz, 2H), 1.44 (t, J=7.1 Hz, 3H); MS (ES) m/z: 264 (M+H$^+$). Anal. Calcd. For C$_{12}$H$_{10}$N$_3$O$_2$Cl: C, 54.66; H, 3.82; N, 15.94. Found: C, 54.78; H, 3.76; N, 15.54.

EXAMPLE 15

COMPOUND 12

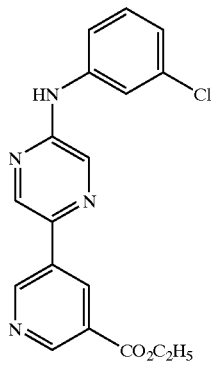

A mixture of Cmd 11 (567 mg, 2.15 mmol), 3-chloroaniline (359 mg, 2.8 mmol), Pd$_2$(dba)$_3$ (56 mg, 0.054 mmol), DPPF (95 mg, 0.172 mmol), and Cs$_2$CO$_3$ (1.4 g, 4.3 mmol) in anhydrous dioxane (7 mL) was stirred at 110° C. for 24 h under nitrogen. Dichloromethane (10 mL) was added to the cooled reaction mixture and filtered through celite. The celite cake was washed with more dichloromethane and the combined filtrate was concentrated. The product was purified by column chromatography (EtOAc/hexane as solvent) followed by recrystallization from EtOAc/hexane to give 416 mg (55%) of Cmd 12 as an off-white solid; $^1$H NMR (300 MHz, CDCl$_3$) δ9.31 (d, J=2.0 Hz, 1H), 9.13 (d, J=2.2 Hz, 1H), 8.65 (t, J=2.1 Hz, 1H), 8.22 (m, 2H), 7.67 (brs, 1H), 7.26 (m, 2H), 7.04 (m 1H), 6.63 (s, 1H), 4.45 (q, J=7.1 Hz, 2H), 1.43 (t, J=7.1 Hz, 3H); MS (ES) m/z: 355 (M+H$^+$). Anal. Calcd. For C$_{18}$H$_{15}$N$_4$O$_2$Cl: C, 60.94; H, 4.26; N, 15.79. Found: C, 61.07; H, 4.24; N, 15.60.

EXAMPLE 16

COMPOUND 13

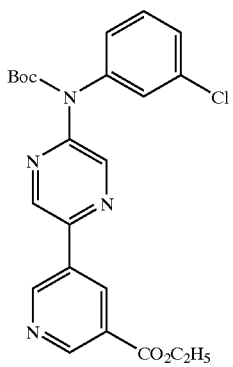

A mixture of Cmd 12 (400 mg, 1.13 mmol), Boc$_2$O (493 mg, 2.26 mmol), and DMAP (20 mg, cat.) in dichloromethane (20 mL) was stirred at 20° C. for 16 h. The reaction mixture was concentrated and the product was purified by column chromatography (EtOAc/hexane as solvent) to give 504 mg (98%) of Cmd 13 as a yellowish oil; $^1$H NMR (300 MHz, CDCl$_3$) δ9.26 (d, J=2.0 Hz, 1H), 9.12 (d, J=2.2 Hz, 1H), 8.68 (m, 1H), 8.64 (t, J=2.1 Hz, 1H), 8.56 (d, J=2.4 Hz, 1H), 7.21 (m, 3H), 7.02 (brd, J=7.9 Hz, 1H), 4.42 (q, J=7.1 Hz, 2H), 1.39 (t, J=7.1 Hz, 3H), 1.26 (s, 9H); MS (ES) m/z: 455 (M+H$^+$). Anal. Calcd. For C$_{23}$H$_{23}$N$_4$O$_4$Cl: C, 60.73; H, 5.10; N, 12.32. Found: C, 61.47; H, 5.29; N, 11.92.

EXAMPLE 17

COMPOUND 14

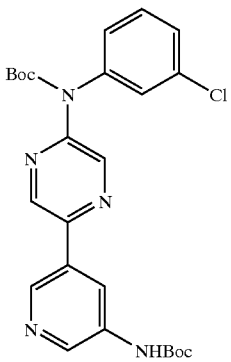

Compound Cmd 13 (485 mg, 1.07 mmol) was dissolved in methanol (13 mL) and stirred for 10 min then cooled to 0° C. A NaOH$_{(aq)}$ (1 N, 8 mL) solution was added slowly and the mixture was stirred at 0° C. for 20 min then stirred at 20° C. for another 18 h. Glacial acetic acid (7 mL) was added to the reaction mixture at 0° C. slowly followed by the addition of water. A white solid was formed. The white solid was collected through filtration, and washed with water (3×), dried in vacuum oven overnight to give 262 mg (58%) of Cmd 64 as an off-white solid; MS (ES) m/z: 425 (M−H$^+$). A mixture of Cmd 64 (262 mg, 0.615 mmol), DPPA (203 mg, 0.74 mmol), triethylamine (106 mg, 1.05 mmol), and t-BuOH (2.7 mL) in toluene (2 mL) was stirred under nitrogen at 70° C. for 30 min then stirred at 100° C. for 4 h. The reaction mixture was concentrated under vacuum. The product was purified by column chromatography (EtOAc/hexane as solvent) to give 224 mg (74%) of Cmd 14 as a white foam; $^1$H NMR (300 MHz, CDCl$_3$) δ8.64 (d, J=2.1 Hz, 2H), 8.54 (d, J=2.5 Hz, 1H), 8.50 (d, J=2.3 Hz, 1H), 8.31 (brs, 1H), 7.26–7.00 (m, 4H), 6.57 (s, 1H), 1.52 (s, 9H), 1.27 (s, 9H); MS (ES) m/z: 498 (M+H$^+$). Anal. Calcd. For C$_{25}$H$_{28}$N$_5$O$_4$Cl: C, 60.30; H, 5.67; N, 14.06. Found: C, 60.69; H, 5.80; N, 13.73.

EXAMPLE 18

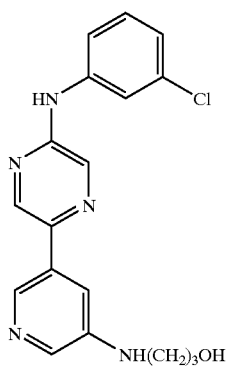

COMPOUND 15

3-[[5-[5-[(3-chlorophenyl)amino]pyrazinyl]-
3-pyridinyl]amino]-1-propanol (Cmd 15)

A mixture of Cmd 14 (82 mg, 0.165 mmol), (3-bromopropoxy)-t-butyl-dimethylsilane (63 mg, 0.248 mmol) and $Cs_2CO_3$ (161 mg, 0.5 mmol) in DMF (3 mL) was stirred at 70° C. under nitrogen for 36 h. The reaction mixture was diluted with water, extracted with ether (3×), dried ($Na_2SO_4$) and concentrated. The product was purified by column chromatography (EtOAc/hexane as solvent) to give 73 mg of the silylated-product as oil. The silylated-product was dissolved in TFA (3 mL) and stirred at 20° C. for 1 hour before it was concentrated. An ammonium hydroxide solution was added to the residue until the pH was about 10–11. Water was added and a yellow-orange solid was formed. The yellow-orange solid was collected through filtration, washed with water and dried under vacuum. The product was purified by column chromatography (dichloromethane/methanol as solvent) to give 30 mg (51%) of Cmd 15 as a light yellow oil; $^1$H NMR (300 MHz, $CDCl_3$) δ8.15 (brs, 2H), 8.08 (d, J=2.6 Hz, 1H), 7.97 (d, J=2.6 Hz, 1H), 7.72 (brs, 1H), 7.33 (d, J=8.2 Hz, 1H), 7.20 (m, 2H), 7.09 (brs, 1H), 6.99 (d, J=7.9 Hz, 1H), 4.57 (m, 1H), 3.77 (t, J=5.6 Hz, 2H), 3.27 (m, 2H), 1.86 (m, 2H); MS (ES) m/z: 356 (M+H$^+$). Anal. Calcd. For $C_{18}H_{18}N_5$° Cl0.2$H_2O$: C, 60.15; H, 5.16; N, 19.48 Found: C, 60.09; H, 5.56; N, 19.45.

EXAMPLE 19

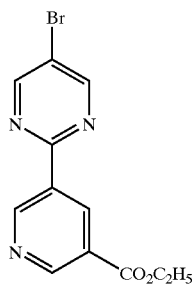

COMPOUND 16

A mixture of 1B (441 mg, 1 mmol), 5-bromo-2-iodopyrimidine (285 mg, 1 mmol), dichloro-bis(triphenylphosphine)palladium (35 mg, 0.05 mmol) and LiCl (210 mg, 5 mmol) in anhydrous toluene (5 mL) was stirred at 100° C. for 23 h under nitrogen. The cooled reaction mixture was concentrated under vacuum. Aqueous sodium carbonate was added to the residue and stirred for 10 min. then extracted with dichloromethane (3×). The combined dichloromethane solution was filtered through celite, dried ($Na_2SO_4$) and concentrated. The product was purified by column chromatography (EtOAc/hexane as solvent) to give 55 mg (18%) of Cmd 16 as a yellow solid; $^1$H NMR (300 MHz, $CDCl_3$) δ9.76 (d, J=2.1 Hz, 1H), 9.33 (d, J=2.0 Hz, 1H), 9.24 (t, J=2.1 Hz, 1H), 8.91 (s, 2H), 4.46 (q, J=7.1 Hz, 2H), 1.45 (t, J=7.1 Hz, 3H); MS (ES) m/z: 310 (M+H$^+$).

EXAMPLE 20

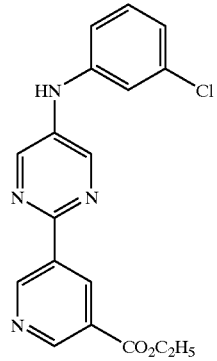

COMPOUND 17

A mixture of Cmd 16 (173 mg, 0.56 mmol), 3-chloroaniline (86 mg, 0.67 mmol), $Pd_2(dba)_3$ (14 mg, 0.014 mmol), DPPF (25 mg, 0.045 mmol), and $Cs_2CO_3$ (365 mg, 1.12 mmol) in anhydrous dioxane (2 mL) was stirred at 110° C. for 23 h under nitrogen. Dichloromethane (20 mL) was added to the cooled reaction mixture. The mixture was filtered through celite. The celite cake with more dichloromethane and the combined filtrate was concentrated to give a yellow-brown solid. The product was purified by column chromatography (EtOAc/hexane as solvent) to give 55 mg (27%) of Cmd 17 as yellow solid; $_1$H NMR (300 MHz, $CDCl_3$) δ9.71 (d, J=2.1 Hz, 1H), 9.27 (d, J=2.0 Hz, 1H), 9.19 (t, J=2.1 Hz, 1H), 8.66 (s, 2H), 7.29 (m, 1H), 7.15 (t, J=1.9 Hz, 1H), 7.04 (m, 2H), 5.90 (s, 1H), 4.46 (q, J=7.1 Hz, 2H), 1.45 (t, J=7.1 Hz, 3H); MS (ES) m/z: 355 (M+H$^+$).

EXAMPLE 21

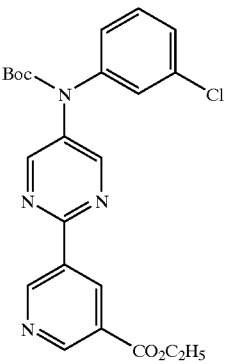

COMPOUND 18

A mixture of Cmd 17 (53 mg, 0.15 mmol), $Boc_2O$ (195 mg, 0.89 mmol), and DMAP (5 mg, cat.) in dichloromethane (23 mL) was stirred at 20° C. for 4 h. The reaction mixture was concentrated and the product was purified by column chromatography (EtOAc/hexane as solvent) to give 59 mg (87%) of Cmd 18 as a yellowish oil; $^1$H NMR (300 MHz, $CDCl_3$) δ9.75 (d, J=2.0 Hz, 1H), 9.30 (d, J=1.9 Hz, 1H), 9.23

(t, J=2.0 Hz, 1H), 8.73 (s, 2H), 7.33 (m, 3H), 7.15 (brd, J=7.6 Hz, 1H), 4.46 (q, J=7.1 Hz, 2H), 1.51 (s, 9H), 1.45 (t, J=7.1 Hz, 3H); MS (ES) m/z: 455 (M+H$^+$).

EXAMPLE 22

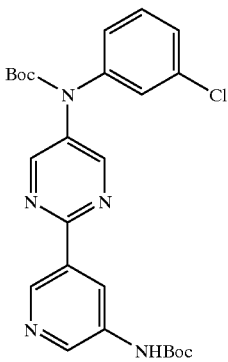

COMPOUND 19

Compound Cmd 18 (59 mg, 0.13 mmol) was dissolved in methanol (1.6 mL) and stirred for 10 min then cooled to 0° C. A NaOH$_{(aq)}$ (1 N, 0.9 mL) solution was added slowly and the mixture was stirred at 0° C. for 20 min then stirred at 20° C. for another 18 h. Glacial acetic acid (0.9 mL) was slowly added to the reaction mixture at 0° C. followed by the addition of water (2 mL). A yellow solid was formed. The yellow solid was collected through filtration, washed with water (3×), dried in vacuum oven overnight to give 45 mg (81%) of Cmd 65 as a yellow solid; MS (ES) m/z: 425 (M–H$^+$). A mixture of Cmd 65 (45 mg, 0.106 mmol), DPPA (35 mg, 0.127 mmol), triethylamine (18 mg, 0.18 mmol), t-BuOH (0.5 mL) in toluene (0.4 mL) was stirred under nitrogen at 70° C. for 30 min then stirred at 100° C. for 4 h. The reaction mixture was concentrated under vacuum. The product was purified by column chromatography (EtOAc/hexane as solvent) to give 40 mg (76%) of Cmd 19 as a yellowish foam; $^1$H NMR (300 MHz, CDCl$_3$) δ9.28 (d, J=1.7 Hz, 1H), 8.90 (s, 1H), 8.67 (s, 2H), 8.65 (brs, 1H), 7.41–7.12 (m, 5H), 1.55 (s, 9H), 1.50 (s, 9H); MS (ES) m/z: 498 (M+H$^+$).

EXAMPLE 23

COMPOUND 20

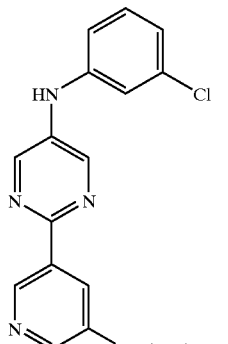

3-[[5-[5-[(3-chlorophenyl)amino]-2-pyrimidinyl]-3-pyridinyl]amino]-1-propanol (Cmd 20)

A mixture of Cmd 19 (39 mg, 0.078 mmol), (3-bromopropoxy)-t-butyl-dimethylsilane (30 mg, 0.117 mmol) and Cs$_2$CO$_3$ (76 mg, 0.234 mmol) in DMF (2 mL) was stirred at 70° C. under nitrogen for 36 h. The reaction mixture was diluted with water, extracted with ether (3×), dried (Na$_2$SO$_4$) and concentrated. The product was purified by column chromatography (EtOAc/hexane as solvent) to give 34 mg of the silylated-product as oil. The silylated-product was dissolved in TFA (2 mL) and stirred at 20° C. for 2 hours before it was concentrated. An ammonium hydroxide solution was added to the residue until the pH was about 10–11, water was added and a yellow solid was formed. The yellow solid was collected through filtration, washed with water and dried under vacuum. The product was purified by column chromatography (dichloromethane/methanol as solvent) to give 18 mg (65%) of Cmd 20 as a foam; $^1$H NMR (300 MHz, D$^6$-DMSO) δ8.91 (s, 1H), 8.71 (s, 2H), 8.64 (brs, 1H), 8.01 (d, J=2.6 Hz, 1H), 7.72 (brs, 1H), 7.31 (t, J=8.0 Hz, 1H), 7.16 (s, 1H), 7.14 (d, J=8.2 Hz, 1H), 6.97 (d, J=7.0 Hz, 1H), 6.04 (t, J=5.3 Hz, 1H), 4.55 (t, J=5.1 Hz, 1H), 3.53 (q, J=5.4 Hz, 2H), 3.14 (q, J=5.9 Hz, 2H), 1.74 (m, 2H); MS (ES) m/z: 356 (M+H$^+$). Anal. Calcd. For C$_{18}$H$_{18}$N$_5$OCl.0.5H$_2$O: C, 59.26; H, 5.25; N, 19.20. Found: C, 59.49; H, 5.22; N, 18.97.

EXAMPLE 24

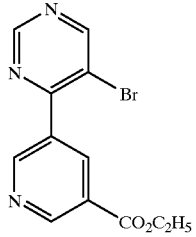

COMPOUND 21

A mixture of 1B (2.7 g, 6.1 mmol), 4-chloro-5-bromo-pyrimidine (2.71 g, 14.06 mmol), dichloro-bis(triphenylphosphine)palladium (428 mg, 0.61 mmol) and LiCl (1.28 g, 30.5 mmol) in anhydrous toluene (27 mL) was stirred at 100° C. for 23 h under nitrogen. The cooled reaction mixture was concentrated under vacuum. Aqueous sodium carbonate was added to the residue and stirred for 10 min. then extracted with dichloromethane (3×). The combined dichloromethane solution was filtered through celite, dried (Na$_2$SO$_4$) and concentrated. The product was purified by column chromatography (EtOAc/hexane as solvent) to give 303 mg (16%) of Cmd 21 as an off-white solid; $^1$H NMR (300 MHz, CDCl$_3$) δ9.35 (d, J=2.0 Hz, 1H), 9.24 (m, 2H), 9.00 (s, 1H), 8.78 (t, J=2.1 Hz, 1H), 4.46 (q, J=7.1 Hz, 2H), 1.44 (t, J=7.1 Hz, 3H); MS (ES) m/z: 310 (M+H$^+$). Anal. Calcd. For C$_{12}$H$_{10}$N$_3$O$_2$Br: C, 46.77; H, 3.27; N, 13.64. Found: C, 46.86; H, 3.28; N, 13.56.

EXAMPLE 25

COMPOUND 22

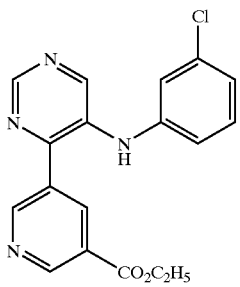

A mixture of Cmd 21 (303 mg, 0.98 mmol), 3-chloroaniline (176 mg, 1.37 mmol), Pd$_2$(dba)$_3$ (25 mg, 0.0245 mmol), DPPF (43 mg, 0.078 mmol), and Cs$_2$CO$_3$ (639 mg, 1.96 mmol) in anhydrous dioxane (3 mL) was stirred at 110° C. for 24 h under nitrogen. Dichloromethane (20 mL) was added to the cooled reaction mixture. The mixture was was filtered through celite. The celite cake was washed with more dichloromethane and the combined filtrate was concentrated to give a yellow-brown solid. The product was purified by column chromatography (EtOAc/hexane as solvent) to give 293 mg (84%) of Cmd 22 as a yellow-brown foam; $^1$H NMR (300 MHz, CDCl$_3$) δ9.14 (brs, 2H), 8.97 (d, J=1.3 Hz, 1H), 8.79 (s, 1H), 8.67 (d, J=1.5 Hz, 1H), 7.19 (t, J=8.4 Hz, 1H), 6.99 (m, 2H), 6.86 (brd, J=8.0 Hz, 1H), 6.21 (brs, 1H), 4.40 (q, J=7.1 Hz, 2H), 1.40 (t, J=7.1 Hz, 3H); MS (ES) m/z: 355 (M+H$^+$).

EXAMPLE 26

COMPOUND 23

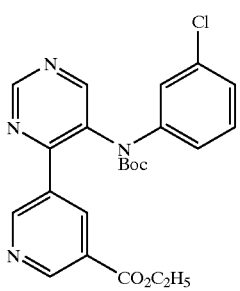

A mixture of Cmd 22 (290 mg, 0.82 mmol), Boc$_2$O (560 mg, 257 mmol), and DMAP (20 mg, cat.) in dichloromethane (5 mL) was stirred at 20° C. for 24 h. The reaction mixture was concentrated and the product was purified by column chromatography (EtOAc/hexane as solvent) to give 349 mg (94%) of Cmd 23 as a light-brown oil; $^1$H NMR (300 MHz, CDCl$_3$) δ9.27 (d, J=2.0 Hz, 1H), 9.26 (s, 1H), 9.11 (d, J=2.2 Hz, 1H), 8.75 (s, 1H), 8.61 (t, J=2.1 Hz, 1H), 7.13 (m, 3H), 6.90 (brd, J=7.8 Hz, 1H), 4.42 (q, J=7.1 Hz, 2H), 1.39 (t, J=7.1 Hz, 3H), 1.33 (s, 9H); MS (ES) m/z: 455 (M+H$^+$).

EXAMPLE 27

COMPOUND 24

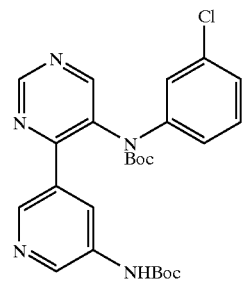

Compound Cmd 23 (348 mg, 0.767 mmol) was dissolved in methanol (9.3 mL) and stirred for 10 min then cooled to 0° C. A NaOH$_{(aq)}$ (1 N, 5.5 mL) solution was added slowly and the mixture was stirred at 0° C. for 20 min then stirred at 20° C. for another 2 h. Glacial acetic acid (5 mL) was slowly added to the reaction mixture at 0° C. followed by the addition of water (20 mL). A yellow solid was formed. The yellow solid was collected through filtration, and washed with water (2x), then dried in a vacuum oven overnight to give 336 mg (99%) of Cmd 66 as a yellow solid; $^1$H NMR (300 MHz, CDCl$_3$) δ9.35 (d, J=1.7 Hz, 1H), 9.28 (s, 1H), 9.18 (d, J=2.1 Hz, 1H), 8.78 (s, 1H), 8.72 (t, J=2.0 Hz, 1H), 7.11 (m, 3H), 6.90 (brd, J=7.4 Hz, 1H), 1.35 (s, 9H); MS (ES) m/z: 425 (N—H$^+$). A mixture of Cmd 66 (326 mg, 0.767 mmol), DPPA (253 mg, 0.92 mmol), triethylamine (132 mg, 1.3 mmol), and t-BuOH (3.3 mL) in toluene (2.5 mL) was stirred under nitrogen at 70° C. for 30 min then stirred at 100° C. for 4 h. The reaction mixture was concentrated under vacuum. The product was purified by column chromatography (EtOAc/hexane as solvent) to give 310 mg (81%) of Cmd 24 as a yellowish foam; $^1$H NMR (300 MHz, CDCl$_3$) δ9.22 (s, 1H), 8.70 (s, 1H), 8.58 (d, J=1.9 Hz, 1H), 8.52 (d, J=2.4 Hz, 1H), 8.34 (brs, 1H), 7.16 (m, 3H), 6.90 (d, J=7.9 Hz, 1H), 6.69 (s, 1H), 1.52 (s, 9H), 1.34 (s, 1H); MS (ES) m/z: 498 (M+H$^+$). Anal. Calcd. For C$_{25}$H$_{28}$N$_5$O$_4$Cl: C, 60.30; H, 5.67; N, 14.06. Found: C, 59.91; H, 5.70; N, 13.66.

EXAMPLE 28

COMPOUND 25

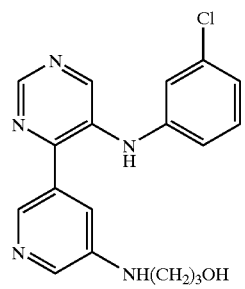

3-[[5-[5-[(3-chlorophenyl)amino]-4-pyrimidinyl]-3-pyridinyl]amino]-1-propanol (Cmd 25)

A mixture of Cmd 24 (83 mg, 0.167 mmol), (3-bromopropoxy)-t-butyl-dimethylsilane (63 mg, 0.25 mmol) and Cs$_2$CO$_3$ (163 mg, 0.5 mmol) in DMF (2 mL) was stirred at 70° C. under nitrogen for 36 h. The reaction mixture was diluted with water, extracted with ether (3x), dried (Na$_2$SO$_4$) and concentrated. The product was purified by column chromatography (EtOAc/hexane as solvent) to give 92 mg of the silylated-product as an oil. The silylated-product was dissolved in TFA (2 mL) and stirred at 20° C. for 4 h before concentration. An ammonium hydroxide solution was added to the residue until the pH was about 10–11. Water was added and a yellow solid was formed. The yellow solid was collected through filtration, washed with water and dried under vacuum. The product was purified by column chromatography (dichloromethane/methanol as solvent) to give 30 mg (51%) of Cmd 25 as a light yellow solid; $^1$H NMR (300 MHz, CD$_3$OD) δ8.88 (s, 1H), 8.75 (s, 1H), 8.22 (d, J=1.6 Hz, 1H), 7.97 (d, J=2.7 Hz, 1H), 7.18 (m, 2H), 7.03 (m, 2H), 6.90 (dd, J=7.7, 1.5 Hz, 1H), 6.24 (s, 1H), 4.40 (brt, J=5.1 Hz, 1H), 3.79 (t, J=5.7 Hz, 2H), 3.27 (q, J=5.7 Hz, 2H), 1.88 (m, 2H); MS (ES) m/z: 356 (M+H$^+$). Anal. Calcd. For C$_{18}$H$_{18}$N$_5$OCl.0.4H$_2$O: C, 59.55; H, 5.22; N, 19.29. Found: C, 59.22; H, 5.36; N, 19.57.

EXAMPLE 29

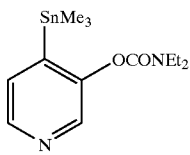

Intermediate Compound 2C

3-Pyridyl diethyl carbamate (1.0 g, 5.1 mmol, JACS 73 1210 1951) was dissolved in THF (10 mL) and was cooled to −78° C. 1.3 M of sec BuLi (5.7 mmol) and TMEDA (0.66 g, 5.7 mmol) was added under nitrogen. The reaction mixture was stirred at −78° C. for 1 hour. Trimethyltin chloride (1.2 g, 6.2 mmol) in dry THF (5 mL) was added slowly and the reaction was warmed up to 20° C. overnight. NH$_4$Cl$_{(aq)}$ was added to quench the reaction and the product was extracted into EtOAc, dried (Na$_2$SO$_4$) and concentrated under vacuum. The product was purified by column chromatography (EtOAc/hexane as solvent) to give 1.2 g (65%) of 2C as a yellow oil; $^1$H NMR (300 MHz, CDCl$_3$) δ8.36 (m, 2H), 7.38 (brt, J=4.5 Hz, 1H), 3.42 (m, 4H), 1.24 (m, 6H), 0.35 (s, 9H); MS (ES) m/z: 359 (M+H$^+$).

EXAMPLE 30

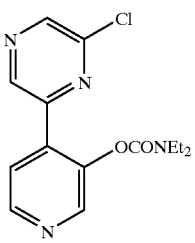

Intermediate Compound 2D

A mixture of 2C (0.11 g, 0.321 mmol), 2,6-dichloropyrazine (0.0478 g, 0.321 mmol), tris-2-furyl phosphine (0.015 g, 0.064 mmol), CuI (0.006 g, 0.032 mmol) and Pd$_2$(dba)$_3$ (0.015 g, 0.016 mmol) in anhydrous NMP (1 mL) was stirred at 60° C. overnight under nitrogen. The cooled reaction mixture was concentrated under vacuum. The product was purified by column chromatography (EtOAc/hexane as solvent) to give 0.06 g (64%) of 2D as a solid; $^1$H NMR (300 MHz, CDCl$_3$) δ8.83 (s, 1H), 8.60 (m, 3H), 7.71 (d, J=5.0 Hz, 1H), 3.46 (q, J=7.1 Hz, 2H), 3.32 (q, J=7.1 Hz, 2H), 1.24 (t, J=7.0 Hz, 3H), 1.13 (t, J=7.1 Hz, 3H); MS (ES) m/z: 307 (M+H$^+$).

EXAMPLE 31

COMPOUND 27

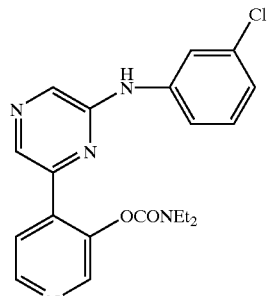

4-[6-[(3-chlorophenyl)amino]pyrazinyl]-3-pyridinyl carbamic acid, diethyl-ester (Cmd 27)

A mixture of 2D (0.1 g, 0.326 mmol), 3-chloroaniline (0.05 g, 0.391 mmol), Pd$_2$(dba)$_3$ (0.0085 g, 0.008 mmol), DPPF (0.015 g, 0.026 mmol), and Cs$_2$CO$_3$ (0.21 g, 0.652 mmol) in anhydrous dioxane (2 mL) was stirred at 100° C. overnight under nitrogen. Dichloromethane (100 mL) was added to the cooled reaction mixture, then the mixture was filtered through celite. The celite cake was washed with more dichloromethane and the combined filtrate was concentrated to give a yellow solid. The solid was purified by column chromatography (EtOAc/hexane as solvent) to give 0.088 g (68%) of Cmd 27 as a yellow solid; $^1$H NMR (300 MHz, CDCl$_3$) δ8.56 (d, J=4.4 Hz, 2H), 8.39 (s, 1H), 8.08 (s, 1H), 7.74 (d, J=5.0 Hz, 1H), 7.54 (t, J=1.6 Hz, 1H), 7.32 (d, J=8.0 Hz, 1H), 7.23 (t, J=8.0 Hz, 1H), 7.04 (m, 2H), 3.46 (q, J=7.0 Hz, 2H), 3.34 (q, J=7.1 Hz, 2H), 1.24 (t, J=7.0 Hz, 3H), 1.15 (t, J=7.0 Hz, 3H); MS (ES) m/z: 398 (M+H$^+$).

EXAMPLE 32

COMPOUND 28

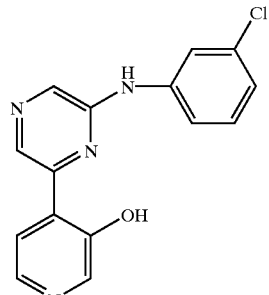

4-[6-[(3-chlorophenyl)amino]pyrazinyl]-3-pyridinol (Cmd 28)

Cmd 27 (1.0 g, 2.5 mmol) was treated with absolute EtOH (50 mL) and 10% NaOH$_{(aq)}$ (50 mL). The reaction mixture was refluxed overnight. The solvent was removed and the residue was acidified with 1 N HCl and then basified back to pH=10. A yellow suspension was formed. The product was extracted into CH$_2$Cl$_2$ and dried (Na$_2$SO$_4$). Solvent was removed to give 0.4 g (53%) of Cmd 28 as a yellow solid; $^1$H NMR (300 MHz, D$^6$-DMSO) δ9.90 (s, 1H), 8.80 (s, 1H), 8.35 (s, 1H), 8.26 (s, 1H), 8.19 (d, J=4.4 Hz, 1H), 7.93 (brs, 1H), 7.85 (d, J=4.9 Hz, 1H), 7.56 (d, J=7.3 Hz, 1H), 7.37 (t, J=8.1 Hz, 1H), 7.05 (d, J=9.1 Hz, 1H); MS (ES) m/z: 299 (M+H$^+$).

EXAMPLE 33

COMPOUND 29

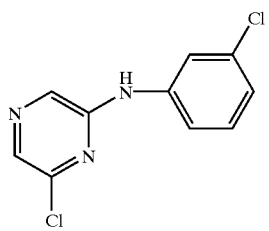

Palladium acetate (0.121 g, 0.537 mmol), BINAP (0.368 g 0.591 mmol), t-BuONa (3.609 g, 37.6 mmol), 2,6-dichloropyrazine (4 g, 26.85 mmol), 3-chloroaniline (3.44 g, 26.85 mmol) in toluene (100 mL) was stirred at 80° C. for 22 h under $N_2$. $CH_2Cl_2$ was added, the reaction mixture was filtered through celite and the solvent was evaporated. Product was purified by column chromatography (EtOAc/hexane as solvent) to give 5.8 g (90%) of Cmd 29; $^1$H NMR (300 MHz, CDCl$_3$) δ8.11 (s, 1H), 8.03 (s, 1H), 7.49 (s, 1H), 7.30 (m, 2H), 7.12 (m, 1H), 6.60 (brs, 1H); MS (ES) m/z: 241 (M+H$^+$). Anal. Calcd. For $C_{10}H_7N_3Cl.0.13H_2O$: C, 49.54; H, 3.02; N, 17.33. Found: C, 49.38; H, 2.86; N, 17.22.

EXAMPLE 34

COMPOUND 30

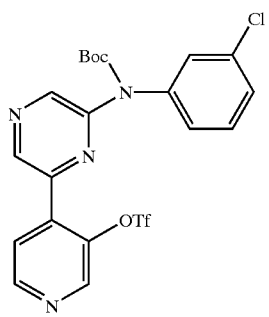

($CF_3SO_2$)$_2$O (0.12 g, 0.4 mmol) and triethylamine (0.04 g, 0.4 mmol) was added to a solution of Cmd 28 (0.1 g, 0.33 mmol) in anhydrous $CH_2Cl_2$ (5 mL) at 0° C. The reaction was stirred under nitrogen at 20° C. for 8 h under $N_2$. The reaction mixture was concentrated under vacuum. The product was purified by column chromatography (EtOAc/hexane as solvent) to give 0.072 g (51%) of triflate as an oil. The triflate was dissolved in $CH_2Cl_2$ (2 mL), and treated with Boc$_2$O (0.041 g, 0.19 mmol) and DMAP (0.002 g, 0.019 mmol). The reaction mixture was stirred overnight at 20° C. under nitrogen. The solvent was removed under vacuum and the product was purified by column chromatography (EtOAc/Hex as solvent) to give 0.078 g (88%) of Cmd 30 as an oil. $^1$H NMR (300 MHz, CDCl$_3$) δ9.16 (s, 1H), 8.73 (s, 1H), 8.68 (s, 1H), 8.67 (d, J=4.9 Hz, 1H), 7.49 (d, J=5.0 Hz, 1H), 7.29 (m, 3H), 7.14 (dt, J=7.0, 2.0 Hz, 1H), 1.48 (s, 9H); MS (ES) m/z: 531 (M+H$^+$).

EXAMPLE 35

COMPOUND 31

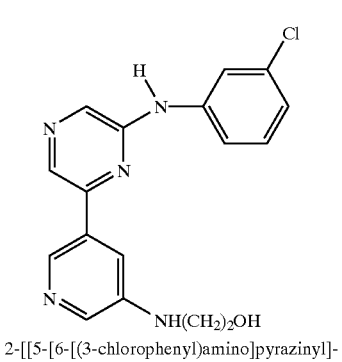

2-[[5-[6-[(3-chlorophenyl)amino]pyrazinyl]-3-pyridinyl]amino]-ethanol (Cmd 31)

A mixture of Cmd 67 (0.1 g, 0.2 mmol), (2-bromoethoxy)-t-butyl-dimethylsilane (0.07 g, 0.3 mmol) and Cs$_2$CO$_3$ (0.197 g, 0.6 mmol) in DMF (4 mL) was stirred at 70° C. under nitrogen for 22 h. The reaction mixture was diluted with water, extracted with ether (3×), dried (Na$_2$SO$_4$) and concentrated. The product was purified by column chromatography (EtOAc/hexane as solvent) to give 0.05 g of the silylated-product as an oil. The silylated-product was dissolved in TFA (1.5 mL) and stirred at 20° C. for 2 h before it was concentrated. An ammonium hydroxide solution was added to the residue until the pH was about 10–11 and a yellow solid was formed. The yellow solid was collected through filtration, washed with water and dried under vacuum to give 0.029 g (43%) of Cmd 31 as a light yellow solid; $^1$H NMR (300 MHz, D$^6$-DMSO) δ9.87 (s, 1H), 8.59 (s, 1H), 8.46 (s, 1H), 8.22 (s, 1H), 8.12 (m, 2H), 7.61 (d, J=8.2 Hz, 1H), 7.52 (s, 1H), 7.37 (t, J=8.1 Hz, 1H), 7.03 (d, J=7.8 Hz, 1H), 6.10 (t, J=5.3 Hz, 1H), 4.79 (t, J=5.3 Hz, 1H), 3.63 (m, 2H), 3.25 (m, 2H); MS (ES) m/z: 342 (M+H$^+$).

EXAMPLE 36

COMPOUND 32

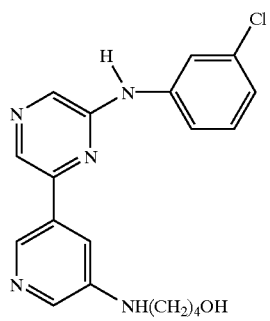

4-[[5-[6-[(3-chlorophenyl)amino]pyrazinyl]-3-pyridinyl]amino]-1-butanol (Cmd 32)

A mixture of Cmd 67 (0.034 g, 0.068 mmol), (4-bromobutoxy)-t-butyl-dimethylsilane (0.023 g, 0.1 mmol) and Cs$_2$CO$_3$ (0.067 g, 0.2 mmol) in DMF (2 mL) was stirred at 70° C. under nitrogen for 5 days. The reaction mixture was diluted with water, extracted with ether (3×), dried (Na$_2$SO$_4$) and concentrated. The product was purified by column chromatography (EtOAc/hexane as solvent) to give 0.037 g of the silylated-product as an oil. The silylated-product was dissolved in TFA (1.5 mL) and stirred at 20° C. for 2 h before it was concentrated. An ammonium hydroxide solution was added to the residue until the pH was about 10–11 and a yellow solid was formed. The yellow solid was collected through filtration, washed with water and dried under vacuum to give 0.016 g (64%) of Cmd 32 as a light yellow solid; $^1$H NMR (300 MHz, D$^6$-DMSO) δ9.88 (s, 1H), 8.60 (s, 1H), 8.45 (s, 1H), 8.20 (m, 2H), 8.08 (d, J=2.5 Hz, 1H), 7.56 (d, J=8.2 Hz, 1H), 7.48 (s, 1H), 7.36 (t, J=8.0 Hz, 1H), 7.03 (dd, J=7.7, 1.4 Hz, 1H), 6.12 (t, J=5.2 Hz, 1H), 4.45 (t, J=5.1 Hz, 1H), 3.44 (q, J=6.1 Hz, 2H), 3.15 (q, J=6.2 Hz, 2H), 1.59 (m, 4H); MS (ES) m/z: 370 (M+H$^+$).

EXAMPLE 37

COMPOUND 33

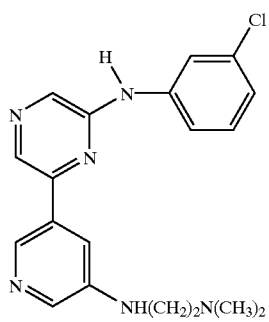

N$^1$-[5-[6-[(3-chlorophenyl)amino]pyrazinyl]-3-pyridinyl]-N$^2$,N$^2$-dimethyl-1,2-ethanediamine (Cmd 33)

A mixture of Cmd 67 (0.05 g, 0.1 mmol), 2-dimethylaminoethylchloride hydrochloride (0.022 g, 0.15 mmol) and Cs$_2$CO$_3$ (0.1 g, 0.3 mmol) in DMF (2 mL) and triethylamine (0.02 g 0.2 mmol) was stirred at 70° C. under nitrogen for 23 h. The reaction mixture was diluted with water, extracted with ether (3×), dried (Na$_2$SO$_4$) and concentrated. The product was purified by column chromatography (CH$_2$Cl$_2$/MeOH as solvent) to give 0.025 g of the dimethylamino product as an oil. The dimethylamino-product was dissolved in TFA (1.0 mL) and stirred at 20° C. for 2 hours before it was concentrated. An ammonium hydroxide solution was added to the residue until the pH was about 10–11. The product was extracted into CH$_2$Cl washed with water and dried (Na$_2$SO$_4$). The product was further recrystallized from CH$_2$Cl$_2$/Hexane to give 0.015 g (41%) of Cmd 33 as a light yellow solid; $^1$H NMR (300 MHz, CD$_3$OD) δ8.44 (m, 2H), 8.13 (m, 2H), 8.02 (d, J=2.7 Hz, 1H), 7.65 (m, 1H), 7.52 (dd, J=2.0, 0.9 Hz, 1H), 7.29 (t, J=8.0 Hz, 1H), 7.00 (dd, J=2.0, 0.9 Hz, 1H), 3.36 (t, J=6.5 Hz, 2H), 2.64 (t, J=6.5 Hz, 2H), 2.32 (s, 6H); MS (ES) m/z: 369 (M+H$^+$).

EXAMPLE 38

COMPOUND 34

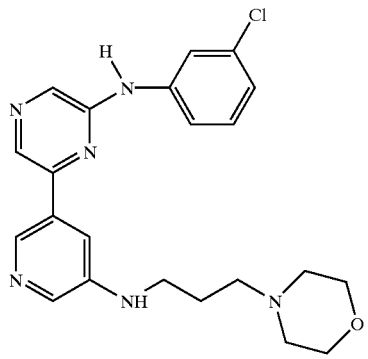

N-[5-[6-[(3-chlorophenyl)amino]pyrazinyl]-3-pyridinyl]-4-morpholinepropanamine (Cmd 34)

A mixture of Cmd 67 (0.1 g, 0.2 mmol), morpholinopropyl chloride (0.049 g, 0.3 mmol) and Cs$_2$CO$_3$ (0.197 g, 0.6 mmol) in DMF (4 mL) was stirred at 70° C. under nitrogen for 20 hours. The reaction mixture was diluted with water, extracted with ether (3×), dried (Na$_2$SO$_4$) and concentrated. The product was purified by column chromatography (CH$_2$Cl$_2$/MeOH as solvent) to give 0.1 g of product as a hard foam. The hard foam was dissolved in TFA (2.0 mL) and stirred at 20° C. for 2 h before it was concentrated. An ammonium hydroxide solution was added to the residue until the pH was about 10–11 and a yellow solid was formed. The yellow solid was collected through filtration, washed with water and dried under vacuum to give 0.053 g (62%) of Cmd 34 as a yellow solid; $^1$H NMR (300 MHz, CD$_3$OD) δ8.43 (s, 1H), 8.39 (d, J=1.5 Hz, 1H), 8.16 (d, J=1.9 Hz 1H), 8.09 (s, 1H), 7.99 (d, J=2.3 Hz, 1H), 7.64 (s, 1H), 7.47 (d, J=7.8. Hz, 1H), 7.27 (t, J=8.0 Hz, 1H), 6.98 (d, J=7.9 Hz, 1H), 3.66 (m, 4H), 3.28 (m, 2H), 2.49 (m, 6H), 1.85 (m, 2H); MS (ES) m/z: 425 (M+H$^+$). Anal. Calcd. For C$_{22}$H$_{21}$N$_6$OCl.0.55H$_2$O: C, 60.77; H, 6.05; N, 19.33. Found: C, 60.81; H, 5.70; N, 19.00.

EXAMPLE 39

COMPOUND 35

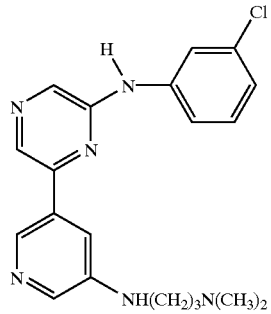

N$^1$-[5-[6-[(3-chlorophenyl)amino]pyrazinyl]-3-pyridinyl]-N$^3$,N$^3$-dimethyl-1,3-propanediamine (Cmd 35)

A mixture of Cmd 67 (0.15 g, 0.3 mmol), (3-chloro-N,N-dimethylpropylamine (0.071 g, 0.45 mmol) and Cs$_2$CO$_3$ (0.3 g, 0.9 mmol) in DMF (6 mL) and triethylamine (0.06 g, 0.6 mmol) was stirred at 70° C. under nitrogen for 2 days. The reaction mixture was diluted with water, extracted with ether (3×), dried (Na$_2$SO$_4$) and concentrated. The product was purified by column chromatography (CH$_2$Cl$_2$/MeOH as solvent) to give 0.08 g of the dimethylamino product as an oil. The dimethylamino-product was dissolved in TFA (3.0 mL) and stirred at 20° C. for 1.5 h before concentration. An ammonium hydroxide solution was added to the residue until the pH was about 10–11. Water was added and the product was extracted into CH$_2$Cl$_2$, washed with water and dried (Na$_2$SO$_4$). The product was further recrystallized from CH$_2$Cl$_2$/hexane to give 0.047 g (43%) of Cmd 35 as a light yellow solid; $^1$H NMR (300 MHz, CD$_3$OD) δ8.42 (m, 2H), 8.16 (t, J=2.0 Hz, 1H), 8.10 (s, 1H), 8.00 (d, J=2.6 Hz, 1H), 7.63 (t, J=2.0 Hz, 1H), 7.48 (dd, J=7.5, 1.2 Hz, 1H), 7.28 (t, J=8.0 Hz, 1H), 6.98 (dd, J=7.2, 1.1 Hz, 1H), 3.27 (m, 2H), 2.54 (brt, J=7.5 Hz, 2H), 2.30 (s, 6H), 1.88 (m, 2H); MS (ES) m/z: 383 (M+H$^+$). Anal. Calcd. For C$_{20}$H$_{23}$N$_6$OCl .0.9H$_2$O: C, 60.19; H, 6.26; N, 21.06. Found: C, 60.40; H, 5.96; N, 20.68.

EXAMPLE 40

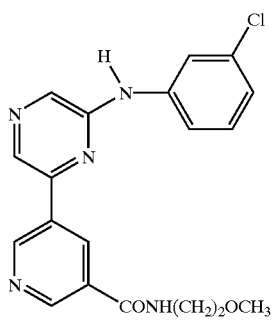

COMPOUND 36

5-[6-[(3-chlorophenyl)amino]pyrazinyl]-
N-(2-methoxyethyl)-3-pyridinecarboxamide(Cmd 36)

A mixture of Cmd 3 (0.05 g, 0.12 mmol), 2-methoxyethylamine (0.009 g, 0.12 mmol) diisopropylethylamine (0.06 g, 0.47 mmol) and HATU (0.045 g, 0.12 mmol) in DMF (2 mL) was stirred at 20° C. under N$_2$ overnight. Solvent was removed and product was purified by column chromatography (CH$_2$Cl$_2$/MeOH as solvent) to give 0.033 g of product as a solid. The above product was dissolved in TFA (2.0 mL) and stirred at 20° C. for 2 h before it was concentrated. An ammonium hydroxide solution was added to the residue until the pH was about 10–11, a light tan solid was formed. The tan solid was collected through filtration, washed with water and dried under vacuum to give 0.010 g (22%) of Cmd 36 as a light tan solid; $^1$H NMR (300 MHz, CD$_3$OD) δ9.36 (s, 1H), 9.02 (s, 1H), 8.85 (s, 1H), 8.56 (s, 1H), 8.16 (s, 1H), 8.02 (s, 1H), 7.59 (d, J=8.0 Hz, 1H), 7.30 (t, J=8.0 Hz, 1H), 7.02 (d, J=7.9 Hz, 1H), 3.62 (s, 4H), 3.39 (s, 3H); MS (ES) m/z: 384 (M+H$^+$).

EXAMPLE 41

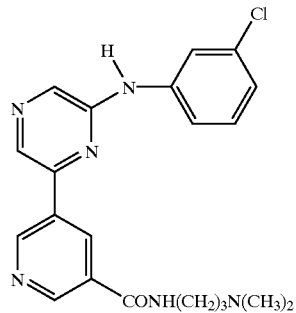

COMPOUND 37

5-[6-[(3-chlorophenyl)amino]pyrazinyl]-
N-(3-methoxpropyl)-3-pyridinecarboxamide(Cmd 37)

A mixture of Cmd 3 (0.075 g, 0.176 mmol), 3-dimethylaminopropylamine (0.018 g, 0.176 mmol) diisopropylethylamine (0.09 g, 0.69 mmol) and HATU (0.067 g, 0.176 mmol) in DMF (4 mL) was stirred at 20° C. under N$_2$ overnight. Solvent was removed and product was purified by column chromatography (CH$_2$Cl$_2$/MeOH/Acetic acid as solvent) to give 0.015 g of product. The above product was dissolved in TFA (2.0 mL) and stirred at 20° C. for 2 h before it was concentrated. An ammonium hydroxide solution was added to the residue until the pH was about 10–11 and a yellow solid was formed. The yellow solid was collected through filtration, washed with water and dried under vacuum to give 0.009 g (13%) of Cmd 37 as a yellow solid; $^1$H NMR (300 MHz, CD$_3$OD) δ9.30 (s, 1H), 9.02 (s, 1H), 8.87 (s, 1H), 8.59 (s, 1H), 8.20 (s, 1H), 8.08 (s, 1H), 7.59 (d, J=6.4 Hz, 1H), 7.32 (t, J=8.0 Hz, 1H), 7.02 (d, J=5.9 Hz, 1H), 3.48 (t, J=7.0 Hz, 2H), 2.50 (brt, J=7.9 Hz, 2H), 2.31 (s, 6H), 1.87 (m, 2H); MS (ES) m/z: 411 (M+H$^+$).

EXAMPLE 42

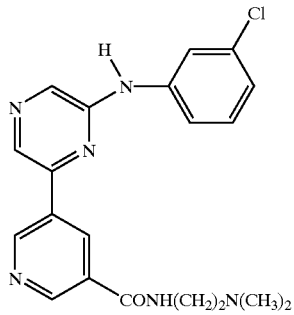

COMPOUND 38

5-[6-[(3-chlorophenyl)amino]pyrazinyl]-
N-[(2-dimethylamino)ethyl]-3-pyridinecarboxamide(Cmd 38)

A mixture of Cmd 3 (0.05 g, 0.12 mmol), N,N-dimethylethylenediamine (0.01 g, 0.12 mmol) diisopropylethylamine (0.06 g, 0.47 mmol) and HATU (0.045 g, 0.12 mmol) in CH$_2$Cl$_2$ (2 mL) was stirred at 20° C. under N$_2$ for 2 days. Solvent was removed and the product was purified by column chromatography (CH$_2$Cl$_2$/MeOH/Acetic acid as solvent) to give 0.02 g of product. The above product was dissolved in TFA (1.0 mL) and stirred at 20° C. for 1 h before concentration. An ammonium hydroxide solution was added to the residue until the pH was about 10–11 and a yellow solid was formed. The yellow solid was collected through filtration, washed with water and dried under vacuum to give 0.005 g (11%) of Cmd 38 as a yellow solid; $^1$H NMR (300 MHz, CD$_3$OD) δ9.39 (s, 1H), 9.06 (s, 1H), 8.91 (s, 1H), 8.59 (s, 1H), 8.19 (s, 1H), 8.07 (s, 1H), 7.59 (d, J=8.3 Hz, 1H), 7.32 (t, J=8.1 Hz, 1H), 7.02 (d, J=7.8 Hz, 1H), 3.60 (t, J=6.7 Hz, 2H), 2.63 (t, J=6.7 Hz, 2H), 2.34 (s, 6H); MS (ES) m/z: 397 (M+H$^+$).

EXAMPLE 43

COMPOUND 39

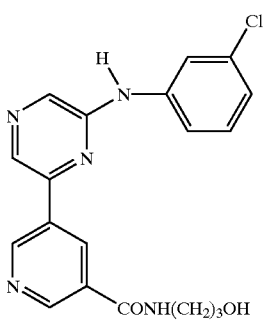

5-[6-[(3-chlorophenyl)amino]pyrazinyl]-N-(3-hydroxypropyl)-3-pyridinecarboxamide (Cmd 39)

A mixture of Cmd 3 (0.025 g, 0.06 mmol), 3-amino-1-propanol (0.0045 g, 0.006 mmol) diisopropylethylamine (0.03 g, 0.23 mmol) and HATU (0.022 g, 0.06 mmol) in DMF (2 mL) was stirred at 20° C. under N$_2$ for 2 days. Solvent was removed and the product was purified by column chromatography (CH$_2$Cl$_2$/MeOH as solvent) to give 0.019 g of product. The above product was dissolved in TFA (1.0 mL) and stirred at 20° C. for 2 h before concentration. An ammonium hydroxide solution was added to the residue until the pH was about 10–11 and a yellow solid was formed. The yellow solid was collected through filtration, washed with water and dried under vacuum to give 0.009 g (41%) of Cmd 39 as a yellow solid; $^1$H NMR (300 MHz, CD$_3$OD) δ9.38 (d, J=2.0 Hz, 1H), 9.02 (d, J=2.0 Hz, 1H), 8.86 (t, J=2.0 Hz, 1H), 8.58 (s, 1H), 8.19 (s, 1H), 8.06 (t, J=2.0 Hz, 1H), 7.59 (dd, J=8.2, 1.3 Hz, 1H), 7.31 (t, J=8.0 Hz, 1H), 7.02 (dd, J=7.9, 1.1 Hz, 1H), 3.68 (t, J=6.2 Hz, 2H), 3.55 (m, 2H), 1.88 (t, J=6.6 Hz, 2H); MS (ES) m/z: 384 (M+H$^+$).

EXAMPLE 44

COMPOUND 40

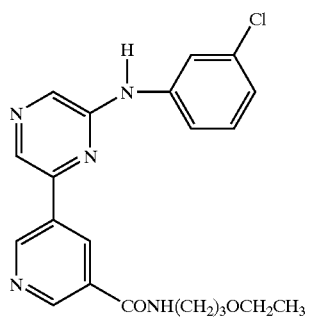

5-[6-[(3-chlorophenyl)amino]pyrazinyl]-N-(3-ethoxypropyl)-3-pyridinecarboxamide (Cmd 40)

A mixture of Cmd 3 without the Boc group (0.05 g, 0.15 mmol), 3-ethoxypropylamine (0.016 g, 0.15 mmol), diisopropylethylamine (0.079 g, 0.61 mmol) and HATU (0.058 g, 0.15 mmol) in DMF (3 mL) was stirred at 20° C. under N$_2$ overnight. Solvent was removed and product was purified by column chromatography (CH$_2$Cl$_2$/MeOH as solvent) to give 0.057 g (90%) of Cmd 40 as a yellow solid; $^1$H NMR (300 MHz, CD$_3$OD) δ9.36 (s, 1H), 9.01 (s, 1H), 8.85 (s, 1H), 8.57 (s, 1H), 8.18 (s, 1H), 8.05 (s, 1H), 7.58 (dd, J=8.3, 1.0 Hz, 1H), 7.30 (t, J=8.0 Hz, 1H), 7.00 (dd, J=8.0, 1.0 Hz, 1H), 3.71 (m, 1H), 3.52 (m, 6H), 3.21 (q, J=7.4 Hz, 1H), 1.93 (m, 2H), 1.18 (t, J=7.0 Hz, 3H); MS (ES) m/z: 412 (M+H$^+$).

EXAMPLE 45

COMPOUND 41

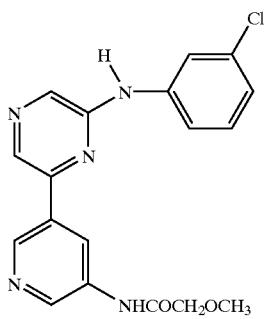

N-[5-[6-[(3-chlorophenyl)amino]pyrazinyl]-3-pyridinyl]-2-methoxy-acetamide (Cmd 41)

Cmd 67 (0.052 g, 0.1 mmol) dissolved in anhydrous THF (3 mL) at 0° C. and NaH (60% oil dispersion 0.03 g, 0.7 mmol) was added. After 10 min, methoxyacetylchloride (0.08 g, 0.7 mmol) was added and the reaction was stirred for 2–3 hours at 0° C. under $N_2$ then allowed to warm up to 20° C. overnight. $NH_4Cl_{(aq)}$ was added to quench the reaction. Solvent was removed and the product was extracted into $CH_2Cl_2$, washed with water and dried ($Na_2SO_4$). Product was purified by column chromatography (Hex/EtOAc as solvent) to give 0.023 g of a yellow solid. The above product was dissolved in TFA (1.0 mL) and stirred at 20° C. for 1.5 h before concentration. An ammonium hydroxide solution was added to the residue until the pH was about 10–11 and a yellow solid was formed. The yellow solid was collected through filtration, washed with water and dried under vacuum to give 0.008 g (21%) of Cmd 41 as a yellow solid; $^1H$ NMR (300 MHz, $CD_3OD$) δ8.98 (s, 1H), 8.86 (brs, 2H), 8.48 (s, 1H), 8.15 (s, 1H), 7.92 (s, 1H), 7.72 (d, J=8.1 Hz, 1H), 7.32 (t, J=8.0 Hz, 1H), 6.99 (d, J=7.8 Hz, 1H), 4.11 (s, 2H), 3.52 (s, 3H); MS (ES) m/z: 370 (M+H$^+$).

EXAMPLE 46

COMPOUND 42

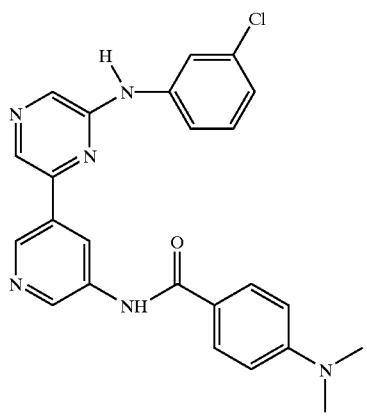

N-[5-[6-[(3-chlorophenyl)amino]pyrazinyl]-
3-pyridinyl]-4-(dimethylamino)-benzamide(Cmd 42)

Cmd 67 (0.05 g, 0.1 mmol) was dissolved in anhydrous THF (3 mL) at 0° C. and NaH (60% oil dispersion 0.04 g, 1.0 mmol) was added. After 10 min, 4-dimethylaminobenzoylchloride (0.18 g, 1.0 mmol) was added and the reaction was stirred for 2–3 hours at 0° C. under $N_2$ then warmed to 20° C. overnight. $NH_4Cl_{(aq)}$ was added to quench the reaction. Solvent was removed and the product was extracted into $CH_2Cl_2$, washed with water and dried ($Na_2SO_4$). Product was purified by column chromatography (Hex/EtOAc as solvent) to give 0.042 g of product. The above product (0.036 g 0.056 mmol) was dissolved in TFA (1.0 mL) and stirred at 20° C. for 1.5 h before it was concentrated. An ammonium hydroxide solution was added to the residue until the pH was about 10–11 and a tan solid was formed. The tan solid was collected through filtration, washed with water and dried under vacuum to give 0.0215 g (49%) of Cmd 42 as a tan solid; $^1H$ NMR (300 MHz, D$^6$-DMSO) δ8.97 (m, 3H), 8.63 (s, 1H), 8.27 (s, 1H), 7.96 (m, 3H), 7.92 (s, 1H), 7.84 (dd, J=8.2, 1.3 Hz, 1H), 7.41 (t, J=8.0 Hz, 1H), 7.04 (dd, J=7.9, 1.4 Hz, 1H), 6.79 (d, J=9.0 Hz, 2H), 3.02 (s, 6H); MS (ES) m/z: 445 (M+H$^+$). Anal. Calcd. For $C_{24}H_{21}N_6OCl.1.15H_2O$: C, 61.91; H, 5.04; N, 18.05. Found: C, 62.27; H, 4.83; N, 17.67.

EXAMPLE 47

COMPOUND 43

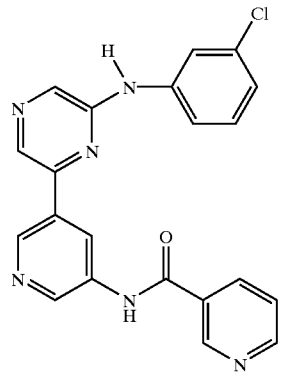

N-[5-[6-[(3-chlorophenyl)amino]pyrazinyl]-
3-pyridinyl]-3-pyridinecarboxamide(Cmd 43)

Cmd 67 (0.05 g, 0.1 mmol) was dissolved in anhydrous THF (3 mL) at 0° C. and NaH (60% oil dispersion 0.04 g, 1.0 mmol) was added. After 10 min, nicotinoyl chloride (0.18 g, 1.0 mmol) was added and the reaction was stirred for 2–3 hours at 0° C. under $N_2$ then allowed to warm to 20° C. overnight. $NH_4Cl_{(aq)}$ was added to quench the reaction. Solvent was removed and the product was extracted into $CH_2Cl_2$, washed with water and dried ($Na_2SO_4$). Product was purified by column chromatography (Hex/EtOAc as solvent) to give 0.02 g of product. The above product was dissolved in TFA (1.0 mL) and stirred at 20° C. for 2 h before it was concentrated. An ammonium hydroxide solution was added to the residue until the pH was about 10–11 and a yellow solid was formed. The yellow solid was collected through filtration, washed with water and dried under vacuum to give 0.006 g (15%) of Cmd 43 as a yellow solid; $^1H$ NMR (300 MHz, $CD_3OD$) δ9.17 (brs, 1H), 9.02 (brs, 2H), 8.94 (brs, 1H), 8.77 (m, 1H), 8.52 (s, 1H), 8.45 (m, 1H), 8.17 (s, 1H), 7.94 (brs, 1H), 7.76 (d, J=8.6 Hz, 1H), 7.65 (m, 1H), 7.34 (t, J=8.2 Hz, 1H), 7.05 (m, 1H); MS (ES) m/z: 403 (M+H$^+$).

EXAMPLE 48

Intermediate Compound 3B

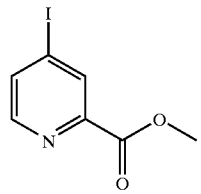

A mixture of 4-iodopicolinic acid (hemi-hydroiodide hydrate) (Lohse, Olivier, *Synthetic Communications*, 1996, 26(10), 2017–2025) (10 g, 30.2 mmol), CDI (20 g, 123 mmol) in THF (200 mL) was stirred for 60 h at room temperature. The reaction mixture was cooled in an ice bath. After methanol (200 mL) was added, triethylamine (25.4 g, 251 mmol) was added dropwise. The reaction stirred for 40 h at room temperature. The reaction mixture was concentrated under vacuum. The product was purified by column chromatography (EtOAc/hexane as solvent) to give 7.3 g (92%) of 3B as a tan solid; $^1H$ NMR (300 MHz, $CDCl_3$)

δ8.52 (d, J=1.6 Hz, 1H), 8.40 (d, J=5.1 Hz, 1H), 7.88 (dd, J=5.1, 1.7 Hz, 1H), 4.02 (s, 3H); MS (ES) m/z: 264 (M+H⁺).

EXAMPLE 49

Intermediate Compound 3C

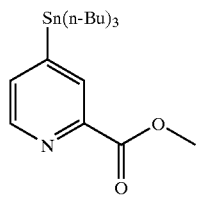

A mixture of 3B (7.3 g, 27.7 mmol), bis(tributyltin) (19.4 g, 33.4 mmol), palladium acetate (0.28 g, 1.25 mmol), tri-o-tolylphosphine (2.2 g, 7.23 mmol) and triethylamine (5.6 g, 55.7 mmol) in acetonitrile (89 mL) was stirred at 80–90° C. for 24 h under nitrogen. The cooled reaction mixture was concentrated under vacuum. The residue was purified by column chromatography (EtOAc/hexane as solvent) to give 8.91 g (75%) of 3C as a yellow oil; $^1$H NMR (300 MHz, CDCl$_3$) δ8.61 (m, 1H), 8.22 (m, 1H), 7.56 (m, 1H), 4.01(s, 3H), 1.60–0.90 (m, 18H), 0.89 (t, J=7.3 Hz, 9H); MS (ES) m/z: 428 (M+H⁺).

EXAMPLE 50

Intermediate Compound 3E

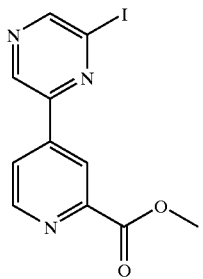

A mixture of 3C (96.7 mg, 0.227 mmol) 2,6-diiodopyrazine (151 mg, 0.454 mmol; Turch, A. et al, *J Heterocycl. Chem.* 1994, 31(6), 1449–53), Pd$_2$(dba)$_3$(6 mg, 0.0057 mmol) and triphenylarsine (14 mg, 0.0454 mmol) in THF (1 mL) was stirred at reflux for 18 h under nitrogen. Aqueous sodium carbonate was added and stirred for 5 min. and then extracted with dichloromethane. The product was purified by column chromatography (EtOAc/hexane as solvent) to give 16.8 mg (22%) of 3E as an off-white solid; $^1$H NMR (300 MHz, CDCl$_3$) δ9.08 (s, 1H), 8.92 (m, 2H), 8.72 (d, J=1.7 Hz, 1H), 8.10 (d, J=5.0 Hz, 1H), 4.08 (s, 3H); MS (ES) m/z: 342 (M+H⁺).

EXAMPLE 51

COMPOUND 44

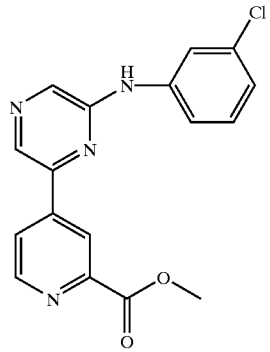

A mixture of 3E (416 mg, 1.22 mmol), 3-chloroaniline (234 mg, 1.83 mmol), Pd$_2$(dba)$_3$ (31.6 mg, 0.003 mmol), DPPF (54 mg, 0.096 mmol), Cs$_2$CO$_3$ (795 mg, 2.44 mmol) in anhydrous dioxane (3.6 mL) was stirred at 100° C. for 24 h under nitrogen. The reaction mixture was concentrated under vacuum. The residue was purified by column chromatography (acetone/dichloromethane as solvent) to give 16 mg (3.8%) of Cmd 44 as a yellow solid; $^1$H NMR (300 MHz, CDCl$_3$) δ8.90 (d, J=5.1 Hz, 1H), 8.76 (brs, 1H), 8.65 (s, 1H), 8.30 (s, 1H), 8.12 (dd, J=5.1, 1.8 Hz, 1H), 7.78 (brs, 1H), 7.40–7.30 (m, 2H), 7.12 (d, J=7.5 Hz, 1H), 6.73 (s, 1H), 4.07 (s, 3H); MS (ES) m/z: 341 (M+H⁺).

EXAMPLE 52

COMPOUND 45

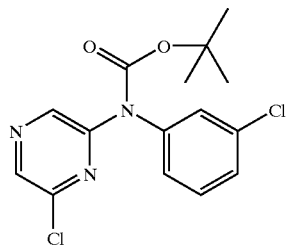

A mixture of Cmd 29 (1.1 g, 4.6 mmol), Boc$_2$O (3 g, 13.8 mmol) and DMAP (200 mg, cat) in dichloromethane (65 mL) was stirred at 20° C. for 16 h. The reaction mixture was concentrated and the product was purified by column chromatography (EtOAc/hexane as solvent) to give 1.6 g (100%) of Cmd 45 as a tan wax; $^1$H NMR (300 MHz, CDCl$_3$) δ8.87 (s, 1H), 8.32 (s, 1H), 7.34–7.27 (m, 2H), 7.21 (brs, 1H), 7.10 (dt, J=6.9, 2.1 Hz, 1H), 1.46 (s, 9H); MS m/z: 362 (M+Na⁺).

EXAMPLE 53

COMPOUND 46

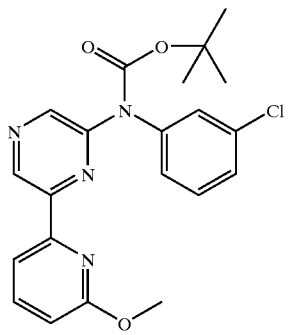

A mixture of 2-methoxy-6-(tributyltin)pyridine (WO9321178, published Oct. 28, 1993 by Pfizer Limited; 384 mg, 1.13 mmol), Cmd 45 (502 mg, 1.26 mmol), $Pd_2(dba)_3$ (27 mg, 0.026 mmol), triphenylarsine (64 mg, 0.21 mmol) and THF (4.5 mL) was refluxed for 4 days under nitrogen. The product was purified by column chromatography (EtOAc/hexane as solvent) and recrystallized from hexane to give 233 mg (45%) of Cmd 46 as a white solid; $^1$H NMR (300 MHz, $CDCl_3$) δ9.36 (s, 1H), 8.92 (s, 1H), 7.59 (m, 1H), 7.50 (dd, J=7.4, 0.8 Hz, 1H), 7.37–7.26 (m, 3H), 7.20 (dt, J=7.3, 1.9 Hz, 1H), 6.77 (dd, J=8.1, 0.8 Hz, 1H), 4.03 (s, 3H), 1.49 (s, 9H); MS (ES) m/z: 413 (M+H$^+$).

EXAMPLE 54

COMPOUND 47

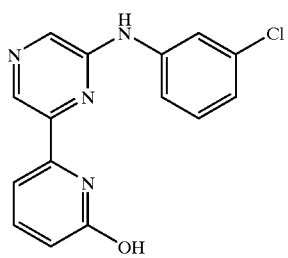

A mixture of Cmd 46 (230 mg, 0.56 mmol) and pyridine hydrochloride (1.6 g, 14 mmol) was heated under nitrogen at 220° C. for 40 min. The cooled reaction mixture was triturated in a mixture of dichloromethane and 30% ammonium hydroxide. Dichloromethane was removed under vacuum and the solid was collected through filtration and dried under vacuum to give 108 mg (65%) Cmd 47 as an off-white solid; $^1$H NMR (300 MHz, D$^6$-DMSO) δ11.2 (brs, 1H), 9.92 (brs, 1H), 8.70 (brs, 1H), 8.28 (brs, 1H), 7.99 (brs, 1H), 7.70–7.50 (m, 2H), 7.38–7.30 (m, 2H), 7.06 (brs, 1H), 6.60 (brs, 1H); MS (ES) m/z: 298 (M+H$^+$).

EXAMPLE 55

COMPOUND 48

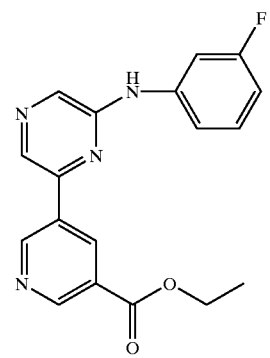

A mixture of 1D (320 mg, 1.22 mmol), 3-fluoroaniline (205 mg, 1.83 mmol), $Pd_2(dba)_3$ (31.6 mg, 0.03 mmol), DPPF (54 mg, 0.096 mmol), $Cs_2CO_3$ (795 mg, 2.44 mmol) in anhydrous dioxane (3.6 mL) was stirred at 110° C. for 46 h under nitrogen. Dichloromethane (2 mL) was added to the cooled reaction mixture. The mixture was filtered through celite. The celite cake was washed with more dichloromethane and the combined filtrate was concentrated to give a yellow solid. A small amount of EtOAc was added, and the solid (45 mg) was collected by filtration. The filtrate was concentrated and purified by column chromatography to give 288 mg of Cmd 48 as a yellow solid (total yield 80%); $^1$H NMR (300 MHz, $CDCl_3$) δ9.42 (d, J=2.2 Hz, 1H), 9.30 (d, J=2.0 Hz, 1H), 8.91 (t, J=2.1 Hz, 1H), 8.58 (s, 1H), 8.26 (s, 1H), 7.54 (d, J=10.9 Hz, 1H), 7.38–7.24 (m, 1H), 6.91 (s, 1H), 6.83 (t, J=8.1 Hz, 1H), 4.48 (q, J=7.1 Hz, 2H), 1.46 (t, J=7.1 Hz, 3H); MS (ES) m/z: 339 (M+H$^+$).

EXAMPLE 56

COMPOUND 49

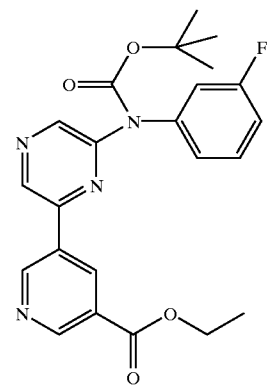

A mixture of Cmd 48 (293 mg, 0.87 mmol), $Boc_2O$ (378 mg, 1.73 mmol), and DMAP (40 mg, cat.) in dichloromethane (5.4 mL) was stirred at 20° C. for 18 h. The reaction mixture was concentrated and the product was purified by column chromatography (EtOAc/hexane as solvent) to give 301 mg (79%) of Cmd 49 as a yellowish oil; $^1$H NMR (300 MHz, $CDCl_3$) δ9.22 (d, J=2.0 Hz, 1H), 9.15 (d, J=2.2 Hz, 1H), 9.10 (s, 1H), 8.84 (s, 1H), 8.65 (t, J=2.1 Hz, 1H), 7.39 (q, J=6.3 Hz, 1H), 7.10–7.00 (m, 3H), 4.43 (q, J=7.1 Hz, 2H), 1.49 (s, 9H), 1.43 (t, J=7.1 Hz, 3H); MS (ES) m/z: 439 (M+H$^+$). Anal. Calcd. For $C_{23}H_{23}N_4O_4F.0.1H_2O$: C, 62.75; H, 5.31; N, 12.73. Found: C, 62.74; H, 5.19; N, 12.82.

EXAMPLE 57

COMPOUND 50

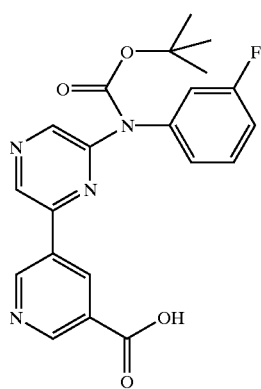

A mixture of Cmd 49 (410 mg, 0.64 mmol) was dissolved in methanol (6.3 mL) and stirred for 10 min then cooled to 0° C. NaOH$_{(aq)}$ (1 N, 1.06 mL) was added slowly and the mixture was stirred at 0° C. for 10 min then stirred at 20° C. for another 18 h. Glacial acetic acid (0.86 mL) was added to the reaction mixture at 0° C. slowly followed by the addition of water (3.2 mL). A yellow solid was formed. The yellow solid was collected through filtration, washed with water (5×), and dried in a vacuum oven overnight to give 222 mg (85%) of Cmd 50 as a yellow solid; $^1$H NMR (300 MHz, CDCl$_3$) δ9.29 (brs, 1H), 9.20 (brs, 1H), 9.13 (brs, 1H), 8.86 (brs, 1H), 8.73 (brs, 1H), 7.44–7.27 (m, 1H), 7.07–6.91 (m, 3H); MS (ES) m/z: 409 (M−H$^+$).

EXAMPLE 58

COMPOUND 51

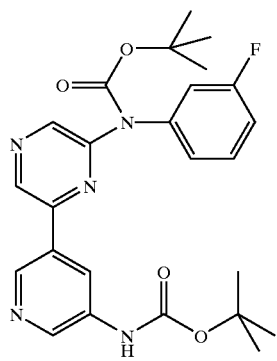

A mixture of Cmd 50 (210 mg, 0.513 mmol), DPPA (169 mg, 0.616 mmol), triethylamine (103 mg, 1.02 mmol), and t-BuOH (2.16 mL) in toluene (1.54 mL) was stirred under nitrogen at 100° C. for 3 h. The reaction mixture was concentrated under vacuum. The product was purified by column chromatography (EtOAc/hexane as solvent) to give 77 mg (31%) of Cmd 51 as a yellowish gum; $^1$H NMR (300 MHz, CDCl$_3$) δ8.99 (s, 1H), 8.80 (s, 1H), 8.68 (d, J=1.9 Hz, 1H), 8.46 (d, J=2.5 Hz, 1H), 8.38 (brs, 1H), 7.41–7.27 (m, 1H), 7.06–7.01 (m, 3H), 6.58 (brs, 1H), 1.54 (s, 9H), 1.49 (s, 9H); FAB-HRMS (M+H$^+$). Calcd. for C$_{25}$H$_{21}$N$_5$O$_4$F 482.2204, found 482.2204.

EXAMPLE 59

COMPOUND 52

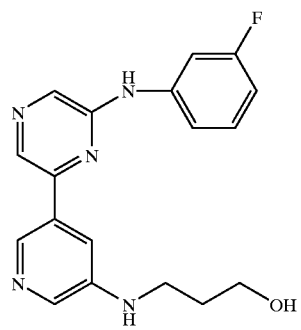

3-[[5-[6-[(3-fluorophenyl)amino]pyrazinyl]-3-pyridinyl]amino]-1-propanol(Cmd 52)

A mixture of Cmd 51 (73 mg 0.152 mmol), (3-bromopropoxy)-t-butyl-dimethylsilane (57.8 mg, 0.228 mmol) and Cs$_2$CO$_3$ (148 mg, 0.456 mmol) in DMF (1.9 mL) was stirred at 70° C. under nitrogen for 36 h. The reaction mixture was diluted with water, extracted with ether (3×), dried (Na$_2$SO$_4$) and concentrated. The product was purified by column chromatography (EtOAc/hexane as solvent) to give 66 mg of the silylated-product as an orange oil. The silylated-product was dissolved in TFA (0.7 mL) and stirred at 20° C. for 1 h before it was concentrated. An ammonium hydroxide solution was added to the residue until the pH was about 10–11 and a yellow solid was formed. The yellow solid was collected through filtration, washed with water and dried under vacuum. The yellow solid was recrystallized from CH$_3$OH/EtOAc to give 14 mg (27% two steps) of Cmd 52 as a light yellow solid; $^1$H NMR (300 MHz, CD$_3$OD) δ8.46 (s, 1H), 8.43 (d, J=1.8 Hz, 1H), 8.13 (brs, 1H), 8.01 (d, J=2.7 Hz, 1H), 7.90 (dt, J=12.1, 2.1 Hz, 1H), 7.68 (t, J=2.1 Hz, 1H), 7.42–7.28 (m, 2H), 6.73 (t, J=8.3 Hz, 1H), 3.72 (t, J=6.2 Hz, 2H), 3.31 (m, 2H), 1.91 (m, 2H); FAB-HRMS (M+H$^+$). Calcd. for C$_{18}$H$_{19}$N$_5$OF 340.1574, found 340.1586.

EXAMPLE 60

COMPOUND 53

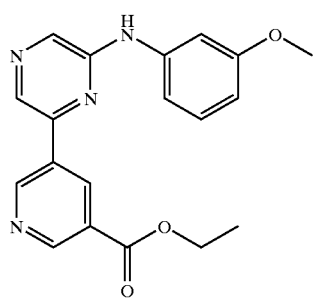

A mixture of 1D (400 mg, 1.53 mmol), 3-methoxyaniline (281 mg, 2.29 mmol), Pd$_2$(dba)$_3$ (39.5 mg, 0.038 mmol), DPPF (67.5 mg, 0.119 mmol), Cs$_2$CO$_3$ (993 mg, 3.05 mmol) in anhydrous dioxane (4.5 mL) was stirred at 110° C. for 47h under nitrogen. Dichloromethane (2 mL) was added to the cooled reaction mixture. The mixture was filtered through celite. The celite cake was washed with more dichloromethane and the combined filtrate was concentrated to give a yellow solid. A small amount of EtOAc was added, the solid (226 mg) was collected by filtration and the filtrate was concentrated and purified by column chromatography to give 62 mg of Cmd 53 as a yellow solid (total yield 65%); $^1$H NMR (300 MHz, CDCl$_3$) δ9.42 (d, J=2.1 Hz, 1H), 9.28 (d, J=2.0 Hz, 1H), 8.89 (t, J=2.1 Hz, 1H), 8.53 (s, 1H), 8.27 (s, 1H), 7.3–7.27 (m, 2H), 7.05 (dd, J=7.9, 1.3 Hz, 1H), 6.78 (brs, 1H), 6.69 (brd, J=7.6 Hz, 1H), 4.48 (q, J=7.1 Hz, 2H), 3.85 (s, 3H), 1.56 (t, J=7.1 Hz, 3H); Anal. Calcd for C$_{19}$H$_{18}$N$_4$O$_3$·0.5H$_2$O: C, 63.82; H, 5.33; N, 15.59. Found: C, 63.90; H, 5.20; N 15.35.

EXAMPLE 61

COMPOUND 54

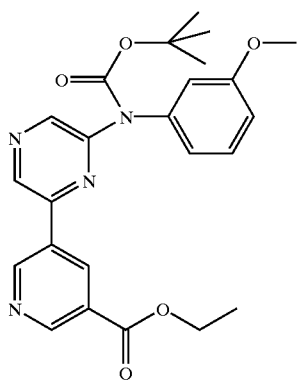

A mixture of Cmd 53 (456 mg, 1.3 mmol), Boc$_2$O (568 mg, 2.6 mmol), and DMAP (~60 mg, cat.) in dichloromethane (8.7 mL) was stirred at 20° C. for 4 days. The reaction mixture was concentrated and the product was purified by column chromatography (EtOAc/hexane as solvent) to give 521 mg (89%) of Cmd 54 as a yellowish oil; $^1$H NMR (300 MHz, CDCl$_3$) δ9.22 (d, J=1.6 Hz, 1H), 9.17 (d, J=1.9 Hz, 1H), 9.02 (s, 1H), 8.81 (s, 1H), 8.68 (brs, 1H), 7.33 (t, J=8.1 Hz, 1H), 6.90–6.82 (m, 3H), 4.44 (q, J=7.1 Hz, 2H), 3.81 (s, 3H), 1.49 (s, 9H), 1.43 (t, J=7.1 Hz, 3H); MS (ES) m/z: 451 (M+H$^+$). Anal. Calcd. For C$_{24}$H$_{26}$N$_4$O$_5$: C, 63.99; H, 5.82; N, 12.44. Found: C, 63.85; H, 5.40; N, 12.14 (error=0.42%); FAB-HRMS (M+H$^+$). Calcd. for C$_{24}$H$_{27}$N$_4$O$_5$ 451.1981, found 451.2007.

EXAMPLE 62

COMPOUND 55

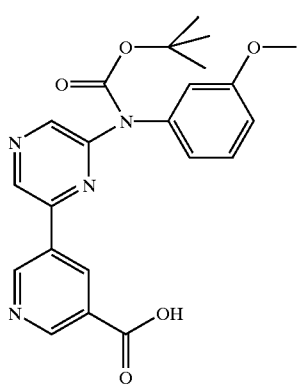

A mixture of Cmd 54 (521 mg, 1.16 mmol) was dissolved in methanol (11.4 mL) and stirred for 10 min then cooled to 0° C. NaOH$_{(aq)}$ (1 N, 1.92 mL) was added slowly and the mixture was stirred at 0° C. for 10 min then stirred at 20° C. for another 18 h. Glacial acetic acid (1.6 mL) was added to the reaction mixture at 0° C. slowly followed by the addition of water (6 mL). A yellow solid was formed. The yellow solid was collected through filtration, washed with water (5×), and dried in a vacuum oven overnight to give 399 mg (80%) of Cmd 55 as a yellow solid; $^1$H NMR (300 MHz, CD$_3$OD) δ9.16 (d, J=2.2 Hz, 1H), 9.11 (d, J=1.9 Hz, 1H,), 9.04 (s, 1H), 8.98 (s, 1H), 8.82 (t, J=2.1 Hz, 1H), 7.35 (t, J=8.0 Hz, 1H), 6.96–6.85 (m, 3H), 3.81 (s, 3H), 1.48 (s, 9H); MS (ES) m/z: 421 (M–H$^+$). Anal. Calcd. For C$_{22}$H$_{22}$N$_4$O$_5$·0.3H$_2$O: C, 61.76; H, 5.32; N, 13.10. Found: C, 61.88; H, 5.21; N, 12.98.

EXAMPLE 63

COMPOUND 56

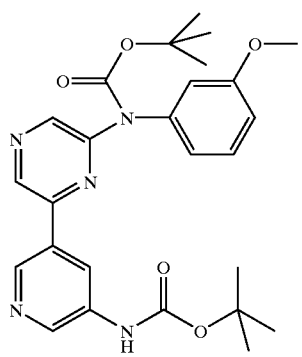

A mixture of Cmd 55 (392 mg, 0.928 mmol), DPPA (307 mg, 1.12 mmol), triethylamine (188 mg, 1.86 mmol), and t-BuOH (3.9 mL) in toluene (2.8 mL) was stirred under nitrogen at 70° C. for 30 min. and then 100° C. for 3 h. The reaction mixture was concentrated under vacuum. The product was purified by column chromatography (EtOAc/hexane as solvent) to give 343 mg (75%) of Cmd 56 as a yellowish gum; $^1$H NMR (300 MHz, CDCl$_3$) δ8.91 (s, 1H), 8.78 (s, 1H), 8.71 (d, J=1.9 Hz, 1H), 8.49 (d, J=2.5 Hz, 1H), 8.38 (brs, 1H), 7.31 (t, J=8.2 Hz, 1H), 6.87–6.82 (m, 3H), 6.63 (brs, 1H), 3.81 (s, 3H), 1.54 (s, 9H), 1.49 (s, 9H); MS (ES) m/z: 494 (M+H$^+$).

EXAMPLE 64

COMPOUND 57

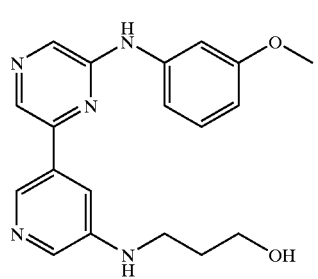

3-[[5-[6-[(3-methoxyphenyl)amino]pyrazinyl]-3-pyridinyl]amino]-1-propanol (Cmd 57)

A mixture of Cmd 56 (343 mg, 0.70 mmol), (3-bromopropoxy)-t-butyl-dimethylsilane (354 mg, 1.4 mmol) and Cs$_2$CO$_3$ (684 mg, 2.1 mmol) in DMF (8.8 mL) was stirred at 70° C. under nitrogen for 18 h. The reaction mixture was diluted with water, extracted with ether (3×), dried (Na$_2$SO$_4$) and concentrated. The product was purified by column chromatography (EtOAc/hexane as solvent) to give 246 mg of the silylated-product as an orange oil.

The silylated-product was dissolved in TFA (2.6 mL) and stirred at 20° C. for 18 h before it was concentrated. An ammonium hydroxide solution was added to the residue until the pH was about 10–11 and a yellow solid was formed. The yellow solid was collected through filtration, washed with water and dried under vacuum. The yellow solid was recrystallized from CH$_3$OH/EtOAc to give 24.3 mg (9.9% two steps) of Cmd 57 as a light yellow solid; $^1$H NMR (300 MHz, CD$_3$OD) δ8.44 (d, J=1.6 Hz, 1H), 8.39 (s, 1H), 8.10 (s, 1H), 8.00 (d, J=2.8 Hz, 1H), 7.67 (brs, 1H), 7.65 (brs, 1H), 7.23–7.20 (m, 2H), 6.62–6.58 (m, 1H), 3.81 (s, 3H), 3.72 (t, J=6.2 Hz, 2H) 3.31 (m, 2H), 1.90 (m, 2H); Anal. Calcd. For C$_{19}$H$_{21}$N$_5$O$_2$.0.5H$_2$O: C, 63.32; H, 6.15; N, 19.43. Found: C, 63.51; H, 5.93; N, 19.31.

EXAMPLE 65

COMPOUND 58

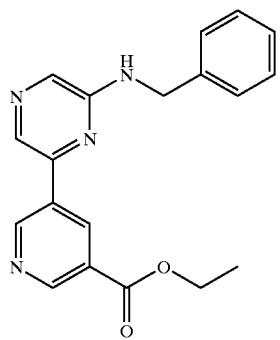

A mixture of 1D (320 mg, 1.22 mmol), benzylamine (144 mg, 1.34 mmol), Pd$_2$(dba)$_3$ (32 mg 0.03 mmol), DPPF (54 mg, 0.096 mmol), and Cs$_2$CO$_3$ (795 mg, 2.44 mmol) in anhydrous dioxane (3.6 mL) was stirred at 110° C. for 39 h under nitrogen. The cooled reaction mixture was concentrated and purified by column chromatography to give 130 mg of Cmd 58 as a green oil (total yield 28%); $^1$H NMR (300 MHz, CDCl$_3$) δ9.35 (d, J=2.2 Hz, 1H), 9.25 (d, J=2.0 Hz, 1H), 8.84 (t, J=2.0 Hz, 1H), 8.37 (s, 1H), 7.94 (s, 1H), 7.43–7.38 (m, 5H), 5.13 (m, 1H), 4.68 (d, J=5.7 Hz, 2H), 4.46 (q, J=7.2 Hz, 2H), 1.45 (t, J=7.2 Hz, 3H); FAB-HRMS (M+H$^+$). Calcd. for C$_{19}$H$_{19}$N$_4$O$_2$ 335.1508, found 335.1515.

EXAMPLE 66

COMPOUND 59

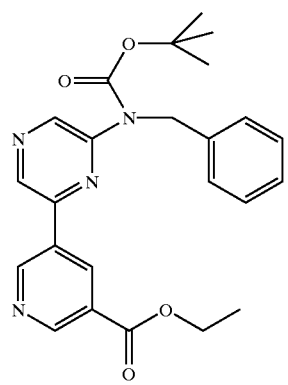

A mixture of Cmd 58 (220 mg, 1.658 mmol), Boc$_2$O (431 mg, 1.98 mmol), and DMAP (~30 mg, cat.) in dichloromethane (4.1 mL) was stirred at 20° C. for 4 days. The reaction mixture was concentrated and the product was purified by column chromatography (EtOAc/hexane as solvent) to give 195 mg (68%) of Cmd 59 as a white solid; $^1$H NMR (300 MHz, CDCl$_3$) δ9.27 (dd, J=7.9, 2.2 Hz, 2H), 9.22 (s, 1H), 8.78 (t, J=2.1 Hz, 1H), 8.74 (s, 1H), 7.35–7.21 (m, 5H), 5.30 (s, 2H), 4.46 (q, J=7.1 Hz, 2H), 1.50 (s, 9H), 1.43 (t, J=7.1 Hz, 3H); FAB-HRMS (M+H$^+$). Calcd. for C$_{24}$H$_{27}$N$_4$O$_4$ 435.2032, found 435.2058.

EXAMPLE 67

COMPOUND 60

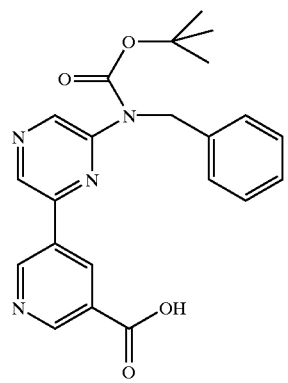

A mixture of Cmd 59 (195 mg, 0.449 mmol) was dissolved in methanol (4.4 mL) and stirred for 10 min then cooled to 0° C. NaOH$_{(aq)}$ (1 N, 0.94 mL) was added slowly and the mixture was stirred at 0° C. for 10 min then stirred at 20° C. for another 18 h. Glacial acetic acid (0.8 mL) was added to the reaction mixture at 0° C. slowly followed by the addition of water (3 mL). A solid was formed and was collected by filtration, washed with water (5×), and dried in vacuum oven overnight to give 399 mg (80%) of Cmd 60 as a white solid; $^1$H NMR (300 MHz, CD$_3$OD) δ9.29 (d, J=2.0 Hz, 1H), 9.17 (s, 1H), 9.15 (d, J=1.6 Hz, 1H), 8.94 (t, J=2.1 Hz, 1H), 8.90 (s, 1H), 7.42–7.19 (m, 5H), 5.30 (s, 2H), 1.50 (s, 9H); MS (ES) m/z: 405 (M–H$^+$); Anal. Calcd. For C$_{22}$H$_{22}$N$_4$O$_4$·0.4H$_2$O: C, 63.88; H, 5.56; N, 13.54. Found: C, 63.85; H, 5.44; N, 13.30.

EXAMPLE 68

COMPOUND 61

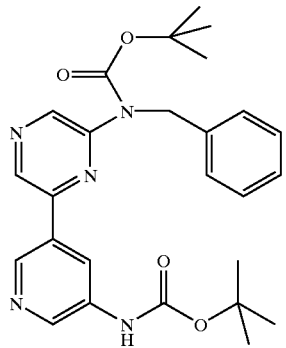

A mixture of Cmd 60 (128 mg, 0.315 mmol), DPPA (104 mg, 0.38 mmol), triethylamine (64 mg, 0.68 mmol), and t-BuOH (1.33 mL) in toluene (0.95 mL) was stirred under nitrogen at 70° C. for 30 min. and then at 100° C. for 19 h. The reaction mixture was concentrated under vacuum. The product was purified by column chromatography (EtOAc/hexane as solvent) to give 89 mg (59%) of Cmd 61 as a white solid; $^1$H NMR (300 MHz, CDCl$_3$) δ9.13 (s, 1H), 8.81 (d, J=1.8 Hz, 1H), 8.69 (s, 1H), 8.55 (d, J=2.4 Hz, 1H), 8.38 (brs, 1H), 7.35–7.21 (m, 5H), 6.56 (brs, 1H), 5.28 (s, 2H), 1.55 (s, 9H), 1.50 (s, 9H); MS (ES) m/z 478 (M+H$^+$).

EXAMPLE 69

COMPOUND 62

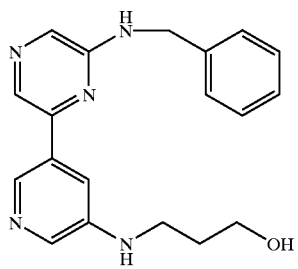

3-[[5-[6-[(phenylmethyl)amino]pyrazinyl]-3-pyridinyl]amino]-1-propanol (Cmd 62)

A mixture of Cmd 61 (83 mg, 0.174 mmol), (3-bromopropoxy)-t-butyl-dimethylsilane (66 mg, 0.26 mmol) and Cs$_2$CO$_3$ (170 mg, 0.522 mmol) in DMF (2.1 mL) was stirred at 70° C. under nitrogen for 3 days. The reaction mixture was diluted with water, extracted with dichloromethane (3×), dried (Na$_2$SO$_4$) and concentrated. The product was purified by column chromatography (EtOAc/hexane as solvent) to give 54 mg of the silylated-product as orange oil. The silylated-product was dissolved in TFA (0.6 mL) and stirred at 20° C. for 4 h before it was concentrated. An ammonium hydroxide solution was added to the residue until the pH was about 10–11 and a greenish solid was formed. The greenish solid was collected by filtration, washed with water, and dried under vacuum. The greenish solid was recrystallized from CH$_3$OH/EtOAc to give 10 mg (17% two steps) of Cmd 62 as a light greenish solid; $^1$H NMR (300 MHz, CD$_3$OD) δ8.30 (s, 1H), 8.15 (s, 1H), 7.93 (brs, 1H), 7.86 (s, 1H), 7.54 (s, 1H), 7.42–7.20 (m, 5H), 4.64 (s, 2H), 3.70 (t, J=6.1 Hz, 2H), 3.24 (t, J=6.6 Hz, 2H), 1.86 (m, 2H); MS (ES) m/z: 336 (M+H$^+$).

EXAMPLE 70

COMPOUND 63

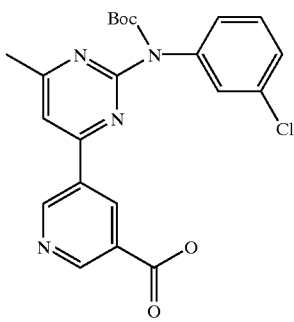

Refer to Example 12 for preparation of Cmd 63, an intermediate for Cmd 9. Characterized as a light-brown solid; MS (ES) m/z: 439 (M–H$^+$). Anal. Calcd. For C$_{22}$H$_{21}$N$_4$O$_4$Cl·0.5H$_2$O: C, 58.73; H, 4.93; N, 12.45. Found: C, 59.04; H, 4.88; N, 12.23

EXAMPLE 71

COMPOUND 64

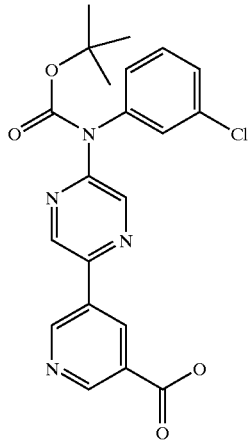

Refer to Example 17 for the preparation of Cmd 64, an intermediate for Cmd 14. Characterized as an off-white solid; MS (ES) m/z: 425 (H$^+$).

EXAMPLE 72

COMPOUND 65

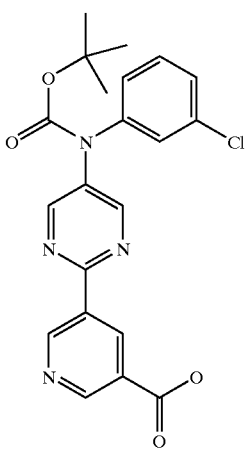

Refer to Example 22 for the preparation of Cmd 65, an intermediate for Cmd 19. Characterized as a yellow solid; MS (ES) m/z: 425 (M–H$^+$).

EXAMPLE 73

COMPOUND 66

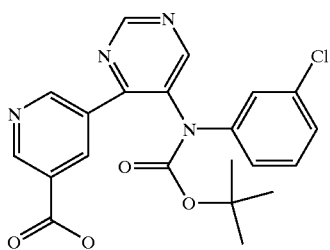

Refer to Example 27 for the preparation of Cmd 66, an intermediate for Cmd 24. Characterized as a yellow solid; $^1$H NMR (300 MHz, CDCl$_3$) δ9.35 (d, J=1.7 Hz, 1H), 9.28 (s, 1H), 9.18 (d, J=2.1 Hz, 1H), 8.78 (s, 1H), 8.72 (t, J=2.0 Hz, 1H), 7.11(m, 3H), 6.90 (brd, J=7.4 Hz, 1H), 1.35 (s, 9H); MS (ES) m/z: 425 (M–H$^+$).

EXAMPLE 74

COMPOUND 68

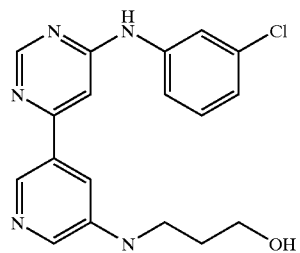

3-[[5-[6-[(3-chlorophenyl)amino-4-pyrimidinyl]-3-pyridinyl]amino]-1-propanol (Cmd 68)

A mixture of 4,6-dichloropyrimidine Compound 74a (4 g, 26.9 mmol), 3-chloroaniline (3.44 g, 26.9 mmol), palladium acetate (121 mg, 38 mmol), BINAP (368 mg, 59 mmol) and NaO-t-Bu (3.61 g, 217 mmol) in toluene (100 mL) was stirred at 90° C. for 40 h under nitrogen. The cooled reaction mixture was concentrated under vacuum. The residue was diluted with dichloromethane, filtered thru celite, the celite washed with acetone and the combined filtrates were concentrated under vacuum. The product was purified by column chromatography (100% dichloromethane as solvent) to give 250 mg (4%) of Compound 74b as a solid; $^1$H NMR (300 MHz, D$^6$-DMSO) δ8.56 (s, 1H), 7.94 (s, 1H), 7.44 (d, J=8.4 Hz, 1H), 7.38 (t, J=8.0 Hz, 1H), 7.12 (d, J=8.2 Hz, 1H), 6.84 (s, 1H); MS (ES) m/z: 240 (M+H$^+$). A mixture of Compound 74b (240 mg, 1 mmol), Boc$_2$O (436 mg, 2 mmol), DMAP (cat.) in CH$_2$Cl$_2$ was stirred at 20° C. for 3 h and concentrated. The product was purified by column chromatography (EtOAc/hexane as solvent) to give 308 mg (91%) of Compound 74c as an oil; MS (ES) m/z: 362 (M+Na). Anal. Calcd. For C$_{15}$H$_{15}$N$_3$O$_2$Cl$_2$: C, 52.96; H, 4.44; N, 12.35. Found: C, 52.91; H, 4.43; N, 12.23.

A mixture of 5-bromonicotinic acid Compound 74d (7.14 g, 35.4 mmol), t-BuOH (155 mL), triethylamine (6.08 g, 60 mmol), DPPA (10.69 g, 38.9 mmol) in toluene (115 mL) was stirred at 65° C. for 30 min then warmed up to 95° C. for 15 h under nitrogen. The cooled reaction mixture was concentrated under vacuum. The product was purified by column chromatography (SiO$_2$, ethylacetate/hexane as solvent) to give 2.9 g (30%) of Compound 74e as a white solid; $^1$H NMR (300 MHz, CDCl$_3$) δ8.32 (m, 3H), 6.97 (brs, 1H), 1.53 (s, 9H); MS (ES) m/z: 273, 275 (M+H$^+$). Anal. Calcd. For C$_{10}$H$_{13}$N$_2$O$_2$Br: C, 43.98; H, 4.80; N, 10.26. Found: C, 43.88; H, 4.52; N, 10.20. A mixture of Compound 74e (2.85 g, 10.44 mmol), (3-bromopropoxy)-t-butyldimethylsilane (3.96 g, 15.66 mmol) and Cs$_2$CO$_3$ (10.21 g, 31.3 mmol), in anhydrous DMF (55 mL) was stirred at 70° C. for 23 h under nitrogen. The cooled reaction mixture was diluted with water and extracted with ether (3×), dried (Na$_2$SO$_4$) and concentrated. The product was purified by column chromatography (EtOAc/hexane as solvent) to give 4.2 g (90%) of Compound 74f as yellow oil; $^1$H NMR (300 MHz, CDCl$_3$) δ8.45 (brs, 2H), 7.77 (brs, 1H), 3.73 (brt, J=7.3 Hz, 2H), 3.62 (t, J=5.9 Hz, 2H), 1.81 (m, 2H), 1.45 (s, 9H), 0.84 (s, 9H), 0.00 (s, 6H); MS (ES) m/z: 445, 447 (M+H$^+$). Anal. Calcd. For C$_{19}$H$_{33}$N$_2$O$_3$BrSi: C, 51.23; H, 7.47; N, 6.29. Found: C, 51.45; H, 7.47; N, 6.53.

A mixture of Compound 74f (500 mg, 1.12 mmol), bis(tributyltin) (780 mg, 1.345 mmol), tri-o-tolylphosphine (88.5 mg, 0.29 mmol), palladium acetate (11.3 mg, 0.05 mmol), triethylamine (226 mg, 2.24 mmol) in acetonitrile was stirred at 95–100° C. for 23 h under nitrogen. The cooled reaction mixture was concentrated, sodium carbonate solution was added and stirred for 10 min before extracted with hexane (4×). The combined hexane was filtered thru celite, dried (Na$_2$SO$_4$) and concentrated. The product was purified by column chromatography (EtOAc/hexane as solvent) to give 395 mg (54%) of Compound 74 g as an oil; $^1$H NMR (300 MHz, CDCl$_3$) δ8.39 (d, J=1.2 Hz, 1H), 8.37 (m, 1H), 7.55 (m, 1H), 3.72 (brt, J=7.3 Hz, 2H), 3.63 (t, J=6.2 Hz, 2H), 1.89–1.10 (m, 29H), 0.89 (t, J=7.2 Hz, 9H), 0.85 (s, 9H), 0.00 (s, 6H); MS (ES) m/z: 657 (M+H$^+$). A mixture of Compound 74 g (396 mg, 0.6 mmol), Compound 74c (293 mg, 0.86 mmol), Pd$_2$(dba)$_3$ (16 mg, 0.015 mmol), triphenylarsine (37 mg, 0.12 mmol) in THF (8 mL) was refluxed for 41 h under nitrogen. The reaction mixture was concentrated, sodium carbonate solution was added and stirred for 10 min before extracted with ether (3×). The combined ether layer was dried (Na$_2$SO$_4$) and concentrated. The product was purified by column chromatography (EtOAc/hexane as solvent) to give 63 mg (16%) of the silylated-product as oil; MS (ES) m/z: 670 (M+H$^+$).

The silylated-product was dissolved in TFA (2 mL) and stirred at room temperature for 5 h before it was concentrated. An ammonium hydroxide solution was added to the solution until the pH was about 10–11, water was added and a yellow solid was formed. The yellow solid was collected thru filtration, washed with more water, dried under vacuum. The yellow solid was purified by column chromatography (dry loading, methylene chloride/methanol as solvent) to give 26 mg (77%) of Cmd 68 as yellow solid; $^1$H NMR (300 MHz, D$^6$-DMSO) δ9.94 (s, 1H), 8.79 (s, 1H), 8.36 (s, 1H), 8.08 (brs, 2H), 7.56 (d, J=9.2 Hz, 1H), 7.47 (s, 1H), 7.37 (t, J=8.1 Hz, 1H), 7.24 (s, 1H), 7.07 (d, J=7.8 Hz, 1H), 6.14 (m, 1H), 4.55 (t, J=5 Hz, 1H), 3.53 (m, 2H), 3.17 (m, 2H), 1.75 (m, 2H); MS (ES) m/z: 356 (M+H$^+$). Anal. Calcd. For C$_{18}$H$_{18}$N$_5$OCl·0.2H$_2$O: C, 60.15; H, 5.16; N, 19.48. Found: C, 60.31; H, 5.10; N, 19.15.

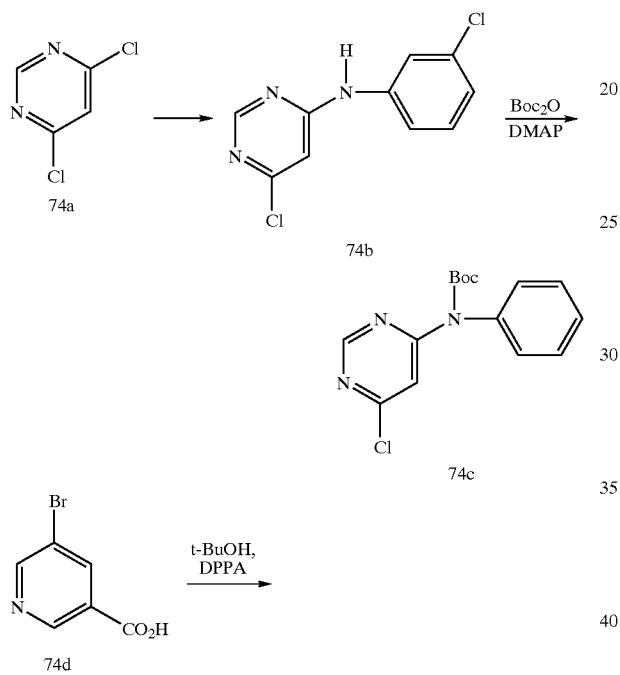

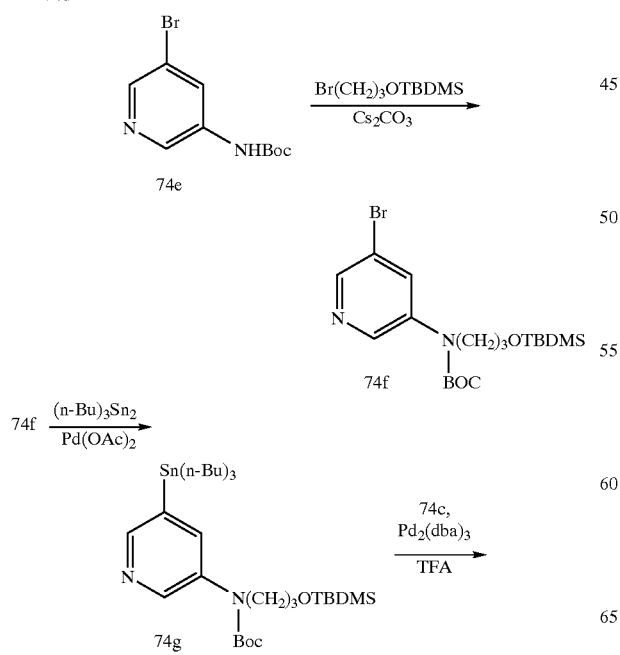

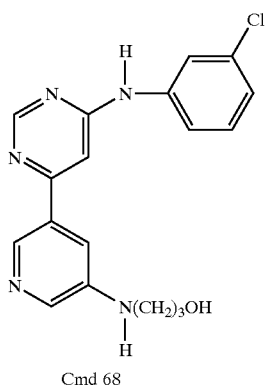

Cmd 68

EXAMPLE 75

COMPOUND 69

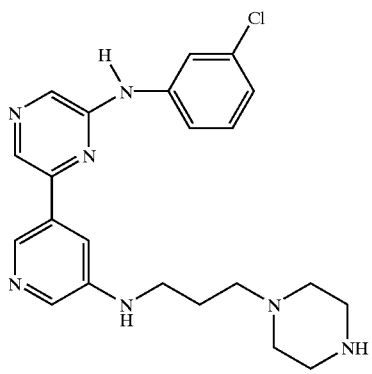

N-(3-chlorophenyl)-6-[5-[[3-(1-piperazinyl)propyl]amino]-3-pyridinyl]-2-pyrazinamine (Cmd 69)

A mixture of Cmd 67 prepared as described in Example 6) (0.1 g, 0.2 mmol), Boc protected 1-(3-chloropropyl) piperazine, (0.079 g, 0.3 mmol) and Cs$_2$CO$_3$ (0.197 g, 0.6 mmol) in DMF (4 mL) was stirred at 70° C. under nitrogen for 20 h. The reaction mixture was diluted with water, extracted with ether (3×), dried (Na$_2$SO$_4$) and concentrated. The product was purified by column chromatography (CH$_2$Cl$_2$/MeOH as solvent) to give 0.192 g of product as an oil. The oil was dissolved in TFA (2.0 mL) and stirred at 20° C. for 2 h before concentrated. Ammonium hydroxide solution was added to the residue until the pH was about 10–11 and a yellow solid was formed. The yellow solid was collected through filtration, washed with water and dried under vacuum to give 0.072 g (65%) of Cmd 69 as a yellow solid; $^1$H NMR (300 MHz, CD$_3$OD) δ8.43 (m, 2H), 8.18 (d, J=2.0 Hz, 1H), 8.11 (s, 1H), 8.00 (d, J=2.5 Hz, 1H), 7.65 (s, 1H), 7.49 (brd, J=8.0 Hz, 1H), 7.29 (t, J=8.0 Hz, 1H), 6.99 (d, J=7.0 Hz, 1H), 3.30 (m, 2H), 2.86 (m, 4H), 2.51 (m, 6H), 1.88 (m, 2H); MS (ES) m/z: 424 (M+H$^+$). Anal. Calcd. For C$_{22}$H$_{26}$N$_7$Cl·0.9H$_2$O: C, 60.03; H, 6.37; N, 22.28. Found: C, 60.24; H, 6.14; N, 21.94.

EXAMPLE 76

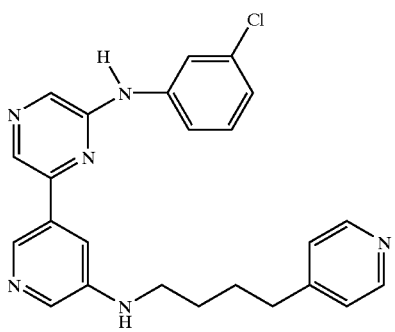

COMPOUND 70

N-(3-chlorophenyl)-6-[5-[[4-(4-pyridinyl)butyl]amino]-3-pyridinyl]-2-pyrazinamine (Cmd 70)

A mixture of Cmd 67 (prepared as described in Example 6) (0.1 g, 0.2 mmol), 4-(4-pyridinyl)butyl chloride (0.05 g, 0.3 mmol, Cheng, Tetrahedron 1993, 49, 5767–5776) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography ($CH_2Cl_2$/MeOH as solvent) to give 0.12 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography ($CH_2Cl_2$/MeOH as solvent) to give 0.06 g (74%) of Cmd 70 as a light yellow solid; $^1$H NMR (300 MHz, $CDCl_3$) δ8.52 (m, 4H), 8.17 (s, 1H), 8.09 (d, J=2.3 Hz, 1H), 7.92 (s, 1H), 7.50 (s, 1H), 7.28 (s, 1H), 7.12 (d, J=5.4 Hz, 1H), 7.06 (m, 1H), 6.83 (s, 1H), 3.81 (brs, 1H), 3.26 (q, J=5.9 Hz, 2H), 2.69 (t, J=7.0 Hz, 2H), 1.77 (m, 4H); MS (ES) m/z: 431 (M+H$^+$). Anal. Calcd. For $C_{24}H_{23}N_6Cl\cdot0.3H_2O$: C, 66.06; H, 5.45; N, 19.26. Found: C, 66.10; H, 5.40; N, 19.11.

EXAMPLE 77

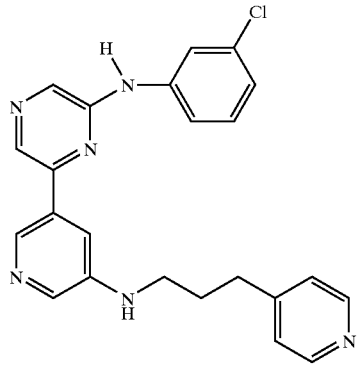

COMPOUND 71

N-(3-chlorophenyl)-6-[5-[[3-(4-pyridinyl)propyl]amino]-3-pyridinyl]-2-pyrazinamine(Cmd 71)

A mixture of Cmd 67 (prepared as described in Example 6) (0.1 g, 0.2 mmol), 4-(3-chloropropyl)pyridine (0.047 g, 0.3 mmol, Eisch, John JOC 1974, 39(21) 3110–4) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/MeOH as solvent) to give 0.074 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography ($CH_2Cl_2$/MeOH as solvent) to give 0.045 g (91%) of Cmd 71 as a yellow solid; $^1$H NMR (300 MHz, $CD_3OD$) δ8.42 (m, 4H), 8.12 (s, 2H), 7.99 (s, 1H), 7.65 (s, 1H), 7.48 (m, 1H), 7.34 (s, 2H), 7.25 (t, J=8.0 Hz, 1H), 6.97 (d, J=6.7 Hz, 1H), 3.30 (m, 2H), 2.83 (m, 2H), 2.03 (m, 2H); MS (ES) m/z: 417 (M+H$^+$).

EXAMPLE 78

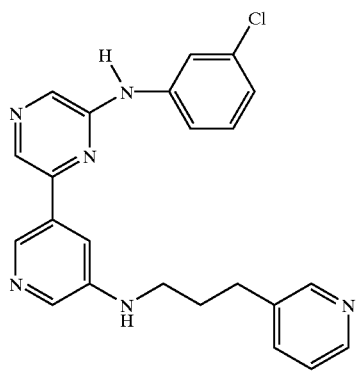

COMPOUND 72

N-(3-chlorophenyl)-6-[5-[[3-(3-pyridinyl)propyl]amino]-3-pyridinyl]-2-[pyrazinamine (Cmd 72)

A mixture of Cmd 67 (prepared as described in Example 6) (0.1 g, 0.2 mmol), 3-(3-chloropropyl)pyridine (0.047 g, 0.3 mmol, Eisch, John, JOC 1974, 39(21), 3110–3114) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO$,) and concentrated. The product was purified by column chromatography ($CH_2Cl_2$/MeOH as solvent) to give 0.093 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography ($CH_2Cl_2$/MeOH as solvent) to give 0.049 g (78%) of Cmd 72 as a yellow solid; $^1$H NMR (300 MHz, $CDCl_3$) δ8.55 (m, 4H), 8.24 (s, 1H), 8.07 (s, 1H), 7.81 (m, 2H), 7.54 (m, 2H), 7.27 (m, 2H), 7.06 (d, J=7.1 Hz, 1H), 3.95 (m, 1H), 3.28 (m, 2H), 2.80 (t, J=7.3 Hz, 2H), 2.05 (m, 2H); MS (ES) m/z: 417 (M+H$^+$). Anal. Calcd. For $C_{23}H_{21}N_6Cl\cdot0.7H_2O$: C, 64.32; H, 5.26; N, 19.57. Found: C, 64.46; H, 4.97; N, 19.25.

EXAMPLE 79

COMPOUND 73

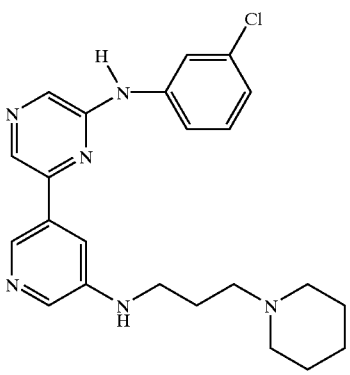

A mixture of Cmd 67 (prepared as described in Example 6) (0.15 g, 0.3 mmol), 1-(3-chloropropyl)piperidine (0.073 g, 0.45 mmol, U.S. Pat. No. 5,414,010) and $Cs_2CO_3$ (0.3 g, 0.9 mmol) in DMF (6 mL) was stirred at 70° C. under nitrogen for 20 h. The reaction mixture was diluted with water, extracted with ether (3×), dried ($Na_2SO_4$) and concentrated. The product was purified by column chromatography ($CH_2Cl_2$/MeOH as solvent) to give 0.12 g of product as an oil. The oil was dissolved in TFA (3.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography ($CH_2Cl_2$/MeOH as solvent) to give 0.067 g (83%) of Cmd 73 as a light yellow solid; $^1$H NMR (300 MHz, $CD_3OD$) δ8.46 (s, 1H), 8.42 (s, 1H), 8.16 (s, 1H), 8.11 (s, 1H), 8.00 (s, 1H), 7.65 (s, 1H), 7.49 (d, J=9.0 Hz, 1H), 7.29 (t, J=8.0 Hz, 1H), 6.99 (d, J=8.0 Hz, 1H) 3.28 (m, 2H), 2.57 (m, 6H), 1.90 (m, 2H), 1.63 (m, 4H), 1.49 (d, J=4.4 Hz, 2H); MS (ES) m/z: 423 (M+H$^+$). Anal. Calcd. For $C_{23}H_{27}N_6Cl.0.7H_2O$: C, 63.42; H, 6.57; N, 19.29. Found: C, 63.21; H, 6.28; N, 18.97.

EXAMPLE 80

COMPOUND 74

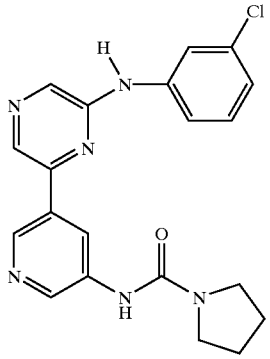

N-[5-[6-[(3-chlorophenyl)amino]pyrazinyl]-3-pyridinyl]-1-pyrrolidinecarboxamide (Cmd 74)

A mixture of Cmd 67 (prepared as described in Example 6) (0.15 g, 0.3 mmol), N-(4-bromobutyl)pyrrolidinium bromide (0.13 g, 0.45 mmol) $Cs_2CO_3$ (0.3 g, 0.9 mmol), and $Et_3N$ (0.06 g, 0.6 mmol) in DMF (6 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.05 g of product as a white solid. The solid was dissolved in TFA (3.0 mL) and stirred at 20° C. for 2 h before concentrated. Ammonium hydroxide solution was added to the residue until the pH was about 10–11 and a yellow solid was formed. The yellow solid was collected through filtration, washed with water and dried under vacuum to give 0.03 g (75%) of Cmd 74 as a yellow solid; $^1$H NMR (300 MHz, $CD_3OD$) δ8.87 (s, 1H), 8.72 (s, 1H), 8.66 (s, 1H), 8.46 (s, 1H), 8.15 (s, 1H), 7.99 (s, 1H), 7.66 (m, 1H), 7.30 (m, 1H), 7.00 (m, 1H), 3.52 (m, 4H), 2.00 (m, 4H); MS (ES) m/z: 395 (M+H$^+$).

EXAMPLE 81

COMPOUND 75

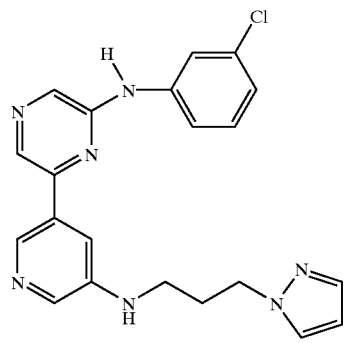

N-(3-chlorophenyl)-6-[5-[[3-(1H-pyrazol-1-yl)propyl]amino]-3-pyrazinyl]-2-pyrazinamine(Cmd 75)

1-Bromo-3-chloropropane (11.3 g, 72 mmol) was added dropwise to a vigorously stirred ice-cooled mixture of pyrazole (5.0 g, 73 mmol), $K_2CO_3$ (10.0 g, 73 mmol) and acetone (95 mL). After 3 h cooling bath was removed and the reaction mixture stirred at 20° C. for 5 days, then filtered. The filtrate was concentrated and product was purified by column chromatography (using EtOAc/hexane as solvent) to give 3.3 g (31%) of Compound 81a as a clear oil; $^1$H NMR (300 MHz, $CDCl_3$) δ7.52 (d, J=1.5 Hz, 1H), 7.42 (d, J=2.1 Hz, 1H), 6.24 (t, J=2.0 Hz, 1H), 4.32 (t, J=6.4 Hz, 2H), 3.45 (t, J=6.0 Hz, 2H), 2.32 (m, 2H); MS (ES) m/z: 145 (M+H$^+$). A mixture of Cmd 67 (prepared as described in Example 6) (0.15 g, 0.3 mmol), 1-(3-chloropropyl)pyrazole Compound 81a (0.065 g, 0.45 mmol) and $Cs_2CO_3$ (0.3 g, 0.9 mmol), in DMF (6 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.12 g of product as an oil. The oil was dissolved in TFA (3.0 mL) and stirred at 20° C. for 2 h before concentrated. Ammonium hydroxide solution was added to the residue until the pH was about 10–11 and a solid was formed. The solid was extracted with $CH_2Cl_2$, dried ($Na_2SO_4$) and concentrated. Product was purified by column chromatography ($CH_2Cl_2$/MeOH as solvent) to give 0.072 g (90%) of Cmd 75 as an off white solid; $^1$H NMR (300 MHz, $CD_3OD$) δ8.43 (s, 2H), 8.10 (d, J=7.9 Hz, 2H), 7.98 (s, 1H), 7.60 (m, 4H), 7.27 (t, J=8.0 Hz, 1H), 6.98 (d, J=7.9 Hz, 1H), 6.26 (s, 1H), 4.31 (t, J=6.7 Hz, 2H), 3.19 (t, J=6.7 Hz, 2H), 2.19 (m, 2H); MS (ES) m/z: 406 (M+H$^+$). Anal. Calcd. For $C_{21}H_{21}N_7Cl.0.3H_2O$ : C, 61.33; H, 5.05; N, 23.84. Found: C, 61.38; H, 4.94; N, 23.75.

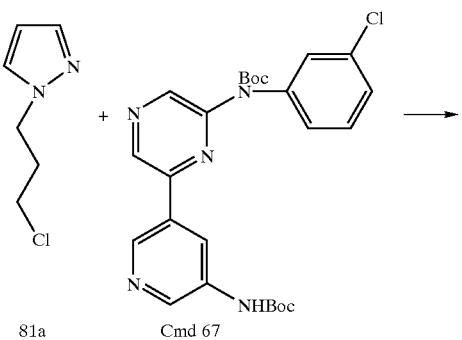

81a  Cmd 67

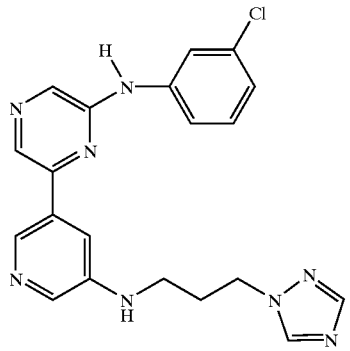

Cmd 75

EXAMPLE 82

COMPOUND 76

N-(3-chlorophenyl)-6-[5-[[3-(1H-1,2,4-triazol-1-yl)propyl]amino]-3-pyridinyl]-2-pyrazinamine(Cmd 76)

1-Bromo-3-chloropropane (11.3 g, 72 mmol) was added dropwise under $N_2$ to a vigorously stirred ice-cooled mixture of 1,2,4-triazole (5.0 g, 72 mmol), $K_2CO_3$ (10.0 g, 73 mmol) and acetone (95 mL). After 3 h, cooling bath was removed and the reaction mixture stirred at 20° C. for 5 days, then filtered. The filtrate was concentrated and product was purified by column chromatography (EtOAc/hexane as solvent) to give 7.1 g (68%) of Compound 82a as a clear oil; $^1$H NMR (300 MHz, CDCl$_3$) δ8.11 (s, 1H), 7.96 (s, 1H), 4.38 (t, J=6.4 Hz, 2H), 3.48 (t, J=6.0 Hz, 2H), 2.35 (m, 2H); MS (ES) m/z: 146 (M+H$^+$). A mixture of Cmd 67 (prepared as described in Example 6) (0.15 g, 0.3 mmol), 1-(3-chloropropyl)-1,2,4-triazole Compound 82a (0.066 g, 0.45 mmol) and $Cs_2CO_3$ (0.3 g, 0.9 mmol), in DMF (6 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.15 g of product as an oil. The oil was dissolved in TFA (3.0 mL) and stirred at 20° C. for 2 h before concentrated. Ammonium hydroxide solution was added to the residue until the pH was about 10–11 and a solid was formed. The solid was then extracted with $CH_2Cl_2$, dried ($Na_2SO_4$) and concentrated. Product was purified by column chromatography ($CH_2Cl_2$/MeOH as solvent) to give 0.086 g (86%) of Cmd 76 as a yellow solid; $^1$H NMR (300 MHz, D$^6$-DMSO) δ9.85 (s, 1H), 8.59 (s, 1H), 8.52 (s, 1H), 8.47 (s, 1H), 8.23 (s, 1H), 8.12 (t, J=1.9 Hz, 1H), 8.08 (d, J=2.6 Hz, 1H), 7.96 (s, 1H), 7.59 (d, J=9.5 Hz, 1H), 7.47 (s, 1H), 7.33 (t, J=8.1 Hz, 1H), 7.02 (dd, J=7.7, 1.6 Hz, 1H), 6.23 (t, J=5.5 Hz, 1H), 4.33 (t, J=6.9 Hz, 1H), 3.15 (m, 2H), 2.12 (m, 2H); MS (ES) m/z: 407 (M+H$^+$). Anal. Calcd. For $C_{20}H_{19}N_8Cl\cdot 0.4H_2O$ : C, 58.01; H, 4.82; N, 27.06. Found: C, 58.25; H, 4.67; N, 26.90.

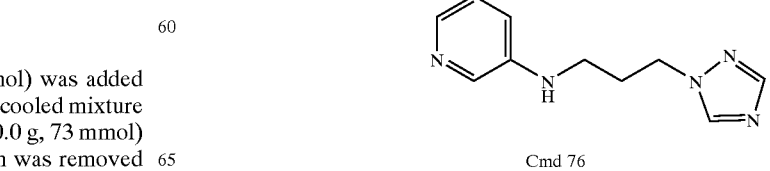

82a  Cmd 67

Cmd 76

EXAMPLE 83

COMPOUND 77

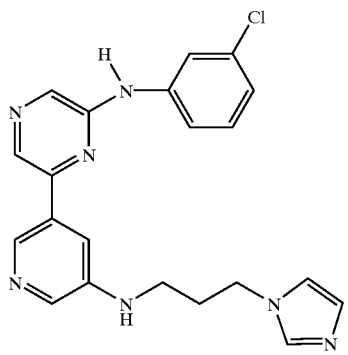

N-(3-chlorophenyl)-6-[5-[[3-(1H-imidazol-1-yl)propyl]amino]-
3-pyridinyl]-2-pyrazinamine(Cmd 77)

A mixture of Cmd 67 (prepared as described in Example 6) (0.15 g, 0.3 mmol), 1-(3-chloropropyl)imidazole (0.065 g, 0.45 mmol) and $Cs_2CO_3$ (0.3 g, 0.9 mmol), in DMF (6 mL) was stirred at 70° C. under nitrogen for 20 h. The reaction mixture was diluted with water, extracted with ether (3×), dried ($Na_2SO_4$) and concentrated. The product was purified by column chromatography (EtOAc/MeOH as solvent) to give 0.15 g of product as an oil. The oil was dissolved in TFA (3.0 mL) and stirred at 20° C. for 2 h before concentrated. Ammonium hydroxide solution was added to the residue until the pH was about 10–11 and a yellow solid was formed. The yellow solid was collected through filtration, washed with water and dried under vacuum to to give 0.064 g (64%) of Cmd 77 as a yellow solid; $^1H$ NMR (300 MHz, $CD_3OD$) δ8.42 (s, 2H), 8.00 (m, 4H), 7.58 (s, 1H), 7.48 (d, J=8.2 Hz, 1H), 7.26 (t, J=8.0 Hz, 2H), 7.07 (brs, 1H), 6.98 (d, J=7.4 Hz, 1H), 4.23 (t, J=6.8 Hz, 2H), 3.22 (t, J=6.5 Hz, 2H), 2.18 (m, 2H); MS (ES) m/z: 406 (M+H$^+$).

EXAMPLE 84

COMPOUND 78

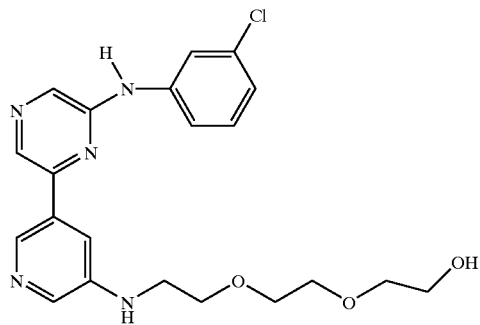

2-[2[2[[5-[6-[(3-chlorophenyl)amino]pyrazinyl]-
3-pyridinyl]amino]ethoxy]-ethanol(Cmd 78)

A mixture of Cmd 67 (prepared as described in Example 6) (0.1 g, 0.2 mmol), (2-chloroethoxy)ethoxyethanol (0.05 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.03 g of product as an oil. The oil was dissolved in TFA (2.0 mL) and stirred at 20° C. for 2 h before concentrated. Ammonium hydroxide solution was added to the residue until the pH was about 10–111 and a yellow solid was formed. The yellow solid was collected through filtration, washed with water and dried under vacuum to give 0.012 g (60%) of Cmd 78 as a light yellow solid; $^1H$ NMR (300 MHz, $D^6$-DMSO) δ9.87 (s, 1H), 8.60 (s, 1H), 8.47 (s, 1H), 8.23 (s, 1HI), 8.13 (d, J=8.3 Hz, 2H), 7.59 (m, 2H), 7.37 (t, J=8.0 Hz, 1H), 7.04 (d, J=7.7 Hz, 1H), 6.18 (brs, 1H), 3.63 (t, J=5.4 Hz, 2H), 3.54 (dd, J=10.0, 3.6 Hz, 4H), 3.44 (m, 6H); MS (ES) m/z: 430 (M+H$^+$).

EXAMPLE 85

COMPOUND 79

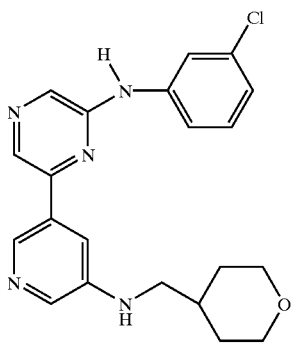

N-(3-chlorophenyl)-6-[5-[[(tetrahydro-2H-pyran-4-yl)methyl]amino]-
3-pyridinyl]-2-pyrazinamine(Cmd 79)

A mixture of Cmd 67 (prepared as described in Example 6) (0.1 g, 0.2 mmol), tetrahydropyranyl-4-methanesulfonate ester (0.04 g, 0.3 mmol, Caldwell, William WO9900385) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.062 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography (EtOAc/MeOH as solvent) to give 0.034 g (83%) of Cmd 79 as an off white solid; $^1H$ NMR (300 MHz, $CDCl_3$) δ8.53 (m, 2H), 8.17 (s, 1H), 8.10 (d, J=2.6 Hz, 1H), 7.90 (brs, 1H), 7.53 (t, J=2.2 Hz, 1H), 7.29 (m, 2H), 7.07 (m, 1H), 6.69 (s, 1H), 4.02 (dd, J=11.3, 4.3 Hz, 2H), 3.92 (brs, 1H), 3.40 (td, J=11.9, 1.8 Hz, 2H), 3.17 (t, J=6.0 Hz, 2H), 1.90 (m, 1H), 1.74 (brd, J=12.8 Hz, 2H), 1.42 (qd, J=12.2, 4.2 Hz, 2H); MS (ES) m/z: 396 (M+H$^+$). Anal. Calcd. For $C_{21}H_{22}N_5ClO \cdot 0.2H_2O$ : C, 63.14; H, 5.65; N, 17.53. Found: C, 62.87; H, 5.47; N, 17.54.

EXAMPLE 86

COMPOUND 80

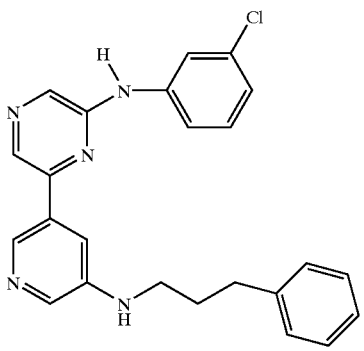

A mixture of Cmd 67 (prepared as described in Example 6) (0.1 g, 0.2 mmol), 1-chloro-3-phenylpropane (0.047 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc as solvent) to give 0.070 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography ($CH_2Cl_2$/Hexane solvent) to give 0.022 g (47%) of Cmd 80 as an off white solid; $^1$H NMR (300 MHz, $D^6$-DMSO) δ9.85 (s, 1H), 8.58 (s, 1H), 8.45 (brs, 1H), 8.22 (s, 1H), 8.16 (s, 1H), 8.09 (brs, 1H), 7.56 (d, J=8.0 Hz, 1H), 7.47 (s, 1H), 7.26 (m, 6H), 7.02 (d, J=7.9 Hz, 1H), 6.19 (t, J=5.5 Hz, 1H), 3.17 (m, 2H), 2.72 (t, J=7.4 Hz, 2H), 1.89 (m, 2H); MS (ES) m/z: 416 (M+H$^+$). Anal. Calcd. For $C_{24}H_{22}N_5Cl.0.1H_2O$: C, 69.01; H, 5.36; N, 16.77. Found: C, 68.64; H, 5.22; N, 16.49.

EXAMPLE 87

COMPOUND 81

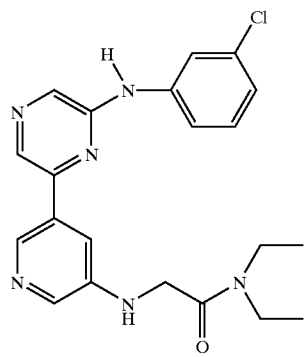

A mixture of Cmd 67 (prepared as described in Example 6) (0.1 g, 0.2 mmol), 2-chloro-N,N-diethylacetamide (0.045 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.1 g of product as an oil. The oil was dissolved in TFA (2.0 mL) and stirred at 20° C. for 2 h before concentrated. Ammonium hydroxide solution was added to the residue until the pH was about 10–11 and a yellow solid was formed. The aqueous layer was extracted with $CH_2Cl_2$. The yellow solid went into the organic layer and was dried ($Na_2SO_4$) and concentrated. Product was purified by column chromatography (EtOAc/MeOH as solvent) to give 0.042 g (63%) of Cmd 81 as a yellow solid; $^1$H NMR (300 MHz, CDCl$_3$) δ8.57 (s, 1H), 8.51 (s, 1H), 8.18 (s, 1H), 8.15 (d, J=2.6 Hz, 1H), 7.84 (t, J=2.0 Hz, 1H), 7.48 (t, J=2.0 Hz, 1H), 7.32 (m, 2H), 7.05 (d, J=7.8 Hz, 1H), 6.84 (s, 1H), 5.26 (brs, 1H), 3.97 (d, J=4.1 Hz, 2H), 3.48 (q, J=7.1 Hz, 2H), 3.35 (q, J=7.1 Hz, 2H), 1.26 (t, J=7.1 Hz, 6H); MS (ES) m/z: 411 (M+H$^+$).

EXAMPLE 88

COMPOUND 82

A mixture of Cmd 67 (prepared as described in Example 6) (0.1 g, 0.2 mmol), benzyl bromide (0.05 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Hexane as solvent) to give 0.025 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was triturated with $CH_2Cl_2$/Hexane to give clean product 0.011 g (69%) of Cmd 82 as a yellow solid; $^1$H NMR (300 MHz, CDCl$_3$) δ8.58 (s, 1H), 8.48 (s, 1H), 8.15 (d, J=4.9 Hz, 2H), 7.85 (s, 1H), 7.57 (s, 1H), 7.35 (m, 6H), 7.05 (d, J=6.8 Hz, 2H), 6.67 (brs, 1H), 4.46 (d, J=5.4 Hz, 2H), 4.26 (brs, 1H); MS (ES) m/z: 388 (M+H$^+$).

EXAMPLE 89

COMPOUND 83

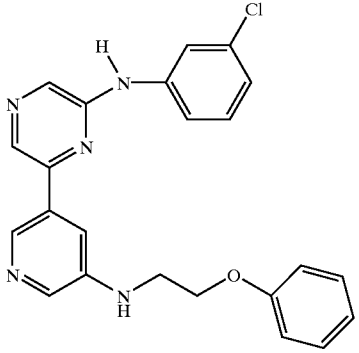

A mixture of Cmd 67 (prepared as described in Example 6) (0.1 g, 0.2 mmol), beta-bromophenetole (0.061 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc as solvent) to give 0.12 g of product as an oil. The oil was dissolved in TFA (2.0 mL) and stirred at 20° C. for 2 h before being concentrated. Ammonium hydroxide solution was added to the residue until the pH was about 10–11 and a yellow solid was formed. The aqueous layer was extracted with $CH_2Cl_2$. The yellow solid went into the organic layer and was dried ($Na_2SO_4$) and concentrated. Product was triturated with $CH_2Cl_2$ to give clean product 0.055 g (68%) of Cmd 83 as a yellow solid; $^1$H NMR (300 MHz, $D^6$-DMSO) δ9.85 (s, 1H), 8.61 (s, 1H), 8.49 (s, 1H), 8.23 (s, 1H), 8.14 (s, 1H), 7.66 (m, 2H), 7.31 (m, 3H), 6.98 (m, 4H), 6.39 (brs, 1H), 4.19 (t, J=5.2 Hz, 2H), 3.59 (d, J=5.3 Hz, 2H); MS (ES) m/z: 418 (M+H$^+$). Anal. Calcd. For $C_{23}H_{20}N_5ClO \cdot 0.2 H_2O$ : C, 65.54; H, 4.88; N, 16.62. Found: C, 65.35; H, 4.72; N, 16.32.

EXAMPLE 90

COMPOUND 84

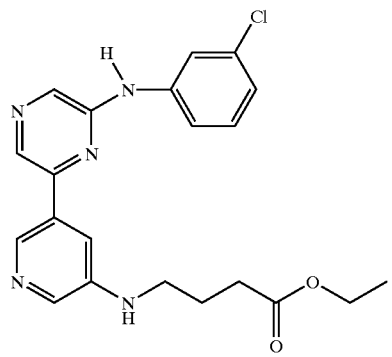

4-[[5-[6-[(3-chlorophenyl)amino]pyrazinyl]-3-pyridinyl]amino]-butanoic acid ethyl ester (Cmd 84)

A mixture of Cmd 67 (prepared as described in Example 6) (0.1 g, 0.2 mmol), ethyl-4-bromobutyrate (0.059 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.013 g of product as an oil. The oil was dissolved in TFA (2.0 mL) and stirred at 20° C. for 2 h before concentrated. Ammonium hydroxide solution was added to the residue until the pH was about 10–11 and a solid was formed. The aqueous layer was extracted with $CH_2Cl_2$. The yellow solid went into the organic layer and was dried ($Na_2SO_4$) and concentrated. Product was triturated with $CH_2Cl_2$/Hexane to give clean product 0.004 g (46%) of Cmd 84 as an off white solid; $^1$H NMR (300 MHz, $CDCl_3$) δ8.53 (m, 2H), 8.17 (s, 1H), 8.09 (brs, 1H), 7.86 (s, 1H), 7.54 (s, 1H), 7.33 (m, 2H), 7.06 (m, 1H), 6.69 (s, 1H), 4.15 (q, J=7.1 Hz, 2H), 4.08 (brs, 1H), 3.32 (m, 2H), 2.47 (t, J=7.0 Hz, 2H) 2.03 (m, 2H), 1.26 (t, J=7.2 Hz, 3H); MS (ES) m/z: 412 (M+H$^+$).

EXAMPLE 91

COMPOUND 85

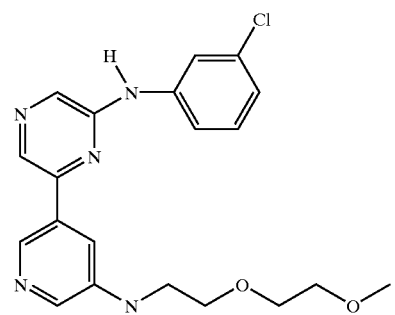

N-(3-chlorophenyl)-6-[5-[[2-(2-methoxyethoxy)ethyl]amino]-3-pyridinyl]-2-pyrazinamine (Cmd 85)

A mixture of Cmd 67 (prepared as described in Example 6) (0.1 g, 0.2 mmol), 1-bromo-2-(2-methoxyethoxy)ethane (0.055 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.1 g of product as an oil. The oil was dissolved in TFA (2.0 mL) and stirred at 20° C. for 2 h before concentrated. Ammonium hydroxide solution was added to the residue until the pH was about 10–11 and a solid was formed. The aqueous layer was extracted with $CH_2Cl_2$. The yellow solid went into the organic layer and was dried ($Na_2SO_4$) and concentrated. Product was purified by column chromatography (EtOAc/Acetone as solvent) to give 0.058 g (87%) of Cmd 85 as a light yellow solid; $^1$H NMR (300 MHz, $D^6$-DMSO) δ9.85 (s, 1H), 8.60 (s, 1H), 8.47 (brs, 1H), 8.23 (s, 1H), 8.14 (s, 1H), 7.59 (m, 2H), 7.37 (t, J=8.0 Hz, 1H), 7.03 (d, J=8.0 Hz, 1H), 6.16 (brs, 1H), 3.63 (t, J=5.6 Hz, 2H), 3.56 (m, 2H), 3.45 (m, 2H), 3.32 (m, 2H), 3.22 (s, 3H); MS (ES) m/z: 400 (M+H$^+$). Anal. Calcd. For $C_{20}H_{22}N_5ClO_2$: C, 60.07; H, 5.55; N, 17.51. Found: C, 59.92; H, 5.41; N, 17.40.

EXAMPLE 92

COMPOUND 86

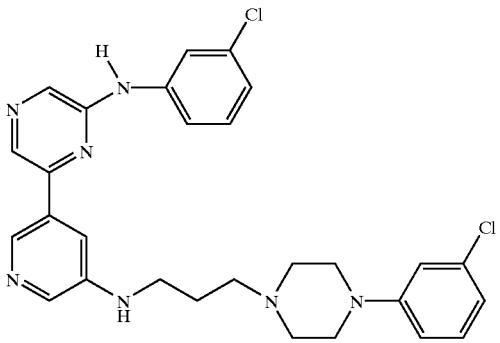

A mixture of Cmd 67 (prepared as described in Example 6) (0.1 g, 0.2 mmol), 1-(3-chlorophenyl)-4-(3-chloropropyl) piperazine (0.093 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product was purified by column chromatography (EtOAc/Acetone as solvent) to give 0.078 g of product as an oil. The oil was dissolved in TFA (2.0 mL) and stirred at 20° C. for 2 h before concentrated. Ammonium hydroxide solution was added to the residue until the pH was about 10–11. The aqueous layer was extracted with $CH_2Cl_2$, dried ($Na_2SO_4$) and concentrated. Product was purified by column chromatography (EtOAc/MeOH as solvent) to give 0.042 g (75%) of Cmd 86 as a light yellow solid; $^1H$ NMR (300 MHz, $CDCl_3$) δ8.51 (s, 2H), 8.15 (s, 1H), 8.08 (s, 1H), 7.91 (s, 1H), 7.54 (s, 1H), 7.26 (m, 2H), 7.15 (t, J=8.0 Hz, 1H), 7.04 (m, 1H), 6.79 (m, 4H), 5.06 (brs, 1H), 3.37 (t, J=6.1 Hz, 2H), 3.20 (t, J=5.0 Hz, 4H), 2.60 (m, 6H), 1.89 (m, 2H); MS (ES) m/z: 534 (M+H+).

EXAMPLE 93

COMPOUND 87

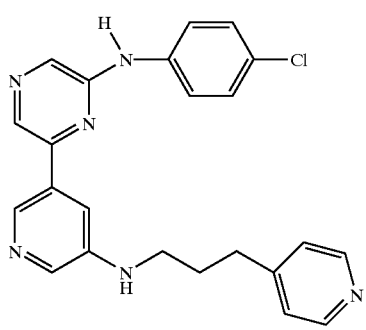

A mixture of Compound 1D (2.7 g, 10.24 mmol), 4-chloroaniline (1.3 g, 15.35 mmol), $Pd_2(dba)_3$ (0.265 g, 0.26 mmol), DPPF (0.45 g, 0.81 mmol), $Cs_2CO_3$ (6.67 g, 24.48 mmol) in anhydrous dioxane (50 mL) was stirred at 100° C. overnight under nitrogen. Dichloromethane (100 mL) was added to the cooled reaction mixture, which was then filtered through celite. The celite cake was washed with more dichloromethane and the combined filtrate was concentrated to give a yellow solid. The solid was purified by column chromatography (EtOAc/hexane as solvent) to give 2.0 g (56%) of Compound 93a as a yellow solid; $^1H$ NMR (300 MHz, $CDCl_3$) δ9.40 (d, J=2.1 Hz, 1H), 9.29 (d, J=1.9 Hz, 1H), 8.87 (t, J=2.0 Hz, 1H), 8.55 (s, 1H), 8.22 (s, 1H), 7.52 (d, J=8.7 Hz, 2H), 7.35 (d, J=8.7 Hz, 2H), 6.71 (s, 1H), 4.47 (q, J=7.1 Hz, 2H), 1.44 (t, J=7.1 Hz, 3H); MS (ES) m/z: 355 (M+H+). Compound 93a (1.5 g, 4.2 mmol) was dissolved in $CH_2Cl_2$ (80 mL), and treated with $Boc_2O$ (1.8 g, 8.4 mmol) and DMAP (catalytic amount). The reaction mixture was stirred at 20° C. under nitrogen for 2 h. The solvent was removed under vacuum and the product was purified by column chromatography (EtOAc/Hex as solvent) to give 1.23 g (65%) of Compound 93b as a hard foam. $^1H$ NMR (300 MHz, $CDCl_3$) δ9.25 (d, J=2.0 Hz, 1H), 9.16 (d, J=1.9 Hz, 1H), 9.10 (s, 1H), 8.82 (s, 1H), 8.62 (t, J=2.0 Hz, 1H), 7.40 (d, J=8.8 Hz, 2H), 7.18 (d, J=8.7 Hz, 2H), 4.45 (q, J=7.1 Hz, 2H), 1.50 (s, 9H), 1.44 (t, J=7.1 Hz, 3H); MS (ES) m/z: 455 (M+H+).

Compound 93b (1.23 g, 2.7 mmol) was treated with MeOH (26 mL). After 3 min 1 N NaOH$_{(aq)}$ (22 mL) was added and the reaction mixture was stirred at 20° C. for 4 h. Glacial acetic acid and water were added to the reaction mixture until a yellow solid was formed. The solid was filtered and washed with water and dried under vacuum to give 1.08 g (94%) of Compound 93c as a yellow solid. Compound 93c (0.5 g, 1.12 mmol), $Et_3N$ (0.24 g, 2.3 mmol), DPPA (1.44 mol), and t-BuOH (5 mL) in toluene (4 mL) was stirred at 70° C. for 40 min under $N_2$ and then at 100° C. for 4 h. The solvent was removed under reduced pressure and product was purified by column chromatography (EtOAc/Hex as solvent) to give 0.32 g (55%) of Compound 93d as a hard foam; $^1H$ NMR (300 MHz, $CDCl_3$) δ9.02 (s, 1H), 8.78 (s, 1H), 8.68 (d, J=1.8 Hz, 1H), 8.44 (d, J=2.4 Hz, 2H), 7.38 (d, J=8.7 Hz, 2H), 7.22 (d, J=8.7 Hz, 2H), 6.56 (brs, 1H), 1.55 (s, 9H), 1.48 (s, 9H); MS (ES) m/z: 498 (M+H+).

A mixture of Compound 93d (0.1 g, 0.2 mmol), 4-(3-chloropropyl)pyridine (0.047 g, 0.3 mmol) and $Cs_2CO_3$ (0.197 g, 0.6 mmol) in DMF (4 mL) was stirred at 70° C. under nitrogen for 20 h. The reaction mixture was diluted with water, extracted with ether (3×), dried ($Na_2SO_4$) and concentrated. The product Compound 93e was purified by column chromatography (EtOAc/MeOH as solvent) to give 0.071 g (59%) of product as an oil. The oil was dissolved in TFA (2.0 mL) and stirred at 20° C. for 2 h before being concentrated. Ammonium hydroxide solution was added to the residue until the pH was about 10–11 and a solid was formed. The yellow solid was collected through filtration, washed with water and dried. Clean product was obtained by recrystallization ($CH_2Cl_2$/Hexane) to give 0.038 g (79%) of Cmd 87 as a light yellow solid; $^1H$ NMR (300 MHz, $CD_3OD$) δ8.39 (m, 4H), 8.10 (s, 1H), 7.98 (s, 1H), 7.77 (m, 2H), 7.61 (s, 1H), 7.33 (d, J=6.1 Hz, 2H), 7.27 (dd, J=6.9,2.1 Hz, 2H), 3.25 (t, J=6.8 Hz, 2H), 2.84 (t, J=7.6 Hz, 2H), 2.04 (m, 2H); MS (ES) m/z: 417 (M+H+).

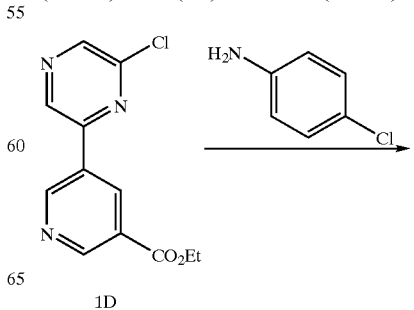

1D

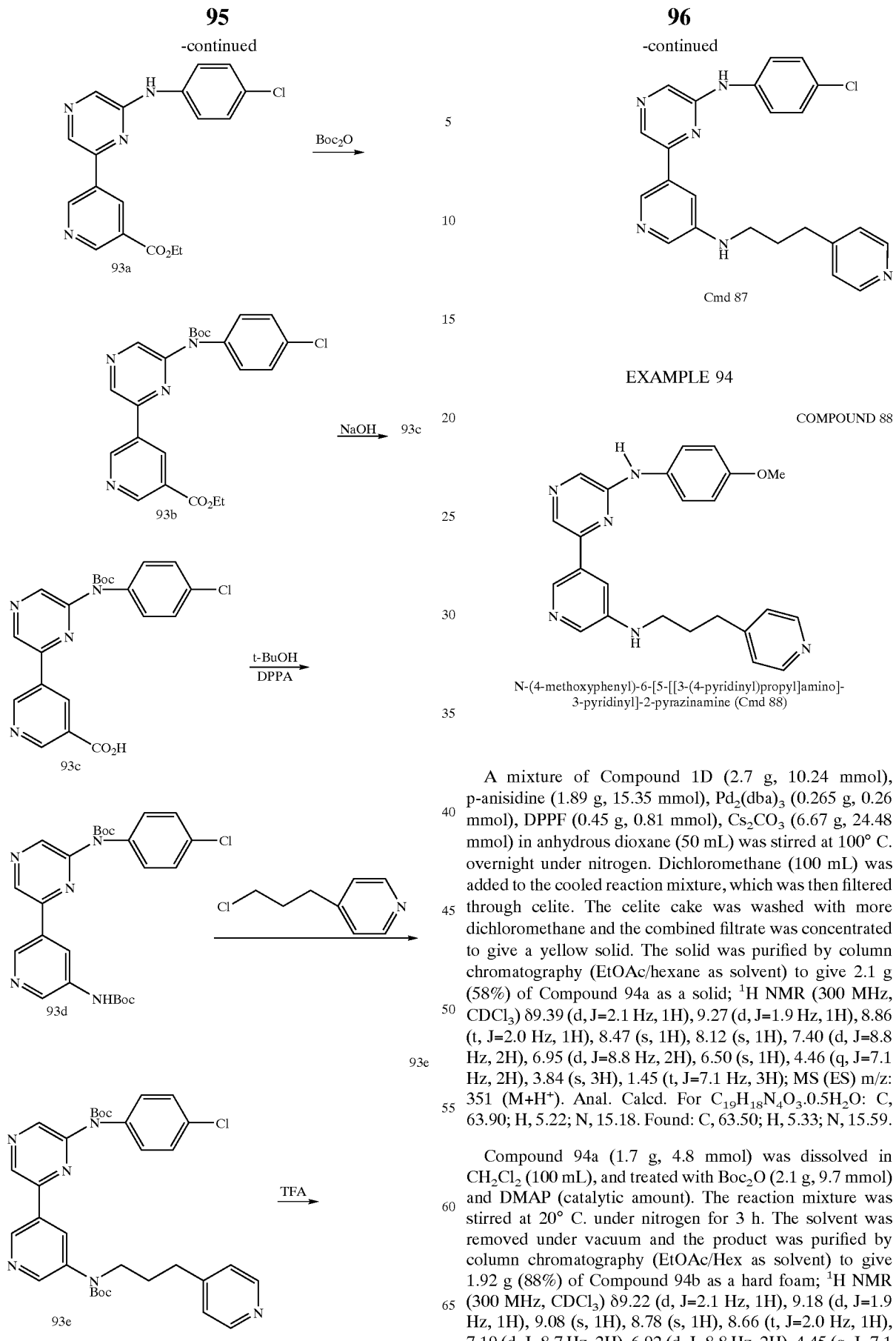

EXAMPLE 94

COMPOUND 88

N-(4-methoxyphenyl)-6-[5-[[3-(4-pyridinyl)propyl]amino]-3-pyridinyl]-2-pyrazinamine (Cmd 88)

A mixture of Compound 1D (2.7 g, 10.24 mmol), p-anisidine (1.89 g, 15.35 mmol), $Pd_2(dba)_3$ (0.265 g, 0.26 mmol), DPPF (0.45 g, 0.81 mmol), $Cs_2CO_3$ (6.67 g, 24.48 mmol) in anhydrous dioxane (50 mL) was stirred at 100° C. overnight under nitrogen. Dichloromethane (100 mL) was added to the cooled reaction mixture, which was then filtered through celite. The celite cake was washed with more dichloromethane and the combined filtrate was concentrated to give a yellow solid. The solid was purified by column chromatography (EtOAc/hexane as solvent) to give 2.1 g (58%) of Compound 94a as a solid; $^1$H NMR (300 MHz, $CDCl_3$) δ9.39 (d, J=2.1 Hz, 1H), 9.27 (d, J=1.9 Hz, 1H), 8.86 (t, J=2.0 Hz, 1H), 8.47 (s, 1H), 8.12 (s, 1H), 7.40 (d, J=8.8 Hz, 2H), 6.95 (d, J=8.8 Hz, 2H), 6.50 (s, 1H), 4.46 (q, J=7.1 Hz, 2H), 3.84 (s, 3H), 1.45 (t, J=7.1 Hz, 3H); MS (ES) m/z: 351 (M+H$^+$). Anal. Calcd. For $C_{19}H_{18}N_4O_3 \cdot 0.5H_2O$: C, 63.90; H, 5.22; N, 15.18. Found: C, 63.50; H, 5.33; N, 15.59.

Compound 94a (1.7 g, 4.8 mmol) was dissolved in $CH_2Cl_2$ (100 mL), and treated with $Boc_2O$ (2.1 g, 9.7 mmol) and DMAP (catalytic amount). The reaction mixture was stirred at 20° C. under nitrogen for 3 h. The solvent was removed under vacuum and the product was purified by column chromatography (EtOAc/Hex as solvent) to give 1.92 g (88%) of Compound 94b as a hard foam; $^1$H NMR (300 MHz, $CDCl_3$) δ9.22 (d, J=2.1 Hz, 1H), 9.18 (d, J=1.9 Hz, 1H), 9.08 (s, 1H), 8.78 (s, 1H), 8.66 (t, J=2.0 Hz, 1H), 7.19 (d, J=8.7 Hz, 2H), 6.92 (d, J=8.8 Hz, 2H), 4.45 (q, J=7.1

Hz, 2H), 3.83 (s, 3H), 1.49 (s, 9H), 1.44 (t, J=7.1 Hz, 3H); MS (ES) m/z: 451 (M+H⁺). Compound 94b (1.92 g, 4.2 mmol) was treated with MeOH (40 mL). After 3 min, 1 N NaOH$_{(aq)}$ (32 mL) was added and the reaction mixture was stirred at 20° C. for 4 h. Glacial acetic acid (25 mL) was added to the reaction mixture along with water until a yellow solid was formed. The solid was filtered and washed with water and then dried under vacuum to give 1.69 g (94%) of Compound 94c as a yellow solid. Compound 94c (0.5 g, 1.2 mmol), Et$_3$N (0.24 g, 2.3 mmol), DPPA (1.44 mol), and t-BuOH (5 mL) in toluene (8 mL) was stirred at 70° C. for 40 min under N$_2$ and then at 100° C. for 2 h. The solvent was removed under reduced pressure and product was was purified by column chromatography (EtOAc/Hex as solvent) to give 0.45 g (77%) of Compound 94d as a hard foam; ¹H NMR (300 MHz, CDCl$_3$) δ8.96 (s, 1H), 8.74 (s, 1H), 8.70 (d, J=1.7 Hz, 1H), 8.48 (d, J=2.4 Hz, 1H), 8.36 (brs, 1H), 7.20 (d, J=8.8 Hz, 2H), 6.92 (d, J=8.8 Hz, 2H), 6.56 (brs, 1H), 3.82 (s, 3H), 1.54 (s, 9H), 1.47 (s, 9H); MS (ES) m/z: 494 (M+H⁺).

A mixture of Compound 94d (0.15 g, 0.3 mmol), 4-(3-chloropropyl)pyridine (0.07 g, 0.45 mmol) and Cs$_2$CO$_3$ (0.3 g, 0.9 mmol) in DMF (6 mL) was stirred at 70° C. under nitrogen for 20 h. The reaction mixture was diluted with water, extracted with ether (3×), dried (Na$_2$SO$_4$) and concentrated. The product Compound 94e was purified by column chromatography (EtOAc/MeOH as solvent) to give 0.122 g (66%) of product as an oil. The oil was dissolved in TFA (2.0 mL) and stirred at 20° C. for 2 h before concentrated. Ammonium hydroxide solution was added to the residue until the pH was about 10–11 and a solid was formed. The yellow solid was collected through filtration, washed with water and dried. Clean product was obtained by recrystallization (CH$_2$Cl$_2$/Hexane) to give 0.063 g (77%) of Cmd 88 as a light yellow solid; ¹H NMR (300 MHz, CD$_3$OD) δ8.39 (d, J=4.4 Hz, 3H), 8.30 (s, 1H), 8.01 (s, 1H), 7.96 (d, J=2.5 Hz, 1H), 7.62 (m, 3H), 7.31 (d, J=5.8 Hz, 2H), 6.89 (d, J=9.0 Hz, 2H), 3.76 (s, 3H), 3.31 (t, J=1.5 Hz, 2H), 2.82 (t, J=7.3 Hz, 2H), 2.03 (m, 2H); MS (ES) m/z: 413 (M+H⁺).

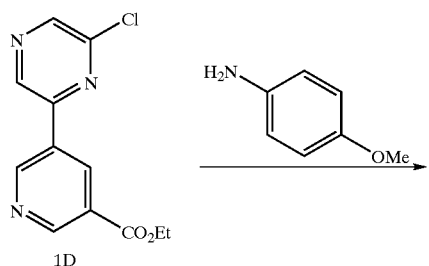

1D

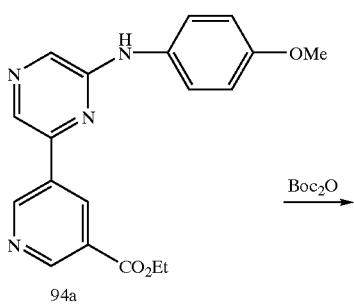

94a

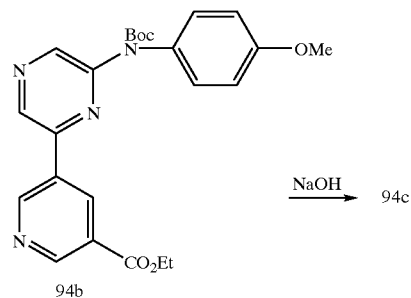

94b

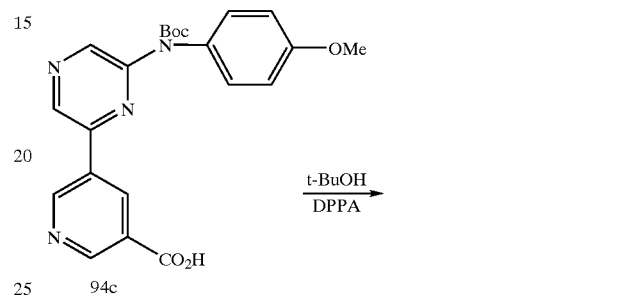

94c

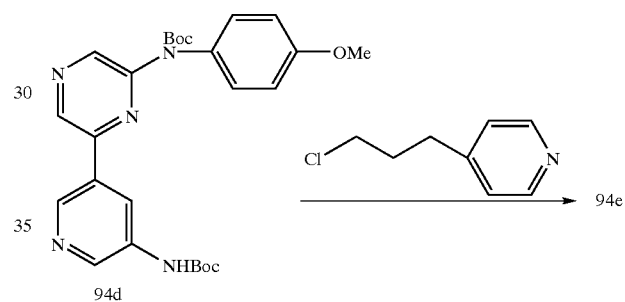

94d

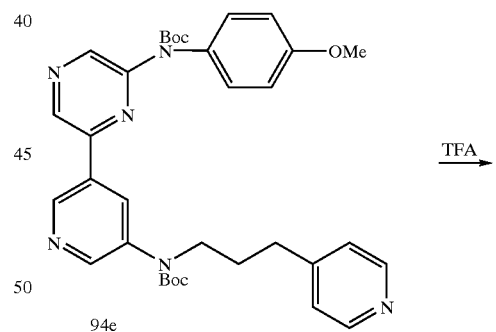

94e

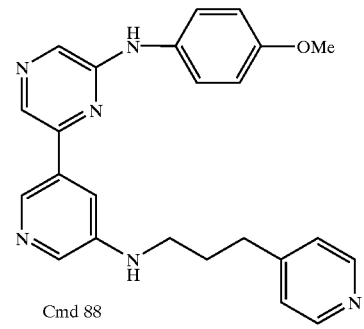

Cmd 88

EXAMPLE 95

COMPOUND 89

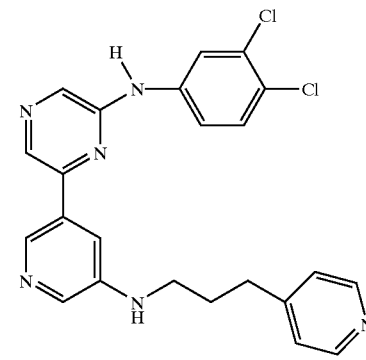

N-(3,4-dichlorophenyl)-6-[5-[[3-(4-pyridinyl)propyl]amino]-3-pyridinyl]-2-pyrazinamine (Cmd 89)

A mixture of Compound 1D (2.7 g, 10.24 mmol), 3,4-dichloroaniline (1.89 g, 15.35 mmol), PQ(dba)$_3$ (0.265 g, 0.26 mmol), DPPF (0.45 g, 0.81 mmol), Cs$_2$CO$_3$ (6.67 g, 24.48 mmol) in anhydrous dioxane (50 mL) was stirred at 100° C. overnight under nitrogen. Dichloromethane (100 mL) was added to the cooled reaction mixture, which was then filtered through celite. The celite cake was washed with more dichloromethane and the combined filtrate was concentrated to give a yellow solid. The solid was purified by column chromatography (EtOAc/hexane as solvent) to give 1.0 g (24%) of Compound 95a as a solid. Compound 95a (0.86 g, 1.77 mmol) was dissolved in CH$_2$Cl$_2$ (35 mL), and treated with Boc$_2$O (0.76 g, 3.54 mmol) and DMAP (catalytic amount). The reaction mixture was stirred at 20° C. under nitrogen for 3 h. The solvent was removed under vacuum and the product was purified by column chromatography (EtOAc/Hex as solvent) to give 1.0 g (93%) of Compound 95b as a hard foam; $^1$H NMR (300 MHz, CDCl$_3$) δ9.24 (d, J=1.8 Hz, 1H), 9.16 (d, J=2.1 Hz, 1H), 9.09 (s, 1H), 8.85 (s, 1H), 8.63 (t, J=2.0 Hz, 1H), 7.50 (d, J=8.5 Hz, 1H), 7.40 (d, J=2.4 Hz, 1H), 7.14 (dd, J=8.0, 1.9 Hz, 1H), 4.44 (q, J=7.1 Hz, 2H), 1.49 (s, 9H), 1.43 (t, J=7.1 Hz, 3H); MS (ES) m/z: 489 (M+H$^+$).

Compound 95b (0.45 g, 0.92 mmol) was treated with MeOH (10 mL). After 3 min 1 N NaOH$_{(aq)}$ (8 mL) was added and the reaction mixture was stirred at 20° C. for 4 h. Glacial acetic acid (7 mL) acid was added to the reaction mixture along with water until a yellow solid was formed. The solid was filtered and washed with water and dried under vacuum to give 0.38 g (90%) of Compound 95c as a yellow solid. Compound 95c (0.38 g, 0.83 mmol), Et$_3$N (0.17 g, 1.7 mmol), DPPA (1.06 mol), and t-BuOH (3.7 mL) in toluene (3 mL) was stirred at 70° C. for 40 min under N$_2$ and then at 100° C. for 3 h. The solvent was removed under reduced pressure and product was purified by column chromatography (EtOAc/Hex as solvent) to give 0.099 g (23%) of Compound 95d as a hard foam; $^1$H NMR (300 MHz, CDCl$_3$) δ8.99 (s, 1H), 8.81 (s, 1H), 8.69 (brs, 1H), 8.45 (brs, 2H), 7.49 (d, J=8.6 Hz, 1H), 7.40 (d, J=2.4 Hz, 1H), 7.16 (dd, J=8.6 2.4 Hz, 1H), 6.59 (brs, 1H), 1.54 (s, 9H), 1.49 (s, 9H); MS (ES) m/z: 532 (M+H$^+$).

A mixture of Compound 95d (0.1 g, 0.2 mmol), 4-(3-chloropropyl)pyridine (0.047 g, 0.3 mmol) and Cs$_2$CO$_3$ (0.19 g, 0.6 mmol) in DMF (4 mL) was stirred at 70° C. under nitrogen for 20 h. The reaction mixture was diluted with water, extracted with ether (3×), dried (Na$_2$SO$_4$) and concentrated. The product Compound 95e was purified by column chromatography (EtOAc/Acetone as solvent) to give 0.051 g (39%) of product as an oil. The oil was dissolved in TFA (3.0 mL) and stirred at 20° C. for 2 h before concentrated. Ammonium hydroxide solution was added to the residue until the pH was about 10–11 and a solid was formed. The yellow solid was collected through filtration, washed with water and dried to give 0.010 g (29%) of Cmd 89 as a light yellow solid; $^1$H NMR (300 MHz, D$^6$-DMSO) δ9.97 (s, 1H), 8.62 (s, 1H), 8.46 (s, 2H), 8.34 (d, J=2.1 Hz, 1H), 8.23 (s, 1H), 8.08 (s, 1H), 7.58 (m, 3H), 7.31 (m, 2H), 3.18(m, 2H), 2.76(t, J=7.7 Hz, 2H), 1.93(m, 2H); MS (ES) m/z: 451 (M+H$^+$).

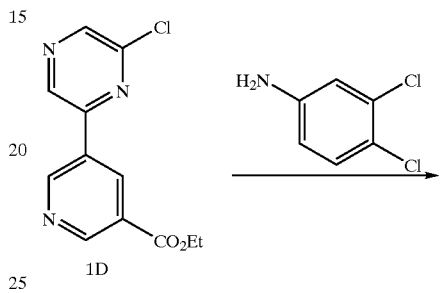

1D

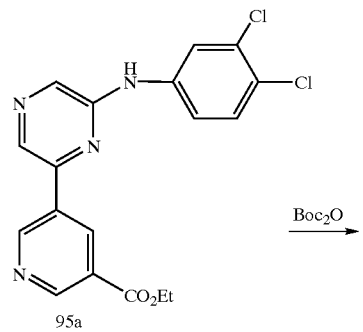

95a

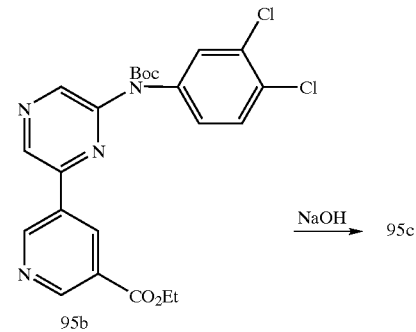

95b

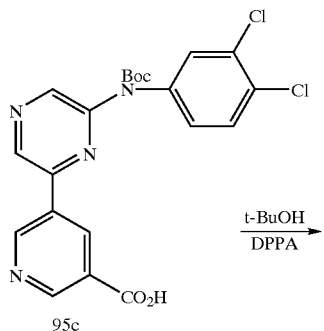

95c

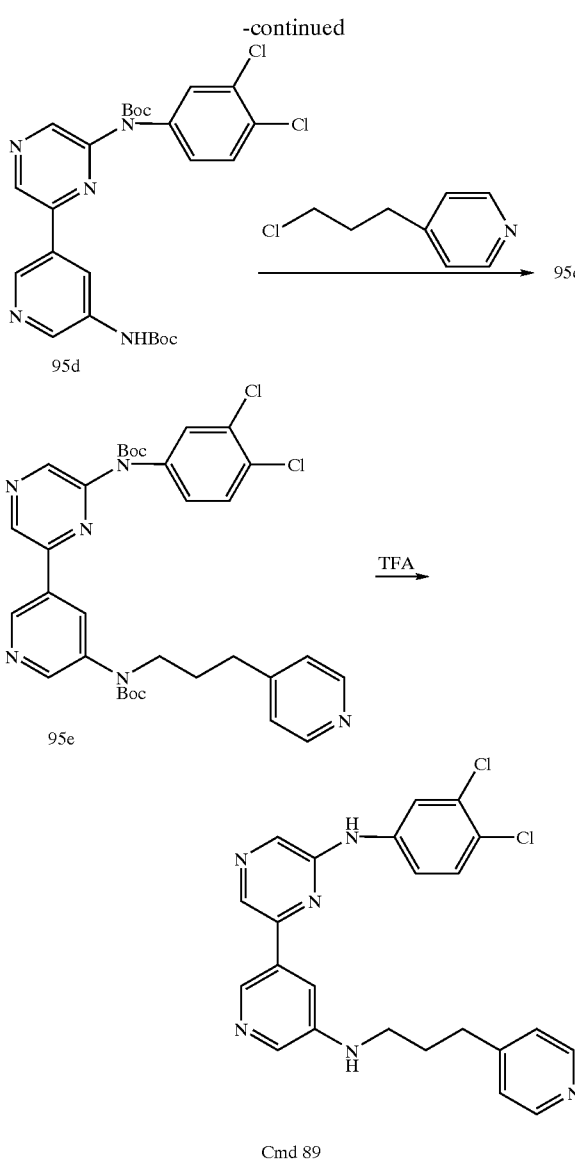

EXAMPLE 96

COMPOUND 90

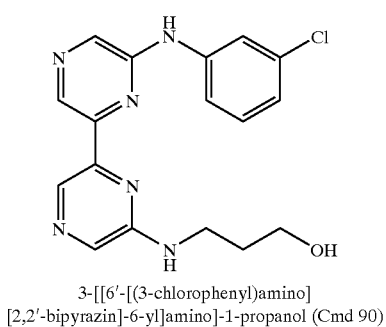

3-[[6'-[(3-chlorophenyl)amino]
[2,2'-bipyrazin]-6-yl]amino]-1-propanol (Cmd 90)

A mixture of methyl 6-chloro-2-pyrazinecarboxylate Compound 96a (4.50 g, 26.1 mmol; Sato, N. *J Heterocyc. Chem.* 1994, 31, 1177), bis(trimethyltin) (10.0 g, 30.5 mmol), tetrakis(triphenylphosphine) palladium (1.51 g, 1.31 mmol), LiCl (3.32 g, 78.3 mmol), and 2,6-di-tert-butyl-4-methylphenol (0.230 g, 1.04 mmol) in anhydrous 1,4-dioxane (80 mL) was refluxed at 100° C. for 4.5 h under nitrogen. After cooled to room temperature, the reaction mixture was filtered. The solid was washed with dichloromethane and the filtrate was concentrated and flash chromatographed (ethyl acetate/hexane as solvent) to give 5.60 g (71%) of methyl 6-trimethylstannyl-2-pyrazinecarboxylate Compound 96b as a yellow oil; $^1$H NMR (300 MHz, CDCl$_3$) δ9.09 (s, 1H), 8.73 (s, 1H), 4.02 (s, 3H), 0.44 (s, 9H). A mixture of the methyl 6-trimethylstannyl-2-pyrazinecarboxylate Compound 96b (536 mg, 1.78 mmol), N-(tert-butoxycarbonyl)-N-(3-chlorophenyl)-2-amino-6-chloropyrazine Cmd 45 (666 mg, 1.96 mmol), dichlorobis(triphenylphosphine) palladium (125 mg, 0.178 mmol), and LiCl (230 mg, 5.42 mmol) in anhydrous toluene (15 mL) was stirred at 100° C. for 6.5 h under nitrogen. The cooled reaction mixture was concentrated under vacuum and purified by flash chromatography (EtOAc/hexane as solvent) to give 593 mg (75%) of Compound 96c as an off-white solid; $^1$H NMR (300 MHz, CDCl$_3$) δ9.40 (s, 1H), 9.27 (s, 1H), 9.20 (s, 1H), 9.17 (s, 1H), 7.41–7.32 (m, 2H), 7.29 (m, 1H), 7.19–7.16 (m, 1H), 4.07 (s, 3H), 1.49 (s, 9H); MS (ES) m/z: 464 (M+Na$^+$). Anal. Calcd. For C$_{21}$H$_{20}$N$_5$O$_4$Cl: C, 57.08; H, 4.56; N, 15.85. Found: C, 57.02; H, 4.46; N, 15.41.

Compound 96c (1.31 g, 2.97 mmol) was treated with LiOH (0.110 g, 4.58 mmol) in THF (10 mL) and water (2.5 mL) for 2 h at room temperature. Acetic acid (0.55 mL) was added and the solution was concentrated to about half of the original volume. After the addition of water, some solid formed. The solid was collected through filtration, washed with water, and dried under vacuum overnight to give 1.22 g (96%) of a carboxylic acid as a yellow solid; MS (ES) m/z: 450 (M+Na$^+$). A mixture of the carboxylic acid (350 mg, 0.819 mmol), DPPA (340 mg, 1.24 mmol), and triethylamine (0.230 mL, 1.65 mmol) in t-BuOH (5 mL) and toluene (4 mL) was heated at 60° C. for 30 min, then the temperature was slowly increased to 80° C. for 2 h and 90° C. for 1 h. After concentration, the reaction mixture was purified by flash chromatography (EtOAc/hexane as solvent) to give 278 mg (68%) of Compound 96d as a yellow solid; $^1$H NMR (300 MHz, CDCl$_3$) δ9.31 (s, 1H), 9.23 (s, 1H), 9.16 (s, 1H), 8.70 (s, 1H), 7.96 (brs, 1H), 7.39–7.30 (m, 2H), 7.27 (m, 1H), 7.19–7.15 (m, H), 1.57 (s, 9H), 1.48 (s, 9H); MS (ES) m/z: 521 (M+Na$^+$).

A mixture of Compound 96d (60 mg, 0.12 mmol), (3-bromopropoxy)-tert-butyldimethylsilane (40 mg, 0.16 mmol), and Cs$_2$CO$_3$ (80 mg, 0.25 mmol) in dry DMF (1 mL) was heated at 70° C. for 3.5 h. The reaction mixture was concentrated and purified by column chromatography (EtOAc/hexane as solvent) to give 71 mg (88%) of the N-akylated product as an off-white solid; Anal. Calcd. For C$_{33}$H$_{47}$N$_6$O$_5$ClSi: C, 59.04; H, 7.06; N, 12.52. Found: C, 59.24; H, 7.00; N, 12.11. The N-akylated product (250 mg, 0.373 mmol) was dissolved in TFA (4 mL) and the solution was stirred at room temperature for 3 h before concentration. A saturated NH$_4$OH solution was added to the residue until the mixture was made basic followed by the addition of water. The precipitated solid was collected through filtration, again washed with water and dried under vacuum. The product was purified by flash chromatography on silica gel (EtOAc/MeOH as solvent) to provide 112 mg (84%) of Cmd 90 as a yellow solid; $^1$H NMR (300 MHz, DMSO-d$_6$) δ9.89 (s, 1H), 8.79 (s, 1H), 8.47 (s, 1H), 8.28 (s, 1H), 8.13 (s, 1H), 8.00 (s, 1H), 7.62 (d, J=8.2 Hz, 1H), 7.39 (t, J=8.0 Hz, 1H), 7.29 (m, 1H), 7.04 (d, J=8.1 Hz, 1H), 4.51 (brs, 1H), 3.53 (m, 2H), 3.47–3.41 (m, 2H), 1.82–1.73 (m, 2H); MS (ES) m/z: 357 (M+H$^+$).

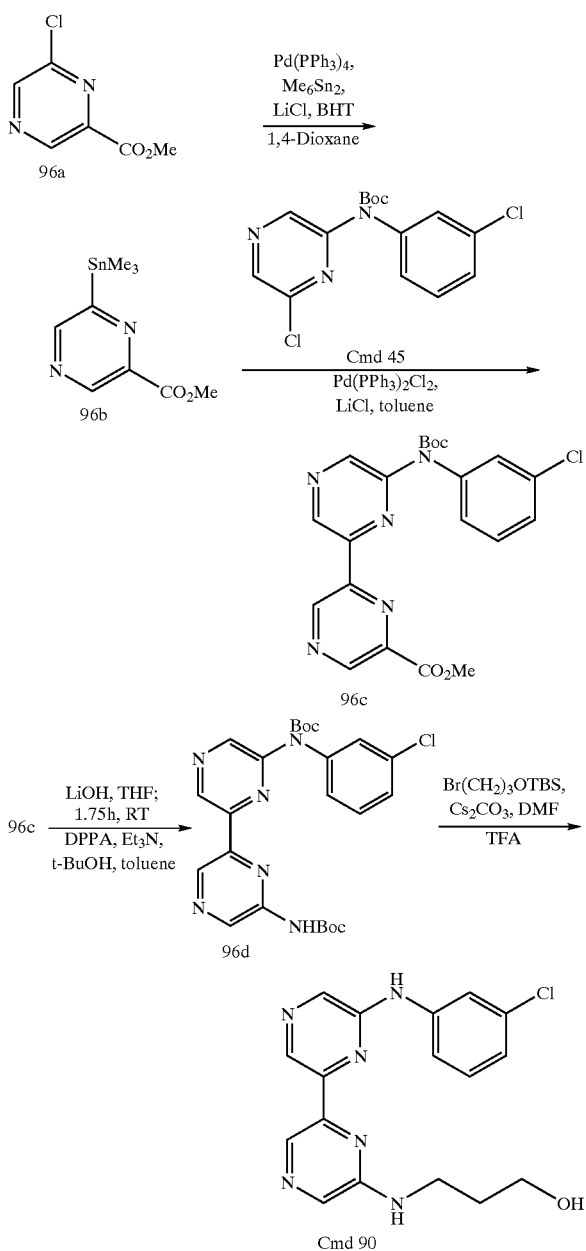

EXAMPLE 97

COMPOUND 91

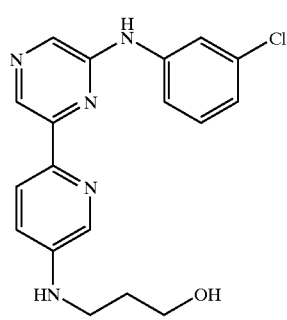

A mixture of methyl 6-(trifluoromethylsulphonyloxy) nicotinate Compound 97a (2.00 g, 7.02 mmol; Torrado, A.

*Synthesis* 1995, 285; *J. Org. Chem.* 1996, 61, 8940), bis (trimethyltin) (3.50 g, 10.7 mmol), tetrakis (triphenylphosphine)palladium (0.810 g, 0.700 mmol), anhydrous LiCl (0.900 g, 21.2 mmol), and 2,6-di-tert-butyl-4-methylphenol (0.062 g, 0.28 mmol) in anhydrous 1,4-dioxane (60 mL) was refluxed at 100° C. for 2 h under nitrogen. After cooled to room temperature, the reaction mixture was filtered through celite and washed with dichloromethane. The filtrate was concentrated under vacuum. Water and $Et_2O$ were added to the residue and the resulting mixture was filtered again through celite. The filtrate was separated and the aqueous layer was extracted with $Et_2O$. The organic layers were combined and washed with 15% $NH_4OH$ (×2) and the aqueous layer was back extracted with $Et_2O$. The combined organic phases were dried over $Na_2SO_4$, filtered, and concentrated to give 2.31 g of crude methyl 6-(trimethylstannyl)nicotinate Compound 97b as a brown oil.

N-(tert-butoxycarbonyl)-N-(3-chlorophenyl)-2-amino-6-chloropyrazine Cmd 45 (2.20 g, 6.47 mmol), dichlorobis (triphenylphosphine) palladium (0.780 g, 1.11 mmol), LiCl (0.900 g, 21.2 mmol) and anhydrous toluene (80 mL) were added to the crude Compound 97b. The reaction mixture was heated at 100° C. for 1 h under nitrogen and then left at room temperature overnight. After filtration through Celite, the filtrate was concentrated and flash chromatographed (EtOAc/hexane as solvent) to give 1.19 g (38%, two steps) of Compound 97c as a white solid; $^1H$ NMR (300 MHz, $CDCl_3$) δ9.43 (s, 1H), 9.24 (d, J=2.1 Hz, 1H), 9.06 (s, 1H), 8.31 (dd, J=8.3, 2.1 Hz, 1H), 7.93 (d, J=8.3 Hz, 1H), 7.39–7.31 (m, 3H), 7.19–7.15 (m, 1H), 3.97 (s, 3H), 1.49 (s, 9H); MS (ES) m/z: 463 (M+$Na^+$). Anal. Calcd. For $C_{22}H_{21}N_4O_4Cl$: C, 59.93; H, 4.80; N, 12.71. Found: C, 60.03; H, 4.67; N, 12.25.

A mixture of Compound 97c (540 mg, 1.22 mmol) and LiOH (44 mg, 1.8 mmol) in THF (16 mL) and water (4 mL) was stirred for 1 h at room temperature. More LiOH (30 mg, 1.3 mmol) was added to the cloudy solution. After another 3 h at room temperature, the solution became clear. Acetic acid (0.30 mL) was added and the solution was concentrated to about half of the original volume. After the addition of water, some solid formed. The solid was collected through filtration, washed with water, and dried under vacuum overnight to give 522 mg (100%) of a carboxylic acid as a yellow solid; MS (ES) m/z: 425 (M−$H^+$). A mixture of the carboxylic acid (522 mg, 1.22 mmol), DPPA (500 mg, 1.82 mmol), and triethylamine (0.340 mL, 2.44 mmol) in t-BuOH (9 mL) and toluene (9 mL) was heated at 60° C. for 30 min, then the temperature was slowly increased to 80° C. for 2 h and 90° C. for 1 h. After concentration, the reaction mixture was purified by flash chromatography (EtOAc/hexane as solvent) to give 393 mg (65%) of Compound 97d as a yellow solid; $^1H$ NMR (300 MHz, $CDCl_3$) δ9.31 (s, 1H), 8.92 (s, 1H), 8.45 (d, J=2.4 Hz, 1H), 8.03 (brd, J=8.5 Hz, 1H), 7.84 (d, J=8.6 Hz, 1H), 7.37–7.29 (m, 3H), 7.19–7.16 (m, 1H), 6.67 (s, 1H), 1.54 (s, 9H), 1.49 (s, 9H); MS (ES) m/z: 520 (M+$Na^+$). Anal. Calcd. For $C_{25}H_{28}N_5O_4Cl$: C, 60.30; H, 5.67; N, 14.06. Found: C, 60.16; H, 5.61;N, 13.81.

A mixture of Compound 97d (43 mg, 0.086 mmol), (3-bromopropoxy)-tert-butyldimethylsilane (30 mg, 0.12 mmol), and $Cs_2CO_3$ (45 mg, 0.14 mmol) in dry DMF (1 mL) was heated at 65° C. for 2 h then 80° C. for 2.5 h. The reaction mixture was concentrated and purified by column chromatography (EtOAc/hexane as solvent) to give 51 mg (88%) of a N-akylated product as a clear oil. The N-akylated product (385 mg, 0.575 mmol) was dissolved in TFA (6 mL) and the solution was stirred at room temperature for 3 h before concentration. A saturated NH$_4$OH solution was added to the residue until the mixture was made basic, followed by the addition of water. The precipitated solid was collected through filtration, washed with water and dried under vacuum. The product was purified by flash chromatography on silica gel (CH$_2$Cl$_2$/MeOH as solvent) to provide 176 mg (86%) of Cmd 91 as a yellow solid; $^1$H NMR (300 MHz, DMSO-d$_6$) δ 9.70 (s, 1H), 8.74 (s, 1H), 8.11–8.08 (m, 3H), 7.99 (d, J=8.6 Hz, 1H), 7.63 (d, J=8.4 Hz, 1H), 7.37 (t, J=8.1 Hz, 1H), 7.06 (dd, J=8.6, 2.6 Hz, 1H), 7.01 (d, J=7.9 Hz, 1H), 6.37 (m, 1H), 4.52 (t, J=5.0 Hz, 1H), 3.53 (m, 2H), 3.18 (m, 2H), 1.74 (m, 2H); MS (ES) m/z: 356 (M+H$^+$). Anal. Calcd. For C$_{18}$H$_{18}$N$_5$O C.1.0.24H$_2$O: C, 60.03; H, 5.17N, 19.45. Found: C, 60.45; H, 5.24; N, 19.03.

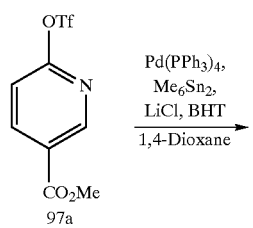

97a

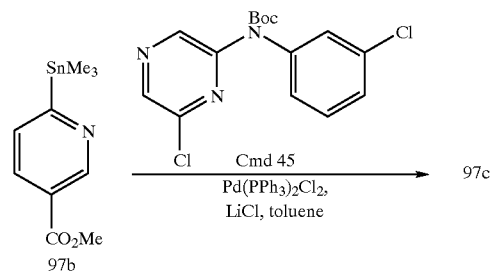

97b

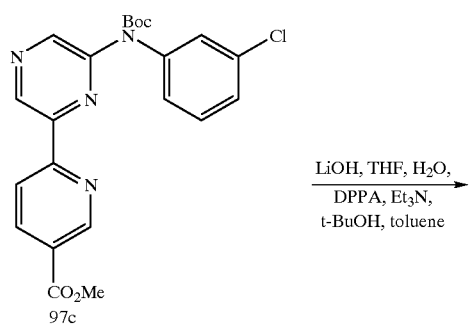

97c

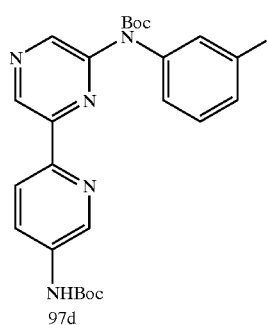

97d

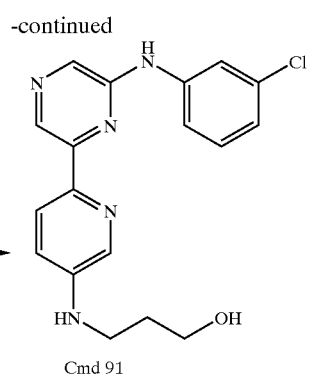

Cmd 91

EXAMPLE 98

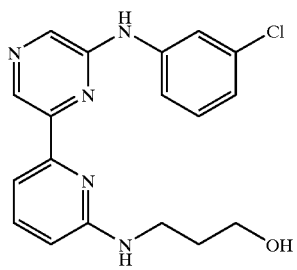

COMPOUND 92

A mixture of 2-amino-6-bromopyridine Compound 98a (3.46 g, 20.0 mmol), di-tert-butyl dicarbonate (4.80 g, 22.0 mmol), and 4-(dimethylamino)pyridine (0.244 g, 2 mmol) in t-BuOH (50 mL) was stirred at room temperature for more than 24 h. The solution was concentrated and purified by flash chromatography (EtOAc/hexane as solvent) to give 1.36 g (25%) of N-(tert-butoxycarbonyl)-2-amino-6-bromopyridine as clear crystals; $^1$H NMR (300 MHz, CDCl$_3$) δ 7.88 (d, J=8.2 Hz, 1H), 7.50 (t, J=8.0 Hz, 1H), 7.22 (brs, 1H), 7.12 (d, J=7.7 Hz, 1H), 1.51 (s, 9H). (3-Bromopropoxy)-tert-butyldimethylsilane (1.50 g, 5.93 mmol) and Cs$_2$CO$_3$ (2.43 g, 7.46 mmol) were added to the solution of crystals in dry DMF (20 mL). After stirring at 70° C. for 18 h, the solvent was evaporated under reduced pressure and the residue was purified by column chromatography (EtOAc/hexane) to provide 1.93 g (88%) of Compound 98b as a clear oil; $^1$H NMR (300 MHz, CDCl$_3$) δ 7.66 (d, J=8.2 Hz, 1H), 7.44 (m, 1H), 7.15 (d, J=7.6 Hz, 1H), 3.99 (t, J=7.3 Hz, 2H), 3.67 (t, J=6.4 Hz, 2H), 1.86 (m, 2H), 1.51 (s, 9H), 0.88 (s, 9H), 0.03 (s, 6H); MS (ES) m/z: 467 (M+Na$^+$). Anal. Calcd. For C$_{19}$H$_{33}$N$_2$O$_3$BrSi: C, 51.23; H. 7.47; N. 6.29. Found: C, 51.15; H, 7.80; N, 6.24. A mixture of Compound 98b (150 mg, 0.337 mmol), bis(tributyltin) (0.340 mL, 0.673 mmol), tetrakis(triphenylphosphine) palladium (40 mg, 0.035 mmol), LiCl (43 mg, 1.0 mmol), and 2,6-di-tert-butyl-4-methylphenol (3 mg, 0.014 mmol) in anhydrous 1,4-dioxane (3 mL) was refluxed at 100° C. for 4 h under nitrogen. The solvent was removed under reduced pressure and the residue was chromatographed over silica gel (ethyl acetate/hexane as solvent) to give 152 mg (69%) of Compound 98c as a clear oil; $^1$H NMR (300 MHz, CDCl$_3$) δ7.49 (d, J=8.5 Hz, 1H), 7.42 (m, 1H), 7.08 (d, J=7.7 Hz, 1H), 4.03 (t, J=7.3 Hz, 2H), 3.65 (t, J=6.6 Hz, 2H), 1.88 (m, 2H), 1.61–1.50 (m, 6H), 1.52 (s, 9H), 1.37–1.26 (m, 6H), 1.10–1.05 (m, 6H), 0.88 (t, J=7.4 Hz, 9H), 0.87 (s, 9H), 0.02 (s, 6H); MS (ES) m/z: 656 (M+H$^+$).

A mixture of Compound 98c (103 mg, 0.157 mmol), N-(tert-butoxycarbonyl)-N-(3-chlorophenyl)-2-amino-6-chloropyrazine Cmd 45 (61 mg, 0.18 mmol), dichlorobis(triphenylphosphine)palladium (13 mg, 0.018 mmol) and LiCl (23 mg, 0.54 mmol) in anhydrous toluene (3 mL) was stirred at 100° C. for 3 h under nitrogen. The cooled reaction mixture was concentrated under vacuum and purified by flash chromatography (EtOAc/hexane as solvent) to give 63 mg (62%) of Compound 98d as a yellow oil; $^1$H NMR (300 MHz, CDCl$_3$) δ9.29 (s, 1H), 8.93 (s, 1H), 7.73 (dd, J=7.8, 1.3 Hz, 1H), 7.65 (m, 1H), 7.61–7.58 (m, 1H), 7.37–7.28 (m, 3H), 7.19–7.15 (m, 1H), 4.12 (t, J=7.4 Hz, 2H), 3.71 (t, J=6.2 Hz, 2H), 2.01–1.92 (m, 2H), 1.53 (s, 9H), 1.49 (s, 9H), 0.85 (s, 9H), 0.02 (s, 6H); MS (ES) m/z: 692 (M+Na$^+$). Anal. Calcd. For C$_{34}$H$_{48}$N$_5$O$_5$ClSi: C, 60.92; H, 7.22; N, 10.45. Found: C, 60.82; H, 7.10; N, 10.18. Compound 98d (53 mg, 0.079 mmol) was dissolved in TFA (1.5 mL) and the solution was stirred at room temperature for 2 h before concentration. A saturated NH$_4$OH solution was added to the residue until the mixture was made basic followed by the addition of water. The precipitated solid was collected through filtration, washed with water and Et$_2$O, and dried under vacuum to provide 28 mg (100%) of Cmd 92 15 as a yellow solid; $^1$H NMR (300 MHz, DMSO-d$_6$) δ9.80 (s, 1H), 8.85 (s, 1H), 8.24 (s, 1H), 8.12 (s, 1H), 7.64 (d, J=8.1 Hz, 1H), 7.56 (m, 1H), 7.40–7.35 (m, 2H), 7.02 (d, J=7.7 Hz, 1H), 6.71 (brs, 1H), 6.57 (d, J=8.3 Hz, 1H), 4.48 (brs, 1H), 3.53 (t, J=6.3 Hz, 2H), 3.40 (m, 2H), 1.76 (m, 2H); MS (ES) m/z: 356 (M+H$^+$). Anal. Calcd. For C$_{18}$H$_{18}$N$_5$OCl.0.55H$_2$O : C, 59.11; H, 5.26; N, 19.15. Found: C, 59.46; H, 4.99; N, 18.78.

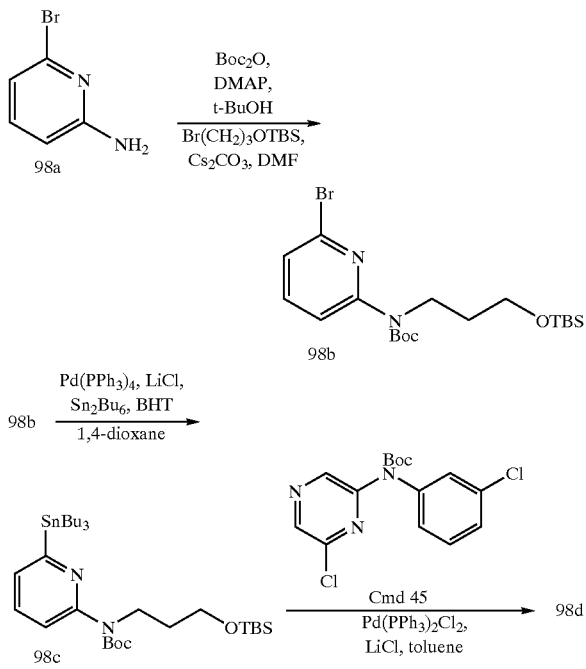

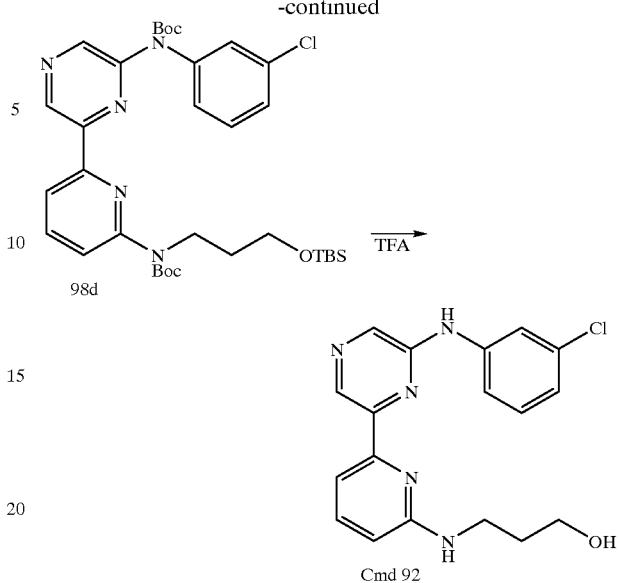

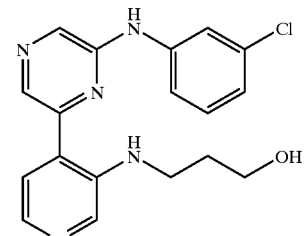

3-[[4-[6-[(3-chlorophenyl)amino]pyrazinyl]-3-pyridinyl]amino]-1-propanol(Cmd 93)

EXAMPLE 99

COMPOUND 93

A mixture of 4-(trimethylstannyl)nicotinic acid Compound 99a (300 mg, 1.05 mmol; Kelly, T. R. J. Org. Chem. 1992, 57, 1593), DPPA (433 mg, 1.57 mmol), and triethylamine (0.250 mL, 1.79 mmol) in t-BuOH (2 mL) and toluene (2 mL) was heated at 60° C. for 1.5 h, then 90° C. for 3.5 h. After concentration, the reaction mixture was purified by flash chromatography (EtOAc/hexane as solvent) to give 213 mg (57%) of Compound 99b as a white solid; $^1$H NMR (300 MHz, CDCl$_3$) δ8.54 (s, 1H), 8.31 (d, J=4.5 Hz, 1H), 7.34 (d, J=4.5 Hz, 1H), 6.30 (brs, 1H), 1.51 (s, 9H), 0.37 (s, 9H). Anal. Calcd. For C$_{13}$H$_{22}$N$_2$O$_2$Sn: C, 43.73; H, 6.21; N, 7.85. Found: 43.53; H, 6.12; N, 7.76. A mixture of Compound 99b (162 mg, 0.454 mmol), N-(tert-butoxycarbonyl)-N-(3-chlorophenyl)-2-amino-6-chloropyrazine Cmd 45 (155 mg, 0.454 mmol), dichlorobis(triphenylphosphine)palladium (64 mg, 0.091 mmol) and LiCl (60 mg, 1.42 mmol) in anhydrous toluene (10 mL) was stirred at 100° C. for 4 h under nitrogen. The reaction mixture was concentrated and purified by flash chromatography (EtOAc/hexane as solvent) to give 156 mg (69%) of Compound 99c as a white solid; $^1$H NMR (300 MHz, CDCl$_3$) δ9.37 (s, 1H), 9.23 (s, 1H), 9.05 (s, 1H), 8.71 (s, 1H), 8.37 (d, J=5.1 Hz, 1H), 7.47–7.27 (m, 3H), 7.20 (dd, J=7.0, 2.0 Hz, 1H), 1.56 (s, 9H), 1.48 (s, 9H); MS (ES) m/z: 498 (M+H$^+$).

A mixture of Compound 99c (29 mg, 0.058 mmol), (3-bromopropoxy)-tert-butyldimethylsilane (22 mg, 0.087 mmol), and $Cs_2CO_3$ (38 mg, 0.12 mmol) in dry DMF (1 mL) was heated at 70° C. for 2 h. The reaction mixture was concentrated and purified by column chromatography (EtOAc/hexane as solvent) to give 32 mg (82%) of a N-akylated product Compound 99d as a yellow oil; MS (ES) m/z: 670 (M+H$^+$). Anal. Calcd. For $C_{34}H_{41}N_5O_5ClSi$: C, 60.92; H, 7.22; N, 10.45. Found: C, 60.49; H, 7.18; N, 10.30. The N-akylated product Compound 99d (60 mg, 0.089 mmol) was dissolved in TFA (2 mL) and the solution was stirred at room temperature for 1.5 h before concentration. A saturated $NH_4OH$ solution was added to the residue until the mixture was made basic followed by the addition of water. The precipitated solid was collected through filtration, washed with water and dried under vacuum. The product was purified by flash chromatography on silica gel ($CH_2Cl_2$/MeOH as solvent) to provide 28 mg (88%) of Cmd 93 as a yellow solid; $^1$H NMR (300 MHz, DMSO-d$_6$) δ9.90 (s, 1H), 8.51 (s, 1H), 8.28 (s, 1H), 8.22 (s, 1H), 7.95 (brd, J=4.4 Hz, 1H), 7.83 (s, 1H), 7.58 (d, J=4.8 Hz, 1H), 7.51 (d, J=8.5 Hz, 1H), 7.41 (t, J=8.0 Hz, 1H), 7.11 (m, 2H), 4.48 (m, 1H), 3.37(m, 2H), 3.29(m, 2H), 1.08 (m, 2H); MS (ES) m/z: 356 (M+H$^+$). Anal. Calcd. For $C_{18}H_{18}N_5OCl.0.6H_2O$ : C, 58.97; H, 5.28; N, 19.10. Found: C, 58.94; H, 5.53; N, 19.10.

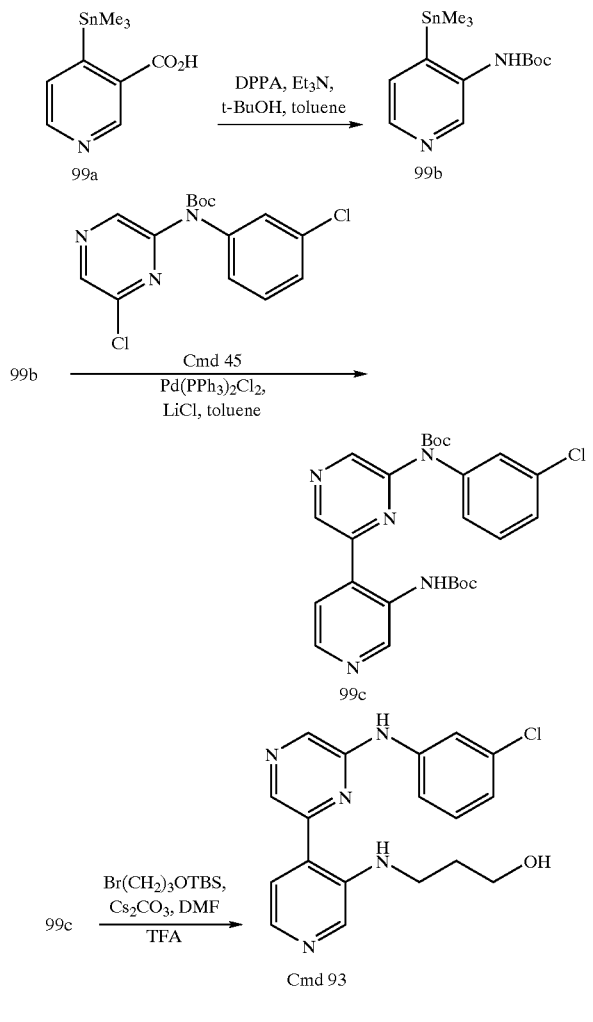

EXAMPLE 100

COMPOUND 94

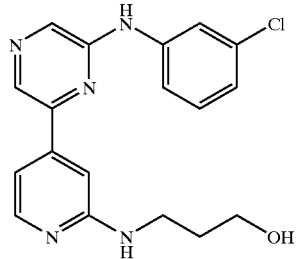

A mixture of 4-iodopicolinic acid Compound 100a (1.00 g, 3.30 mmol; Lohse, O. *Synth. Commun.* 1996, 26, 2017), DPPA (1.36 g, 4.95 mmol), and triethylamine (1.4 mL, 10 mmol) in t-BuOH (5.5 mL) and toluene (5 mL) was heated at 65° C. for 1.5 h, then 100° C. for 4 h. After concentration, the reaction mixture was purified by flash chromatography (EtOAc/hexane as solvent) to give 515 mg (50%) of Compound 100b as a white solid; $^1$H NMR (300 MHz, CDCl$_3$) δ9.17 (brs, 1H), 8.48 (s, 1H), 7.98 (dd, J=5.2, 1.5 Hz, 1H), 7.34 (dd, J=5.2,1.3 Hz, 1H), 1.56 (s, 9H). MS (ES) m/z: 343 (M+Na$^+$). A mixture of Compound 100b (330 mg, 1.03 mmol), (3-bromopropoxy)-tert-butyldimethylsilane (340 mg, 1.34 mmol), and $Cs_2CO_3$ (504 mg, 1.55 mmol) in dry DMF (4 mL) was stirred at 70° C. for 3 h. The solvent was evaporated under reduced pressure and the residue was purified by column chromatography (EtOAc/hexane) to provide 450 mg (89%) of Compound 100c as a clear oil; $^1$H NMR (400 MHz, CDCl$_3$) δ8.11 (s, 1H), 8.00 (d, J=5.2 Hz, 1H), 7.33 (dd, J=5.2, 1.3 Hz, 1H), 3.99 (t, J=7.3 Hz, 2H), 3.65 (t, J=6.3 Hz, 2H), 1.84 (m, 2H), 1.52 (s, 9H), 0.87 (s, 9H), 0.02 (s, 6H); MS (ES) m/z: 515 (M+Na$^+$).

A mixture of Compound 100c (650 mg, 1.32 mmol), bis(trimethyltin) (870 mg, 2.66 mmol), tetrakis(triphenylphosphine)palladium (150 mg, 0.130 mmol), LiCl (170 mg, 4.00 mmol), and 2,6-di-tert-butyl-4-methylphenol (12 mg, 0.054 mmol) in anhydrous 1,4-dioxane (12 mL) was heated at 90° C. for 1.5 h under nitrogen. The solvent was removed under reduced pressure and the residue was chromatographed over silica gel (EtOAc/hexane as solvent) to give 590 mg (84%) of Compound 100d as a clear oil; $^1$H NMR (300 MHz, CDCl$_3$) δ8.09 (d, J=4.7 Hz, 1H), 7.56 (s, 1H), 7.10 (d, J=4.7 Hz, 1H), 3.97 (t, J=7.2 Hz, 2H), 3.64 (t, J=6.5 Hz, 2H), 1.85 (m, 2H), 1.49 (s, 9H), 0.86 (s, 9H), 0.33 (s, 9H), 0.00 (s, 6H); MS (ES) m/z: 527 (M–H). Anal. Calcd. For $C_{22}H_{42}N_2O_3SiSn$: C, 49.92; H, 8.00; N, 5.29. Found: C, 50.32; H, 7.88; N, 5.20.

A mixture of Compound 100d (550 mg, 1.04 mmol), N-(tert-butoxycarbonyl)-N-(3-chlorophenyl)-2-amino-6-chloropyrazine Cmd 45 (360 (360 mg, 1.06 mmol), dichlorobis(triphenylphosphine)palladium (73 mg, 0.104 mmol) and LiCl (132 mg, 3.11 mmol) in anhydrous toluene (20 mL) was stirred at 90° C. for 1 h then 100° C. for 2 h under nitrogen. The cooled reaction mixture was concentrated under vacuum and purified by flash chromatography (EtOAc/hexane as solvent) to give 380 mg (55%) of Compound 100e as a yellow oil; $^1$H NMR (300 MHz, CDCl$_3$) δ9.00 (s, 1H), 8.82 (s, 1H), 8.40 (d, J=5.2 Hz, 1H), 8.04 (s, 1H), 7.37–7.28 (m, 4H), 7.16 (brd, J=7.3 Hz, 1H), 4.02 (m, 2H), 3.65 (t, J=6.3 Hz, 2H), 1.85 (m, 2H), 1.50 (s, 9H), 1.49 (s, 9H), 0.85 (s, 9H), 0.00 (s, 6H); MS (ES) m/z: 670 (M+H$^+$). Anal. Calcd. For $C_{34}H_{48}N_5O_5ClSi.0.3H_2O$ : C, 60.43; H, 7.25; N, 10.36. Found: C, 60.22; H, 7.04; N, 10.15.

A solution of Compound 100e (350 mg, 0.522 mmol) and TFA (4 mL) was left at room temperature overnight before concentration. A saturated $NH_4OH$ solution was added to the residue until the mixture was made basic followed by the addition of water. The precipitated solid was collected through filtration, washed with water, dried under vacuum, and purified by flash chromatography ($CH_2Cl_2$/MeOH as solvent) to provide 143 mg (77%) of Cmd 94 as a yellow solid; $^1$H NMR (300 MHz, DMSO-$d_6$) δ9.88 (s, 1H), 8.54 (s, 1H), 8.27 (s, 1H), 8.10 (d, J=5.8 Hz, 1H), 8.00 (s, 1H), 7.73 (d, J=8.2 Hz, 1H), 7.39 (t, J=8.1 Hz, 1H), 7.10 (s, 2H), 7.04 (dd, J=7.9, 1.0 Hz, 1H), 6.69 (brt, J=5.3 Hz, 1H), 4.55 (brs, 1H), 3.51 (t, J=6.2 Hz, 2H), 3.36 (m, 2H), 1.73 (m, 2H); MS (ES) m/z: 356 (M+H$^+$). Anal. Calcd. For $C_{18}H_{18}N_5OCl.0.3$ $H_2O$ : C, 59.85; H, 5.19; N, 19.39. Found: C, 60.03; H, 5.08; N, 19.20.

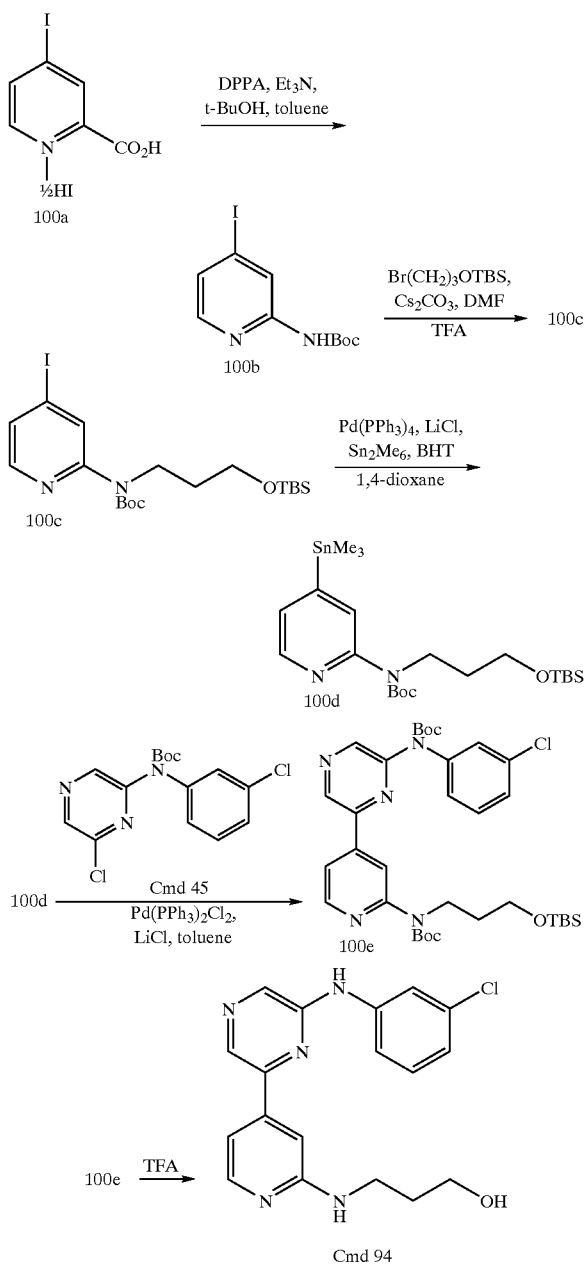

EXAMPLE 101

COMPOUND 95

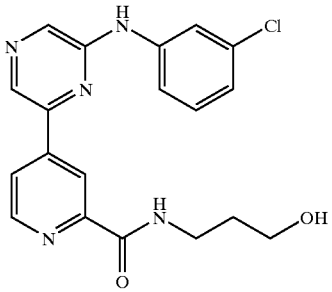

3-[[5-[6-[(3-chlorophenyl)amino]pyrazinyl]-2-thiazolyl]amino]-1-propanol(Cmd 95)

A mixture of methyl 4-iodopicolinate Compound 101a (0.800 g, 3.04 mmol; Lohse, O. *Synth. Commun.* 1996, 26, 2017), bis(trimethyltin) (1.70 g, 5.19 mmol), tetrakis (triphenylphosphine)palladium (350 mg, 0.303 mmol), LiCl (0.390 g, 9.19 mmol), and 2,6-di-tert-butyl-4-methylphenol (27 mg, 0.12 mmol) in anhydrous 1,4-dioxane (20 mL) was refluxed at 100° C. for 1 h under nitrogen. The solvent was removed under reduced pressure and the residue was chromatographed over silica gel (EtOAc/hexane as solvent) to give 404 mg (44%) of methyl 4-trimethylstannylpicolinate Compound 101b as a yellow oil; $^1$H NMR (400 MHz, CDCl$_3$) δ8.64 (d, J=4.6 Hz, 1H), 8.25 (s, 1H), 7.59 (d, J=4.5 Hz, 1H), 4.01 (s, 3H), 0.38 (s, 9H); MS (ES) m/z: 324 (M+Na$^+$). Anal. Calcd. For $C_{10}H_{15}NO_2Sn$: C, 40.04; H, 5.04; N, 4.67. Found: C, 40.17; H, 4.63; N, 4.60. A mixture of methyl 4-trimethylstannylpicolinate Compound 101b (350 mg, 1.17 mmol), N-(tert-butoxycarbonyl)-N-(3-chlorophenyl)-2-amino-6-chloropyrazine Cmd 45 (400 mg, 1.18 mmol), dichlorobis(triphenylphosphine)palladium (82 mg, 0.12 mmol) and LiCl (150 mg, 3.54 mmol) in anhydrous toluene (15 mL) was stirred at 100° C. for 4 h under nitrogen. The cooled reaction mixture was concentrated under vacuum and purified by flash chromatography (EtOAc/hexane as solvent) to give 260 mg (51%) of Compound 101c as a yellow solid; $^1$H NMR (300 MHz, CDCl$_3$) δ9.17 (s, 1H), 8.90 (s, 1H), 8.80 (d, J=4.9 Hz, 1H), 8.52 (s, 1H), 7.82 (dd, J=5.0, 1.6 Hz, 1H), 7.40–7.38 (m, 2H), 7.30 (s, 1H), 7.18 (brd, J=6.8 Hz, 1H), 4.04 (s, 3H), 1.50 (s, 9H); MS (ES) m/z: 441 (M+H$^+$). Anal. Calcd. For $C_{22}H_{21}N_4O_4Cl.0.25H_2O$ : C, 59.33; H, 4.87; N, 12.58. Found: C, 59.14; H, 4.60; N, 12.48.

Compound 101c (260 mg, 0.590 mmol) was treated with LiOH (30 mg, 1.25 mmol) in THF (8 mL) and water (2 mL) for 40 min at room temperature. Acetic acid (10 drops) was added and the solution was concentrated to about half of the original volume. After the addition of water, some solid formed. The solid was collected through filtration, washed with water, and dried under vacuum overnight to give 235 mg (93%) of a carboxylic acid product as a yellow solid; MS (ES) m/z: 427 (M+H$^+$). A mixture of the carboxylic acid product (220 mg, 0.515 mmol), DPPA (213 mg, 0.775 mmol), and triethylamine (0.150 mL, 1.08 mmol) in t-BuOH (4 mL) and toluene (4 mL) was heated at 65° C. for 1 h, then the temperature was slowly increased to 80° C. for 1 h and 100° C. for 1 h. After removal of solvents, the reaction mixture was purified by flash chromatography (EtOAc/hexane as solvent) to give 140 mg of an amide (containing impurities) as a white solid. (3-Bromopropoxy)-tertbutyldimethylsilane (100 mg, 0.395 mmol), Cs$_2$CO$_3$ (180 mg, 0.552 mmol) and DMF (4 mL) were added to the amide. After stirring at 70° C. for 17 h, the reaction mixture was concentrated and purified by column chromatography (EtOAc/hexane as solvent) to give 27 mg (8%, 3 steps) of Compound 101d as a yellow solid; $^1$H NMR (400 MHz, CDCl$_3$) δ9.08 (s, 1H), 8.94 (s, 1H), 8.62 (d, J=1.0 Hz, 1H), 8.56 (d, J=5.0 Hz, 1H), 8.44 (brt, J=5.4 Hz, 1H), 7.73 (dd, J=5.0, 1.7 Hz, 1H), 7.40–7.33 (m, 2H), 7.29 (t, J=1.8 Hz, 1H), 7.18 (dt, J=7.6, 1.6 Hz, 1H), 3.80 (t, J=5.6 Hz, 2H), 3.62 (m, 2H), 1.86 (m, 2H), 1.49 (s, 9H), 0.92 (s, 9H), 0.10 (s, 6H); MS (ES) m/z: 669 (M–H$^+$). A solution of Compound 101d (27 mg, 0.047 mmol) and TFA (1 mL) was left at room temperature overnight before concentration. A saturated NH$_4$OH solution was added to the residue until the mixture was made basic followed by the addition of water. The precipitated solid was filtered, washed with water, dried under vacuum, and purified by flash chromatography (CH$_2$Cl$_2$/MeOH as solvent) to provide 13 mg (72%) of Cmd 95 as a yellow solid; $^1$H NMR (400 MHz, DMSO-d$_6$) δ9.98 (s, 1H), 8.90 (brt, J=5.4 Hz, 1H), 8.80 (s, 2H), 8.68 (s, 1H), 8.35 (s, 1H), 8.24 (d, J=4.7 Hz, 1H), 8.02 (s, 1H), 7.70 (d, J=7.8 Hz, 1H), 7.39 (t, J=8.0 Hz, 1H), 7.07 (d, J=7.5 Hz, 1H), 4.57 (t, J=5.1 Hz, 1H), 3.50 (m, 2H), 3.41 (m, 2H), 1.72 (t, J=6.4 Hz, 2H); MS (ES) m/z: 384 (M+H$^+$).

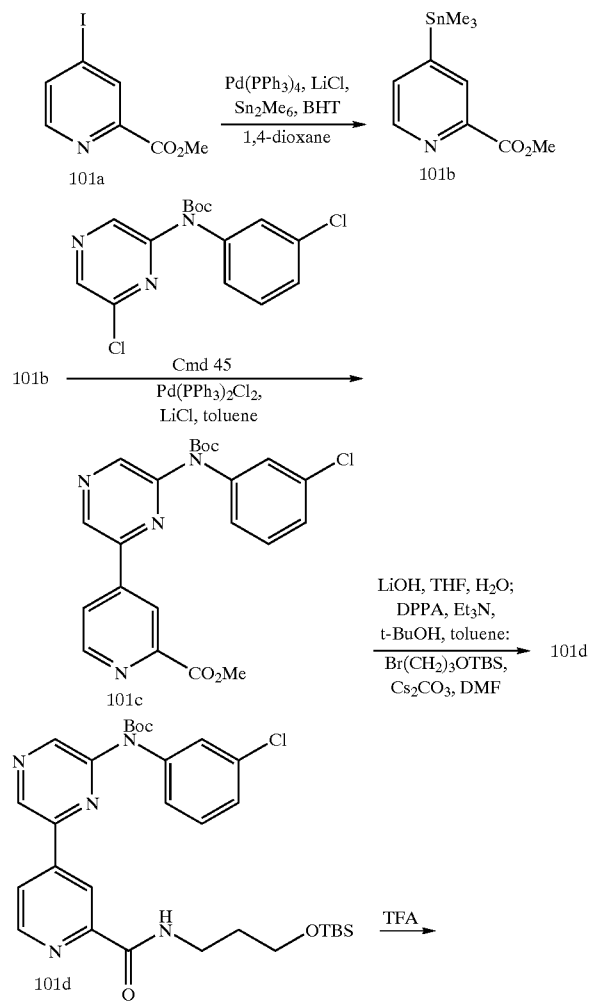

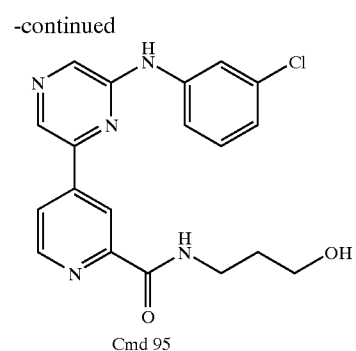

Cmd 95

EXAMPLE 102

COMPOUND 96

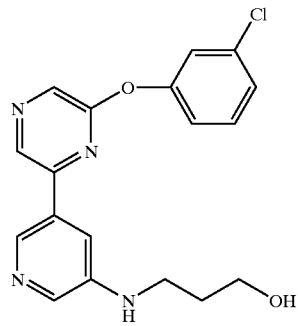

A mixture of Cmd 1D (450 mg, 1.71 mmol), 3-chlorophenol (330 mg, 2.56 mmol), Pd$_2$(dba)$_3$ (44.2 mg, 0.042 mmol), DPPF (75.6 mg, 0.134 mmol), Cs$_2$CO$_3$ (1.11 g, 3.41 mmol) in anhydrous dioxane (5 mL) was stirred at reflux for 18 h under nitrogen. The reaction mixture was filtered thru celite and the filter cake was washed with dichloromethane. The filtrate was concentrated under vacuum. The residue was purified by column chromatography (EtOAc/hexane as solvent) and recrystallized from ethyl acetate/hexane to give 168 mg (27%) of Compound 102a as a solid; $^1$H NMR (300 MHz, CDCl$_3$) δ9.26 (brs, 2H), 8.85 (s, 1H), 8.73 (t, J=2.1 Hz, 1H), 8.46 (s, 1H), 7.39 (t, J=8.4 Hz, 1H), 7.30–7.25 (m, 2H), 7.16 (brd, J=8.2 Hz, 1H), 4.44 (q, J=7.1 Hz, 2H), 1.43 (t, J=7.1 Hz, 3H); Anal. Calcd. For C$_{18}$H$_{14}$ClN$_3$O$_3$: C, 60.77; H, 3.97; N, 11.81. Found: C, 60.67; H, 3.92; N, 11.64. A mixture of Compound 102a (150 mg, 0.44 mmol) was dissolved in methanol (4.3 mL) and stirred for 10 min then cooled to 0° C. NaOH$_{(aq)}$ (1 N, 0.74 mL) was added slowly and the mixture was stirred at 0° C. for 10 min then stirred at 20° C. for another 18 h. Glacial acetic acid (0.7 mL) was added to the reaction mixture followed by the addition of water (2.2 mL). A solid was formed. The solid was collected thru filtration, and washed with water (5×), dried in vacuum oven overnight to give 122 mg (85%) of Compound 102b as a solid; $^1$H NMR (300 MHz, CD$_3$OD) δ9.23 (s, 1H), 9.14 (s, 1H), 9.00 (s, 1H), 8.85 (t, J=2.1 Hz, 1H), 8.50 (s, 1H), 7.47 (t, J=8.1 Hz, 1H), 7.39–7.23 (m, 3H); MS (ES) m/z: 326 (M–H); Anal. Calcd. For C$_{16}$H$_{10}$ClN$_3$O$_3$: C, 58.67; H, 3.08; N, 12.82. Found: C, 58.55; H, 3.01; N, 12.66.

A mixture of Compound 102b (107.7 mg, 0.33 mmol), DPPA (108 mg, 0.39 mmol), triethylamine (66 mg, 0.65 mmol), t-BuOH (1.4 mL) in toluene (1 mL) was stirred under nitrogen at 70° C. for 0.5 h then heated at reflux for 4 h. The reaction mixture was concentrated under vacuum.

The product was purified by column chromatography (EtOAc/hexane as solvent) and recrystallized from EtOAc/hexane to give 51 mg (40%) of Compound 102c as a solid; $^1$H NMR (300 MHz, CDCl$_3$) δ 8.81 (s, 1H), 8.78 (d, J=1.9 Hz, 1H), 8.51 (d, J=2.5 Hz, 1H), 8.44 (brs, 1H), 8.40 (s, 1H), 7.39 (t, J=8.2 Hz, 1H), 7.27–7.24 (m, 1H), 7.17 (d, J=7.6 Hz, 1H), 6.57 (brs, 2H), 1.54 (s, 9H); FAB-HRMS (M+H$^+$). Calcd. for C$_{20}$H$_{19}$ClN$_4$O$_3$ 399.1224, found 399.1241. A mixture of Compound 102c (51 mg 0.128 mmol), (3-bromopropoxy)-t-butyl-dimethylsilane (48.6 mg, 0.192 mmol) and Cs$_2$CO$_3$ (125 mg, 0.384 mmol) in DMF (1.5 mL) was stirred at 70° C. under nitrogen for 36 h. The reaction mixture was diluted with water, extracted with ether (3×), dried (Na$_2$SO$_4$) and concentrated. The product was purified by column chromatography (EtOAc/hexane as solvent) to give 28.8 mg of the silylated-product as an oil. The silylated-product was dissolved in TFA (0.34 mL) and stirred at 20° C. for 18 h before concentrated. Ammonium hydroxide solution was added to the residue until the pH was about 10–11 and a yellow solid was formed. The yellow solid was collected thru filtration, washed with water and dried under vacuum. The solid was recrystallized from CH$_3$OH/EtOAc to give 15 mg (33% two steps) of Compound 102d as a solid; $^1$H NMR (300 MHz, CD$_3$OD) δ 8.87 (s, 1H), 8.4 (s, 1H), 8.28 (s, 1H), 7.96 (d, J=2.7 Hz, 1H), 7.49–7.21 (m, 5H), 3.67 (t, J=6.3 Hz, 2H), 3.20 (t, J=6.9 Hz, 2H), 1.82 (m, 2H); MS (ES) m/z: 357 (M+H$^+$).

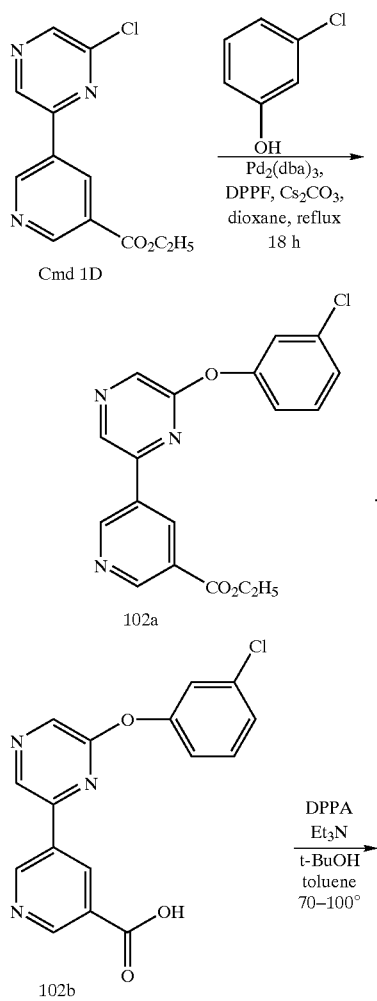

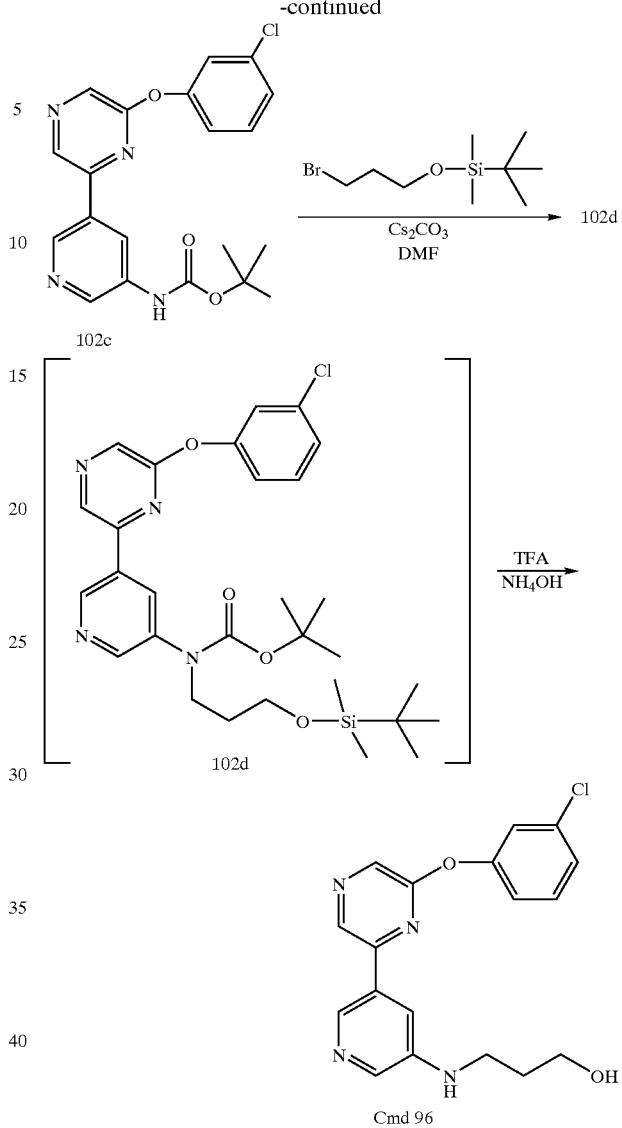

Cmd 96

EXAMPLE 103

COMPOUND 97

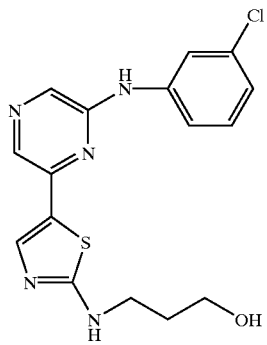

A mixture of (2-amino-5-bromothiazole HBr) Compound 103a (10 g, 38.4 mmol), Boc$_2$O (8.39 g, 38.4 mmol), DMAP (440 mg, 3.6 mmol) and NaHCO$_3$ (9.6 g, 114 mmol) in t-BuOH (100 mL) was stirred at 20° C. for 16 h. The reaction mixture was concentrated and the product was purified by column chromatography (EtOAc/hexane as solvent) and recrystallized from ethyl acetate/hexane to give 3.41 g (32%) of Compound 103b as a white solid; $^1$H NMR (300 MHz, D$^6$-DMSO) δ11.70 (brs, 1H), 7.43 (s, 1H), 1.48 (s, 9H); Anal. Calcd. For C$_8$H$_{11}$BrN$_2$O$_2$S: C, 34.42; H, 3.97; N, 10.04. Found: C, 34.59; H, 3.95; N, 9.92. A mixture of Compound 103b (2.2 g, 7.91 mmol), (3-bromopropoxy)-t-butyl-dimethylsilane (3.46 g, 12.7 mmol) and Cs$_2$CO$_3$ (7.7 g, 23.7 mmol) in DMF (24 mL) was stirred at 70° C. under nitrogen for 18 h. The reaction mixture was diluted with water, extracted with ether (3×), dried (Na$_2$SO$_4$) and concentrated. The product was purified by column chromatography (EtOAc/hexane as solvent) to give 2.6 g (72%) of the silylated-product Compound 103c as an oil. $^1$H NMR (300 MHz, CDCl$_3$) δ7.22 (s, 1H), 4.08 (t, J=7.5 Hz, 2H), 3.65 (t, J=6.3 Hz, 2H), 1.85 (m, 2H), 1.53 (s, 9H), 0.85 (s, 9H), 0.01 (s, 6H); Anal. Calcd. For C$_{17}$H$_{31}$BrN$_2$O$_3$SSi: C, 45.22; H, 6.92; N, 6.20. Found: C, 45.08; H, 6.72; N, 6.12.

A mixture of Compound 103c (152 mg, 0.337 mmol), bis(tributyltin) (390 mg, 0.34 mmol), tetrakis(triphenylphosphine) palladium (40 mg, 0.035 mmol), LiCl (43 mg, 1.0 mmol) and BHT (3 mg, 0.014 mmol) in dioxane (3 mL) was stirred at 100° C. for 4 h under nitrogen. The cooled reaction mixture was concentrated under vacuum. The residue was purified by column chromatography (EtOAc/hexane as solvent) to give 56 mg (25%) of Compound 103d as an oil; $^1$H NMR (300 MHz, CDCl$_3$) δ7.27 (s, 1H), 4.15 (t, J=7.4 Hz, 2H), 3.67 (t, J=6.3 Hz, 2H), 1.87(m, 2H), 1.54–1.46 (m, 15H), 1.28 (m, 6H), 1.05 (t, J=8.3 Hz, 6H), 0.85 (m, 18H), 0.01 (s, 6H); MS (ES) m/z: 663 (M+1+).

A mixture of Compound 103d (140 mg, 0.21 mmol), Cmd 45 (72 mg, 0.21 mmol), Pd(PPh$_3$)$_2$Cl$_2$ (15 mg, 0.021 mmol) and LiCl (27 mg, 0.62 mmol) in toluene (3.5 mL) was stirred at 100° C. for 3 h under nitrogen. The cooled reaction mixture was concentrated under vacuum. The residue was purified by column chromatography (EtOAc/hexane as solvent) to give 96 mg (68%) of the silylated-product Compound 103e as an oil. The silylated-product Compound 103e was dissolved in dichloromethane (2 mL) and TFA (2.6 mL) and stirred at 20° C. for 18 h before concentrated. Ammonium hydroxide solution was added to the residue until the pH was about 10–11 and a yellow solid was formed. The yellow solid was collected thru filtration, washed with water and dried under vacuum to give Cmd 97 as a light yellow solid; $^1$H NMR (300 MHz, CD$_3$OD) δ8.23 (s, 1H), 8.10 (t, J=2.0 Hz, 1H), 7.84 (s, 1H), 7.74 (s, 1H), 7.45 (dd, J=8.3, 1.3 Hz, 1H), 7.26 (t, J=8.1 Hz, 1H), 6.97 (dd, J=7.8, 1.1 Hz, 1H), 3.68 (t, J=6.2 Hz, 2H), 3.46 (t, J=6.9 Hz, 2H), 1.88 (m, 2H); MS (ES) m/z: 362 (M+1$^+$).

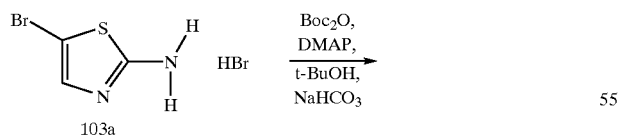

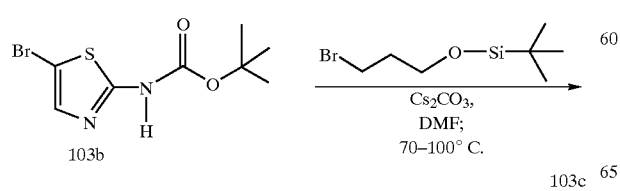

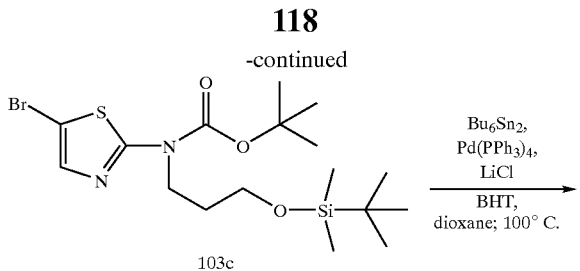

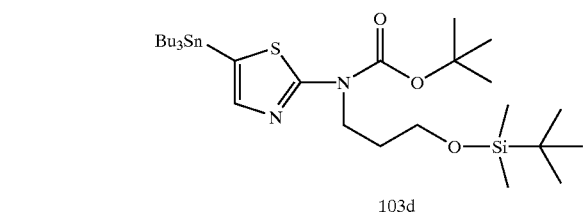

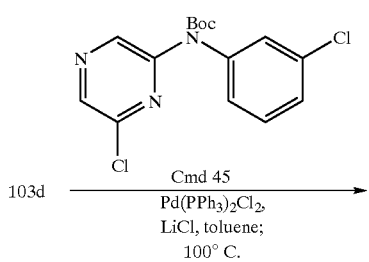

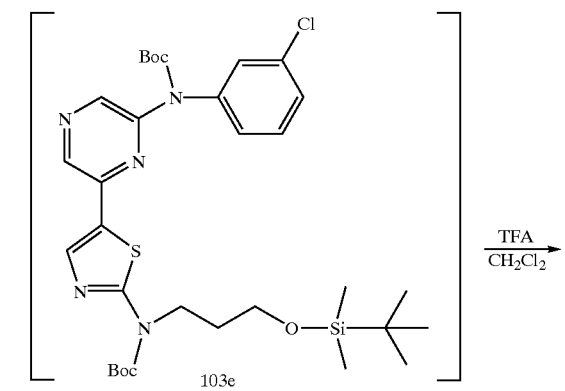

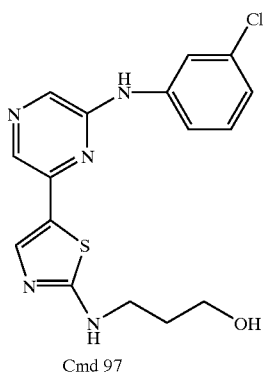

EXAMPLE 104

COMPOUND 98

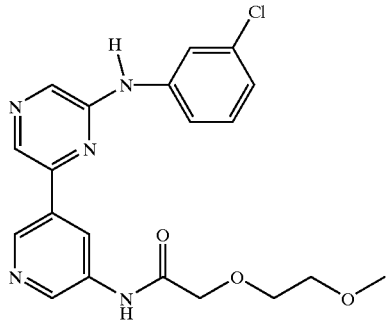

N-[5-[6-[(3-chlorophenyl)amino]pyrazinyl]-
3-pyridinyl]-2-(2-methoxyethoxy)-acetamide(Cmd 98)

A mixture of Cmd 67 (156 mg, 0.3 mmol) and 60% NaH (166 mg, 3.9 mmol), in THF (9 mL) was stirred under nitrogen at 20° C. for 10 min then (2-methoxyethoxy)acetyl chloride Compound 104a (where R = O⌒⌒O⌒CH₃);

(594 mg, 3.9 mmol) was added. The reaction was then stirred at reflux for 1 h. Saturated NaHCO₃ was added. The resulting THF layer was dried (Na₂SO₄) then concentrated under vacuum and purified by column chromatography (EtOAc/hexane as solvent) to give 122 mg (89%) of the Boc-protected amide Compound 104b as an oil. The Boc-protected amide Compound 104b was stirred in TFA (1 mL) at 20° C. for 18 h before concentrated. Ammonium hydroxide solution was added to the residue until the pH was about 10–11 and a yellow solid was formed. The solid was collected thru filtration, washed with water and dried under vacuum and purified by column chromatography (EtOAc/acetone as solvent) to give 20 mg (16%) of Cmd 98

(Compound 104c where R = O⌒⌒O⌒CH₃);

as an off-white solid; ¹H NMR (300 MHz, CD₃OD) δ9.00 (d, J=1.8 Hz, 1H), 8.88 (brs, 1H), 8.85 (brs, 1H), 8.49 (s, 1H), 8.16 (s, 1H), 7.91 (t, J=2.0 Hz, 1H), 7.74 (dd, J=8.2, 1.1 Hz, 1H), 7.33 (t, J=8.0 Hz, 1H), 7.00 (d, J=7.6 Hz, 1H), 4.57 (brs, 1H), 4.21 (s, 2H), 3.80 (m, 2H), 3.67 (m, 2H), 3.43 (s, 3H); Anal. Calcd. For $C_{20}H_{20}ClN_5O_3 \cdot 0.3H_2O$ : C, 57.29; H, 4.95; N, 16.70. Found: C, 57.33; H, 4.84; N, 16.51.

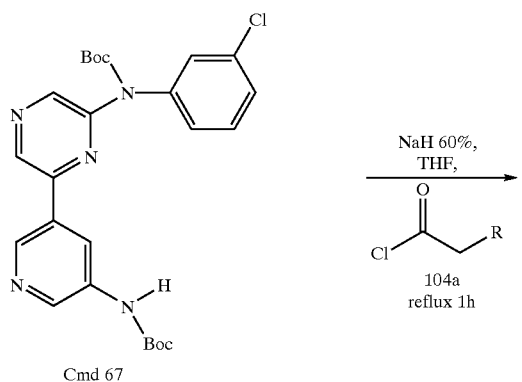

Cmd 67

NaH 60%, THF,

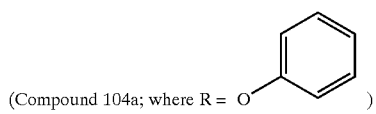

104a
reflux 1h

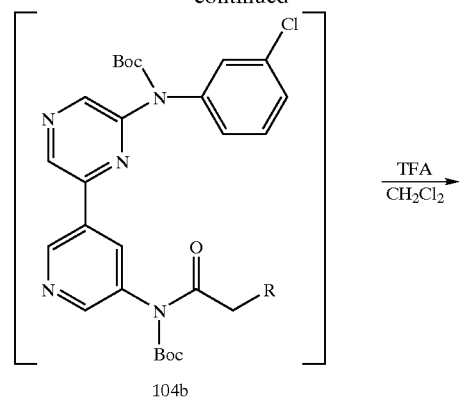

104b

TFA / CH₂Cl₂

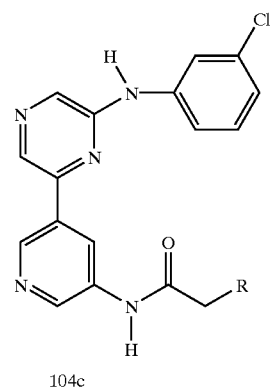

104c

R = O⌒⌒O⌒CH₃

EXAMPLE 105

COMPOUND 99

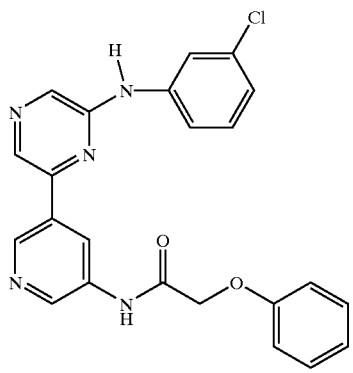

Following the procedure of Example 104, a mixture of Cmd 67 (156 mg, 0.3 mmol) and 60% NaH (90 mg, 2.1 mmol), in THF (9 mL) was stirred under nitrogen at 20° C. for 10 min then phenoxyacetyl chloride Compound 105a (Compound 104a; where R = O—C₆H₅ )

(358 mg, 2.1 mmol) was added. The reaction was then stirred at reflux for 0.5 h. Aqueous NaHCO₃ was added then extracted with ether. The ether layer was dried (Na₂SO₄) then concentrated under vacuum and purified by column chromatography (EtOAc/hexane as solvent) to give 134 mg of the Boc-protected amide Compound 105b as an oil. The Boc-protected amide Compound 105b was stirred in TFA (1 mL) at 20° C. for 48 h before concentrated. Ammonium hydroxide solution was added to the residue until the pH was about 10–11 and was then extracted with ethyl acetate. The ethyl acetate layer was dried on $Na_2SO_4$ then concentrated under vacuum and purified by column chromatography (EtOAc/acetone as solvent) to give 30 mg (23%) of Cmd 99

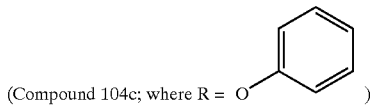

(Compound 104c; where R = )

as an off-white solid; $^1$H NMR (300 MHz, $D^6$-DMSO) δ10.48 (s, 1H), 9.89 (s, 1H), 9.00 (d, J=1.6 Hz, 1H), 8.86 (brs, 2H), 8.62 (s, 1H), 8.26 (s, 1H), 7.87 (s, 1H), 7.84 (s, 1H), 7.34 (t, J=7.6 Hz, 3H), 7.07–6.97 (m, 4H), 4.79 (s, 2H); FAB-HRMS (M+H$^+$). Calcd. for $C_{23}H_{18}ClN_5O_2$ 432.1227, found 432.1238.

EXAMPLE 106

COMPOUND 100

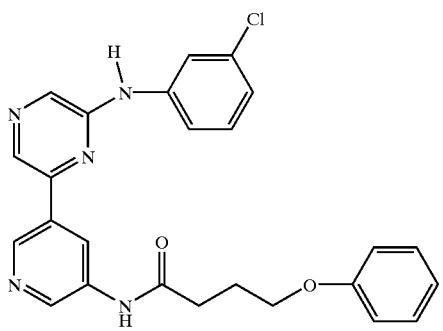

Following the procedure of Example 104, a mixture of Cmd 67 (250 mg, 0.5 mmol) and 60% NaH (150 mg, 3.5 mmol), in THF (9 mL) was stirred under nitrogen at 20° C. for 10 min then 4-phenoxybutyryl chloride Compound 106a

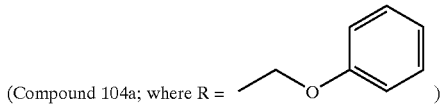

(Compound 104a; where R = )

(580 mg, 2.9 mmol) was added. The reaction was then stirred at reflux for 1 h. Aqueous $NaHCO_3$ was added then extracted with ether. The ether layer was dried on $Na_2SO_4$ then concentrated under vacuum and purified by column chromatography (EtOAc/hexane as solvent) to give 188 mg of the Boc-protected amide Compound 106b. The Boc-protected amide Compound 106b was stirred in dichloromethane (3 mL) and TFA (1 mL) at 20° C. for 48 h before concentrated. Ammonium hydroxide solution was added to the residue until the pH was about 10–11 and was then extracted with hot ethyl acetate. The ethyl acetate layer was dried ($Na_2SO_4$) then concentrated under vacuum and purified by recrystallization from ethyl acetate to give 30 mg (31%) of Cmd 100

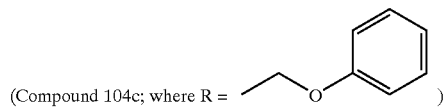

(Compound 104c; where R = )

as an off-white solid; $^1$H NMR (300 MHz, $D^6$-DMSO) δ10.36 (s, 1H), 9.89 (s, 1H), 8.95 (s, 1H), 8.83 (s, 1H), 8.76 (s, 1H), 8.60 (s, 1H), 8.26 (s, 1H), 7.88–7.84 (m, 2H), 7.38 (t, J=8.1 Hz, 1H), 7.31–7.25 (m, 2H), 7.02 (d, J=7.9 Hz, 1H), 6.95–6.90 (m, 3H), 4.05 (t, J=6.3 Hz, 2H), 2.59 (t, J=7.3 Hz, 2H), 2.08 (m, 2H); FAB-HRMS (M+H$^+$). Calcd. for $C_{25}H_{22}ClN_5O_2$ 460.1540, found 460.1542.

EXAMPLE 107

COMPOUND 101

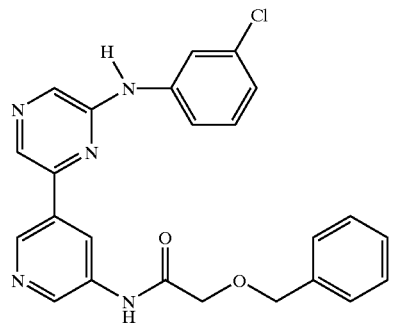

Following the procedure of Example 104, a mixture of Cmd 67 (250 mg, 0.5 mmol) and 60% NaH (150 mg, 3.5 mmol), in THF (9 mL) was stirred under nitrogen at 20° C. for 1 h then benzyloxyacetyl chloride Compound 107a

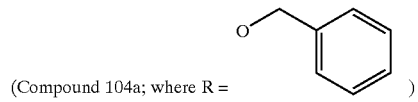

(Compound 104a; where R = )

(646 mg, 3.5 mmol) was added. The reaction was then stirred at reflux for 1 h. Saturated $NaHCO_{3(aq)}$ was added then extracted with ether. The ether layer was dried ($Na_2SO_4$) then concentrated under vacuum and purified by column chromatography (EtOAc/hexane as solvent) to give 264 mg of the Boc-protected amide Compound 107b as an oil. The Boc-protected amide Compound 107b was stirred in dichloromethane (4.2 mL) and TFA (1.4 mL) at 20° C. for 4 h before concentrated. Ammonium hydroxide solution was added to the residue until the pH was about 10–11 and was then extracted with ethyl acetate. The ethyl acetate layer was dried ($Na_2SO_4$) then concentrated under vacuum and purified by recrystallization from ethyl acetate to give 50 mg (22%) of Cmd 101

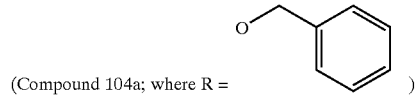

(Compound 104a; where R = )

(AD-12 as an off-white solid; $^1$H NMR (300 MHz, $D^6$-DMSO) δ10.21 (s, 1H), 9.89 (s, 1H), 8.99 (d, J=1.7 Hz, 1H), 8.86 (brs, 1H), 8.61 (s, 1H), 8.27 (s, 1H), 7.90 (brs, 1H), 7.86 (d, J=8.1 Hz, 1H), 7.45–7.30 (m, 6H), 7.03 (d, J=9.4 Hz, 1H), 4.67 (s, 2H), 4.18 (s, 2H); Anal. Calcd. For $C_{24}H_{20}ClN_5O_2 \cdot 0.2H_2O$ : C, 64.13; H, 4.57; N, 15.58. Found: C, 64.22; H, 4.45; N, 15.61.

EXAMPLE 108

COMPOUND 102

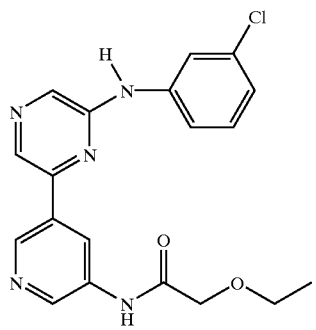

N-[5-[6[(3-chlorophenyl)amino]pyrazinyl]-
3-2-pyridinyl]-2-ethoxy-acetamide(Cmd 102)

A mixture of Cmd 67 (250 mg, 0.5 mmol) and 60% NaH (150 mg, 3.5 mmol), in THF (6 mL) was stirred under nitrogen at 20° C. for 1 h then ethoxyacetyl chloride Compound 108a (where R=ethoxyene) (427 mg, 3.5 mmol) in THF (3 mL) was added. The reaction was then stirred at reflux for 18 h. Water was added then extracted with ethyl acetate. The ether layer was dried (Na$_2$SO$_4$) then concentrated under vacuum and purified by column chromatography (EtOAc/hexane as solvent) to give 80 mg (42%) of Cmd 102 (Compound 108b; where R=ethoxyene) as an off-white solid; $^1$H NMR (300 MHz, D$^6$-DMSO) δ10.08 (s, 1H), 9.89 (s, 1H), 8.99 (s, 1H), 8.89 (s, 1H), 8.82 (s, 1H), 8.61 (s, 1H), 8.27 (s, 1H), 7.92 (d, J=1.6 Hz, 1H), 7.39 (t, J=8.0 Hz, 1H), 7.04 (d, J=7.9 Hz, 1H), 4.11 (s, 2H), 3.62(q, J=7.0 Hz, 2H), 1.22 (t, J=7.0 Hz, 3H); Anal. Calcd. For C$_{19}$H$_{18}$ClN$_5$O$_2$.0.1H$_2$O: C, 59.18; H, 4.76; N, 18.16. Found: C, 59.06; H, 4.49; N, 17.98.

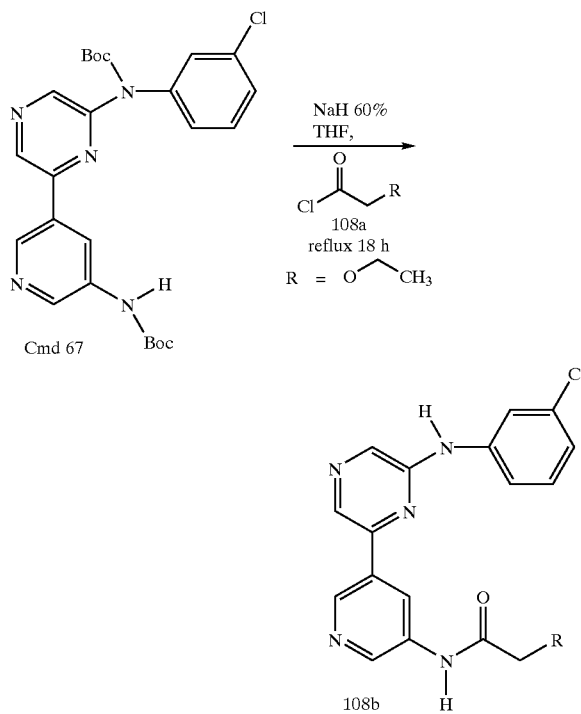

EXAMPLE 109

COMPOUND 103

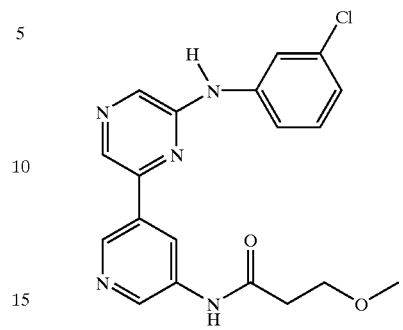

N-[5-[6-[(3-chlorophenyl)amino]pyradinyl]-
3-pyridinyl]-3-methoxy-propanamide(Cmd 103)

Following the procedure of Example 108, a mixture of Cmd 67 (250 mg, 0.5 mmol) and 60% NaH (150 mg, 3.5 mmol), in THF (6 mL) was stirred under nitrogen at 20° C. for 0.5 h then 3-methoxypropanoyl chloride Compound 109a (Compound 108a; where R=(1-methoxy)methylene) (427 mg, 3.5 mmol) in THF (3 mL) was added. The reaction was then stirred at reflux for 18 h. Water was added then extracted with ethyl acetate. The ether layer was dried (Na$_2$SO$_4$) then concentrated under vacuum and purified by column chromatography (EtOAc/acetone as solvent) to give 50 mg (26%) of Cmd 103 (Compound 108b; where R=(1-methoxy)methylene) as an off-white solid; $^1$H NMR (300 MHz, D$^6$-DMSO) δ10.35 (s, 1H), 9.89 (s, 1H), 8.96 (s, 1H), 8.81 (s, 1H), 8.78 (s, 1H), 8.60 (s, 1H), 8.26 (s, 1H), 7.88 (brs, 1H), 7.84 (brs, 1H), 7.40 (t, J=8.1 Hz, 1H), 7.04 (dd, J=7.8, 1.1 Hz, 1H), 3.66 (t, J=6.1 Hz, 2H), 3.26 (s, 3H), 2.63 (t, J=6.1 Hz, 2H); Anal. Calcd. For C$_{19}$H$_{18}$ClN$_5$O$_2$.0.2H$_2$O: C, 58.90; H, 4.79; N, 18.08. Found: C, 59.07; H, 4.69; N, 17.93.

EXAMPLE 110

COMPOUND 104

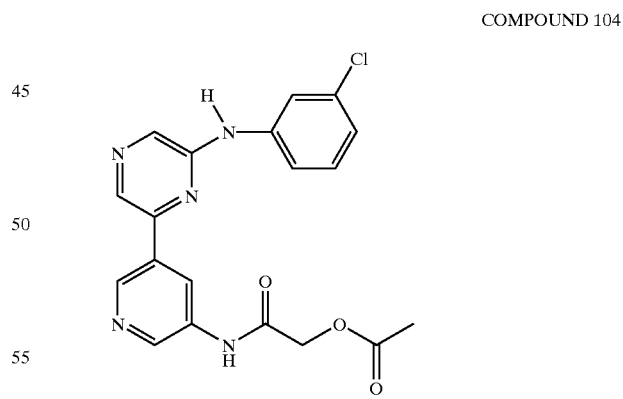

Following the procedure of Example 104, a mixture of Cmd 67 (250 mg, 0.5 mmol) and 60% NaH (150 mg, 3.5 mmol), in THF (9 mL) was stirred under nitrogen at 20° C. for 0.5 h then acetoxyacetyl chloride Compound 110a (Compound 104a; where R=acetyloxyene) (478 mg, 3.5 mmol) was added. The reaction was then stirred at reflux for 18 h (conditions changed from Example 104). Water was added then extracted with ethyl acetate. The ether layer was dried (Na$_2$SO$_4$) then concentrated under vacuum and purified by column chromatography (EtOAc/acetone as solvent) to give 70 mg of the Boc-protected amide Compound 110b as an oil. The Boc-protected amide Compound 110b was stirred in dichloromethane (1.3 mL) and TFA (0.42 mL) at 20° C. for 60 h before concentrated. Ammonium hydroxide solution was added to the residue until the pH was about 10–11 and was then extracted with ethyl acetate. The ethyl acetate layer was dried ($Na_2SO_4$) then concentrated under vacuum and purified by column chromatography (EtOAc/acetone as solvent) to give 26 mg (13%) of Cmd 104 (Compound 104c; where R=acetyloxyene) AD-15 as an off-white solid; $^1$H NMR (300 MHz, $CD_3OD$) δ8.91 (brs, 1H), 8.75 (brs, 2H), 8.42 (brs, 1H), 8.10 (brs, 1H), 7.83–7.56 (m, 2H), 7.28 (m, 1H), 6.96 (m, 1H), 4.85 (s, 2H), 2.21 (s, 3H); MS (ES) m/z: 398 (M+1$^+$).

EXAMPLE 111

COMPOUND 105

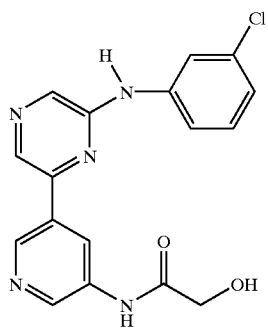

N[5-[6-[(3-chlorophenyl)amino]pyrazinyl]-3-pyridinyl]-2-hydroxy-acetamide(Cmd 105)

A mixture of Cmd 104 (prepared according to the procedure of Example 110) (26 mg, 0.065 mmol), $K_2CO_3$ (5.4 mg, 0.04 mmol), $H_2O$ (0.1 mL) and methanol (3.4 mL) was heated at reflux for 1 min. Crystals were recovered by filtration and purified by recrystallization from methanol to give 5 mg (22%) of Cmd 105 as an off-white solid; $^1$H NMR (300 MHz, $CD_3OD$) δ10.10 (s, 1H), 9.89 (s, 1H), 8.98–8.88 (m, 3H), 8.60 (s, 1H), 8.26 (s, 1H), 7.89–7.86 (m, 2H), 7.40 (t, J=8.2 Hz, 1H), 7.04 (d, J=7.2 Hz, 1H), 5.81 (m, 1H), 4.08 (d, J=5.5 Hz, 2H); FAB-HRMS (M+H$^+$). Calcd. for $C_{17}H_{14}ClN_5O_2$ 356.0914, found 356.0927.

EXAMPLE 112

COMPOUND 106

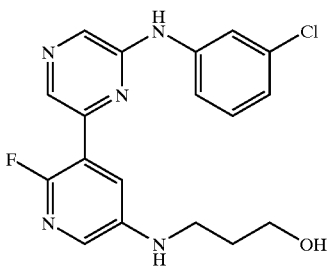

Bromine (2.3 mL, 44.6 mmol) was added dropwise to a suspension of the 6-aminonicotinic acid Compound 112a (5.08 g, 36.8 mmol) in water (20 mL) at 4° C. After the completion of the addition, the cooling bath was removed and the reaction mixture was stirred at room temperature for 4.5 h. Saturated $Na_2S_2O_5$ was added slowly to the stirred mixture. The solid was collected through filtration, washed with water, and dried under vacuum overnight to give 9.30 g of 6-amino-5-bromonicotinic acid along with 3,5-dibromo-2-aminopyridine in ~1:1 ration as a greenish solid; MS (ES) m/z: 217 (M+H$^+$). A mixture of the solid (4.00 g) containing 6-amino-5-bromonicotinic acid, DPPA (6.08 g, 22.1 mmol), triethylamine (2.80 g, 27.7 mmol), benzyl alcohol (3.8 mL, 36.8 mmol), and toluene (50 mL) was heated at 70° C. for 1 h, then 100° C. for 1 h. After concentration, the reaction mixture was purified by flash chromatography (EtOAc/hexane as solvent) to give 1.31 g (26% in 2 steps) of Compound 112b as a yellow solid; $^1$H NMR (300 MHz, $CDCl_3$) δ7.99 (brs, 1H), 7.91(d, J=2.3 Hz, 1H), 7.39–7.34 (m, 5H), 6.50 (brs, 1H), 5.19 (s, 2H), 4.79 (brs, 2H); MS (ES) m/z: 324 (M+H$^+$). Anal. Calcd. For $C_{13}H_{12}BrN_3O_2 \cdot 0.1H_2O$ : C, 48.20; H, 3.80; N, 12.97. Found: C, 48.40; H, 3.90; N, 12.64.

A mixture of Compound 112b (685 mg, 2.13 mmol), (3-bromopropoxy)-tert-butyldiphenylsilane (965 mg, 2.56 mmol), and $Cs_2CO_3$ (1.04 g, 3.19 mmol) in dry DMF (20 mL) was heated at 70° C. for 3 h. The reaction mixture was concentrated and purified by column chromatography (EtOAc/hexane as solvent) to give 1.06 g (81%) of Compound 112c as a yellow oil; $^1$H NMR (300 MHz, $CDCl_3$) δ7.88 (brs, 1H), 7.61–7.58 (m, 5H), 7.51 (brs, 1H), 7.41–7.30 (m, 10H), 5.12 (s, 2H), 4.93 (s, 2H), 3.74 (t, J=7.4 Hz, 2H), 3.65 (t, J=6.0 Hz, 2H), 1.82–1.73 (m, 2H), 1.00 (s, 9H); MS (ES) m/z: 620 (M+H$^+$). Nitrosonium tetrafluoroborate (170 mg, 1.45 mmol) was added to the solution of Compound 112c (680 mg, 1.10 mmol) in $CH_2Cl_2$ (20 mL) at 4° C. After 1 h at 4° C., more $NOBF_4$ (50 mg, 0.43 mmol) was added followed by the same amount of $NOBF_4$ (50 mg, 0.43 mmol) after another 1 h. After stirring for total 3 h at 4° C., water was added. The aqueous solution was extracted with $CH_2Cl_2$. The combined organic layers were dried, concentrated, and flash chromatographed (EtOAc/hexane) to give 425 mg (62%) of Compound 112d as a yellow oil; $^1$H NMR (300 MHz, $CDCl_3$) δ8.24 (d, J=2.3 Hz, 1H), 7.84 (brs, 1H), 7.59–7.56 (m, 5 H), 7.45–7.27 (m, 10H), 5.15 (s, 2H), 3.83 (m, 2H), 3.65 (t, J=5.9 Hz, 2H), 1.79 (m, 2H), 1.00 (s, 9H); MS (ES) m/z: 645 (M+Na$^+$). Anal. Calcd. For $C_{32}H_{34}BrFN_2O_3Si \cdot 0.50H_2O$ : C, 60.95; H, 5.59; N, 4.44. Found: C, 60.65; H, 5.24; N, 4.35.

A mixture of Compound 112d (405 mg, 0.652 mmol), bis(trimethyltin) (427 mg, 1.30 mmol), tetrakis (triphenylphosphine) palladium (76 mg, 0.066 mmol), LiCl (110 mg, 2.59 mmol), and 2,6-di-tert-butyl-4-methylphenol (6 mg, 0.03 mmol) in anhydrous 1,4-dioxane (10 mL) was refluxed at 100° C. for 4.5 h under nitrogen. After removal of solvent under reduced pressure, the mixture was purified by flash chromatography (EtOAc/hexane as solvent) to give 375 mg (82%) of Compound 112e as a clear oil; $^1$H NMR (400 MHz, $CDCl_3$) δ8.17 (s, 1H), 7.59–7.57 (m, 5H), 7.53 (s, 1H), 7.44–7.27 (m, 10H), 5.14 (s, 2H), 3.84 (t, J=7.5 Hz, 2H), 3.66 (t, J=5.8 Hz, 2H), 1.82 (m, 2H), 0.98 (s, 9H), 0.38 (s, 9H); MS (ES) m/z: 729 (M+Na$^+$). A mixture of Compound 112e (370 mg, 0.525 mmol), N-(tert-butoxycarbonyl)-N-(3-chlorophenyl)-2-amino-6-chloropyrazine Cmd 45 (200 mg, 0.588 mmol), dichlorobis (triphenylphosphine)palladium (74 mg, 0.11 mmol), and LiCl (89 mg, 2.10 mmol) in anhydrous toluene (5 mL) was stirred at 100° C. for 19 h under nitrogen. After removal of solvent under reduced pressure, the residue was purified by flash chromatography (EtOAc/hexane as solvent) to give 140 mg (32%) of Compound 112f as a yellow solid; $^1$H NMR (400 MHz, CDCl$_3$) δ9.15 (s, 1H), 8.94 (d, J=1.6 Hz, 1H), 8.06 (s, 1H), 7.89 (brs, 1H), 7.59–7.52 (m, 5H), 7.41–7.20 (m, 13H), 7.06–7.04 (m, 1H), 5.13 (s, 2H), 3.78 (t, J=7.3 Hz, 2H), 3.62 (t, J=5.9 Hz, 2H), 1.76–1.70 (m, 2H), 1.48 (s, 9H), 0.95 (s, 9H); MS (ES) m/z: 868 (M+Na$^+$).

The mixture of Compound 112f (100 mg, 0.118 mmol), 10% Pd/C (100 mg), EtOH (9 mL), and EtOAc (3 mL) was hydrogenated under 22 psi for 46 h at room temperature. After removal of solvents under reduced pressure, the residue was purified by flash chromatography (ethyl acetate/hexane as solvent) to give 55 mg (65%) of Compound 112f as the des-Cbz yellow oil. Anal. Calcd. For C$_{39}$H$_{43}$ClFN$_5$O$_3$Si.0.30H$_2$O : C, 65.26; H, 6.12; N, 9.76. Found: C, 65.50; H, 6.30; N, 9.44. A solution of the yellow oil (68 mg, 0.096 mmol), TFA (1 mL), and CH$_3$SO$_3$H (3 drops) was stirred at room temperature for 5 h and then concentrated. A saturated NH$_4$OH solution was added to the residue until the mixture was made basic followed by the addition of water. The precipitated solid was collected through filtration, washed with water, and dried under vacuum. The product was purified by flash chromatography on silica gel (using EtOAc/MeOH as the solvent) to provide 30 mg (84%) of Cmd 106 as a yellow solid; $^1$H NMR (300 MHz, DMSO-d$_6$) δ9.90 (s, 1H), 8.42 (s, 1H), 8.25 (s, 1H), 8.05 (s, 1H), 7.64 (s, 1H), 7.62 (s, 2H), 7.36 (t, J=8.1 Hz, 1H), 7.03 (d, J=7.8 Hz, 1H), 6.02 (brs, 1H), 4.52 (brs, 1H), 3.54 (t, J=5.9 Hz, 2H), 3.17 (m, 2H), 1.76 (m, 2H); MS (ES) m/z: 374 (M+H$^+$).

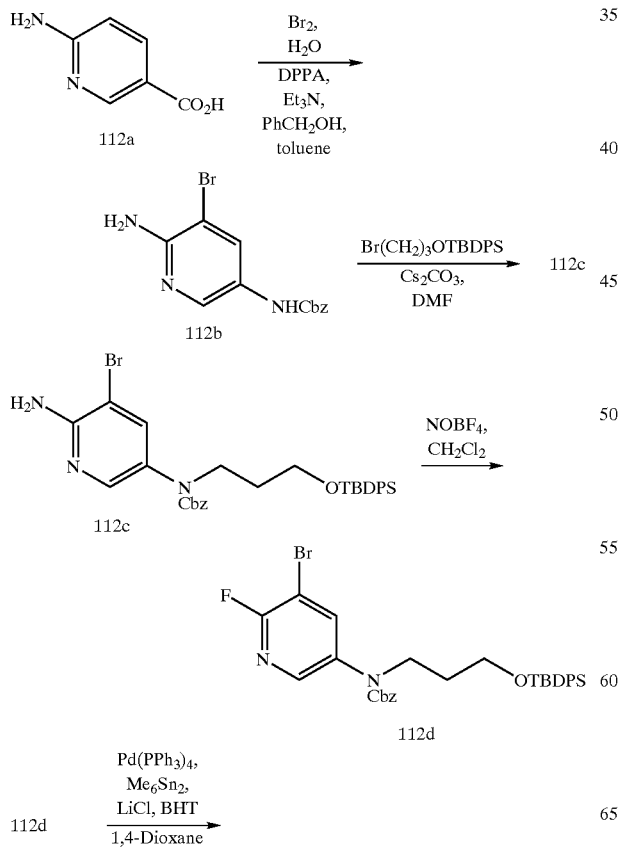

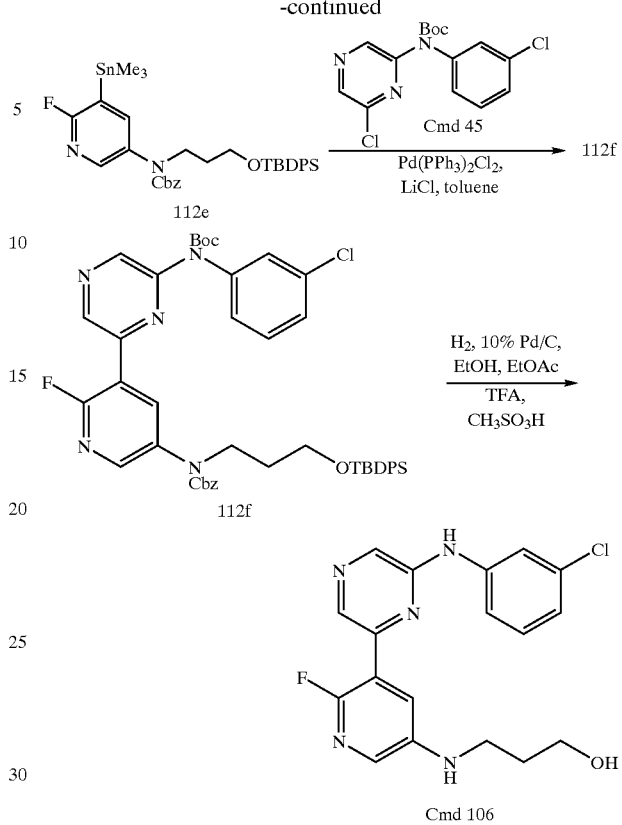

EXAMPLE 113

COMPOUND 107

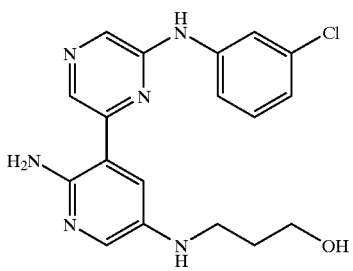

A mixture of Compound 113a (1.25 g, 2.02 mmol), bis(trimethyltin) (1.00 g, 3.05 mmol), tetrakis(triphenylphosphine) palladium (240 mg, 0.208 mmol), LiCl (260 mg, 6.13 mmol), and 2,6-di-tert-butyl-4-methylphenol (20 mg, 0.091 mmol) in anhydrous 1,4-dioxane (25 mL) was refluxed at 100° C. for 3 h under nitrogen. After removal of solvent under reduced pressure, the residue was purified by flash chromatography (EtOAc/hexane as solvent) to give 1.05 g (74%) of Compound 113b as a yellow oil; $^1$H NMR (300 MHz, CDCl$_3$) δ7.86 (brs, 1H), 7.61–7.58 (m, 5H), 7.43–7.28 (m, 11H), 5.11 (brs, 2H), 4.40 (s, 2H), 3.75 (t, J=7.6 Hz, 2H), 3.66 (t, J=6.0 Hz, 2H), 1.85–1.76 (m, 2H), 0.99 (s, 9H), 0.34 (s, 9H); MS (ES) m/z: 704 (M+H$^+$). A mixture of Compound 113b (1.05 g, 1.50 mmol), N-(tert-butoxycarbonyl)-N-(3-chlorophenyl)-2-amino-6-chloropyrazine Cmd 45 (510 mg, 1.50 mmol), dichlorobis(triphenylphosphine)palladium (105 mg, 0.150 mmol), and LiCl (190 mg, 4.48 mmol) in anhydrous toluene (30 mL)

was stirred at 100° C. for 2.5 h under nitrogen. After removal of solvent under reduced pressure, the residue was purified by flash chromatography (EtOAc/hexane as solvent) to give 830 mg (66%) of Compound 113c as a yellow oil; $^1$H NMR (300 MHz, CDCl$_3$) δ9.00 (s, 1H), 8.52 (brs, 1H), 7.93 (s, 1H), 7.66 (brs, 1H), 7.59–7.55 (m, 5H), 7.41–7.27 (m, 13H), 7.14 (m, 1H), 5.89 (s, 2H), 5.11 (brs, 2H), 3.77 (t, J=7.4 Hz, 2H), 3.65 (t, J=5.9 Hz, 2H), 1.84–1.75 (m, 2H), 1.48 (s, 9H), 0.97 (s, 9H); MS (ES) m/z: 843 (M+H$^+$). Anal. Calcd. For C$_{47}$H$_{51}$ClN$_6$O$_5$Si.1.70H$_2$O: C, 64.58; H, 6.27; N, 9.61. Found: C, 64.93; H, 6.18; N, 9.23. A solution of Compound 113c (70 mg, 0.083 mmol), CF$_3$SO$_3$H (0.4 mL), and CH$_2$Cl$_2$ (1 mL) was stirred at room temperature for 1.5 h and then concentrated. A saturated NH$_4$OH solution was added to the residue at 4° C. until the mixture was made basic followed by the addition of water. The aqueous solution was discarded. The gummy material left in the reaction flask was washed with water, dried under vacuum, and purified by flash chromatography (CH$_2$Cl$_2$/MeOH as solvent) to provide 37 mg (76%) of Cmd 107 as a dark yellow oil; $^1$H NMR (300 MHz, MeOH-d$_4$) δ8.31 (s, 1H), 8.07 (s, 1H), 7.71 (s, 1H), 7.61 (d, J=2.5 Hz, 1H), 7.47 (m, 2H), 7.29 (t, J=8.0 Hz, 1H), 7.01 (d, J=6.6 Hz, 1H), 3.71 (t, J=6.2 Hz, 2H), 3.19 (t, J=6.9 Hz, 2H), 1.85 (m, 2H); MS (ES) m/z: 371 (M+H$^+$).

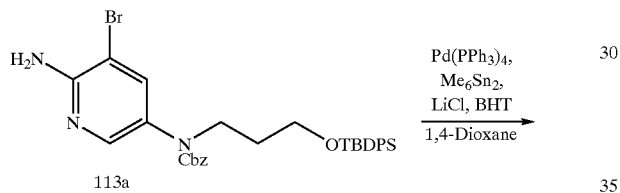

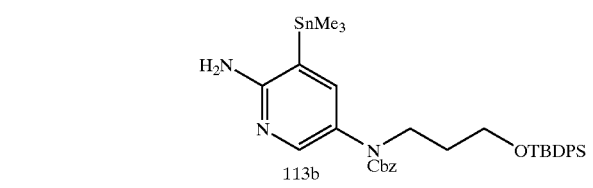

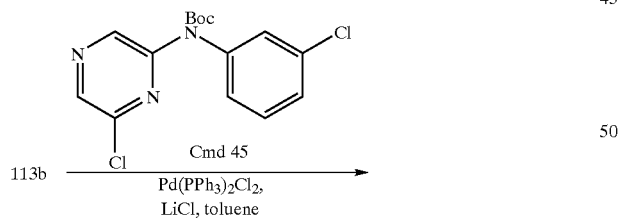

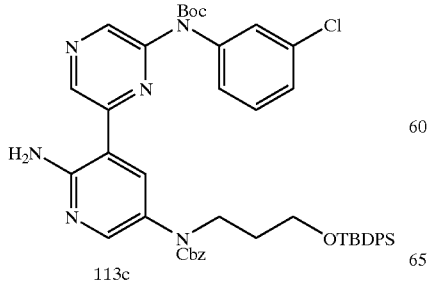

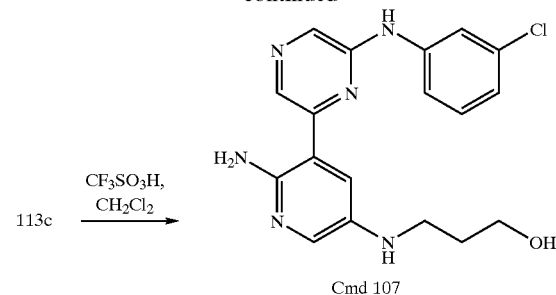

Cmd 107

EXAMPLE 114

COMPOUND 108

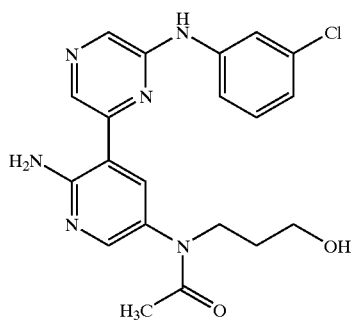

A solution of Compound 113c (128 mg, 0.152 mmol) and 30% HBr in AcOH (1.5 mL) was stirred at room temperature for 7 h and then concentrated. A saturated NH$_4$OH solution was added to the residue at 4° C. until the pH was ~11. The aqueous solution was discarded. The gummy material left in the reaction flask was washed with water, dried under vacuum, and purified by flash chromatography (EtOAc/MeOH as solvent) to provide 62 mg (60%) of Cmd 108 as a yellow oil; $^1$H NMR (300 MHz, CDCl$_3$) δ8.37 (s, 1H), 8.14 (s, 1H), 7.71 (d, J=2.6 Hz, 1H), 7.52 (s, 1H), 7.33–7.25 (m, 4H), 7.09–7.06 (m, 2H), 5.77 (brs, 2H), 4.22 (t, J=6.2 Hz, 2H), 3.23 (t, J=6.8 Hz, 2H), 2.08 (s, 3H), 1.97 (m, 2H); MS (ES) m/z: 413 (M+H$^+$).

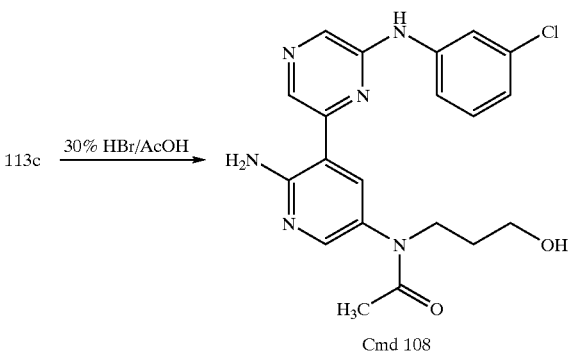

Cmd 108

EXAMPLE 115

COMPOUND 109

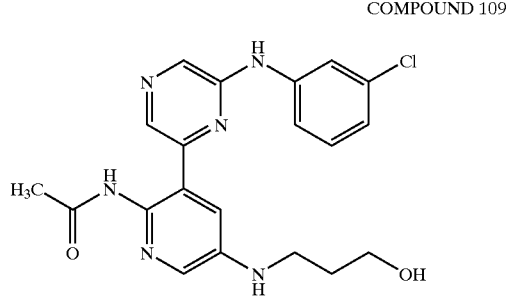

A solution of Compound 113c (58 mg, 0.069 mmol) in CH₃CN (2 mL) was added to a solution of tert-butyl nitrite (0.018 mL, 0.14 mmol), CuBr₂ (23 mg, 0.10 mmol) and CH₃CN (0.5 mL) at room temperature. After stirring for 1.5 h, the solvent was evaporated and the residue was partitioned between Et₂O and diluted HCl aqueous solution. The organic layer was dried, concentrated, and flash chromatographed (EtOAc/hexane) to provide 32 mg (53%) of Compound 115a as a yellow oil; $^1$H NMR (300 MHz, CDCl₃) δ9.96 (s, 1H), 8.81 (s, 1H), 8.44 (brs, 1H), 8.38 (d, J=2.2 Hz, 1H), 7.74 (brs, 1H), 7.60–7.57 (m, 5H), 7.43–7.20 (m, 14H), 5.17 (s, 2H), 3.88 (t, J=7.3 Hz, 2H), 3.67 (t, J=6.0 Hz, 2H), 2.21 (s, 3H), 1.84 (m, 2H), 1.49 (s, 9H), 0.98 (s, 9H); MS (ES) m/z: 885 (M+H⁺). A solution of Compound 115a (83 mg, 0.094 mmol), CH₃SO₃H (0.5 mL), and CH₂Cl₂ (1 mL) was stirred at room temperature for 6 h and then concentrated. A saturated NH₄OH solution was added to the residue at 4° C. until the pH was 10. The aqueous solution was discarded. The gummy material left in the reaction flask was washed with water, dried under vacuum, and purified by flash chromatography (CH₂Cl₂/MeOH as solvent) to provide 28 mg (72%) of Cmd 109 as a yellow solid; $^1$H NMR (300 MHz, MeOH-d₄) δ8.18 (s, 1H), 8.09 (s, 1H), 7.87 (m, 2H), 7.62 (d, J=7.3 Hz, 1H), 7.38 (d, J=2.4 Hz, 1H), 7.27 (t, J=8.1 Hz, 1H), 6.97 (dd, J=7.9, 1.1 Hz, 1H), 3.70 (t, J=6.1 Hz, 2H), 3.29 (m, 2H), 1.90 (s, 3H), 1.88 (m, 2H); MS (ES) m/z: 413 (M+H⁺).

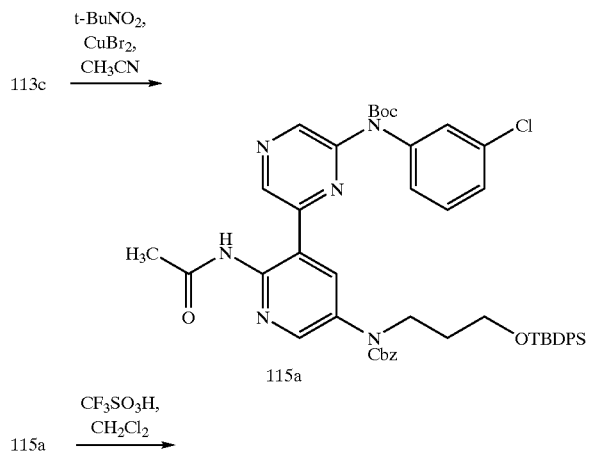

-continued

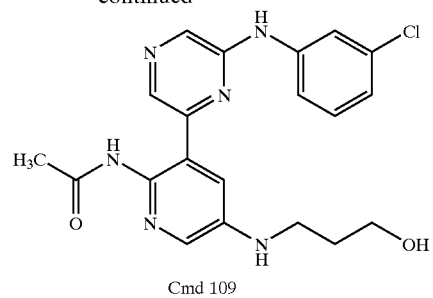

Cmd 109

EXAMPLE 116

COMPOUND 110

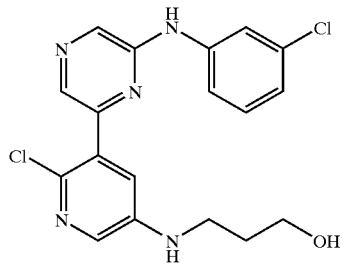

Bromine (4.2 mL, 81.4 mmol) was added dropwise to the suspension of 6-hydroxynicotinic acid Compound 116a (8.00 g, 57.6 mmol) in water (30 mL) at 4° C. After the completion of the addition, the cooling bath was removed and the reaction mixture was stirred at room temperature for 4 h. Saturated Na₂SO₅ was added slowly to the stirred mixture until the brown mixture became white. The solid was collected through filtration, washed with water, and dried under vacuum overnight to give 12.17 g (97%) of 6-hydroxy-5-bromonicotinic acid as an off-white solid; $^1$H NMR (300 MHz, DMSO-d₆) δ12.95 (brs, 1H), 12.55 (brs, 1H), 8.16 (s, 1H), 8.04 (s, 1H). Quinoline (1.0 mL, 8.47 mmol) was slowly added to the solution of POCl₃ (2.0 mL, 21.5 mmol), followed by 6-hydroxy-5-bromonicotinic acid (3.92 g, 18.0 mmol) at room temperature. After heating at 120° C. for 2 h, the reaction was quenched by addition of water dropwise at 10° C. After the mixture was cooled at 4° C. for a few hours, the solid was collected through filtration, washed with water, and dried under vacuum overnight to give 3.68 g (87%) of Compound 116b as an off-white solid; $^1$H NMR (300 MHz, DMSO-d₆) δ8.86 (s, 1H), 8.55 (s, 1H); MS (ES) m/z: 236 (M−H⁺).

A mixture of Compound 116b (2.00 g, 8.46 mmol), DPPA (3.49 g, 12.7 mmol), triethylamine (2.56 g, 25.3 mmol), t-BuOH (18 mL), and toluene (20 mL) was heated at 65° C. for 3 h, then 100° C. for 1.5 h. After removal of solvent under reduced pressure, the reaction mixture was purified by flash chromatography (EtOAc/hexane as solvent) to give 3.04 g of Compound 116c (containing impurities) as an off-white solid; $^1$H NMR (300 MHz, CDCl₃) δ8.36 (s, 1H), 8.19 (d, J=2.3 Hz, 1H), 7.01 (brs, 1H), 1.52 (s, 9H); MS (ES) m/z: 309 (M+H⁺). Anal. Calcd. For C₁₀H₁₂BrClN₂O₂: C, 39.05; H, 3.93; N, 9.11. Found: C, 38.94; H, 4.01; N, 9.06. A mixture of Compound 116c (710 mg, 2.31 mmol), 3-bromo-1-propanol (400 mg, 2.88 mmol), and Cs₂CO₃ (1.13 g, 3.47 mmol) in dry CH₃CN (10 mL) was heated at 65° C. for 17 h. The reaction mixture was concentrated and purified by column chromatography (EtOAc/hexane as solvent) to give 255 mg (30%) of Compound 116d as a clear oil; ¹H NMR (300 MHz, CDCl₃) δ8.22 (d, J=2.4 Hz, 1H), 7.84 (d, J=2.3 Hz, 1H), 3.80 (t, J=6.5 Hz, 2H), 3.67 (m, 2H), 1.74 (m, 2H), 1.44 (s, 9H); MS (ES) m/z: 389 (M+Na⁺). A mixture of Compound 116d (145 mg, 0.396 mmol), bis (trimethyltin) (260 mg, 0.794 mmol), tetrakis (triphenylphosphine) palladium (46 mg, 0.040 mmol), LiCl (68 mg, 1.6 mmol), and 2,6-di-tert-butyl-4-methylphenol (4 mg, 0.02 mmol) in anhydrous 1,4-dioxane (5 mL) was refluxed at 100° C. for 3 h under nitrogen. After removal of solvent under reduced pressure, the residue was purified by flash chromatography (CH₂Cl₂/EtOAc as solvent) to give 149 mg (84%) of Compound 116e as a clear oil; ¹H NMR (300 MHz, CDCl₃) δ8.13 (d, J=2.9 Hz, 1H), 7.50 (d, J=2.9 Hz, 1H), 3.79 (t, J=6.3 Hz, 2H), 3.67 (m, 2H), 1.71 (m, 2H), 1.42 (s, 9H), 0.42 (s, 9H); MS (ES) m/z: 451 (M+H⁺).

A mixture of Compound 116e (145 mg, 0.323 mmol), N-(tert-butoxycarbonyl)-N-(3-chlorophenyl)-2-amino-6-chloropyrazine Cmd 45 (120 mg, 0.353 mmol), dichlorobis (triphenylphosphine)palladium (23 mg, 0.033 mmol), and LiCl (55 mg, 1.3 mmol) in anhydrous toluene (4 mL) was stirred at 110° C. for 32 h under nitrogen. After removal of solvent under reduced pressure, the residue was purified by flash chromatography (EtOAc/hexane as solvent) to give 28 mg (15%) of the coupling compound as a yellow solid. A solution of the yellow solid (28 mg, 0.047 mmol), TFA (1 mL), and CH₂Cl₂ (1 mL) was stirred at room temperature for 1.5 h and then concentrated. A saturated NH₄OH solution was added to the residue until the mixture was made basic, followed by the addition of water. The precipitated solid was collected through filtration, washed with water, and dried under vacuum. The product was purified by flash chromatography on silica gel (EtOAc/CH₂Cl₂ as solvent) to provide 13 mg (70%) of Cmd 110 as a yellow solid; ¹H NMR (300 MHz, DMSO-d₆) δ9.89 (s, 1H), 8.26 (s, 2H), 8.07 (s, 1H), 7.86 (d, J=2.9 Hz, 1H), 7.57 (d, J=8.3 Hz, 1H), 7.32 (t, J=8.1 Hz, 1H), 7.20 (d, J=2.9 Hz, 1H), 6.99 (d, J=6.0 Hz, 1H), 6.26 (t, J=5.2 Hz, 1H), 4.50 (brs, 1H), 3.50 (m, 2H), 3.15 (m, 2H), 1.72 (m, 2H); MS (ES) m/z: 390 (M+H⁺).

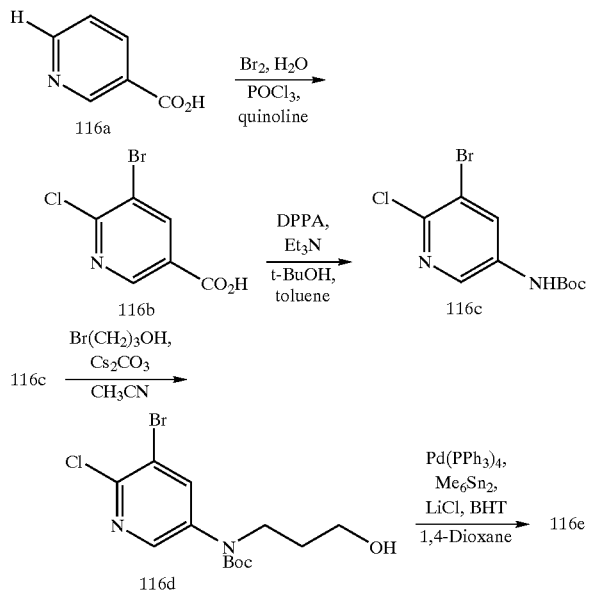

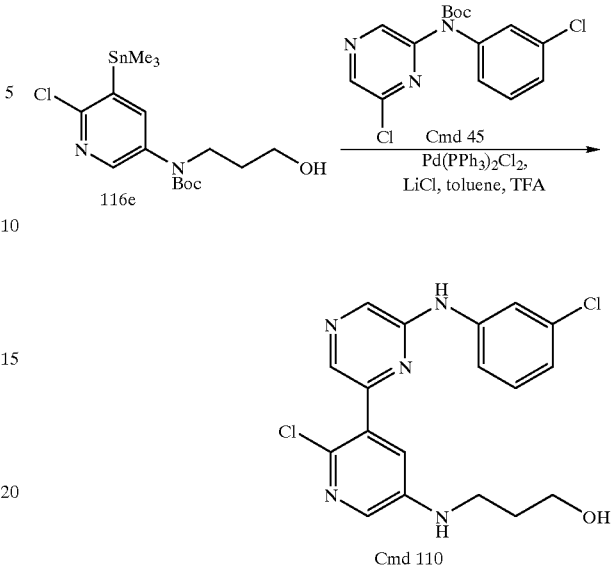

EXAMPLE 117

Compound 111

2.0 M TMSCHN₂ in hexane (6.4 mL, 12.8 mmol) was slowly added to a suspension of Compound 116b (2.00 g, 8.46 mmol) in C₆H₆ (10 mL) and MeOH (10 mL) at 4° C. After 15 min, the cooling bath was removed. The solution was stirred at room temperature for 1 h, concentrated under reduced pressure, and flash chromatographed to give 2.03 g (96%) of methyl 5-bromo-6-chloronicotinic acid as a white solid. The mixture of methyl 5-bromo-6-chloronicotinic acid (4.00 g, 16.0 mmol), KF (2.78 g, 47.9 mmol), tetraphenylphosphonium bromide (3.35 g, 8.0 mmol) and CH₃CN (100 mL) was heated at 80° C. for 4.5 days and filtered. The filtrate was concentrated and flash chromatographed (EtOAc/hexane as solvent) to provide 2.40 g (64%) of Compound 117a as white crystals; ¹H NMR (300 MHz, CDCl₃) δ8.78 (m, 1H), 8.58 (dd, J=8.2, 2.1 Hz, 1H), 3.97 (s, 3H); MS (ES) m/z: 235 (M+H⁺). Anal. Calcd. For C₇H₅BrFNO₂: C, 35.93; H, 2.15; N, 5.99. Found: C, 36.10; H, 2.43; N, 5.90. A mixture of Compound 117a (2.02 g, 8.63 mmol), bis(trimethyltin) (3.40 g, 10.4 mmol), tetrakis (triphenylphosphine) palladium (0.500 g, 0.433 mmol), LiCl (1.10 g, 25.9 mmol), and 2,6-di-tert-butyl-4-methylphenol (76 mg, 0.34 mmol) in anhydrous 1,4-dioxane (40 mL) was refluxed at 100° C. for 2 h under nitrogen. After removal of solvent under reduced pressure, the mixture was purified by flash chromatography (EtOAc/hexane as solvent) to give 2.72 g (99%) of Compound 117b as white crystals; ¹H NMR (300 MHz, CDCl₃) δ8.81 (d, J=2.4 Hz, 1H), 8.42 (dd, J=6.4, 2.5 Hz, 1H), 3.94 (s, 3H), 0.42 (s, 9H); MS (ES) m/z: 320 (M+H⁺).

A mixture of Compound 117b (285 mg, 0.896 mmol), N-(tert-butoxycarbonyl)-N-(3-chlorophenyl)-2-amino-6-chloropyrazine Cmd 45 (335 mg, 0.985 mmol), dichlorobis (triphenylphosphine)palladium (63 mg, 0.090 mmol), and LiCl (152 mg, 3.58 mmol) in anhydrous toluene (5 mL) was stirred at 100° C. for 32 h under nitrogen. After removal of solvent under reduced pressure, the residue was purified by flash chromatography (EtOAc/hexane as solvent) to give 234 mg (57%) of Compound 117c as a white solid; ¹H NMR (300 MHz, CDCl₃) δ9.13 (s, 1H), 8.95 (d, J=2.3 Hz, 1H), 8.86 (m, 1H), 8.67 (dd, J=9.1, 2.4 Hz, 1H), 7.42–7.37 (m, 2H), 7.31 (m, 1H), 7.16 (m, 1H), 3.96 (s, 3H), 1.50 (s, 9H); MS (ES) m/z: 481 (M+Na⁺). Anal. Calcd. For $C_{22}H_{20}ClFN_4O_4$: C, 57.58; H, 4.39; N, 12.21. Found: C, 57.67; H, 4.44; N, 12.03. The mixture of NaCN (60 mg, 1.22 mmol) and DMF (2 mL) was stirred at 100° C. for 1.5 h. After cooling to 4° C., the solution of Compound 117c (187 mg, 0.407 mmol) in DMF (3 mL) was added. After stirring at room temperature for 1 h, water was added. The aqueous solution was extracted with $Et_2O$ (×3), and the combined organic layers were washed with water, dried, concentrated, and flash chromatographed (EtOAc/hexane as solvent) to give 135 mg (71%) of Compound 117d as a yellow oil; $^1H$ NMR (300 MHz, CDCl₃) δ9.29 (s, 1H), 9.26 (d, J=1.9 Hz, 1H), 8.87 (s, 1H), 8.52 (d, J=1.9 Hz, 1H), 7.39–7.28 (m, 3H), 7.21–7.18 (m, 1H), 4.01 (s, 3H), 1.49 (s, 9H); MS (ES) m/z: 488 (M+Na⁺).

The solution of Compound 117d (165 mg, 0.354 mmol), 1.0 M LiOH (0.5 mL, 0.5 mmol), THF (4 mL), and water (0.5 mL) was stirred at room temperature for 1.5 h. More LiOH (12 mg, 0.5 mmol) was added, and the solution was stirred for another 1 h then concentrated. AcOH was added to the residue until the pH was 5–6. The precipitated solid was collected through filtration, rinsed with water, and dried overnight to give 155 mg (97%) of acid. A mixture of the acid (155 mg, 0.343 mmol), DPPA (123 mg, 0.447 mmol), triethylamine (70 mg, 0.69 mmol), t-BuOH (2 mL), and toluene (4 mL) was heated at 70° C. for 1 h, then 100° C. for 2.5 h. After removal of the solvents under reduced pressure, the reaction mixture was purified by flash chromatography (EtOAc/hexane as solvent) to give 124 mg (69%) of Compound 117e as a clear oil; $^1H$ NMR (300 MHz, CDCl₃) δ9.17 (s, 1H), 8.82 (s, 1H), 8.48 (d, J=2.5 Hz, 1H), 8.33 (d, J=2.4 Hz, 1H), 7.37–7.27 (m, 3H), 7.22–7.18 (m, 1H), 6.82 (brs, 1H), 1.53 (s, 9H), 1.49 (s, 9H); MS (ES) mn/z: 545 (M+Na⁺). A mixture of Compound 117e (114 mg, 0.218 mmol), (3-bromopropoxy)-tert-butyldimethylsilane (110 mg, 0.435 mmol), and $Cs_2CO_3$ (170 mg, 0.521 mmol) in dry DMF (5 mL) was heated at 70° C. for 1 h. The reaction mixture was concentrated and purified by column chromatography (EtOAc/hexane as solvent) to give 144 mg (95%) of the N-alkylated compound as a clear oil. A solution of the oil (144 mg, 0.207 mmol) and TFA (2 mL) was stirred at room temperature for 2 h and then concentrated. A saturated NH₄OH solution was added to the residue until the mixture was made basic followed by the addition of water. The precipitated solid was collected through filtration, washed with water, and dried under vacuum. The product was purified by flash chromatography on silica gel (EtOAc/MeOH as solvent) to provide 8 mg (10%) of Cmd 111 as a yellow solid; $^1H$ NMR (300 MHz, DMSO-d₆) δ9.96 (s, 1H), 8.38 (s, 1H), 8.34 (s, 1H), 8.15 (d, J=1.7 Hz, 1H), 8.12 (s, 1H), 7.63 (d, J=8.1 Hz, 1H), 7.33 (t, J=8.1 Hz, 1H), 7.19 (m, 2H), 7.01 (d, J=7.8 Hz, 1H), 4.55 (t, J=5.0 Hz, 1H), 3.51 (m, 2H), 3.26 (m, 2H), 1.74 (m, 2H); MS (ES) m/z: 381 (M+H⁺).

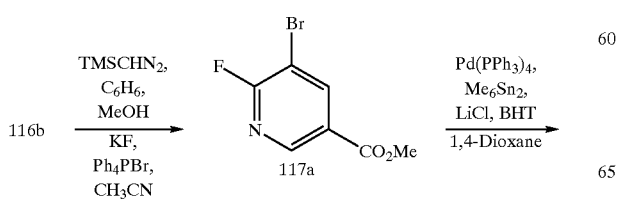

-continued

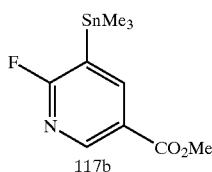

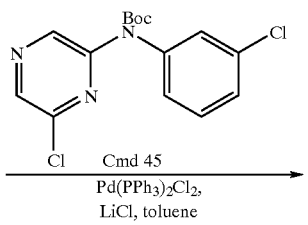

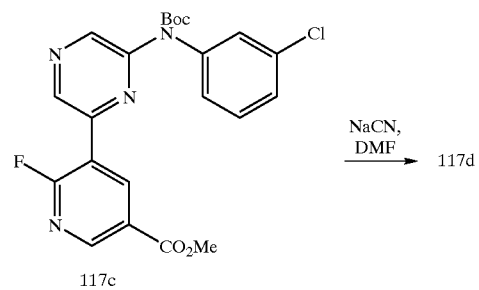

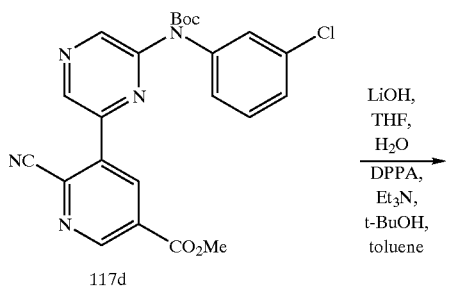

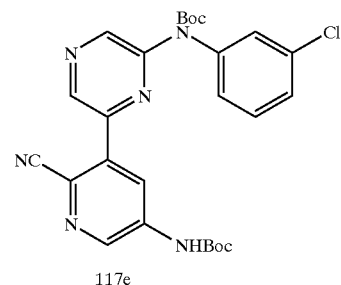

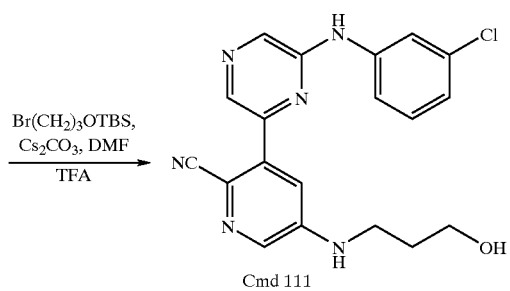

EXAMPLE 118
VEGF-R Screening Assay

A kinase reaction mixture was prepared containing 50 mM Tris-HCl pH=8, 10 mM $MgCl_2$, 0.1 mM $NAPO_4$, 1 mM DTT, 10 μM ATP, 0.025 μM biotinylated peptide substrate and 0.8 μCuries per well $^{33P}$-γ-ATP [2000–3000 Ci/mmol]. 70 μl of the kinase reaction mixture was dispensed into the well of a streptavidin coated FlashPlate™ (Cat. # SMP103, NEN, Boston, Mass.). Then 1 μl of test compound stock in 100% DMSO was added to the wells resulting in a final concentration of 1% DMSO in the reaction with a 100 μl final reaction volume. Next, soluble rat tyrosine kinase containing an N-terminal 6×HIS tag was diluted in 50 mM Tris-HCl pH=8.0, 0.1% BSA at a concentration of 5 ng per microliter and 30 μl (150 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The PLCI biotinylated peptide substrate becomes immobilized on the Flashplate™ and the incorporation of $^{33}P$-γ-ATP was measured by reading the plate on a scintillation counter. Inhibition of the enzymatic activity of the VEGF-R was measured by observing a reduced amount of $^{33}P$-γ-ATP incorporated into the immobilized peptide.

$IC_{50}$ data for VEGF-R and CDK are shown in Tables 1 to 3. $IC_{50}$ values listed as >10 or >100 indicate no observed 50% inhibition at the highest dose tested, nor was an inhibition maxima observed. The term n.d. means not tested.

Compared to VEGF-R kinase inhibitory pyrazine derivative 3-[[5-[6-[(3-chlorophenyl)amino]pyrazinyl]-3-pyridinyl]amino]-1-propanol (Cmd 4), compounds 52, 57, 62, 87, 88 and 89 were prepared with variations on the Y position.

TABLE 1

X-[Y-phenyl-$(CH_2)_n$]-6-(5-$R_8$-3-pyridinyl)-2-pyrazinamine derivatives

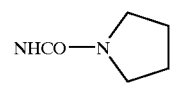

| Cmd | X | n | $R_7$ | $R_8$ | Y | CDK $IC_{50}$ (uM) | VEGF-R $IC_{50}$ (uM) |
|---|---|---|---|---|---|---|---|
| 1 | NH | 0 | H | $CO_2C_2H_5$ | 3-Cl | >10 | nd |
| 4 | NH | 0 | H | $NH(CH_2)_3OH$ | 3-Cl | 5.96 | 0.08 |
| 5 | NH | 0 | H | $NH_2$ | 3-Cl | 11.69 | 1.16 |
| 31 | NH | 0 | H | $NH(CH_2)_2OH$ | 3-Cl | ~10 | 0.15 |
| 32 | NH | 0 | H | $NH(CH_2)_4OH$ | 3-Cl | >100 | 0.06 |
| 33 | NH | 0 | H | $NH(CH_2)_2N(CH_3)_2$ | 3-Cl | ~10 | 0.07 |
| 34 | NH | 0 | H | $NH(CH_2)_3$-(morpholine) | 3-Cl | >100 | 0.18 |
| 35 | NH | 0 | H | $NH(CH_2)_3N(CH_3)_2$ | 3-Cl | ~10 | 0.09 |
| 36 | NH | 0 | H | $CONH(CH_2)_2OCH_3$ | 3-Cl | >100 | ~10 |
| 37 | NH | 0 | H | $CONH(CH_2)_3N(CH_3)_2$ | 3-Cl | >100 | 5.5 |
| 38 | NH | 0 | H | $CONH(CH_2)_2N(CH_3)_2$ | 3-Cl | 3.69 | 4.3 |
| 39 | NH | 0 | H | $CONH(CH_2)_3OH$ | 3-Cl | 34.8 | 2.5 |
| 40 | NH | 0 | H | $CONH(CH_2)_3OC_2H_5$ | 3-Cl | >100 | >100 |
| 41 | NH | 0 | H | $NHCOCH_2OCH_3$ | 3-Cl | >100 | 0.36 |
| 42 | NH | 0 | H | NHCO-(4-$N(CH_3)_2$-phenyl) | 3-Cl | >100 | >100 |
| 43 | NH | 0 | H | NHCO-3-pyridine | 3-Cl | >100 | 1.12 |
| 52 | NH | 0 | H | $NH(CH_2)_3OH$ | 3-F | ~100 | 0.17 |
| 57 | NH | 0 | H | $NH(CH_2)_3OH$ | 3-$OCH_3$ | 81.38 | 0.81 |
| 62 | NH | 1 | H | $NH(CH_2)_3OH$ | H | 34.38 | 1.05 |
| 69 | NH | 0 | H | $NH(CH_2)_3$-piperazine | 3-Cl | >10 | 0.364 |
| 70 | NH | 0 | H | $NH(CH_2)_4$-(4-pyridine) | 3-Cl | 10 | 0.295 |
| 71 | NH | 0 | H | $NH(CH_2)_3$-(4-pyridine) | 3-Cl | >10 | 0.052 |
| 72 | NH | 0 | H | $NH(CH_2)_3$-(3-pyridine) | 3-Cl | >10 | 0.089 |
| 73 | NH | 0 | H | $NH(CH_2)_3$-(1-piperidine) | 3-Cl | 3.24 | 0.105 |
| 74 | NH | 0 | H | 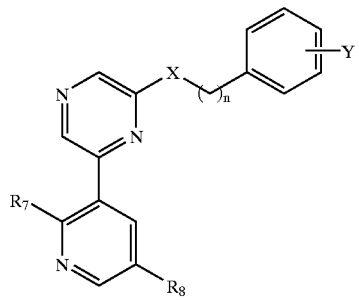 | 3-Cl | >10 | 0.578 |
| 75 | NH | 0 | H | $NH(CH_2)_3$-(1-pyrazole) | 3-Cl | >10 | 0.079 |
| 76 | NH | 0 | H | $NH(CH_2)_3$-(1,2,4-triazole) | 3-Cl | >10 | 0.052 |
| 77 | NH | 0 | H | $NH(CH_2)_3$-(1-imidazole) | 3-Cl | >10 | 0.030 |

TABLE 1-continued

X-[Y-phenyl-(CH$_2$)$_n$]-6-(5-R$_8$-3-pyridinyl)-2-pyrazinamine derivatives

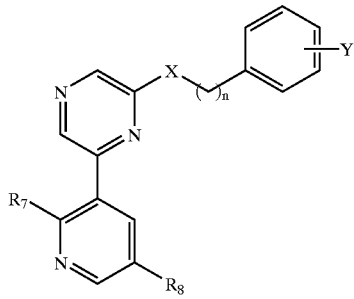

| Cmd | X | n | R$_7$ | R$_8$ | Y | CDK IC$_{50}$ (uM) | VEGF-R IC$_{50}$ (uM) |
|---|---|---|---|---|---|---|---|
| 78 | NH | 0 | H | NH(CH$_2$)$_2$O(CH$_2$)$_2$O(CH$_2$)$_2$OH | 3-Cl | >10 | 0.282 |
| 79 | NH | 0 | H | HN—CH$_2$-tetrahydropyran | 3-Cl | >10 | 0.475 |
| 80 | NH | 0 | H | NH(CH$_2$)$_3$—C$_6$H$_5$ | 3-Cl | >10 | 2.277 |
| 81 | NH | 0 | H | NHCH$_2$CON(C$_2$H$_5$)$_2$ | 3-Cl | >10 | 1.102 |
| 82 | NH | 0 | H | NHCH$_2$C$_6$H$_5$ | 3-Cl | >10 | 4.3 |
| 83 | NH | 0 | H | NH(CH$_2$)$_2$OC$_6$H$_5$ | 3-Cl | >10 | >10 |
| 84 | NH | 0 | H | NH(CH$_2$)$_3$CO$_2$C$_2$H$_5$ | 3-Cl | 2.03 | 0.125 |
| 85 | NH | 0 | H | NH(CH$_2$)$_2$O(CH$_2$)$_2$OCH$_3$ | 3-Cl | >10 | 0.085 |
| 86 | NH | 0 | H | NH(CH$_2$)$_3$-piperazine-(3-Cl-phenyl) | 3-Cl | >10 | >10 |
| 87 | NH | 0 | H | NH(CH$_2$)$_3$-(4-pyridine) | 4-Cl | >10 | 1.0 |
| 88 | NH | 0 | H | NH(CH$_2$)$_3$-(4-pyridine) | 4-OCH$_3$ | >10 | 0.154 |
| 89 | NH | 0 | H | NH(CH$_2$)$_3$-(4-pyridine) | 3,4-Cl$_2$ | >10 | 0.268 |
| 96 | O | 0 | H | NH(CH$_2$)$_3$OH | 3-Cl | >10 | >10 |
| 98 | NH | 0 | H | NHCOCH$_2$O(CH$_2$)$_2$OCH$_3$ | 3-Cl | >10 | 0.99 |
| 99 | NH | 0 | H | NHCOCH$_2$OPh | 3-Cl | >10 | >10 |
| 100 | NH | 0 | H | NHCO(CH$_2$)$_3$OPh | 3-Cl | >10 | >10 |
| 101 | NH | 0 | H | NHCOCH$_2$OCH$_2$Ph | 3-Cl | >10 | >10 |
| 102 | NH | 0 | H | NHCOCH$_2$OCH$_2$CH$_3$ | 3-Cl | >10 | 0.93 |
| 103 | NH | 0 | H | NHCO(CH$_2$)$_2$OCH$_3$ | 3-Cl | >10 | 0.59 |
| 105 | NH | 0 | H | NHCOCH$_2$OH | 3-Cl | >10 | 0.41 |
| 106 | NH | 0 | F | NH(CH$_2$)$_3$OH | 3-Cl | >10 | 0.138–0.365 |
| 107 | NH | 0 | NH$_2$ | NH(CH$_2$)$_3$OH | 3-Cl | >10 | 1.36 |
| 109 | NH | 0 | NHCOCH$_3$ | NH(CH$_2$)$_3$OH | 3-Cl | >10 | >10 |
| 110 | NH | 0 | Cl | NH(CH$_2$)$_3$OH | 3-Cl | >10 | >10 |
| 111 | NH | 0 | CN | NH(CH$_2$)$_3$OH | 3-Cl | >10 | >10 |

TABLE 2

N-(3-chlorophenyl)-6-(R8-Het)-2-pyrazinamine derivatives

| Cmd | Het | R8 | CDK IC50 (uM) | VEGF-R IC50 (uM) |
|---|---|---|---|---|
| 27 | 3,4-pyridine (a=4,b=3) | OCON(Et)2 | >10 | n.d. |
| 28 | 3,4-pyridine | OH | >10 | >10 |
| 90 | 2,6-pyrazine | NH(CH2)3OH | >10 | 0.372 |
| 91 | 2,5-pyridine | NH(CH2)3OH | >10 | >10 |
| 47 | 2,6-pyridine | OH | 5.76 | ~100 |
| 92 | 2,6-pyridine | NH(CH2)3OH | >10 | >10 |
| 93 | 3,4-pyridine | NH(CH2)3OH | 2.218 | 0.761 |
| 94 | 3,4-pyridine | NH(CH2)3OH | ~0.5 | ~0.5 |
| 97 | 2,5-thiazole (dimethyl) | NH(CH2)3OH | 6.15 | 0.416 |

TABLE 3

| Cmd | Het | CDK IC50 (uM) | VEGF-RIC50 (uM) |
|---|---|---|---|
| 10 | 2,6-dimethylpyrimidine | >10 | 0.84 |
| 15 | pyrazine | >10 | >10 |
| 20 | 2-methylpyrimidine | >10 | >10 |

TABLE 3-continued

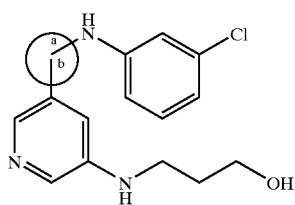

| Cmd | Het | CDK IC$_{50}$ (uM) | VEGF-RIC$_{50}$ (uM) |
|---|---|---|---|
| 25 | (pyrimidine a,b) | >10 | >10 |
| 68 | (pyrimidine a,b) | 2.40 | >10 |

EXAMPLE 119
Kinase Selectivity Assays

Assays to test compound inhibition of other kinases were preformed using methods that measure the amount of phosphorylation of a biotinylated peptide substrate. Biotinylated peptide substrates were selected from the literature as appropriate for the enzyme being evaluated. The general procedure used to assay for kinase activity is as follows: A kinase reaction mix was prepared in 50 mM Tris-HCl pH=8, 10 mM MgCl$_2$, 0.1 mM NaVO$_4$, 1 mM DTT, 5–10 μM ATP, 0.25–1 μM biotinylated peptide substrate, 0.2–0.8 μCuries per well $^{33}$P-γ-ATP [2000–3000 Ci/mmol]. Assay conditions vary slightly for each protein kinase, for example, insulin receptor kinase requires 10 mM MnCl$_2$ for activity and Calmodulin-dependent protein kinase requires calmodulin and 2 mM CaCl$_2$. The reaction mixture was dispensed into the wells of a streptavidin coated Flashplate and 1 μl drug stock in 100% DMSO was added to a 100 μl reaction volume resulting in a final concentration of 1% DMSO in the reaction. Enzyme was diluted in 50 mM Tris-HCl pH=8.0, 0.1% BSA and added to each well. The reaction was incubated for one hour at 30° C. in the presence of compound. After one hour the reaction mix was aspirated from the plate and the plate was washed with PBS containing 100 mM EDTA. The plate was read on a scintillation counter to determine $^{33}$P-γ-ATP incorporated into the immobilized peptide. Test compounds were assayed in duplicate at 8 concentrations [100 tM, 10 μM, 1 μM, 100 nM, 10 nM, 1 nM, 100 μM, 10 μM]. A maximum and minimum signal for the assay was determined on each plate. The IC$_{50}$ was calculated from the dose response curve of the percent inhibition of the maximum signal in the assay according to the formula [max signal−background/test compound signal−background (100)=% inhibition] by graphing the percent inhibition against the log concentration of test compound. Known inhibitor compounds appropriate for the kinase being assayed were also included on each plate.

Definition and Source of Kinase Enzymes.

VEGF-R (vascular endothelial growth factor receptor-2) is a fusion protein containing a polyhistidine tag at the N-terminus followed by amino acids 786–1343 of the rat VEGF-R2 kinase domain (GenBank Accession #U93306). CDK1 (cyclin dependent kinase 1) is isolated from insect cells expressing both the human CDK1 catalytic subunit and its positive regulatory subunit cyclin B (New England Biolabs, Beverly, Mass., Cat. #6020). CDK4 (cyclin dependent kinase 4) contains amino acids 769 to 921 of the mouse R6 protein found in the GST-retinoblastoma protein construct (Santa Cruz Biotechnology, Santa Cruz, Calif.; Cat. #SC-4112). Insulin Receptor Kinase consists of residues 941–1313 of the cytoplasmic domain of the beta-subunit of the human insulin receptor (BIOMOL, Plymouth Meeting, Pa., Cat. #SE-195). Protein Kinase A is the catalytic subunit of cAMP dependent protein kinase-A purified from bovine heart (Upstate Biotech, Lake Placid, N.Y., Cat#14–114). PKC (protein kinase-C) is the gamma or beta isoform of the human protein produced in insect cells (BIOMOL, Plymouth Meeting, Pa., Cat. #SE-143). Casein Kinase 1 is a truncation at amino acid 318 of the C-terminal portion of the rat CK1 delta isoform produced in E.coli (New England Biolabs, Beverly, Mass., Cat. #6030). Casein Kinase 2 includes the alpha and beta subunits of the human CK2 protein produced in E.coli (New England Biolabs, Beverly, Mass., Cat. #6010). Calmodulin Kinase (calmodulin-dependent protein kinase 2) is a truncated version of the alpha subunit of the rat protein produced in insect cells (New England Biolabs, Beverly, Mass., Cat. #6060). Glycogen Synthase Kinase-3 is the beta isoform of the rabbit enzyme produced in E. coli (New England Biolabs, Beverly, Mass., Cat. #6040). MAP Kinase is the rat ERK-2 isoform containing a polyhistidine tag at the N-terminus produced in E. coli. and activated by phosphorylation with MEK1 prior to purification (BIOMOL, Plymouth Meeting, Pa., Cat. #SE-137). EGFR (epidermal growth factor receptor) is purified from human A431 cell membranes (Sigma, St. Louis, Mo., Cat.# E3641). PDGF-R (platelet derived growth factor receptor) is a fusion protein containing a polyhistidine tag at the N-terminus followed by nucleotides 1874–3507 of the human PDGF-R beta subunit kinase domain (Accession #M21616).

| | Peptide Substrates | |
|---|---|---|
| Assay/Seq ID NO: | Kinase | Peptide Substrate |
| 1/1 | VEGF-R | (Biotin)KHKKLAEGSAYEEV-Amide |
| 2/2 | CDK1 | (Biotin)KTPKKAKKPKTPKKAKKL-Amide |
| 3/ | CDK4 | GST-Retinoblastoma protein construct |

-continued

Peptide Substrates

| Assay/Seq ID NO: | Kinase | Peptide Substrate |
|---|---|---|
| 4/3 | EGF-R | (Biotin)DRVYIHPF-Amide |
| 5/4 | Protein Kinase A | (Biotin)GRTGRRNSI-Amide |
| 6/5 | PKC-γ | (Biotin)RFARIKGSLRQKNV-NH2 |
| 7/5 | PKC-β2 | (Biotin)RFARKGSLRQKNV-NH2 |
| 8/6 | Casein Kinase 1 | (Biotin)KRRRALS(phospho)VASLPGL-Amide |
| 9/7 | Casein Kinase 2 | (Biotin)RREEETEEE-Amide |
| 10/8 | Calmodulin Kinase | Biotin)KKALRRQETVDAL-Amide |
| 11/9 | GSK-3 | Biotin)KRREILSRRP(phospho)SYR-Amide |
| 12/10 | MAP Kinase ERK-2 | (Biotin)APRTPGGRR-Amide |
| 13/11 | Insulin Kinase | (Biotin)TRDIYETDYYRK-Amide |
| 14/12 | PDGF-R | (Biotin)KHKKLAEGSAYEEV-Amide |
| 15 | FGF-R2 | (Biotin)Poly(GT) 4:1 |
| 16 | HER2 | (Biotin) Poly(GT) 4:1 |

The $IC_{50}$ data (in $\mu M$) for various kinases is shown in Table 4. $IC_{50}$ values listed as >10 or >100 indicate no observed 50% inhibition at the highest dose tested, nor was an inhibition maxima observed. Values shown as 10 indicate an approximate value based on an observed 50% inhibition. ND means not tested.

TABLE 4

Kinase Selectivity of Pyrazine Derivatives

| Assay | Cmd 4 | Cmd 32 | Cmd 33 | Cmd 35 | Cmd 39 | Cmd 71 | Cmd 72 |
|---|---|---|---|---|---|---|---|
| 1 | 0.042 | 0.059 | 0.07 | 0.094 | 2.5 | 0.052 | 0.089 |
| 2 | >10 | >100 | >10 | >10 | 34.8 | >100 | >100 |
| 3 | 10 | >10 | 10 | 10 | ND | ND | ND |
| 4 | 1.36 | >7.4 | 17.25 | 20.7 | 6.06 | >100 | >100 |
| 5 | >100 | >100 | >100 | >100 | >100 | >100 | >100 |
| 6 | >100 | >100 | 3.96 | 14.49 | >100 | ND | ND |
| 7 | >100 | >100 | >100 | >100 | >100 | ND | ND |
| 8 | >100 | >100 | >100 | >100 | >100 | >100 | >100 |
| 9 | >100 | >100 | >100 | >100 | 10 | >100 | >100 |
| 10 | >100 | >100 | >100 | >100 | >100 | 4.89 | >100 |
| 11 | 0.478 | 4.02 | 11.38 | 8.15 | 0.866 | 0.159 | 0.318 |
| 12 | >100 | >100 | >100 | >100 | >100 | >100 | >100 |
| 13 | 1.69 | >100 | >100 | >100 | 1.8 | >100 | >100 |
| 14 | 0.36 | 2.8 | 29.2 | 2.5 | 2.8 | 1 | 0.876 |
| 15 | 0.207 | 2.36 | 1.4 | 3.07 | 1.8 | 0.317 | 0.293 |
| 16 | ND | ND | ND | ND | ND | >100 | 9.7 |

| Assay | Cmd 73 | Cmd 75 | Cmd 76 | Cmd 77 | Cmd 84 | Cmd 85 |
|---|---|---|---|---|---|---|
| 1 | 0.105 | 0.079 | 0.052 | 0.03 | 0.125 | 0.085 |
| 2 | 6.1 | >100 | >100 | 10 | 2.03 | >10 |
| 3 | ND | ND | ND | ND | ND | ND |
| 4 | >100 | ND | ND | ND | ND | ND |
| 5 | >100 | >100 | >100 | ND | ND | ND |
| 6 | 1.36 | ND | ND | ND | ND | ND |
| 7 | 1.75 | ND | ND | ND | ND | ND |
| 8 | 5.03 | 5.6 | 6.5 | ND | ND | ND |
| 9 | 6.35 | 8.1 | 7.2 | ND | ND | ND |
| 10 | 7.55 | 27 | 15.8 | ND | ND | ND |
| 11 | 0.491 | 0.606 | 0.196 | ND | ND | ND |
| 12 | >100 | >100 | >100 | ND | ND | ND |
| 13 | >100 | >100 | >100 | ND | ND | ND |
| 14 | 0.175 | 1.7 | 0.725 | ND | ND | ND |
| 15 | 0.276 | 0.326 | 0.153 | 0.221 | ND | ND |
| 16 | 7.2 | 3 | 2.24 | 0.966 | ND | ND |

EXAMPLE 120

Cell Proliferation Assay

The ability of a test compound to inhibit the proliferation of cell growth was determined by measuring incorporation of $^{14}C$-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), A375 malignant melanoma (ATCC CRL-1619), SK-OV-3 ovarian adenocarcinoma (ATCC HTB-77) HCT-116 colon carcinoma (CCL-247) and PC-3 prostate adenocarcinoma (ATCC CRL-1435). The method was also used on primary cells such as HUVEC endothelial cells (ATCC CRL-1730). In this way the effect of a compound on cell growth of cells with many different phenotypes can be determined. Cells were trypsinized and counted and 3000–8000 cells were added to each well of a 96-well CytoStar tissue culture treated scintillating microplate (Amersham #RPNQ0160) in complete medium in a volume of 100 $\mu l$. Cells were incubated for 24 hours in complete medium at 37° C. in an atmosphere containing 5% $CO_2$.

Next, 1 $\mu l$ of test compound in 100% DMSO was added to the wells of the plate. DMSO only was added to control wells. Cells were incubated for 24 more hours in complete medium at 37° C. in an atmosphere containing 5% $CO_2$. Methyl $^{14}C$-thymidine 56 mCi/mmol (NEN #NEC568 or Amersham #CFA532) was diluted in complete medium and 0.2 $\mu Ci$/well was added to each well of the CytoStar plate in a volume of 20 µl. The plate was incubated for 24 hours at 37° C. plus 5% $CO_2$ in drug plus $^{14}$C-thymidine. The contents of the plate were discarded into a $^{14}$C radioactive waste container by inverting the plate and the plate was washed twice with 200 µl PBS. 200 µl of PBS is then added to each well. The top of the plate was sealed with a transparent plate sealer and a white plate backing sealer (Packard #6005199) was applied to the bottom of the plate. The degree of Methyl $^{14}$C-thymidine incorporation was quantified on a Packard Top Count.

The $IC_{50}$ data (in µM) for various compounds is shown in Table 5. $IC_{50}$ values listed as >10 or >100 indicate no observed 50% inhibition at the highest dose tested. ND means not tested.

TABLE 5

Inhibition of cell proliferation

| Cell line | Cmd 4 | Cmd 32 | Cmd 33 | Cmd 35 | Cmd 71 |
|---|---|---|---|---|---|
| HeLa | 4.56 | 86.4 | 2.23 | >100 | 3.8 |
| HCT-116 | 8.35 | 23.47 | >100 | >100 | 3.29 |
| SK-OV-3 | 3 | 14.57 | 21.47 | 19.34 | ND |
| MDA-MB-231 | 3.26 | 27.62 | 12.67 | 98.3 | 1.88 |
| PC-3 | 11.34 | 67.64 | 22.87 | >100 | 3.2 |

| Cell line | Cmd 72 | Cmd 73 | Cmd 75 | Cmd 76 |
|---|---|---|---|---|
| HeLa | 5.7 | 2.2 | 12.5 | 4.94 |
| HCT-116 | 4.97 | ND | ND | ND |
| SK-OV-3 | ND | 3.78 | >10 | 12.9 |
| MDA-MB-231 | 2.57 | ND | ND | ND |
| PC-3 | 2.58 | ND | 5.34 | ND |

EXAMPLE 121

Rat Aortic Ring Assay

The rat aortic ring assay is a rapid in vitro assay that measures new capillary growth in an environment that closely approximates the in vivo conditions of the extracellular matrix. The assay was performed as described (Nicosia, R F and Ottinetti, A. Growth of new microvessels in serum-free matrix culture of rat aorta. *Lab Invest.*, 63: 115–122, 1990). Thoracic aortas were removed from 1 to 2-month old male Sprague-Dawley rats and transferred to a culture dish containing serum-free MCDB 131 medium (Clonetics). Extraneous tissue was removed and the aorta was sectioned into rings approximately 1 mm long and rinsed 8–10 times in serum-free medium. A solution of sterile 1.5% agarose (Type VI-A, Sigma, St. Louis, Mo.) was added to the wells of a 6-well plate. The wells were filled with clotting fibrinogen solution and an aortic ring was transferred into the well positioned with the lumen oriented horizontally in the center of the fibrin gel solution. The fibrinogen solution was prepared in MCDB 131 medium with bovine fibrinogen at 3 mg/ml. Clotting was initiated by adding 20 µl of a 50 NIH units/ml bovine thrombin solution and the fibrin gel generally formed within 30 seconds. The fibrinolytic inhibitor amino-n-caproic acid was added to the culture medium at 300 g/ml (microgram per milliliter) for the first four days of the assay and at 50 µg/ml from day 5 to day 8. Once the fibrin gel solution solidified, 5 ml of serum-free MCDB 131 media containing 100 µg/ml penicillin, 100 µg/ml streptomycin and 0.25 µg/ml amphotericin B was added to each well. Explants were incubated at 37° C. with 5% $CO_2$ for 8 days. Medium was replaced every 2–3 days and the assay was analyzed on day 8. Inhibition of vascular sprouting was measured by adding test compounds diluted in DMSO. The final concentration of DMSO in the assay did not exceed 0.2%. As shown in Table 6, the degree of inhibition was quantified using the Vessels image analysis package as described (Nissanov, J, Tuman, R W, Gruver, L M and Fortunato, J M. Automatic vessel segmentation and quantification of the rat aortic ring assay of angiogenesis. *Lab. Invest.* 73, 734–739, 1995).

TABLE 6

Inhibition of Vascular Sprouting

|  | Cmd 4 | Cmd 32 | Cmd 33 | Cmd 35 |
|---|---|---|---|---|
| ($IC_{50}$ µM) | 0.099 | 0.83 | >1 | >1 |

EXAMPLE 122

In vitro Autophosphorylation Assay for Kinase Inhibition VEGF-R Autophosphorylation Assay Growth factor receptors are activated following binding of their cognate ligands which catalyzes autophosphorylation of the receptor. The VEGF receptor is autophosphorylated upon binding to VEGF (Tessler, S., Rockwell, P., Hicklin, D., Cohen, T., Levi, B.-Z., Witte, L. Lemischka, I. R. & Neufeld, G. (1994) *J. Biol. Chem.* 269, 12456–12461) and activation of signal transduction then occurs (Heldin, C.-H. (1995) *Cell* 80, 213–223). As autophosphorylation is essential for a signal to be transduced, an assay to quantitate the degree of phosphorylation of the VEGF receptor measures the ability of a test compound to directly inhibit activation of the VEGF-R and eliminates the possibility of substrate interactions.

A kinase reaction mixture is prepared containing 50 mM Tris-HCl pH=8, 10 mM $MgCl_2$, 0.1 mM $Na_3VO_4$, 1 mM DTT, 5–10 µM ATP, and 0.8 µCuries per well $^{33}$P-γ-ATP [2000–3000 Ci/mmol]. 70 µl of the kinase reaction mixture is dispensed into the well of an NTA-Nickel coated FlashPlate™ (Cat. # SMP107, NEN, Boston, Mass.). Then 1 µl of test compound in 100% DMSO is added to the wells resulting in a final concentration of 1% DMSO in the reaction (100 µl final reaction volume includes subsequent enzyme solution). Then soluble rat tyrosine kinase containing an N-terminal 6xHIS tag is diluted in 50 mM Tris-HCl pH=8.0, 0.1% BSA at a concentration of 5 ng per microliter and 30 µl (150 ng per test well) is added to each well to initiate the reaction. The reaction is incubated for one hour at 30° C. At the end of the 1-hour incubation, the reaction is terminated by aspirating the reaction mixture from the plate and washing the wells twice with PBS containing 100 mM EDTA. The 6× HIS-VEGF receptor becomes immobilized on the Flashplate™ and the incorporation of $^{33}$P-γ-ATP via autophosphorylation is measured by reading the plate on a scintillation counter. Inhibition of the enzymatic activity of the VEGF-R is measured by observing a reduced amount of $^{33}$P-γ-ATP incorporated into the immobilized enzyme.

EXAMPLE 123

In vivo Models—Inhibition of Tumor Growth

The in vivo effect of a compound on the growth of human tumor cells can be evaluated by implanting human tumor cells into the hindflank of athymic mice and administering test compound to the mice. Such assays are useful in identifying and confirming compounds that are useful for inhibiting angiogenesis or to identify compounds that can inhibit VEGF activity and therefor are useful for treating a variety of cancers or other diseases associated with abnormal or aberrant angiogenesis, such as those diseases discussed supra. Human tumor cells originating from a variety of different cancer types, such as A375 human melanoma cells, were implanted subcutaneously into the hindflank of male athymic mice (Charles River) and allowed to establish a sizeable tumor for 6–10 days as determined by caliper measurements. Test compound was then administered by injecting the compound formulated in an appropriate vehicle, here saline was used as the vehicle, intraperitoneally into the mice once a day for 30 days. The test compound can also be administered by other routes such as orally, sub cutaneously or by intravenous infusion. The size of the tumor in this study was measured every four days and the degree of inhibition was determined by comparing drug-treated animals to animals that were injected with vehicle only. FIG. 1 illustrates the results of one study with Cmd 33 indicating a delay of tumor size progression. Similarly the compounds of this invention can be tested in other known models of aberrant angiogenesis, such as models of retinopathy, endometriosis, psoriasis and the like.

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

What is claimed is:

1. A compound of Formula 1.

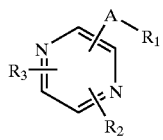

Formula 1 or a pharmaceutically acceptable salt thereof, wherein $R_1$ is aryl or bicyclic aryl, optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkenyl, heterocyclylalkynyl, heterocyclylalkoxy, aryl, arylalkyl, arylalkenyl, arylalkynyl, arylalkoxy, heteroaryl, heteroarylalkyl, heteroarylalkenyl, heteroarylalkynyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri (halo)substituted lower alkoxy), aminosulfonyl, ammosulfonylalkyl, alkylaminosulfonyl, alkylaminosulfonylalkyl, di(alkyl)aminosulfonyl, di(alkyl)aminosulfonylalkyl carboxyl, (hydroxyalkyl)carbonyl, (hydroxyalkoxy)carbonyl, trihalo substituted lower alkyl and trihalo substituted lower alkoxy;

A is —N($R_4$)($CH_2$)$_x$—wherein x is an integer from 0 to 4;

$R_4$ is selected from the group consisting of H, lower alkyl, alkyl, hydroxyalkyl, alkoxyalkyl, arylalkyl, lower alkenyl, alkenyl, aryl and heteroaryl; wherein aryl and heteroaryl are optionally substituted with 1 to 5 substituents independently selected from the group consisting of OH, halogen, cyano, nitro, amino, alkylamino, di(alkyl)amino, (hydroxyalkyl)amino, di(hydroxyalkyl)amino, alkyl, lower alkyl, alkoxy, lower alkoxy, tri(halo)substituted lower alkyl and tri (halo)substituted lower alkoxy;

$R_2$ is selected from the group consisting of pyridinyl, thiazolyl, and pyrazinyl, optionally substituted with 1 to 2 substituents independently selected from $R_7$ and 1 substituent selected from $R_8$;

$R_7$ is selected from the group consisting of alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri (halo)substituted lower alkoxy), carboxyl, (hydroxyalkyl)carbonyl, (hydroxyalkoxy)carbonyl tri (halo)substituted lower alkyl and tri(halo)substituted lower alkoxy;

$R_8$ is selected from the group consisting of alkyl, OH, hydroxyalkyl, halogen, cyano, amino, alkylamino, di(alkyl)amino, (hydroxyalkyl)amino, di(hydroxyalkyl)amino, carbamoyl, alkylcarbonylamino, alkylcarbonyl, alkoxycarbonyl, (hydroxyalkyl) carbonyl, (hydroxyalkoxy)carbonyl, O($CH_2$)$_n$$R_5$, O($CH_2$)$_n$O($CH_2$)$_m$$R_5$, O($CH_2$)$_n$CH[($CH_2$)$_m$$R_5$]$_2$, $O(CH_2)_nN[(CH_2)_mR_5]_2$, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH(CH_2)_nCH(OH)(CH_2)_mOR_5$, $NH(CH_2)_nCH(OH)(CH_2)_mN[(CH_2)_m-R_5]_2$, $NH(CH_2)_nCO(CH_2)_mN[(CH_2)_mR_5]_2$, $NH(CH_2)_nCO_2(CH_2)_mR_5NH(CH_2)_nCO(CH_2)_mSO_2NH(CH_2)_mR_5$, $NHCO(CH_2)_nCH(R_5)_2$, $NHCO(CH_2)_nR_5$, $NHCO(CH_2)_nO(CH_2)_mR_5$, $NHCO(CH_2)_nO(CH_2)_mO(CH_2)_mR_5$, $NHCO(CH_2)_nO(CH_2)_mCO(CH_2)_mR_5$, $NHCO(CH_2)_nN[(CH_2)_mR_5]_2$, $CONH(CH_2)_nO(CH_2)_mR_5$, and $CONH(CH_2)_nN[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino;

$R_5$ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents; and, $R_3$ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

2. The compound of claim 1 wherein $R_1$ is aryl or bicyclic aryl optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkoxy, aryl, arylalkyl, arylalkoxy, heteroaryl, heteroarylalkyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, trihalo substituted lower alkyl and trihalo substituted lower alkoxy.

3. The compound of claim 1 wherein $R_1$ is aryl optionally substituted with 1 to 5 substituents independently selected from the group consisting of lower alkyl, lower alkoxy, heterocyclyl, heterocyclylalkyl, aryl, arylalkyl, heteroaryl, heteroarylalkyl, OH, halogen, cyano, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, carbamoyl, acyl, alkoxycarbonyl, aminosulfonyl, aminosulfonylalkyl, alkylaminosulfonyl, alkylaminosulfonylalkyl, di(alkyl)aminosulfonyl, di(alkyl)aminosulfonylalkyl, carboxyl, trihalo substituted lower alkyl and trihalo substituted lower alkoxy.

4. The compound of claim 1 wherein A is $—N(R_4)-(CH_2)_x—$; wherein x is an integer from 0 to 3.

5. The compound of claim 1 wherein A is $—N(R_4)-(CH_2)_x—$; wherein x is an integer from 0 to 1.

6. The compound of claim 1 wherein $R_4$ is selected from the group consisting of H, alkyl, lower alkyl, alkoxyalkyl, alkenyl, lower alkenyl, hydroxyalkyl, aryl, arylalkyl and heteroaryl.

7. The compound of claim 1 wherein $R_4$ is selected from the group consisting of H, lower alkyl and hydroxyalkyl.

8. The compound of claim 1 wherein $R_4$ is H.

9. The compound of claim 1 wherein $R_2$ is selected from the group consisting of pyridinyl, thiazolyl, and pyrazinyl, optionally substituted with 1 to 2 substituents independently selected from $R_7$ and optionally substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

10. The compound of claim 1 wherein $R_2$ is selected from the group consisting of pyridinyl, thiazolyl, and pyrazinyl, optionally substituted with 1 substituent selected from $R_7$ and optionally substituted with 1 substituent selected from $R_8$; wherein $R_7$ is substituted on the 2 or 6 position from the point of attachment of $R_2$; and, wherein $R_8$ is substituted on a carbon atom at the 4 or 5 position from the point of attachment of $R_2$.

11. The compound of claim 1 wherein $R_7$ is selected from the group consisting of lower alkyl, lower alkoxy, heterocyclylalkyl, aryl, arylalkyl, OH, hydroxyalkyl, halogen, cyano, nitro, amino, alkylamino, di(alkyl)amino, (hydroxyalkyl)amino, di(hydroxyalkyl)amino, acyl, carboxyl, tri(halo)substituted lower alkyl and tri(halo) substituted lower alkoxy.

12. The compound of claim 1 wherein $R_7$ is selected from the group consisting of lower alkyl, OH, halogen, cyano, nitro, amino, tri(halo)substituted lower alkyl and tri(halo) substituted lower alkoxy.

13. The compound of claim 1 wherein $R_7$ is selected from the group consisting of methyl, ethyl, OH, bromine, chlorine, fluorine, cyano, nitro, amino, trifluoromethyl and trifluoromethoxy.

14. The compound of claim 1 wherein $R_8$ is selected from the group consisting of OH, amino, (hydroxyalkyl)amino, alkoxycarbonyl, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO-(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH-(CH_2)_nCH(OH)(CH_2)_mOR_5$, $NH(CH_2)_nCH(OH)(CH_2)_mN[(CH_2)_mR_5]_2$, $NH(CH_2)_nCO(CH_2)_mN[(CH_2)_mR_5]_2$, $NH(CH_2)_nCO_2(CH_2)_mR_5$, $NH(CH_2)_nCO(CH_2)_mSO_2NH(CH_2)_mR_5$, $NHCO(CH_2)_nR_5$, $NHCO(CH_2)_nO(CH_2)_mR_5$, $NHCO(CH_2)_nO(CH_2)_mO(CH_2)_mR_5$, $NHCO(CH_2)_nO-(CH_2)_mCO(CH_2)_mR_5$, $CONH(CH_2)_nO(CH_2)_mR_5$ and $CONH(CH_2)_nN[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino.

15. The compound of claim 1 wherein $R_8$ is selected from the group consisting of OH, amino, (hydroxyalkyl)amino, alkoxycarbonyl, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO-(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH(CH_2)_nCH(OH)(CH_2)_mOR_5$, $NH(CH_2)_nCH(OH)(CH_2)_mN[(CH_2)_mR_5]_2$, $NH(CH_2)_nCO(CH_2)_mN[(CH_2)_mR_5]_2$, $NH(CH_2)_nCO_2(CH_2)_mR_5$, $NH(CH_2)_nCO(CH_2)_mSO_2NH(CH_2)_mR_5$, $NHCO(CH_2)_nR_5$, $NHCO(CH_2)_nO(CH_2)_mR_5$, $NHCO(CH_2)_nO(CH_2)_nO(CH_2)_mR_5$, $NHCO(CH_2)_nO-(CH_2)_mCO(CH_2)_mR_5$, $CONH(CH_2)_nO(CH_2)_mR_5$ and $CONH(CH_2)_nN[(CH_2)_mR_5]_2$; wherein n is an integer from 0 to 5 and m is an integer from 0 to 2; with the proviso, that m is at least 1 when $R_5$ is selected from the group consisting of OH, amino, alkylamino and di(alkyl)amino.

16. The compound of claim 1 wherein $R_8$ is selected from the group consisting of OH, amino, (2-hydroxyethyl)amino, (3-hydroxy-n-propyl)amino, (4-hydroxy-n-butyl)amino, ethoxycarbonyl, $OCON(R_5)_2$, $NH(CH_2)_{1-4}R_5$, $NH(CH_2)_{1-3}SO_2(CH_2)_{0-1}R_5$, $NH(CH_2)_{1-3}O(CH_2)_{0-1}R_5$, $NH(CH_2)_{1-4}OCH[(CH_2)_{1-2}R_5]_2$, $NH(CH_2)_{1-3}O(CH_2)_{1-2}O(CH_2)_{1-2}R_5$, $NH(CH_2)_{1-4}N[(CH_2)_{0-2}R_5]_2$, $NH(CH_2)_{1-4}SO_2NH(CH_2)_{1-2}R_5$, $NH(CH_2)_{1-4}CH(OH)(CH_2)_{1-2}R_5$, $NH(CH_2)_{1-4}CH(OH)(CH_2)_{1-2}OR_5$, $NH(CH_2)_{1-4}CH(OH)(CH_2)_{1-2}N[(CH_2)_{0-1}R_5]_2$, $NH(CH_2)_{1-3}CO(CH_2)_{0-1}N[(CH_2)_{0-1}R_5]_2$, $NH(CH_2)_{1-3}CO_2(CH_2)_{0-1}R_5$, $NH(CH_2)_{1-4}CO(CH_2)_{1-2}SO_2NH(CH_2)_{1-2}R_5$, $NHCO(CH_2)_{0-1}R_5$, $NHCO(CH_2)_{1-3}O(CH_2)_{0-2}R_5$, $NHCO(CH_2)_{1-2}O(CH_2)_{1-2}O(CH_2)_{1-2}R_5$, $NHCO(CH_2)_{1-2}O(CH_2)_{0-1}CO(CH_2)_{1-2}R_5$, $CONH(CH_2)_{1-3}O(CH_2)_{0-2}R_5$ and $CONH(CH_2)_{1-3}N[(CH_2)_{1-2}R_5]_2$; with the proviso, that the $R_5$ alkylene linking group is at least methylene when $R_5$ is selected from the group consisting of OH, amino, alkylamino and di(alkyl)amino.

17. The compound of claim 1 wherein $R_5$ is selected from the group consisting of H, OH, lower alkyl, amino, alkylamino, di(alkyl)amino, aryl, heteroaryl and heterocyclyl; wherein aryl, heteroaryl and heterocyclyl are optionally substituted with 1 to 3 substituents independently selected from the group consisting of lower alkyl, acyl, carboxyl, aryl (optionally substituted with one halogen substituent), di(alkyl)amino; alkylsulfonyl, aminosulfonyl, alkylaminosulfonyl and aminosulfonylalkyl; and, wherein heterocyclyl is further optionally substituted with 1 to 3 oxo substituents.

18. The compound of claim 1 wherein $R_5$ is selected from the group consisting of H, OH, lower alkyl, heteroaryl and heterocyclyl; wherein heterocyclyl is optionally substituted with 1 to 3 substituents independently selected from the group consisting of lower alkyl, acyl, carboxyl, aryl (optionally substituted with one halogen substituent), di(alkyl)amino, alkylsulfonyl, aminosulfonyl, alkylaminosulfonyl, aminosulfonylalkyl and oxo.

19. The compound of claim 1 wherein $R_5$ is selected from the group consisting of H, OH, methyl, ethyl, t-butyl, 1H-azetidinyl, 1H-pyrrolidinyl, 4-tetrahydro-2H-pyranyl, hexahydro-1H-azepinyl, 1,3-dioxolanyl, 1,3-dioxanyl, piperidinyl, piperazinyl, imidazolyl, pyrazolyl, triazolyl and pyridinyl; wherein 1,3-dioxolanyl, 1,3-dioxanyl, piperazinyl and piperidinyl are optionally substituted with 1 to 2 substituents independently selected from the group consisting of methyl, acetyl, carboxyl, phenyl (optionally substituted with chlorine), di(methyl)amino, methylsulfonyl, methylaminosulfonyl and oxo.

20. The compound of claim 1 wherein $R_3$ is selected from the group consisting of H, lower alkyl, lower alkoxy, OH, halogen, cyano, amino, alkylamino and di(alkyl)amino.

21. The compound of claim 1 wherein $R_3$ is selected from the group consisting of H, lower alkyl, lower alkoxy, OH, halogen, amino and di(alkyl)amino.

22. The compound of claim 1 wherein $R_3$ is selected from the group consisting of H and methyl.

23. A compound selected from the group consisting of:
3-[[5-[6-[(3-chlorophenyl)amino]pyrazinyl]-3-pyridinyl]amino]-1-propanol;
3-[[5-[2-[(3-chlorophenyl)amino]-6-methyl-4-pyrimidinyl]-3-pyridinyl]amino]-1-propanol;
2-[[5-[6-[(3-chlorophenyl)amino]pyrazinyl]-3-pyridinyl]amino]-ethanol;
4-[[5-[6-[(3-chlorophenyl)amino]pyrazinyl]-3-pyridinyl]amino]-1-butanol;
3-[[5-[6-[(3-fluorophenyl)amino]pyrazinyl]-3-pyridinyl]amino]-1-propanol;
3-[[5-[6-[(3-methoxyphenyl)amino]pyrazinyl]-3-pyridinyl]amino]-1-propanol;
3-[[5-[6-[(phenylmethyl)amino]pyrazinyl]-3-pyridinyl]amino]-1-propanol;
3-[[6'-[(3-chlorophenyl)amino][2,2'-bipyrazin]-6-yl]amino]-1-propanol;
3-[[4-[6-[(3-chlorophenyl)amino]pyrazinyl]-3-pyridinyl]amino]-1-propanol;
3-[[5-[6-[(3-chlorophenyl)amino]pyrazinyl]-2-thiazolyl]amino]-1-propanol; and,
2-[2-[2-[[5-[6-[(3-chlorophenyl)amino]pyrazinyl]-3-pyridinyl]amino]ethoxy]ethoxy]-ethanol.

24. A compound selected from the group consisting of:
6-(5-amino-3-pyridinyl)-N-(3-chlorophenyl)-2-pyrazinamine; $N^1$-[5-[6-[(3-chlorophenyl)amino]pyrazinyl]-3-pyridinyl]-$N^2$,$N^2$-dimethyl-1,2-ethanediamine;
N-[5-[6-[(3-chlorophenyl)amino]pyrazinyl]-3-pyridinyl]-4-morpholinepropanamine;
$N^1$-[5-[6-[(3-chlorophenyl)amino]pyrazinyl]-3-pyridinyl]-$N^3$,$N^3$-dimethyl-1,3-propanediamine;
N-(3-chlorophenyl)-6-[5-[[3-(1-piperazinyl)propyl]amino]-3-pyridinyl]-2-pyrazinamine;
N-(3-chlorophenyl)-6-[5-[[4-(4-pyridinyl)butyl]amino]-3-pyridinyl]-2-pyrazinamine;
N-(3-chlorophenyl)-6-[5-[[3-(4-pyridinyl)propyl]amino]-3-pyridinyl]-2-pyrazinamine;
N-(3-chlorophenyl)-6-[5-[[3-(3-pyridinyl)propyl]amino]-3-pyridinyl]-2-pyrazinamine;
N-(3-chlorophenyl)-6-[5-[[3-(1H-pyrazol-1-yl)propyl]amino]-3-pyridinyl]-2-pyrazinamme;
N-(3-chlorophenyl)-6-[5-[[3-(1H-1,2,4-triazol-1-yl)propyl]amino]-3-pyridinyl]-2-pyrazinamine;
N-(3-chlorophenyl)-6-[5-[[3-(1H-imidazol-1-yl)propyl]amino]-3-pyridinyl]-2-pyrazinamine;
N-(3-chlorophenyl)-6-[5-[[(tetrahydro-2H-pyran-4-yl)methyl]amino]-3-pyridinyl]-2-pyrazinamine;
N-(3-chlorophenyl)-6-[5-[[2-(2-methoxyethoxy)ethyl]amino]-3-pyridinyl]-2-pyrazinamine;
N-(4-methoxyphenyl)-6-[5-[[3-(4-pyridinyl)propyl]amino]-3-pyridinyl]-2-pyrazinamine;
N-(3,4-dichlorophenyl)-6-[5-[[3-(4-pyridinyl)propyl]amino]-3-pyridinyl]-2-pyrazinamine;
N-[5-[6-[(3-chlorophenyl)amino]pyrazinyl]-3-pyridinyl]-2-(2-methoxyethoxy)-acetamide;
N-[5-[6-[(3-chlorophenyl)amino]pyrazinyl]-3-pyridinyl]-2-ethoxy-acetamide;

N-[5-[6-[(3-chlorophenyl)amino]pyrazinyl]-3-pyridinyl]-3-methoxy-propanamide; and, N-[5-[6-[(3-chlorophenyl)amino]pyrazinyl]-3-pyridinyl]-2-hydroxy-acetamide.

25. A compound selected from the group consisting of:

N-[5-[6-[(3-chlorophenyl)amino]pyrazinyl]-3-pyridinyl]-2-methoxy-acetamide;

N-[5-[6-[(3-chlorophenyl)amino]pyrazinyl]-3-pyridinyl]-3-pyridinecarboxamide;

N-[5-[6-[(3-chlorophenyl)amino]pyrazinyl]-3-pyridinyl]-1-pyrrolidinecarboxamide; and, 4-[[5-[6-[(3-chlorophenyl)amino]pyrazinyl]-3-pyridinyl]amino]-butanoic acid ethyl ester.

26. A compound of Formula 2:

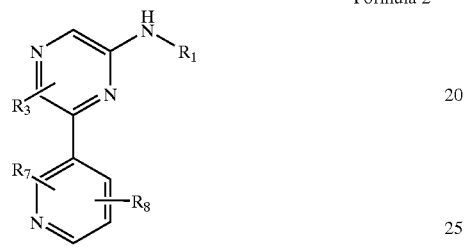

Formula 2 or a pharmaceutically acceptable salt thereof, wherein $R_1$ is aryl or bicyclic aryl, optionally substituted with 1 to 5 substituents independently selected from the group consisting of alkyl, lower alkyl, alkenyl, alkynyl, alkoxy, lower alkoxy, heterocyclyl, heterocyclylalkyl, heterocyclylalkenyl, heterocyclylalkynyl, heterocyclylalkoxy, aryl, arylalkyl, arylalkenyl, arylalkynyl, arylalkoxy, heteroaryl, heteroarylalkyl, heteroarylalkenyl, heteroarylalkynyl, heteroarylalkoxy, OH, hydroxyalkyl, halogen, cyano, nitro, amino, alkylamino, alkylaminoalkyl, alkylaminoalkylamino, aminoalkyl, aminoalkylamino, di(alkyl)amino, di(alkyl)aminoalkyl, di(alkyl)aminoalkylamino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), aminosulfonyl, aminosulfonylalkyl, alkylaminosulfonyl, alkylaminosulfonylalkyl, di(alkyl)aminosulfonyl, di(alkyl)aminosulfonylalkyl, carboxyl, (hydroxyalkyl)carbonyl, (hydroxyalkoxy)carbonyl, trihalo substituted lower alkyl and trihalo substituted lower alkoxy;

$R_7$ is selected from the group consisting of alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy;

$R_8$ is selected from the group consisting of alkyl, OH, hydroxyalkyl, halogen, cyano, amino, alkylamino, di(alkyl)amino, (hydroxyalkyl)amino, di(hydroxyalkyl)amino, carbamoyl, alkylcarbonylamino, alkylcarbonyl, alkoxycarbonyl, (hydroxyalkyl)carbonyl, (hydroxyalkoxy)carbonyl, $O(CH_2)_nR_5$, $O(CH_2)_nO(CH_2)_mR_5$, $O(CH_2)_nCH[(CH_2)_mR_5]_2$, $O(CH_2)_nN[(CH_2)_mR_5]_2$, $OCON[(CH_2)_mR_5]_2$, $NH(CH_2)_nR_5$, $NH(CH_2)_nCH(R_5)_2$, $NH(CH_2)_nSO_2(CH_2)_mR_5$, $NH(CH_2)_nO(CH_2)_mR_5$, $NH(CH_2)_nOCH[(CH_2)_mR_5]_2$, $NH(CH_2)_nO(CH_2)_mO(CH_2)_mR_5$, $NH(CH_2)_nN[(CH_2)_mR_5]_2$, $NH(CH_2)_nSO_2NH(CH_2)_mR_5$, $NH(CH_2)_nCH(OH)(CH_2)_mR_5$, $NH(CH_2)_nCH(OH)(CH_2)_mOR_5$, $NH(CH_2)_nCH(OH)(CH_2)_mN[(CH_2)_m-R_5]_2$, $NH(CH_2)_nCO(CH_2)_mN[(CH_2)_mR_5]_2$, $NH(CH_2)_nCO_2(CH_2)_mR_5$, $NH(CH_2)_nCO(CH_2)_mSO_2NH(CH_2)_mR_5$, $NHCO(CH_2)_nCH(R_5)_2$, $NHCO(CH_2)_nR_5$, $NHCO(CH_2)_nO(CH_2)_mR_5$, $NHCO(CH_2)_nO(CH_2)_mO(CH_2)_mR_5$, $NHCO(CH_2)_nO(CH_2)_mCO(CH_2)_mR_5$, $NHCO(CH_2)_nN[(CH_2)_mR_5]_2$, $CONH(CH_2)_nO(CH_2)_mR_5$, and $CONH(CH_2)_nN[(CH_2)_mR_5]_2$; wherein n is an integer from 0 to 6 and m is an integer from 0 to 4; with the proviso, that m is at least 1 when $R_5$ is selected from the group consisting of OH, amino, alkylamino and di(alkyl)amino;

$R_5$ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents; and, $R_3$ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

27. A compound of Formula 1:

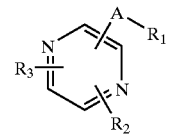

Formula 1 or a pharmaceutically acceptable salt thereof, wherein

R₁ is phenyl, optionally substituted with 1 to 5 halo or methoxy substituents;

A is —N(R₄)(CH₂)ₓ—; wherein x is an integer from 0 to 4;

R₄ is selected from the group consisting of H, lower alkyl, alkyl, hydroxyalkyl, alkoxyalkyl, arylalkyl, lower alkenyl, alkenyl, aryl and heteroaryl; wherein aryl and heteroaryl are optionally substituted with 1 to 5 substituents independently selected from the group consisting of OH, halogen, cyano, nitro, amino, alkylamino, di(alkyl)amino, (hydroxyalkyl)amino, di(hydroxyalkyl)amino, alkyl, lower alkyl, alkoxy, lower alkoxy, tri(halo)substituted lower alkyl and tri(halo)substituted lower alkoxy;

R₂ is selected from the group consisting of pyridinyl, thiazolyl, and pyrazinyl, optionally substituted with 1 to 2 substituents independently selected from R₇ and 1 substituent selected from R₈;

R₇ is selected from the group consisting of H, OH, alkyl, halo, cyano, nitro, amino, acyl, and acylamino;

R₈ is selected from the group consisting of OH, halo, cyano, alkyl, amino, hydroxyalkyl, (hydroxyalkyl)amino, carboxy, carbamoyl, alkoxycarbonyl, NH-(CH₂)ₙR₅, CONH(CH₂)ₙO(CH₂)ₘR₅, CONH(CH₂)ₙN[(CH₂)ₘR₅]₂, NHCO(CH₂)ₙO(CH₂)ₘR₅, NHCO-(CH₂)ₙR₅, NH(CH₂)ₙO(CH₂)ₘO(CH₂)ₘR₅, NH(CH₂)ₙCO₂(CH₂)ₘR₅, NHCO(CH₂)ₙO(CH₂)ₘO(CH₂)ₘR₅NH(CH₂)ₙO(CH₂)ₘR₅, and NH(CH₂)ₙCON(C₂H₅)₂; wherein n is an integer from 0 to 6 and m is an integer from 0 to 4; with the proviso, that m is at least 1 when R₅ is OH or amino;

R₅ is selected from the group consisting of H, OH, lower alkyl, amino, alkylamino, di(alkyl)amino, aryl, heteroaryl, biheteroaryl and heterocyclyl; wherein aryl, heteroaryl and heterocyclyl are optionally substituted with 1 to 3 substituents independently selected from the group consisting of alkyl, lower alkyl, acyl, carboxyl, aryl (optionally substituted with 1 to 5 halogen substituents), OH, halogen, cyano, amino, alkylamino, di(alkyl)amino, (hydroxyalkyl)amino, di(hydroxyalkyl)amino, alkylsulfonyl, aminosulfonyl, alkylaminosulfonyl and aminosulfonylalkyl; and, wherein heterocyclyl is further optionally substituted with 1 to 3 oxo substituents; and, R₃ is selected from the group consisting of H, alkyl, lower alkyl, alkoxy, lower alkoxy, alkenyl, alkynyl, heterocyclyl, heterocyclylalkyl, heterocyclylalkoxy, aryl, arylalkyl, arylalkoxy, OH, hydroxyalkyl, halogen, cyano, nitro, amino, alkylamino, di(alkyl)amino, (hydroxyalkyl)amino, di(hydroxyalkyl)amino, carbamoyl, acyl, acylalkyl, alkoxycarbonyl, alkoxycarbonylalkyl, acylamino, alkylsulfonyl, alkylsulfonylamino, arylsulfonylamino (wherein aryl is substituted with 1 to 3 substituents independently selected from the group consisting of cyano, halogen, hydroxy, nitro, tri(halo)substituted lower alkyl and tri(halo)substituted lower alkoxy), carboxyl, (hydroxyalkyl)carbonyl, (hydroxyalkoxy)carbonyl, tri(halo)substituted lower alkyl and tri(halo)substituted lower alkoxy.

28. A pharmaceutical composition comprising a pharmaceutically acceptable carrier and a compound of claim 1.

29. A pharmaceutical composition comprising a pharmaceutically acceptable carrier and a compound of claim 23.

30. A pharmaceutical composition comprising a pharmaceutically acceptable carrier and a compound of claim 24.

31. A pharmaceutical composition comprising a pharmaceutically acceptable carrier and a compound of claim 25.

32. A method of inhibiting the vascular endothelial growth factor (VEGF) receptor tyrosine kinase in a patient comprising the step of administering a therapeutically effective amount of the compound of claim 1.

33. The method of claim 32 wherein the method is used in a patient with aberrant angiogenesis, tumors, diabetic retinopathy, rheumatoid arthritis, endometriosis or psoriasis.

34. A method of treating aberrant angiogenesis in a subject in need thereof comprising administering a therapeutically effective amount of the compound of claim 1.

35. A method of treating a cancer capable of stimulating angiogenesis in a subject in need thereof comprising administering a therapeutically effective amount of the compound of claim 1.

36. A method of treating diabetic retinopathy in a subject in need thereof comprising administering a therapeutically effective amount of the compound of claim 1.

37. A method of treating rheumatoid arthritis in a subject in need thereof comprising administering a therapeutically effective amount of the compound of claim 1.

38. A method of treating endometriosis in a subject in need thereof comprising administering a therapeutically effective amount of the compound of claim 1.

39. A method of treating psoriasis in a subject in need thereof comprising administering a therapeutically effective amount of the compound of claim 1.

40. A method of inhibiting vascular endothelial growth factor (VEGF) receptor tyrosine kinase in a subject comprising the step of administering a composition of claim 28 in a therapeutically effective amount.

41. The method of claim 40 wherein the method is used to treat a patient with aberrant angiogenesis, tumors, diabetic retinopathy, rheumatoid arthritis, endometriosis and psoriasis.

42. A method of treating aberrant angiogenesis in a subject in need thereof comprising administering a therapeutically effective amount of the composition of claim 28.

43. A method of treating solid-tumor cancer in a subject in need thereof comprising administering a therapeutically effective amount of the composition of claim 28.

44. A method of treating diabetic retinopathy in a subject in need thereof comprising administering a therapeutically effective amount of the composition of claim 28.

45. A method of treating rheumatoid arthritis in a subject in need thereof comprising administering a therapeutically effective amount of the composition of claim 28.

46. A method of treating endometriosis in a subject in need thereof comprising administering a therapeutically effective amount of a pharmaceutical composition of claim 28.

47. A method of treating psoriasis in a subject in need thereof comprising administering a therapeutically effective amount of a pharmaceutical composition of claim 28.

48. A method of inhibiting vascular endothelial growth factor (VEGF) receptor tyrosine kinase in a patient comprising the step of administering a therapeutically effective amount of the composition of claim 29.

49. The method of claim 48 wherein the method is used to treat a patient with aberrant angiogenesis, angiogenesis-dependent tumors, diabetic retinopathy, rheumatoid arthritis endometriosis and psoriasis.

50. A method of treating aberrant angiogenesis in a subject in need thereof comprising administering a therapeutically effective amount of the composition of claim 29.

51. A method of treating a cancer capable of stimulating angiogenesis in a subject in need thereof comprising administering a therapeutically effective amount of the composition of claim 29.

52. A method of treating diabetic retinopathy in subject in need thereof comprising administering a therapeutically effective amount of the composition of claim 29.

53. A method of treating rheumatoid in a subject in need thereof comprising administering a therapeutically effective amount of the composition claim 29.

54. A method of treating endometriosis in a subject in need thereof comprising administering a therapeutically effective amount of the composition of claim 29.

55. A method of treating psoriasis in a subject in need thereof comprising administering a therapeutically effective amount of the composition of claim 29.

56. A method of inhibiting vascular endothelial growth factor (VEGF) receptor tyrosine kinase in a patient comprising the step of administering a therapeutically effective amount of the composition claim 30.

57. The method of claim 56 wherein the method is used to treat a patient with aberrant angiogenesis, angiogenesis-dependent tumors, diabetic retinopathy, rheumatoid arthritis, endometriosis and psoriasis.

58. A method of treating aberrant angiogenesis in a subject in need thereof comprising administering a therapeutically effective amount of the composition claim 30.

59. A method of treating a cancer capable of stimulating angiogenesis in a subject in need thereof comprising administering a therapeutically effective amount of the composition of claim 30.

60. A method of treating diabetic retinopathy in subject in need thereof comprising administering a therapeutically effective amount of the composition of claim 30.

61. A method of treating rheumatoid arthritis in a subject in need thereof comprising administering a therapeutically effective amount of the composition of claim 30.

62. A method of treating endometriosis in a subject in need thereof comprising administering a therapeutically effective amount of the composition of claim 30.

63. A method of treating psoriasis in a subject in need thereof comprising administering a therapeutically effective amount of the composition claim 30.

64. A method of inhibiting vascular endothelial growth factor (VEGF) receptor tyrosine kinase in a patient comprising the step of administering a therapeutically effective amount of the composition claim 31.

65. The method of claim 64 wherein the method is used to treat a patient with aberrant angiogenesis, angiogenesis-dependent tumors, diabetic retinopathy, rheumatoid arthritis, endometriosis and psoriasis.

66. A method of treating aberrant angiogenesis in a subject need thereof comprising administering a therapeutically effective amount of the composition of claim 31.

67. A method of treating a cancer capable of stimulating angiogenesis in subject in need thereof comprising administering a therapeutically effective amount of the composition of claim 31.

68. A method of treating diabetic retinopathy in a subject in need thereof comprising administering a therapeutically effective amount of the composition of claim 31.

69. A method of treating rheumatoid arthritis in a subject in need thereof comprising administering a therapeutically effective amount of the composition claim 31.

70. A method of treating endometriosis in a subject in need thereof comprising administering a therapeutically effective amount of the composition of claim 31.

71. A method of treating psoriasis in a subject in need thereof comprising administering a therapeutically effective amount of the composition of claim 31.

* * * * *